US007145467B2

(12) United States Patent
Abel et al.

(10) Patent No.: US 7,145,467 B2
(45) Date of Patent: Dec. 5, 2006

(54) MEDICAL GAS ALARM SYSTEM

(75) Inventors: Joseph H. Abel, New Palestine, IN (US); William C. Bohlinger, Buffalo City, WI (US); Stanton H. Breitlow, Winona, MN (US); Edward W. Catton, New Palestine, IN (US); Thomas J. Dubisar, Winona, MN (US); James P. Hentges, Fountain City, WI (US); Richard E. Hoffman, Overland Park, KS (US); William J. Kaht, Burlington, KY (US); Nick D. LaBare, Winona, MN (US); Robert O. Moran, Onalaska, WI (US); Thomas R. Pfingsten, Winona, MN (US); Phillip B. Plyler, Atlanta, GA (US); John M. Sharer, Batesville, IN (US); John B. Wilker, Sr., St. Leon, IN (US); Dale T. Wolfe, Onalaska, WI (US)

(73) Assignee: Beacon Medical Products LLC, Charlotte, NC (US)

( * ) Notice: Subject to any disclaimer, the term of this patent is extended or adjusted under 35 U.S.C. 154(b) by 0 days.

(21) Appl. No.: 11/138,867

(22) Filed: May 25, 2005

(65) Prior Publication Data
US 2005/0275548 A1 Dec. 15, 2005

Related U.S. Application Data

(63) Continuation of application No. 09/933,502, filed on Aug. 20, 2001, now Pat. No. 6,987,448.

(51) Int. Cl.
*G08B 17/10* (2006.01)
*G01N 9/00* (2006.01)
*A61B 5/00* (2006.01)
(52) U.S. Cl. ............... 340/632; 340/506; 340/614; 340/500; 600/300; 128/903; 137/551; 137/557; 706/924; 702/24; 73/23.27; 73/23.2
(58) Field of Classification Search ............... 340/632
See application file for complete search history.

(56) References Cited

U.S. PATENT DOCUMENTS 6,987,448 B1 * 1/2006 Catton et al. ............... 340/506
2002/0020444 A1 * 2/2002 Dickerson et al. .......... 137/112

* cited by examiner

*Primary Examiner*—Donnie L. Crosland
(74) *Attorney, Agent, or Firm*—Finnegan, Henderson, Farabow, Garrett & Dunner, LLP

(57) ABSTRACT

A medical gas alarm system for use in a healthcare facility having a medical gas system and having a network of computer devices is provided. The alarm system includes at least one area alarm controller adapted to receive a first signal indicative of a condition of a first portion of the medical gas system. The area alarm controller is adapted to communicate with the network. The alarm system also includes at least one master alarm controller adapted to receive a second signal indicative of a condition of a second portion of the medical gas system. The master alarm controller is adapted to communicate with the network. The area alarm controller is adapted to communicate with the master alarm controller through the network.

15 Claims, 184 Drawing Sheets

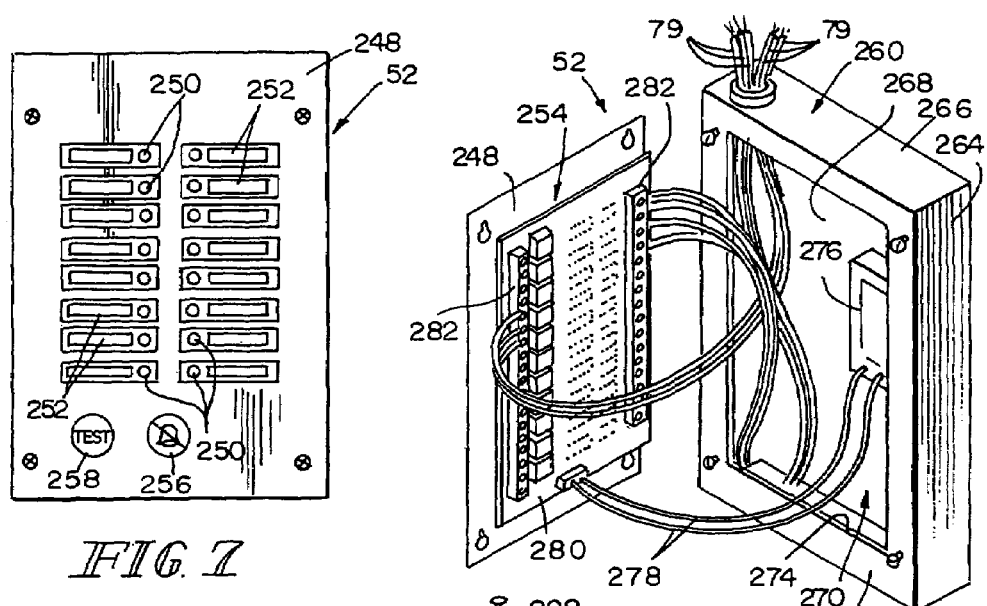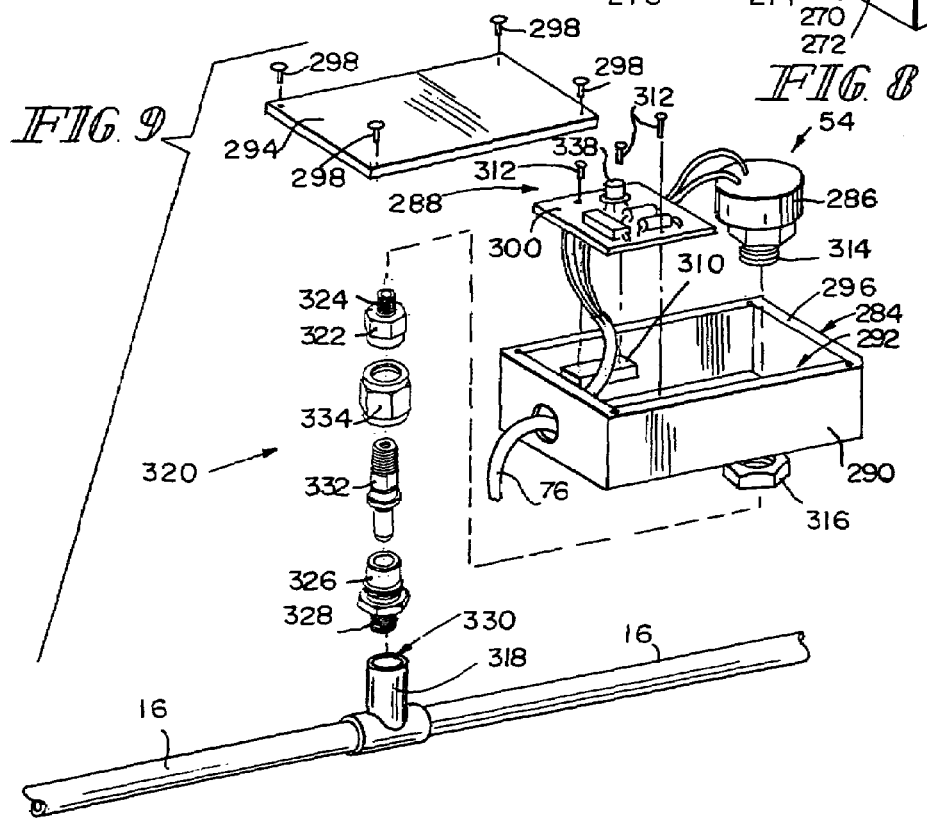

Network Devices    /374 Master Alarm /376

View Master    Data at 06-Aug-2001 09:57:48 Refresh

| | Device | Jump | View | Type | SN | Area | Zone | Floor | Direction | Status | Alarms |
|---|---|---|---|---|---|---|---|---|---|---|---|
| Home | | | | | | | | | | | |
| Alarms | This Master | Jump | View | AreaCombo | 40000 | General | 1 | 1 | North | Ok | Fault |
| Network Devices | Master49000 | Jump | View | AreaComms | 49000 | ER | 3 | 2 | East | Ok | |
| Device information | Area39001 | Jump | View | AreaComms | 39001 | ENG | 2 | 4 | North | Ok | None |
| Event Log | Area39002 | Jump | View | AreaComms | 39002 | OR | 2 | 2 | North | Ok | None |
| Setup Master | Area39003 | Jump | View | AreaComms | 39003 | PACU | 3 | 1 | North | Ok | None |
| Login | Area39004 | Jump | View | AreaComms | 39004 | CCU | 1 | 4 | East | Ok | None |
| Diagnostics | Area39005 | Jump | View | AreaComms | 39005 | ENG | 1 | 1 | North | Ok | None |
| Diagnostics | Area39006 | Jump | View | AreaComms | 39006 | OR | 1 | 1 | South | Ok | None |
| Help | Area39010 | Jump | View | AreaComms | 39010 | PACU | 3 | 2 | East | Ok | None |
| | Area39007 | Jump | View | AreaComms | 39007 | PACU | 3 | 2 | East | Ok | None |
| | Area39008 | Jump | View | AreaComms | 39008 | ER | 3 | 5 | East | Ok | None |
| | Area39009 | Jump | View | AreaComms | 39009 | CCU | 3 | 3 | North | Ok | None |

Device Information            Master Alarm

View Master
Home
Alarms
Network Devices
Device Information
Event Log
Setup Master
Login
Diagnostics
Diagnostics
Help

| | |
|---|---|
| Type | Master Alarm |
| Serial Number | 10013 |
| Model Number | HRMM-0000-0000 |
| Software Version | 0.37 |
| Software Build | 024 |
| Current Time | 28-Jun-2001 13:33:39 |
| Date Code | Week 23, 2001 |
| Name | Master10013 |
| Location | PBX |
| Zone | 1 |
| Floor | 1 |
| Direction | South |
| IP Address | 192.168.1.100 |
| MAC Address | 00:03:aa:00:00:13 |

375

| Specific Area | 387 | Master Alarm | | | | |
|---|---|---|---|---|---|---|

View Master
Home
Alarms
Network Devices
Device Information
Event Log
Setup Master
Login
Diagnostics
Diagnostics
Help Back  Refresh ←376

Area Communication Module                                    ←379

| Name | SN | Area | Zone | Floor | Dir | Status |
|---|---|---|---|---|---|---|
| This Master | 40000 | General | 1 | 1 | North | Ok |

Area Displays                                                ←381

| Gas Type | SN | Trans SN | Item | Value | Units | Alarm | Area | Zone | Floor | Dir | Status |
|---|---|---|---|---|---|---|---|---|---|---|---|
| Nitrogen | 5000 | 0 | Pressure | 0 | PSI | None | ER | 1 | 1 | North | Wiring |
| Nitrogen | 5004 | 0 | Pressure | 0 | PSI | None | OR | 1 | 2 | East | Wiring |

| Specific Area | 387 | Master Alarm | | | | |
|---|---|---|---|---|---|---|

View Master
Home
Alarms
Network Devices
Device Information
Event Log
Setup Master
Login
Diagnostics
Diagnostics
Help Back  Refresh ←376

Area Communication Module                                    ←383

| Name | SN | Area | Zone | Floor | Dir | Status |
|---|---|---|---|---|---|---|
| Area39002 | 39002 | OR | 2 | 2 | North | Ok |

Area Displays                                                ←385

| Gas Type | SN | Trans SN | Item | Value | Units | Alarm | Area | Zone | Floor | Dir | Status |
|---|---|---|---|---|---|---|---|---|---|---|---|
| Oxygen | 29021 | 19021 | Pressure | 26 | PSI | None | ICU | 3 | 4 | South | Ok |
| Medical Air | 29022 | 19022 | Pressure | 58 | PSI | None | ICU | 3 | 4 | South | Ok |
| Medical Air | 29023 | 19023 | Pressure | 60 | PSI | None | CCU | 2 | 5 | South | Ok |
| Oxygen | 29024 | 19024 | Pressure | 39 | PSI | None | CCU | 2 | 4 | South | Ok |
| WAGD | 29025 | 19025 | Pressure | 30 | PSI | None | ICU | 3 | 5 | East | Ok |
| WAGD | 29026 | 19026 | Pressure | 42 | PSI | None | ER | 3 | 5 | South | Ok |

Master Alarm - Device Configuraton

*Master Alarm Configuration Summary*

Device Name - Master10013  /432
Location - no location
Language - English
Alarm Silence - never
IP Addressing - DHCP, Auto IP, Fixed
Firmware version - 0.37  /430

Alarm 1 - Medical Air, Low Line Pressure, led=1, sytem=1
Alarm 2 - Medical Air, Compressor Malfunc., led=1, sytem=1
Alarm 3 - Oxygen, Low Line Pressure, led=2, sytem=1
Alarm 4 - Oxygen, Resrv. Supply in Use, led=2, sytem=1
Alarm 5 - Oxygen, Low Line Pressure, led=2, sytem=2
Alarm 6 - Oxygen, Resrv. Supply in Use, led=2, sytem=2
Alarm7 - Medical Vacuum, Low Vacuum, led=3, sytem=1
Alarm8 - Medical Vacuum, Service Required, led=3, sytem=1
Alarm9 - WAGD, Thermal Shutdown, led=4, sytem=1
Alarm10 - WAGD, Service Required, led=4, sytem=1
Alarm11 - WAGD, Backup Vac. Pump On, led=4, sytem=1
Alarm12 - Unused
Alarm13 - Unused
Alarm14 - Unused
Alarm15 - Unused
Alarm16 - Unused
Alarm17 - Nitrous Oxide, Reserve Supply Low, led=3, sytem=5
Alarm18 - Unused
Alarm19 - Unused
Alarm20 - Unused
Alarm21 - Unused
Alarm22 - Unused
Alarm23 - Unused
Alarm24 - Unused
Alarm25 - Unused
Alarm26 - Unused
Alarm27 - Unused
Alarm28 - Unused
Alarm29 - Unused
Alarm30 - Unused

| Network Statistics | 436 | Master Alarm |
|---|---|---|
| View Master | Refresh | |
| Home | IP Address | 192.168.1.100 |
| | Subnet | 255.255.255.0 |
| Setup Master | Gateway | 192.168.1.1 |
| Login | Fixed IP Address | 192.168.1.1 |
| | Fixed Subnet | 255.0.0.0 |
| Diagnostics | Fixed Gateway | 0.0.0.0 |
| Download Configuration | Mac Address | 00:03:aa:00:00:13 |
| Network Statistics | Receives | 354 |
| Physical Inputs | Unicasts | 332 |
| | Multicasts | 0 |
| Help | Broadcasts | 22 |
| | Rx Errors | 0 |
| | Rx Missed | 0 |
| | Rx CRC Errors | 0 |
| | Rx Drops | 0 |
| | Transmits | 603 |
| | Buffer Defers | 0 |
| | Tx Errors | 0 |
| | Tx Collisions | 0 |
| | Tx Coll. Overflow | 0 |
| | Tx FILO Errors | 0 |
| | Traffic Backoffs | 0 |

Alarm Message Setup — Master Alarm
Click on a number to change an alarm message

View Master
Home

Setup Master 494

Setup Alarm Messages
Setup Device
Email Notification
Set Clock
Administer Users
Setup Network
Clear Network
Update Flash
Transfer Setup

Help

| Alarm Input | Gas Type | Message for Condition | LED | System |
|---|---|---|---|---|
| 1 | Medical Air | Low Line Pressure | 1 | 1 |
| 2 | Medical Air | Compressor Malfunc. | 1 | 1 |
| 3 | Oxygen | Low Line Pressure | 2 | 1 |
| 4 | Oxygen | Resrv. Supply in Use | 2 | 1 |
| 5 | Oxygen | Low Line Pressure | 2 | 2 |
| 6 | Oxygen | Resrv. Supply in Use | 2 | 2 |
| 7 | Medical Vacuum | Low Vacuum | 3 | 1 |
| 8 | Medical Vacuum | Service Required | 3 | 1 |
| 9 | WAGD | Thermal Shutdown | 4 | 1 |
| 10 | WAGD | Service Required | 4 | 1 |
| 11 | WAGD | Backup Vac. Pump Low | 4 | 1 |
| 12 | Unused | Unused | 0 | 1 |
| 13 | Unused | Unused | 0 | 1 |
| 14 | Unused | Unused | 0 | 1 |
| 15 | Unused | Unused | 0 | 1 |
| 16 | Unused | Unused | 0 | 1 |
| 17 | Nitrous Oxide | Reserve Supply Low | 3 | 5 |
| 18 | Unused | Unused | 0 | 1 |
| 19 | Unused | Unused | 0 | 1 |
| 20 | Unused | Unused | 0 | 1 |
| 21 | Unused | Unused | 0 | 1 |
| 22 | Unused | Unused | 0 | 1 |
| 23 | Unused | Unused | 0 | 1 |
| 24 | Unused | Unused | 0 | 1 |
| 25 | Unused | Unused | 0 | 1 |
| 26 | Unused | Unused | 0 | 1 |
| 27 | Unused | Unused | 0 | 1 |
| 28 | Unused | Unused | 0 | 1 |
| 29 | Unused | Unused | 0 | 1 |
| 30 | Unused | Unused | 0 | 1 |

494 (pointing to rows 13, 14, 15); 494 → 17; 494 → 30

```
Setup Alarm Messages Step     Master Alarm
2

View Master            Select the Gas Type that is wired to input 17
Logout->Home                498
                                                    ─512
Setup Master           Gas Type   [Nitrous Oxide  |▼]
Setup Alarm Messages   LED 500→ [3|▼]
Setup Device           System    [5|▼]─512
Email Notification          510/    ─512
Set Clock
Administer Users       [Next]
Setup Network                 ─514
Clear Network
Update Flash
Transfer Setup
Logout
Help
```

```
Setup Alarm Messages Step              Master Alarm
3
View Master            Alarm Number            17
Logout->Home           Gas Type                Nitrous Oxide
                       LED Number              3
Setup Master           System Number           5
Setup Alarm Messages   Alarm message for this input [Reserve Supply Low |▼]
Setup Device                                              520
Email Notification                      518
Set Clock                       522
Administer Users       [Next]
Setup Network
Clear Network
Update Flash
Transfer Setup
Logout
Help
```

Setup Alarm Messages Final                Master Alarm

View Master
Logout->Home              Changes complete

Input Number          17
Setup Master          Gas Type              Nitrous Oxide
Setup Alarm Messages      Alarm Message         Reserve Supply Low
Setup Device              LED Number            3
Email Notification        System Number         5
Set Clock                                              ╱ 525
Administer Users          Return to Alarm Messages
Setup Network
Clear Network
Update Flash
Transfer Setup
Logout
Help

Setup Device                              Master Alarm
                                528
View Master
Logout->Home             Device Name     [Master10013]
                                  530
Setup Master         Location        [PBX        ▽] — 532
Setup Alarm Messages             534
Setup Device             Zone            [1          ]
Email Notification               536
Set Clock                Floor           [1          ]
Administer Users                 538                     — 540
Setup Network            Direction       [South      ▽]
Clear Network            Silenced return time [never  ▽] — 544
Update Flash                      542
Transfer Setup              [Submit]  [Reset]
Logout          544                         — 546
Help

Clock Accepted                          Master Alarm

596

View Master
Home                 Changes were accepted

Setup Master       The clock is now set to 26-Jul-2001 10:54:27
Setup Alarm Messages
Setup Device
Email Notification
Set Clock
Administer Users
Setup Network
Clear Network
Update Flash
Transfer Setup Help

User Administration                      Master Alarm

View Master     These entries are case sensitive
Logout->Home

User Name      Password

Setup Master       User 1 Name   [new]        [ ]
Setup Alarm Messages   User 2 Name   [ ]          [ ]
Setup Device
Email Notification      User 3 Name   [ ]          [ ]
Set Clock                            600            610
Administer Users
Setup Network
Clear Network      612      614
Update Flash
Transfer Setup      [Submit]   [Reset]
Logout Help

| User Name Changes Accepted | Master Alarm |
|---|---|
| View Master | |
| Home | Changes to user name and password were accepted |
| Setup Master | |
| Setup Alarm Messages | |
| Setup Device | |
| Email Notification | |
| Set Clock | |
| Administer Users | |
| Setup Network | |
| Clear Network | |
| Update Flash | |
| Transfer Setup | |
| Help | |

FIG. 33

```
672
   Logout                          Master Alarm
   View Master        Logged out of setup
   Home
   Alarms
   Network Devices
   Device Information
   Event Log Setup Master
   Login Diagnostics
   Diagnostics Help
```

FIG. 41

```
680
                682                  Area Communications
                                            Module
   View Area  684    Home
   Home           686  This page is served from an Area Communications Board
   Gas Readings      688
   Device Information
   Masters ← 690              692
   Alarms ← 692    Active Alarms        686
   Event Log ← 694  Detailed Information from Areas    688
                    Information about this Communication Module
   Setup Area       Master Alarms on this Network
   Log In ← 696     Event History              690
                                    694
   Diagnostics      698
   Network Statistics Help ← 700
```

View Area
Home
Gas Readings
Device Information
Masters
Alarms     726
Event Log  728

Setup Area
Log In

Diagnostics
Network Statistics
Help

Area Display Data

Area Communications Module
725

Data at 12-Jul-2001 15:40:52

| Item | Value |
|---|---|
| Gas Type | Nitrogen |
| Measurement | Pressure |
| Value | 144 PSI |
| Alarm | None |
| Status | Ok |
| Connection | Resolved |
| Area | OR |
| Zone | 1 |
| Floor | 1 |
| Direction | |
| Alarm High | 190 PSI |
| Alarm Low | 140 PSI |
| Display SN | 4100 |
| Transducer SN | 1016 |

730 Direction
732 Alarm High
734 Alarm Low
736 Display SN

*FIG. 45*

| | | |
|---|---|---|
| View Area | | Area Communications |
| Home | Device Info | Module |
| Gas Readings | | |
| Device Information | | |
| Masters | | |
| Alarms | Type: | Area Communications Module |
| Event Log | Serial Number: | 1051 |
| | Model Number: | HRCM-0000-0000 |
| Setup Area | Software Version: | 0:37 |
| Log In | Software Build: | 018 |
| Diagnostics | Current Time: | 12-Jul-2001 15:41:20 |
| Network Statistics | Date Code: | Week 7, 2001 |
| | Name: | Comms11 |
| Help | Area: | OR |
| | Zone: | 1 |
| | Floor: | 1 |
| | Direction: | East |
| | IP Address: | 192.168.1.200 |
| | MAC Address: | 00:03:aa:00:00:11 |

| | | | |
|---|---|---|---|
| View Area | | Area Communications | |
| Home | Masters | Module | |
| Gas Readings | | | 742 |
| Device Information | Refresh Data at 12-Jul-2001 15:41:38 | | |
| Masters | Master | Details | Location |
| Alarms | | | |
| Event Log | Master10013 | | PBX |
| Setup Area | 744 | | |
| Log In | | | |
| Diagnostics | | | |
| Network Statistics | | | |
| Help | | | |

| View Area | Area Display - Network Setup Result |
|---|---|
| Home | |
| Gas Readings | |
| Device Information | |
| Masters | Changes to the network setup where accepted |
| Alarms | |
| Event Log | |
| Setup Area | |
| Setup Device | |
| Setup Network | |
| Set Clock | |
| Administrate Users | |
| Update Flash | |
| Log Out | |
| Diagnostics | |
| Network Statistics | |
| Help | |

FIG. 54

| View Area | Set Clock | Area Communications Module |
|---|---|---|
| Home | | |
| Gas Readings | | |
| Device Information | | |
| Masters | Current Time: 12-Jul-2001 15:47:02 ← 842 | |
| Alarms | 844 ⟶ 856 | |
| Event Log | Year 846 ⟶ [2001 ▽] | |
| Setup Area | Month 848 ⟶ [July ▽] — 856 | |
| Setup Device | Date 850 ⟶ [12 ▽] — 856 | |
| Setup Network | Hour 852 ⟶ [15 ▽] — 856 | |
| Set Clock | Minute 854 ⟶ [47 ▽] — 856 | |
| Administrate Users | Second [2 ▽] — 856 | |
| Update Flash 858 ⟶ | | |
| Log Out | [Submit] [Reset] ← 860 | |
| Diagnostics | | |
| Network Statistics | | |
| Help | | |

View Area
Home
Gas Readings
Device Information
Masters
Alarms
Event Log

Setup Area
Setup Device
Setup Network
Set Clock
Administrate Users
Update Flash
Log Out

Diagnostics
Network Statistics

Help

Confirm Download

Area Communications Module

Verify your intention

Once FLASH programming mode is entered the device will not operate as an alarm system until the download is successfully complete.

Click here to confirm entering FLASH programming mode

| View Area | Communications | Area Communications |
|---|---|---|
| Home | Statistics | Module |
| Gas Readings | Ethernet Refresh ←—896 | 892 |
| Device Information | IP Address | 192.168.1.200 |
| Masters | Subnet | 255.255.255.0 |
| Alarms | Gateway | 192.168.1.1 |
| Event Log | Fixed IP Address | 0.0.0.0 |
| | Fixed Subnet | 0.0.0.0 |
| Setup Area | Fixed Gateway | 0.0.0.0 |
| Setup Device | Mac Address | 00:03:aa:00:00:11 |
| Setup Network | Receives | 662 |
| Set Clock | Unicasts | 590 |
| Administrate Users | Multicasts | 0 |
| Update Flash | Broadcasts | 72 |
| Log Out | Rx Errors | 0 |
| | Rx Missed | 0 |
| Diagnostics | Rx CRC Errors | 0 |
| Network Statistics | Rx Drops | 0 |
| Help | Transmits | 705 |
| | Buffer Defers | 0 |
| | Tx Errors | 0 |
| | Tx Collisions | 0 |
| | Tx Coll. Overflow | 0 |
| | Tx FILO Errors | 0 |
| | Traffic Backoffs | 0 |

*Serial Communications* —894

| Recieves | 11591 |
|---|---|
| Transmits | 11627 |
| Bad CRC | 0 |
| Missed End | 0 |
| Packet Too Long | 0 |

| FIG. 62A | FIG. 62D | FIG. 62G | FIG. 62J | FIG. 62M | FIG. 62P | FIG. 62S |
| --- | --- | --- | --- | --- | --- | --- |
| FIG. 62B | FIG. 62E | FIG. 62H | FIG. 62K | FIG. 62N | FIG. 62Q | FIG. 62T |
| FIG. 62C | FIG. 62F | FIG. 62I | FIG. 62L | FIG. 62O | FIG. 62R | FIG. 62U |

FIG. 62H

| Pin | Signal | | Signal | Pin | |
|---|---|---|---|---|---|
| D(10) | 124 | DATA10 | ADDR13 | 56 | A(13) |
| D(9) | 125 | DATA9 | ADDR11 | 52 | A(12) |
| D(8) | 127 | DATA8 | ADDR12 | 51 | A(11) |
| D(7) | 130 | DATA7 | ADDR10 | 50 | A(10) |
| D(6) | 131 | DATA6 | ADDR9 | 49 | A(9) |
| D(5) | 132 | DATA5 | ADDR8 | 46 | A(8) |
| D(4) | 133 | DATA4 | ADDR7 | 45 | A(7) |
| D(3) | 136 | DATA3 | ADDR6 | 44 | A(6) |
| D(2) | 137 | DATA2 | ADDR5 | 43 | A(5) |
| D(1) | 138 | DATA1 | ADDR4 | 42 | A(4) |
| D(0) | 139 | DATA0 | ADDR3 | 41 | A(3) |
| | 1 | NC1 | ADDR2 | 40 | A(2) |
| | 16 | NC2 | ADDR1 | 39 | A(1) |
| | 17 | NC3 | ADDR0 | 115 | A(0) |
| | 87 | XFC | NC14 | 88 | A(19) |
| | 85 | EXTAL | ADDR23/CS10 | 10 | |
| | 83 | XTAL | ADDR22/CS9/PC6 | 9 | |
| | 18 | NC4 | ADDR21/CS8/PC5 | 8 | |
| | 21 | NC5 | ADDR20/CS7/PC4 | 7 | |
| | 27 | NC6 | ADDR19/CS6/PC3 | 6 | |
| | 94 | BERR | CS5/FC2/PC2 | 5 | |
| | 93 | HALT | CS4/FC1/PC1 | 4 | |
| | 92 | RESET | CS3/FC0/PC0 | 3 | |
| | 79 | BKPT/DSCLK | NC15 | 108 | |
| | 80 | TSC | BGACK/CS2 | 143 | |
| | 34 | NC7 | BG/CS1 | 142 | |
| | 36 | NC8 | BH/CS0 | 141 | |
| | 23 | IC4/OC5/OC1/PGP7 | CSBOOT | 140 | |
| | 24 | OC4/OC1/PGP6 | NC16 | 123 | |
| | 28 | OC3/OC1/PGP5 | R/W | 103 | |
| | 29 | OC2/OC1/PGP4 | CLKOUT | 90 | |
| | 30 | OC1/PGP3 | PWMA | 15 | |
| | 31 | IC3/PGP2 | PWMB | 14 | |
| | 32 | IC2/PGP1 | FREEZE/OOUT | 81 | |
| | 33 | IC1/PGP0 | IPIPE/DS0 | 77 | |
| | 38 | NC9 | IFETCH/DS1 | 78 | |
| | 53 | NC10 | NC17 | 126 | |
| | 22 | PAI | SIZ1/PE7 | 104 | |
| | 13 | PCLK | SIZ0/PE6 | 105 | |

FIG. 63

| FIG. 63A | FIG. 63D | FIG. 63G | FIG. 63J |
|---|---|---|---|
| FIG. 63B | FIG. 63E | FIG. 63H | FIG. 63K |
| FIG. 63C | FIG. 63F | FIG. 63I | FIG. 63L |

FIG. 63B
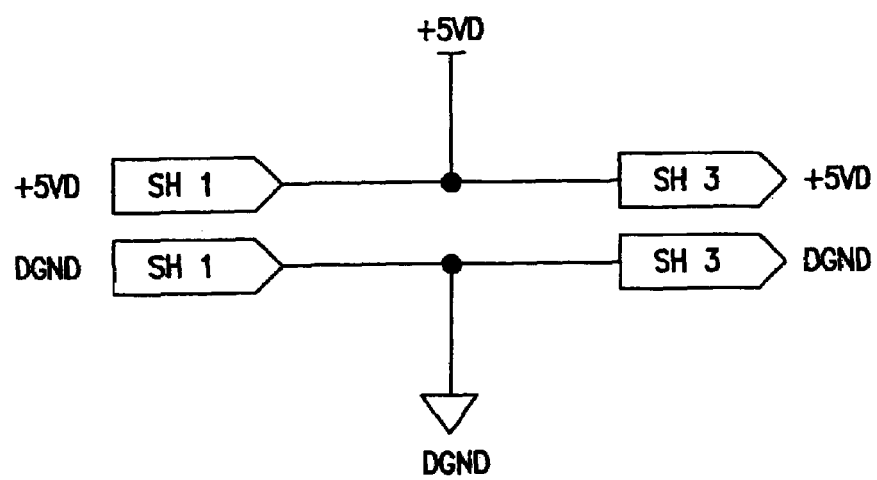
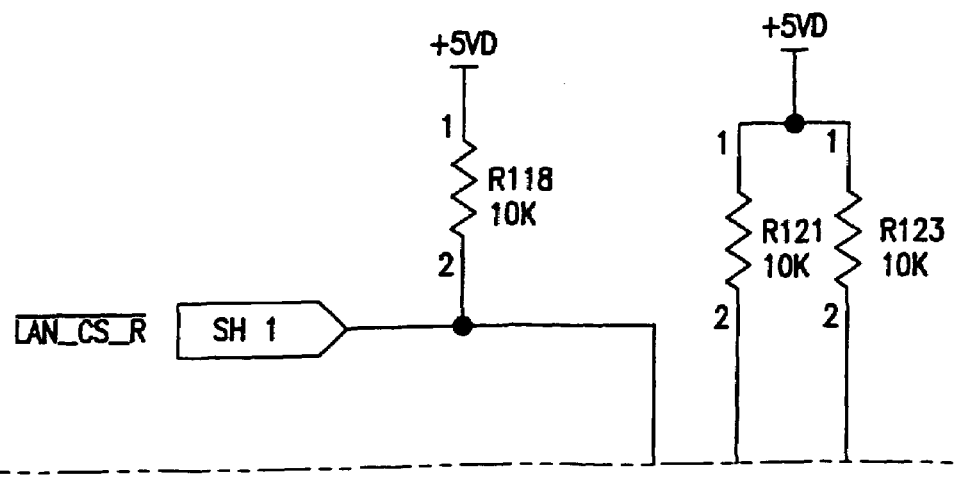

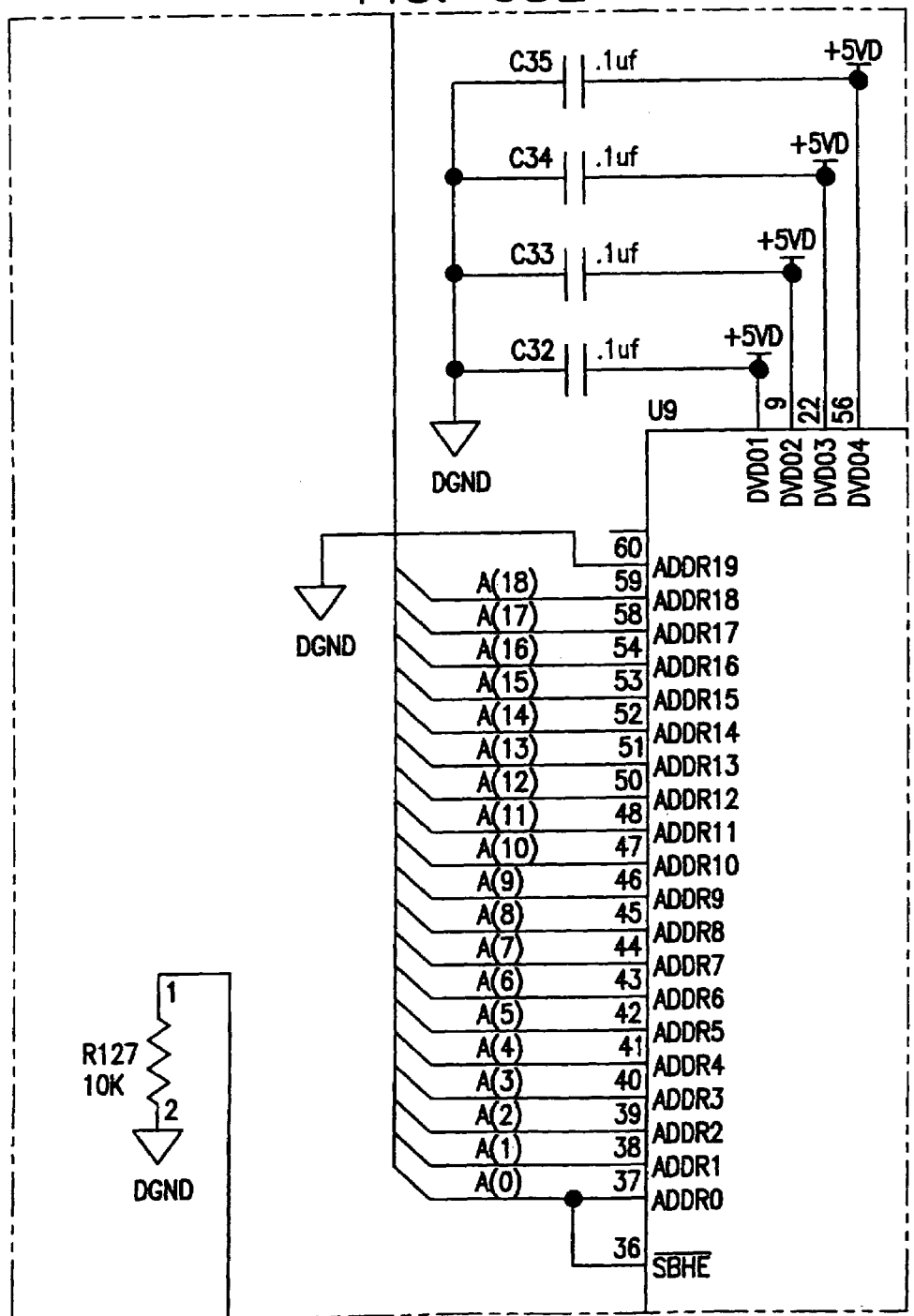

FIG. 64

| FIG. 64A | FIG. 64D | FIG. 64G | FIG. 64J | FIG. 64M | FIG. 64P |
|---|---|---|---|---|---|
| FIG. 64B | FIG. 64E | FIG. 64H | FIG. 64K | FIG. 64N | FIG. 64Q |
| FIG. 64C | FIG. 64F | FIG. 64I | FIG. 64L | FIG. 64O | |

FIG. 65

| FIG. 65C | FIG. 65F | FIG. 65H | FIG. 65J | FIG. 65L |
|---|---|---|---|---|
| FIG. 65A | FIG. 65D | FIG. 65G | FIG. 65I | FIG. 65K |
| FIG. 65B | FIG. 65E | | | |

FIG. 66

|          | FIG. 66E | FIG. 66J | FIG. 66O | FIG. 66S | FIG. 66W |
|----------|----------|----------|----------|----------|----------|
| FIG. 66A | FIG. 66F | FIG. 66K | FIG. 66P | FIG. 66T | FIG. 66X |
| FIG. 66B | FIG. 66G | FIG. 66L | FIG. 66Q | FIG. 66U |          |
| FIG. 66C | FIG. 66H | FIG. 66M | FIG. 66R | FIG. 66V |          |
| FIG. 66D | FIG. 66I | FIG. 66N |          |          |          |

FIG. 66A
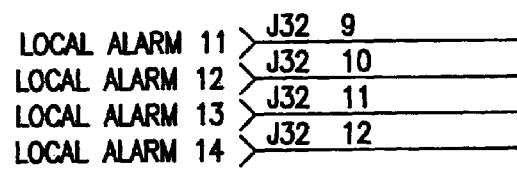
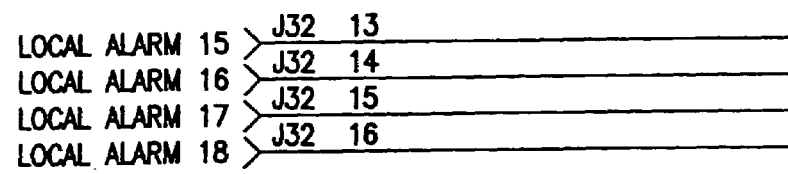

FIG. 66B

LOCAL ALARM 19 >— J32  17
LOCAL ALARM 20 >— J32  18
LOCAL ALARM 30 >— J32  19
LOCAL ALARM 29 >— J32  20

LOCAL ALARM 28 >— J32  21
LOCAL ALARM 27 >— J32  22
LOCAL ALARM 26 >— J32  23
LOCAL ALARM 25 >— J32  24

LOCAL ALARM 24 >— J32  25
LOCAL ALARM 23 >— J32  26
LOCAL ALARM 22 >— J33  1
LOCAL ALARM 21 >— J33  2

FIG. 66C

LOCAL ALARM 1 >—J33  3
LOCAL ALARM 2 >—J33  4
LOCAL ALARM 3 >—J33  5
LOCAL ALARM 4 >—J33  6

LOCAL ALARM 5 >—J33  7
LOCAL ALARM 6 >—J33  8
LOCAL ALARM 7 >—J33  9
LOCAL ALARM 8 >—J33 10

FIG. 67

|  | FIG. 67E | FIG. 67I | FIG. 67M |  |  |
|---|---|---|---|---|---|
| FIG. 67A | FIG. 67B | FIG. 67F | FIG. 67J | FIG. 67N | FIG. 67Q | FIG. 67T |
|  | FIG. 67C | FIG. 67G | FIG. 67K | FIG. 67O | FIG. 67R | FIG. 67U |
|  | FIG. 67D | FIG. 67H | FIG. 67L | FIG. 67P | FIG. 67S |  |

FIG. 67E

AUX_ALARM ⟩—J1  3———————————————10W1→
                                     AUX_ALARM_A

MAIN_ALARM ⟩—J1  4———————————————9  W1→
                                     MAIN_ALARM_A

GUARDED_ACCESS ⟩—J1  8———————————8  W1→
                                     GUARDED_ACCESS_A

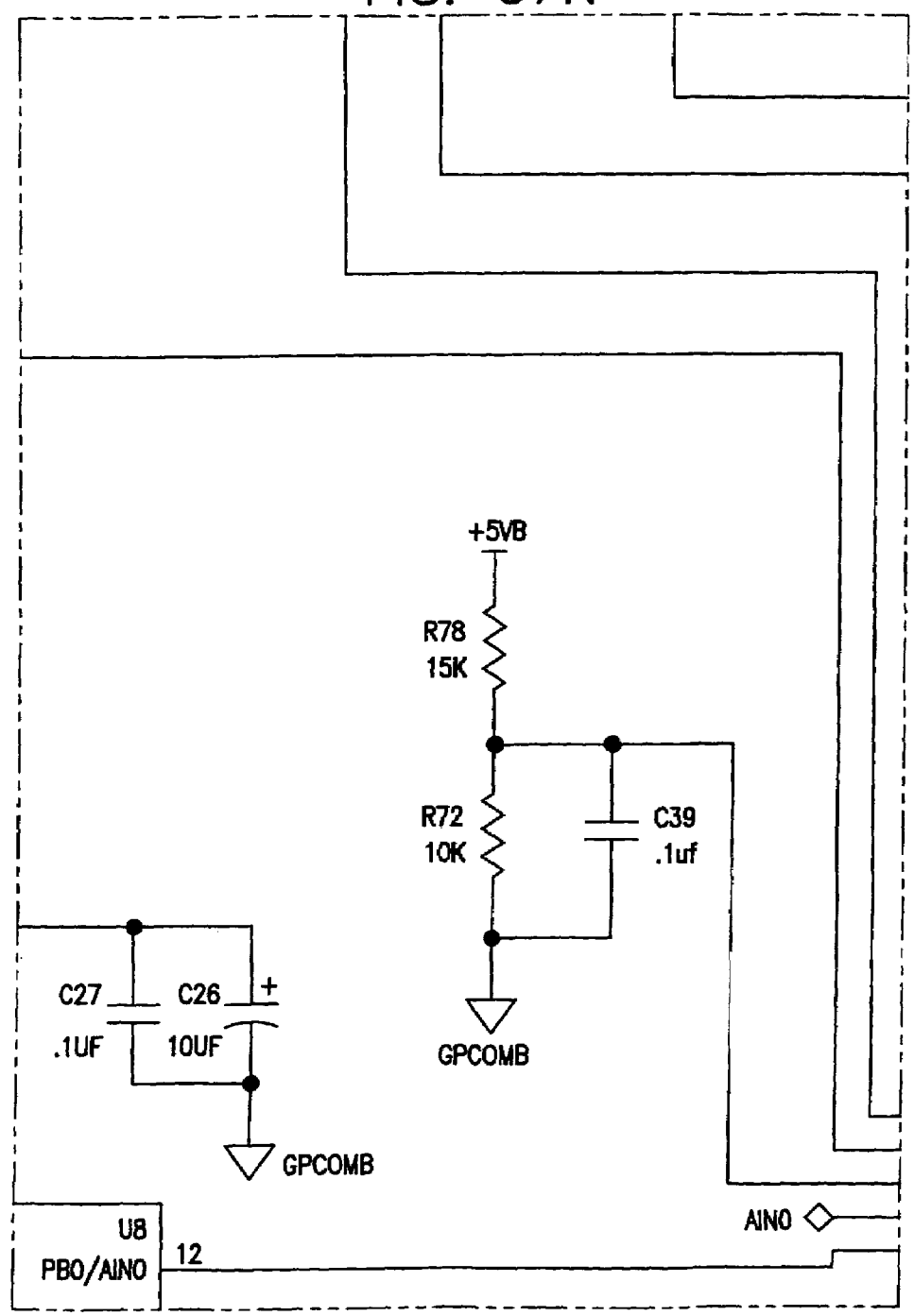

FIG. 68

| FIG. 68B | FIG. 68D | FIG. 68F | FIG. 68H | |
|---|---|---|---|---|
| FIG. 68A | FIG. 68C | FIG. 68E | FIG. 68G | FIG. 68I | FIG. 68J |

FIG. 70

| FIG. 70A | FIG. 70C | FIG. 70E | FIG. 70G | FIG. 70I |
| --- | --- | --- | --- | --- |
| FIG. 70B | FIG. 70D | FIG. 70F | FIG. 70H | FIG. 70J |

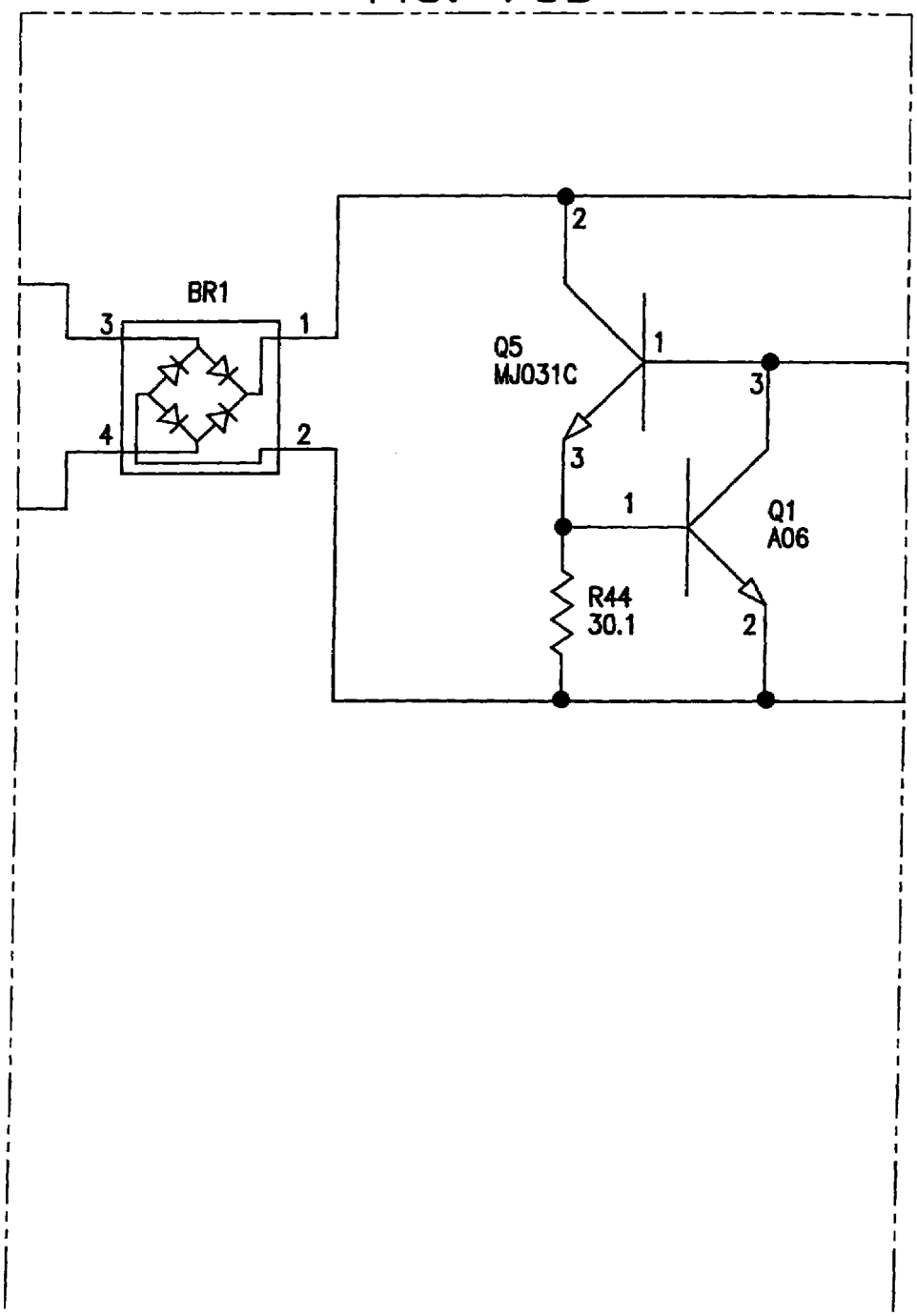

FIG. 71

| FIG. 71A | FIG. 71B | FIG. 71C | FIG. 71D |

MEDICAL GAS ALARM SYSTEM

CROSS-REFERENCE TO THE RELATED APPLICATIONS

The present application is a continuation of U.S. patent application Ser. No. 09/933,502, filed on Aug. 20, 2001, now U.S. Pat. No. 6,987,448.

BACKGROUND AND SUMMARY OF THE INVENTION

The present invention relates to medical gas alarm systems. More particularly, the present invention relates to the design, installation, and operation of alarm system components that monitor a number of conditions of a medical gas system at various points throughout a healthcare facility.

Healthcare facilities, such as hospitals, include medical gas systems that deliver different types of gases and other gas-related services, such as vacuum and waste gas removal, to numerous points throughout the facility. A few examples of such gases include oxygen, nitrogen, carbon dioxide, and nitrous oxide. Conventional medical gas systems include source equipment, such as gas tanks, pumps, compressors, dryers, receivers, and manifolds that provide associated medical gases or vacuum through a network of pipes to service outlets located in rooms throughout the facility. Medical gas alarm systems usually monitor conditions of the source equipment as well as gas pressures at various locations throughout the facility. When certain alarm conditions are detected, the system operates to alert facility personnel of the alarm conditions so that appropriate corrective actions can be taken.

According to this disclosure, a medical gas alarm system for use in a healthcare facility having a medical gas system and having a network of computer devices is provided. The alarm system includes at least one area alarm controller adapted to receive a first signal indicative of a condition of a first portion of the medical gas system. The area alarm controller is adapted to communicate with the network. The alarm system also includes at least one master alarm controller adapted to receive a second signal indicative of a condition of a second portion of the medical gas system. The master alarm controller is adapted to communicate with the network. The area alarm controller is adapted to communicate with the master alarm controller through the network.

Networks included in healthcare facilities usually include a number of network hubs located throughout the facility. These network hubs are coupled, either directly or through other network hubs, to one or more servers of the network. The network hubs provide connection points for the computer devices, such as personal computers, included in the network. According to this disclosure, the area alarm controller and the master alarm controller are each adapted to couple to respective network hubs included in the network.

Also according to this disclosure, a master alarm controller is identified by a network address and is configured to host a website. Some of the pages of the website are password protected. Authorized users that know the network address are able to access the website hosted by the master alarm controller using any personal computer included in the network of the healthcare facility, assuming the personal computer being used is configured with appropriate web browser software. In addition, if the network of the healthcare facility is coupled to the world wide web (aka the Internet), then authorized users are able to access the website hosted by the master alarm controller through the Internet using any computer having appropriate web browser software.

In one embodiment, each area alarm controller is identified by its own, unique network address and is configured to host its own website. In such an embodiment, the website hosted by the master alarm controller is hyperlinked to each of the websites hosted by the area alarm controllers and the websites hosted by each area alarm controller is hyperlinked to the website hosted by the master alarm controller so that authorized users are able to easily navigate all of the websites once any of the websites have been accessed. Healthcare facilities will typically have at least two master alarm controllers and many area alarm controllers. In one embodiment, the master alarm controllers are each identified by the same network address and cooperate with one another to serve a single website.

Authorized users that access any of the websites hosted by the master alarm and area alarm controllers can navigate through various web pages of these websites to view output data from the master alarm controller, to view output data from any associated area alarm controllers, to provide input data to the master alarm controller, and to provide input data to any associated area alarm controllers. Examples of output data viewable via this website include alarm information about alarm conditions occurring in the medical gas system, set-up information regarding the configuration of any alarm controllers in the medical gas alarm system, network address information regarding the network addresses assigned to each of the alarm controllers of the medical gas alarm system, and an event log that lists past alarms. Authorized users provide input data via the websites, for example, to program each master alarm controller and to program each area alarm controller with various operating parameters.

In preferred embodiments, each master alarm controller and each area alarm controller includes a number of input ports that receive associated input signals. Each input signal indicates a respective condition of the medical gas system. The input signals received by each area alarm controller typically indicate gas pressures in respective gas lines being monitored by the associated area alarm controller. The input signals received by each master alarm controller are generally binary signals (i.e. on/off or high/low signals) that indicate the occurrence of some condition in the source equipment of the medical gas system. Examples of the conditions indicated by these binary signals include low line pressure, high line pressure, low vacuum, backup vacuum pump on, liquid level low, and reserve supply in use. A more exhaustive list is provided below in the Detailed Description of the Drawings.

Also in preferred embodiments, each master alarm controller includes a display screen that displays text messages identifying the alarm conditions that occur in the source equipment of the medical gas system. In addition, each master alarm controller may include a set of LED's which visually indicate, such as by turning from green to red, that an alarm condition is occurring in an associated portion of the medical gas system. In such embodiments, the input data provided by authorized users via the website hosted by the master alarm controller assigns to each input port of the master alarm controller an LED of the set of LED's, the type of gas and/or system associated with the respective input signal, and the text message that is to appear on the display screen of the master alarm controller when a respective alarm condition is indicated by the associated input signal.

The input data provided by authorized users via the websites hosted by the area alarm controllers may assign a device name to each area alarm controller and a location in the healthcare facility of each area alarm controller. This information is communicated to the associated master alarm controllers through the network. When any of the area alarm controllers receive an input signal indicative of an alarm condition, the associated device name and location in the facility is displayed on the display screen of the associated master alarm controllers.

In some embodiments, the input data received by the master alarm controller via the website hosted by the master alarm controller configures the master alarm controller to send an e-mail to at least one designated e-mail address to notify a recipient of the e-mail of the occurrence of an alarm condition in the medical gas system. The e-mail sent by the master controller contains information about the alarm condition that caused the e-mail to be sent. In other embodiments, the input data received by the master alarm controller via the website hosted by the master alarm controller configures the master alarm controller to initiate a page to at least one pager carried by a recipient to notify the recipient of the occurrence of an alarm condition in the medical gas system. Such a page may be initiated, for example, by sending an e-mail to a paging service provider with the number to be paged.

It will be appreciated that a method of installing a medical gas alarm system in a healthcare facility having a medical gas system and a network of computer devices is provided in this disclosure. The method includes providing a first alarm controller, coupling to the first alarm controller a first input signal line on which is carried a first input signal indicative of a first condition of a first portion of the medical gas system, and coupling the first alarm controller to the network. The method further includes providing a second alarm controller, coupling to the second alarm controller a second input signal line on which is carried a second input signal indicative of a second condition of a second portion of the medical gas system, and coupling the second alarm controller to the network.

Further according to this disclosure, an alarm controller includes a set of user inputs that are operable to program the alarm controller with operating parameters in lieu of using a personal computer to program these alarm controllers via the websites hosted by the various alarm controllers. One of the user inputs is operable to cause the alarm controller to enter into a programming mode. One or more other user inputs are operable to scroll through various programming options that are displayed on a display screen of the alarm controller. One or more additional user inputs are operable to select a desired programming option appearing on the display screen. In the illustrative embodiment, each master alarm controller and each area alarm controller includes its own set of user inputs that are operable to configure each of these controllers separately without the use of a personal computer.

Additionally according to this disclosure, a sensor module for use in a medical gas alarm system having a gas line through which pressurized gas flows is provided. The sensor module includes a housing and a transducer coupled to the housing. The housing is couplable to the gas line to expose the transducer to a gas pressure in the gas line. The transducer is adapted to generate a pressure signal that indicates a pressure in the gas line. The sensor module further includes an electric circuit coupled to the housing. The electric circuit receives and processes the pressure signal from the transducer. The electric circuit is adapted to output serial data indicating one or more of the following: the pressure in the gas line, the type of gas in the gas line, a serial number assigned to the sensor module, the software revision number of software with which the electric circuit is programmed, status information, information about the characteristic being measures, and a failure code indicating the occurrence of a failure in the sensor module.

Additional features and advantages of the invention will become apparent to those skilled in the art upon consideration of the following detailed description of an illustrative embodiment exemplifying the best mode of carrying out the invention as presently perceived.

BRIEF DESCRIPTION OF THE DRAWINGS

The detailed description particularly refers to the accompanying figures in which:

FIG. 7 is a front elevation view of a local alarm annunciator included in the medical gas alarm system showing the local alarm annunciator having a 2-by-8 array of LED's, a test button beneath the array of LED's, and an alarm silence button beneath the array of LED's;

FIG. 8 is a perspective view of the local alarm annunciator of FIG. 7 showing a front panel of the local alarm annunciator disconnected from a wall-mountable box of the local alarm annunciator to provide access to various electrical components of the local alarm annunciator;

FIG. 9 is an exploded perspective view showing components of one of the sensor modules included in the medical gas alarm system and showing components that couple the sensor module pneumatically to one of the gas lines of the medical gas system;

FIGS. 10–41 are screen printouts of various web pages of a website that is served by the master alarm controllers and that is accessible via the network to view output data from the master and area alarm controllers and to provide input data to the master alarm controllers;

FIG. 10 is a screen printout of a Master Alarm Home page;

FIG. 11 is a screen printout of a Master Alarm Active Alarms page;

FIG. 12A is a screen printout of a Master Alarm Network Devices page;

FIG. 12B is a screen printout of a first Master Alarm Specific Area page:

FIG. 12C is a screen printout of a second Master Alarm Specific Area page;

FIG. 13 is a screen printout of a Master Alarm Device Information page;

FIG. 14 is a screen printout of a Master Alarm Event Log page;

FIG. 15 is a screen printout of a Master Alarm Diagnostics page;

FIG. 16 is a screen printout of a Master Alarm Download Configuration page;

FIG. 17 is a screen printout of a Master Alarm Device Configuration page;

FIG. 18 is a screen printout of a Master Alarm Network Statistics page;

FIG. 19 is a screen printout of a Master Alarm Hardware Diagnostics page;

FIG. 20 is a screen printout of a Master Alarm Login page;

FIG. 21 is a screen printout of a Master Alarm Logged In page;

FIG. 22 is a screen printout of a Master Alarm Alarm Message Setup page;

FIG. 23 is a screen printout of a Master Alarm Setup Alarm Messages Step 2 page;

FIG. 24 is a screen printout of a Master Alarm Setup Alarm Messages Step 3 page;

FIG. 25 is a screen printout of a Master Alarm Setup Alarm Messages Final page;

FIG. 26 is a screen printout of a Master Alarm Setup Device page;

FIG. 27 is a screen printout of a Master Alarm Device Setup Accepted page;

FIG. 28 is a screen printout of a Master Alarm Email Notification page;

FIG. 29 is a screen printout of a Master Alarm Email Changes Accepted page;

FIG. 30 is a screen printout of a Master Alarm Set Clock page;

FIG. 31 is a screen printout of a Master Alarm Clock Accepted page;

FIG. 32 is a screen printout of a Master Alarm User Administration page;

FIG. 33 is a screen printout of a Master Alarm User Name Changes Accepted page;

FIG. 34 is a screen printout of a Master Alarm Network Settings page of the website;

FIG. 35 is a screen printout of a Master Alarm Network Setup page;

FIG. 36 is a screen printout of a Master Alarm Clear Network page;

FIG. 37 is a screen printout of a Master Alarm Changes Accepted page;

FIG. 38 is a screen printout of a Master Alarm Software Update page;

FIG. 39 is a screen printout of a Master Alarm Verify FLASH Download page;

FIG. 40 is a screen printout of a Master Alarm Configuration Transfer page;

FIG. 41 is a screen printout of a Master Alarm Logout page;

FIGS. 42–61 are screen printouts of various web pages of a website that is served by one of the area alarm controllers and that is accessible via the network to view output data from the area alarm controller and to provide input data to the area alarm controller;

FIG. 42 is a screen printout of an Area Alarm Home page;

FIG. 43 is a screen printout of an Area Alarm Active Area Alarms page;

FIG. 44 is a screen printout of a first Area Alarm Area Display Data page;

FIG. 45 is a screen printout of a second Area Alarm Area Display Data page;

FIG. 46 is a screen printout of an Area Alarm Device Info page;

FIG. 47 is a screen printout of an Area Alarm Masters page;

FIG. 48 is a screen printout of an Area Alarm Event Log page;

FIG. 49 is a screen printout of an Area Alarm Login page;

FIG. 50 is a screen printout of an Area Alarm Login Status page;

FIG. 51 is a screen printout of an Area Alarm Device Settings page;

FIG. 52 is a screen printout of an Area Alarm Device Setup Results page;

FIG. 53 is a screen printout of an Area Alarm Network Settings page;

FIG. 54 is a screen printout of an Area Alarm Network Setup Result page;

FIG. 55 is a screen printout of an Area Alarm Set Clock page;

FIG. 56 is a screen printout of an Area Alarm Change Result page;

FIG. 57 is a screen printout of an Area Alarm User Administration page;

FIG. 58 is a screen printout of an Area Alarm Change User Info Result page;

FIG. 59 is a screen printout of an Area Alarm Flash Download page;

FIG. 60 is a screen printout of an Area Alarm Confirm Download page;

FIG. 61 is a screen printout of an Area Alarm Communications Statistics page;

DETAILED DESCRIPTION OF THE DRAWINGS

Figure 1:
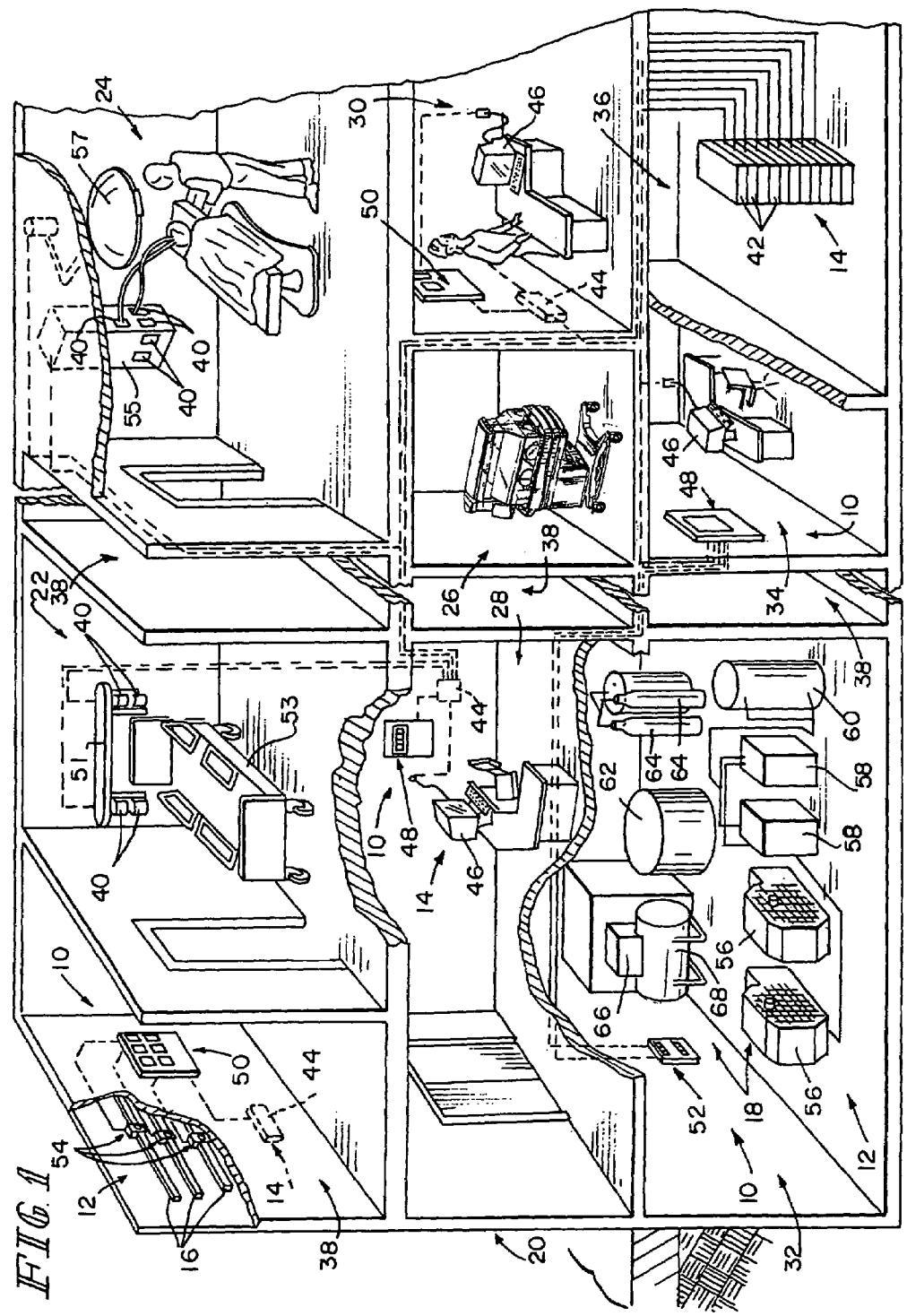
FIG. 1 is a diagrammatic view of a healthcare facility having a medical gas system and a network of computer devices showing various components of a medical gas alarm system in accordance with this disclosure coupled to the medical gas system and coupled to the network.

According to this disclosure, a medical gas alarm system 10 is provided for use in a healthcare facility, such as a hospital. Hospitals are usually large, multi-story buildings having a multitude of rooms that are grouped into various wings, units, or wards. Such a facility 20 is shown diagrammatically in FIG. 1 as having a patient room 22, an operating room 24, a neonatal intensive care unit 26, a security station 28, a nurse station 30, a mechanical equipment room 32, a facilities engineer office 34, a main computer room 36, and a number of corridors 38 interconnecting these rooms and units. Although facility 20 is shown diagrammatically as having only one patient room 22, one operating room 24, etc., hospitals typically have more than one of each of these rooms, as well as having, for example, intensive care units, critical care units, recovery rooms, maternity wards and so on. Thus, it will be appreciated that FIG. 1 is intended to provide a general understanding of the basic environment in which alarm system 10 is used and to provide a general understanding of the interaction of the components of alarm system 10 with other components included in a healthcare facility.

Facility 20 has a medical gas system 12 and an Ethernet or network 14 of computer devices. Alarm system 10 couples to gas system 12 and to network 14 as will be described in further detail below. The computer devices in network 14 include one or more servers 42, a plurality of network hubs 44, and one or more personal computers 46 as shown in FIGS. 1 and 2. Server 42 and personal computers 46 communicate with each other through hubs 44 in a manner well known to those skilled in the art.

Figure 2:
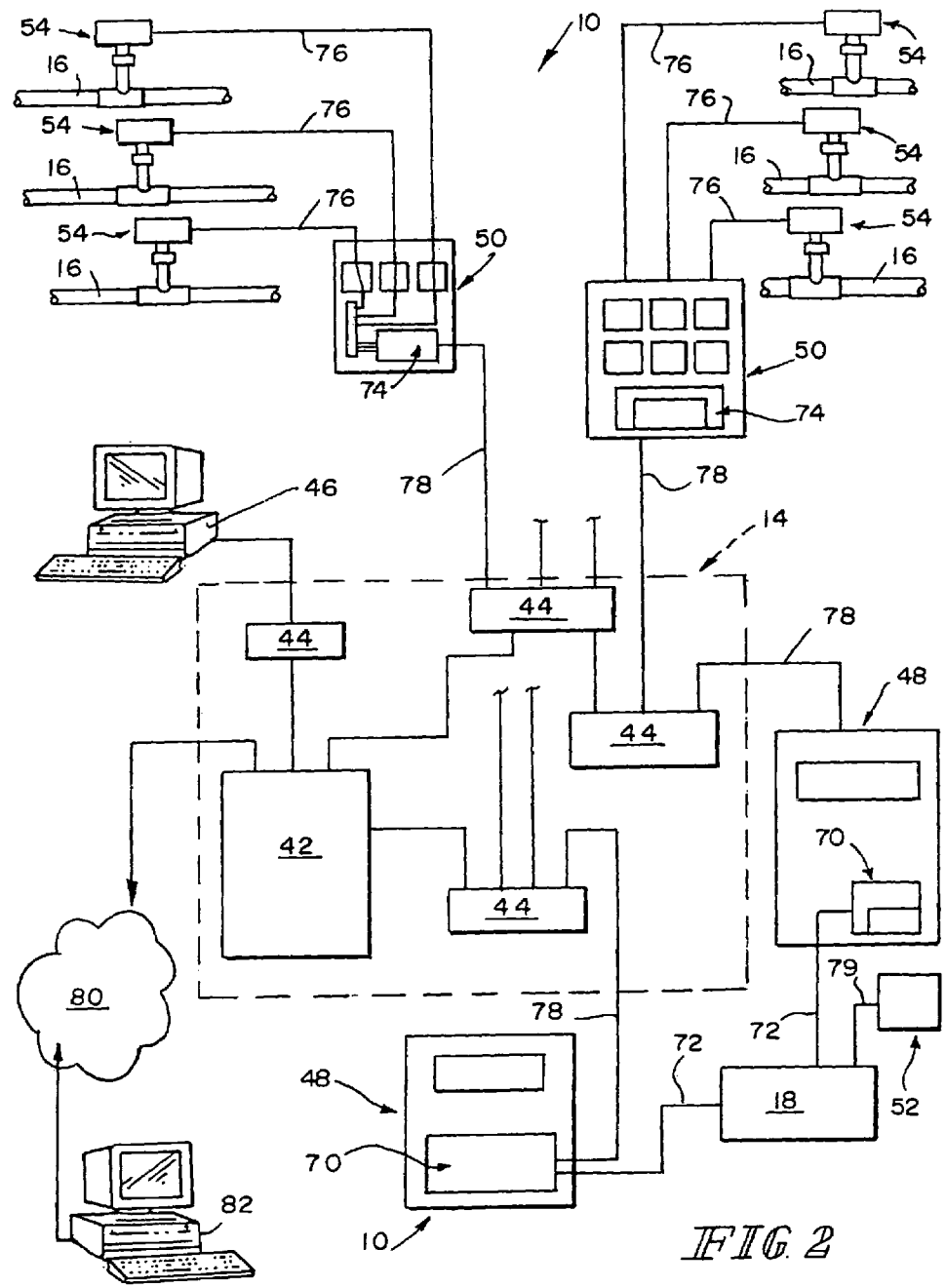
FIG. 2 is a diagrammatic view of the network and the medical gas alarm system of FIG. 1 showing a server of the network and several network hubs of the network surrounded by a dashed box, a pair of area alarm controllers above the dashed box, two sets of three sensor modules above the area alarm controllers, each sensor module being coupled pneumatically to a respective gas line of the medical gas system and coupled electrically to an associated area alarm controller, a first master alarm controller beneath the dashed box, a second master alarm controller to the right of the dashed box, the area alarm controllers and the master alarm controllers each being coupled electrically to a respective network hub, a personal computer of the network coupled to the server through an associated network hub, and a personal computer external to the network coupled to the server via the world wide web.

Medical gas system 12 includes various pieces of source equipment 18 located in room 32 and a network of pipes or lines 16 that are routed throughout facility 20 as shown in FIG. 1. Source equipment 32 operates to deliver different types of gases and gas-related services through lines 16 to associated service outlets 40 located at different points throughout facility 20. For example, some outlets 40 are located in room 22 on a headwall unit 51 that is adjacent a patient bed 53 and some outlets 40 are located in room 24 on a column 55 that extends downwardly from the ceiling adjacent a surgical light 57.

Alarm system 10 monitors various conditions occurring at different points in gas system 12 and provides both a visual alarm and an audible alarm when an alarm condition is detected. In preferred embodiments, the points in gas system 12 that are monitored by alarm system 10 are in accordance with standards set by the National Fire Protection Association (NFPA). See, for example, NFPA 99, Standard for Health Care Facilities, 1999 Edition. Illustrative alarm system 10 includes two master alarm controllers 48 which provide redundant monitoring of conditions occurring in source equipment 18. One of illustrative master alarm controllers 48 is located in facilities engineer office 34 and the other of illustrative master alarm controllers 48 is located at security station 28. Alarm system 10 also includes a number of area alarm controllers 50 that monitor pressures in lines 16. Illustrative alarm system 10 includes two area alarm controllers 50, one located at nurse station 30 and one located in the corridor 38 adjacent to patient room 22. It will be appreciated that a typical healthcare facility will have many more than two area alarm controllers 50. Alarm system 10 further includes a local alarm annunciator 52 located in mechanical equipment room 32 and a plurality of sensor modules 54 that each operate to measure the pressure in associated lines 16 and that each operate to provide a signal to an associated area alarm controller 50.

Source equipment 18 of medical gas system 12 includes, for example, compressors 56, dryers 58, receivers 60, liquid storage tanks 62, gas tanks 64, vacuum pumps 66, and vacuum tanks 68 as shown diagrammatically in FIG. 1. Source equipment 18 also includes a number of other pieces of auxiliary equipment (not shown) such as, for example, manifolds, filters, and valves. Source equipment 18 operates to distribute the various types of gases and gas-related services to associated lines 16 in a manner well known to those skilled in the art.

The various pieces of source equipment 18 are outfitted by their manufacturers with a number of switches (not shown) that change from one state, such as an OFF or low state, to another state, such as an ON or high state, to indicate the occurrence of certain conditions in source equipment 18. Some of these switches include, for example, pressure switches that are configured to change state when pressures in associated lines, pipes, or conduits become either too high or too low, as the case may be. Others of these switches include, for example, liquid level sensors with circuitry that produces output signals that change state when the liquid level in an associated tank 62 drops to a predetermined level or when the liquid level in an associated receiver 60 rises to a predetermined level. Still others of these switches change state when a reserve supply or a second supply of gas is being used instead of a main supply. Source equipment 18 may also include switches that change state as the result of the occurrence of other conditions, such has high dew point, equipment malfunction, high temperature, low temperature, inappropriate chemical concentration, and use of a back-up pump or compressor.

Exemplary gases and gas-related services delivered by source equipment 18 include oxygen, nitrogen, medical air, medical vacuum, nitrous oxide, waste anesthesia gas disposal (WAGD), carbon dioxide, oxygen/carbon dioxide mixture, helium, and argon. Medical air is sometimes referred to as laboratory air or dental air if being used for laboratory or dental purposes, respectively. Similarly, medical vacuum is sometimes referred to as laboratory vacuum or dental vacuum. Other gases or gas-related services may be provided by source equipment 18 for other specialized purposes.

The medical purpose of each gas and gas-related service delivered by source equipment 18 is different. For example, oxygen is sometimes delivered to patients to increase their blood oxygenation, nitrogen is sometimes used to power tools in the operating room, medical air is filtered air that is used to assist patient respiration, medical vacuum is sometimes used during surgery to suction blood and other fluids away from the patient, nitrous oxide is sometimes administered by anesthesiologists to patients during surgery, the WAGD system is sometimes used to remove gases exhaled by patients during surgery, and helium is sometimes used during laproscopic or endoscopic procedures to inflate certain areas within a patient's body to provide room for surgical instruments that are used during these procedures.

Because various pieces of source equipment 18 operate to deliver associated gases or gas-related services (hereinafter referred to collectively as "service" or "services") through an associated subset of lines 16, medical gas system 12 includes a number of subsystems, each of which is associated with the delivery of a particular service. Furthermore, in large healthcare facilities, medical gas system 12 may include more than one subsystem of source equipment 18 and lines 16 that deliver the same type of service to different parts of the facility. Thus, it is not uncommon for medical gas systems included in large healthcare facilities to have more than one oxygen subsystem, more than one medical vacuum subsystem, and so on.

Each master alarm controller 48 includes an electric circuit 70 that receives one or more input signals from the switches of associated pieces of source equipment 18 via electrical conductors or lines 72 as shown diagrammatically in FIG. 2. In accordance with standards set by the NFPA, at least two redundant master controllers 48 are provided to monitor the same conditions of source equipment 18. Thus, the master alarm controller 48 at station 28 monitors the same conditions of source equipment 18 as are being monitored by the master alarm controller 48 in office 34.

Each area alarm controller 50 includes an electric circuit 74 that receives input signals from each respective sensor module 54 via electrical conductors or lines 76. Electric circuits 70, 74 are microcontroller or microprocessor-based circuits that process the respective input signals and determine whether the input signals are indicative of alarm conditions in gas system 12. Circuits 72, 74 of alarm controllers 48, 50, respectively, are configured to be coupled to network 14 via associated electrical conductors 78 as shown diagrammatically in FIG. 2. In addition, local alarm annunciator 52 receives input signals from the switches of associated pieces of source equipment 18 via electrical conductors or lines 79. In preferred embodiments, conductors 72, 76, 79 are shielded, twisted pairs and conductors 78 are RJ-45 cables.

Area alarm controllers 50 communicate with master alarm controllers 48 through server 42 and through respective hubs 44 of network 14. Some of hubs 44 are coupled directly to server 42 and some hubs 44 are included in chains of two or more hubs 44 that couple to server 42 as shown diagrammatically in FIG. 2. Illustrative network hubs 44 are configured to couple to a number of computer devices. Thus, the network hubs 44 to which any of alarm controllers 48, 50 couple may also be coupled to one or more personal computers 46, for example. In alternative embodiments, one or more of alarm controllers 48, 50, as well as one or more personal computers 46, may be coupled directly to server 42.

Server 42 operates in a conventional manner to control the flow of data between the various computer devices coupled to server 42 either directly or via hubs 44.

Each area alarm controller 50 communicates data through network 14 to master alarm controllers 48, including data regarding the pressures sensed by the respective sensor modules 54 associated with each of the area alarm controllers 50. Each master alarm controller 48 caches the data received from the area alarm controllers 50 in memory devices included in respective electric circuits 70. In addition, electric circuit 74 of each area alarm controller 48 has its own memory devices in which data is stored, including data regarding the pressures sensed by the associated sensor modules 54. Furthermore, master alarm controllers 48 and area alarm controllers 50 communicate identifying information to each other through network 14 so that each master alarm controller 48 is made aware of all of the other alarm controllers 48, 50 that are coupled to network 14 and so that each area alarm controller 50 is made aware of the master alarm controllers 48 that are coupled to network 14.

As will be described in further detail below, alarm controllers 48, 50 are each programmed to host or serve a website. In one embodiment, area alarm controllers 50 are each identified by different network addresses and the master alarm controllers 48 are all identified by the same network address. Thus, in this embodiment, master alarm controllers 48 host a single website and area alarm controllers 50 each host their own separate websites. In other embodiments, area alarm controllers 50 are all identified by a single network address and cooperate with each other to host a single website. In still other embodiments, all of the alarm controllers 48, 50 are identified by the same network address such that the alarm controllers 48, 50 cooperate with one another to host a single website. It is also within the scope of this disclosure for each master alarm controllers 48 to be identified by a different network address and to host a website separate from each of the other master alarm controllers 48.

Once alarm controllers 48, 50 are coupled to network hubs 44 and are properly configured with network addresses, as will be described in further detail below, alarm controllers 48, 50 become part of the Ethernet 14 of facility 20 and the websites hosted by alarm controllers 48, 50 are accessible to any of personal computers 46 that are included in network 14 and that are programmed with conventional web browser software. In addition, if network 14 is coupled to the world wide web or Internet, which is illustrated diagrammatically in FIG. 2 at reference numeral 80, then the websites hosted by alarm controllers 48, 50 are accessible to any remote personal computers 82 that are coupled to the Internet 80 and that are programmed with conventional web browser software.

The description below of the various components and the operation of the components of one illustrative master alarm controller 48 is applicable to all illustrative master alarm controllers 48 unless specifically noted otherwise. Similarly, the description below of the various components and the operation of the components of one illustrative area alarm controller 50 is applicable to all illustrative area alarm controllers 50 unless specifically noted otherwise. Likewise, the description below of the components and the operation of components of one illustrative sensor module 54 is applicable to all illustrative sensor modules 54 unless specifically noted otherwise.

Figure 3:
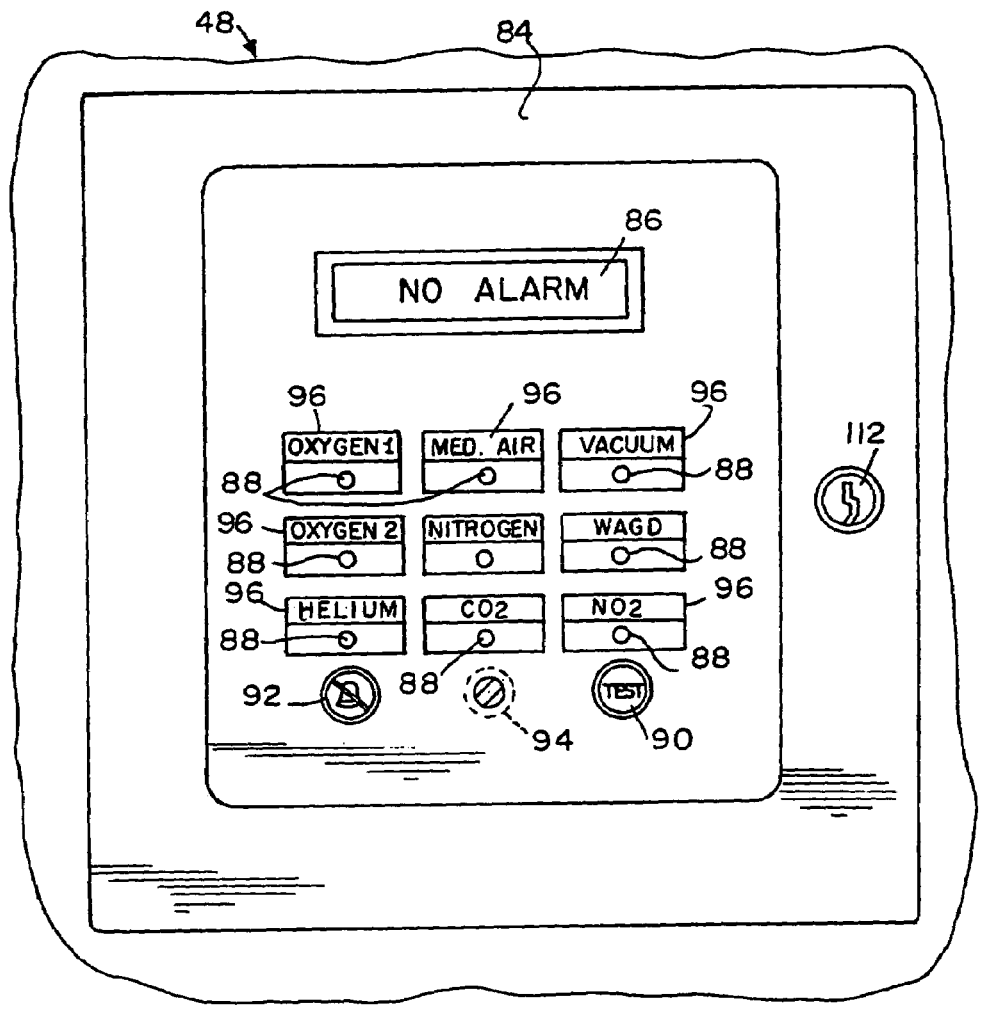
FIG. 3 is a front elevation view of a portion of one of the master alarm controllers of FIG. 2 showing a 3-by-3 array of LED's, each LED being labeled to correspond to a type of gas or gas-related service of the medical gas system, an alarm silence button and a test button beneath the array of LED's, and a display screen above the array of LED's.

Master alarm controller 48 includes a panel 84, a display screen 86 coupled to panel 84, and a plurality of light emitting diodes (LED's) 88 coupled to panel 84 as shown in FIG. 3. Alarm controller 48 also includes a test button 90 and an alarm silence button 92 that are accessible on the front of panel 84. Display screen 84, LED's 88, test button 90, and alarm silence button 92 are some of the components included in electric circuit 70. A set of labels 96 are attached to panel 84, each label 96 being positioned adjacent a respective LED 88 and each label 96 indicating the subsystem of gas system 12 that is associated with the respective LED 88. In the illustrative embodiment, nine LED's 88 are provided on panel 84. If more than one subsystem of gas system 12 delivers the same type of service, then labels 96 may be fashioned in such a manner to indicate this, as is shown in FIG. 3 where the LED 88 associated with a first oxygen subsystem is labeled as "OXYGEN 1" and the LED 88 associated with a second oxygen subsystem is labeled as "OXYGEN 2."

When an alarm condition occurs anywhere in gas system 12 and is detected by alarm system 10, display screen 86 and the LED 88 associated with the subsystem of gas system 12 in which the alarm condition is occurring operate to provide visual indicators of the occurring alarm condition. For example, in one embodiment, a text message providing information about the alarm condition is displayed on display screen 86 and the LED 88 associated with the subsystem in which the alarm condition is occurring changes from green to red and flashes. In this embodiment, if more than one alarm condition occurs in gas system 12, then the text messages displayed on display screen 86 alternate or scroll every so often, such as every two seconds, to provide information about the various alarm conditions. In other embodiments, display screen 86 is configured to display simultaneously a plurality of text messages to convey information about a plurality of alarm conditions occurring in gas system 12. If no alarm conditions are detected by alarm system 10, then screen 86 will display an appropriate message, such as "NO ALARM," as shown in FIG. 3

If more than one alarm condition occurs in gas system 12, then more than one of LED's 88 will visually indicate the occurring alarm conditions by flashing red, assuming that the alarm conditions occur in different subsystems of gas system 12. If more than one alarm condition occurs in the same subsystem of gas system 12, then the one LED 88 associated with the subsystem in which the multiple alarm conditions are occurring will be activated to flash red to provide the visual alarm. Electric circuit 70 also includes a speaker 94 or other suitable sound-producing device that is activated to provide an audible alarm when an alarm condition is sensed anywhere in gas system 12 by alarm system 10. Speaker 94 may be silenced by pressing button 92. In addition, pressing button 92 acknowledges all of the then-existing alarm conditions and causes the associated LED's 88 to stay steadily lit instead of flashing. Each new alarm condition resounds the audible alarm and causes the associated LED 88 to flash red, while the LED's 88 of the previously acknowledged alarm conditions remain steadily lit. In some embodiments, electric circuit 70 is programmed so that the audible alarm generated by speaker 94 resounds after a predetermined period of time, assuming the alarm condition is still occurring after the predetermined period of time.

When test button 90 is pressed, electric circuit 70 of alarm controller 48 runs a self-diagnostic test routine. For a short period of time after the diagnostic test routine starts, all of LED's 88 light, the characters of display screen 86 illuminate, and speaker 94 is activated to sound the audible alarm. Thereafter, a list of text messages for the configured alarms scrolls on display screen 86. If a problem is detected by electric circuit 70 while running the self-diagnostic test, then appropriate error messages are provided on display screen 86 after the test is finished. Of course, if screen 86 fails the diagnostic test and is unable to display any information at all, this will be readily apparent since screen 86 will be blank.

Figure 4:
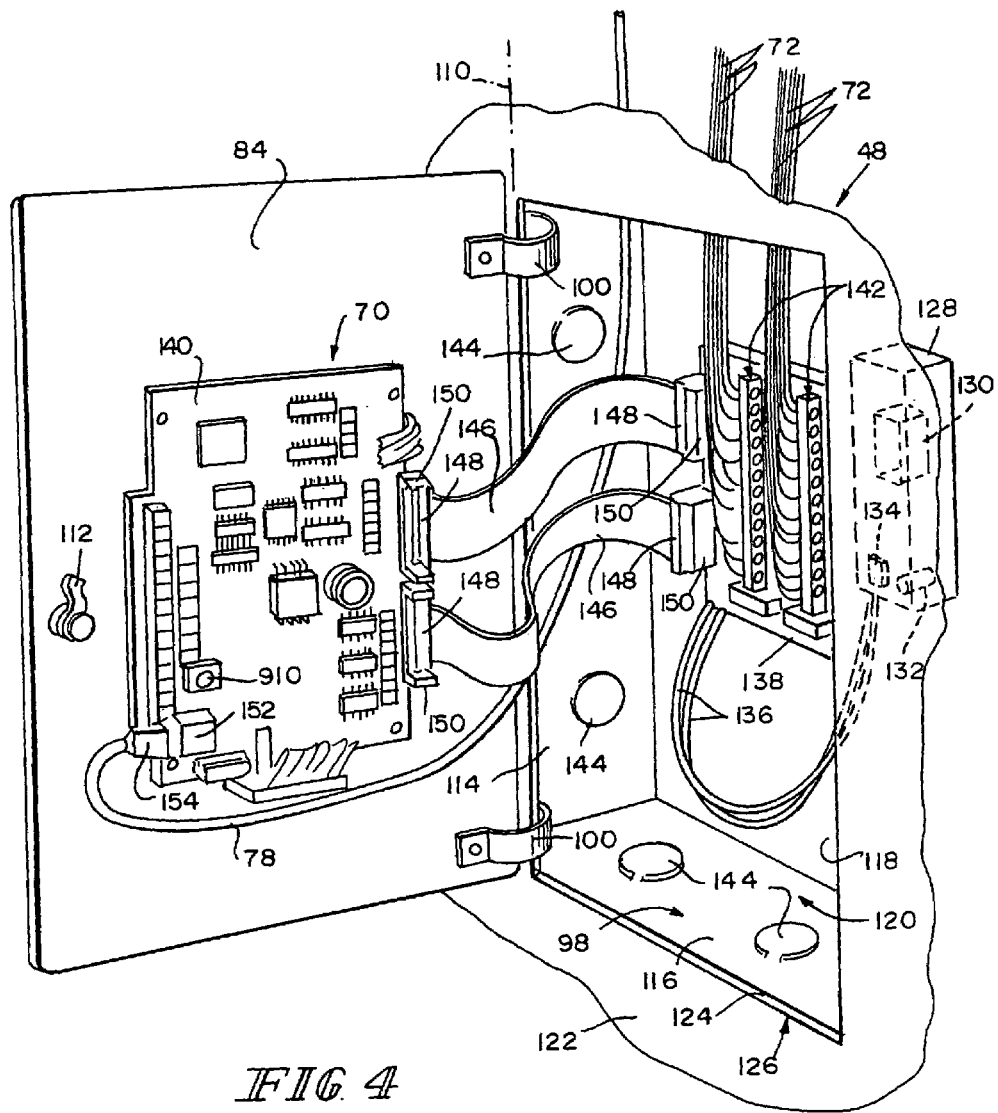
FIG. 4 is a perspective view of a portion of the master alarm controller of FIG. 3 showing a door panel of the master alarm controller moved to an opened position relative to a rough-in box of the master alarm controller to provide access to various electric circuit components of the master alarm controller.

Master alarm controller 48 includes a box 98 and a pair of hinge mechanisms 100 that couple panel 84 to box 98 for pivoting movement about a vertical axis 110 as shown in FIG. 4. Box 98 cooperates with panel 84 to provide a housing 84, 98 of controller 48. A locking device 112 is coupled to panel 84 and is operable to lock panel 84 in a closed position relative to box 98 and to unlock panel 84 for movement about axis 110 between the closed position and an opened position. Thus, panel 84 serves as a door of alarm controller 48.

Box 98 includes side panels 114, end panels 116, and a back panel 118. Panels 114, 116, 118 define an interior region 120 of box 98. Box 98 includes a front panel 122 that is parallel with back panel 118. Panel 122 includes a rectangular edge 124 that defines an opening 126 through which interior region 120 of box 98 is accessed when panel 84 is in the opened position. Panels 114, 116 extend perpendicularly between panels 118, 122. Box 98 is configured so that panels 114, 116, 118 are receivable in an appropriately sized cavity or recess formed in a wall of a facility and so that portions of panel 122 extending perpendicularly outwardly from panels 114, 116 abut the wall of the facility to which alarm controller 48 is mounted.

Electric circuit 70 of master alarm controller 48 includes a power supply 128 that is mounted to back panel 118. Power supply 128 includes a transformer 130, a fuse holder 132, and an ON/OFF switch 134. Power supply 128 receives standard 110 Volt, 60 Hertz power from the healthcare facility and operates in a conventional manner to provide electrical power to the rest of circuit 70 via power lines 136. ON/OFF switch 134 is placed in an ON position during the normal operation of master alarm controller 48 and may be placed in an OFF position during installation, removal, or maintenance of electric circuit 70. Fuse holder 132 contains a fuse (not shown) that operates in a conventional manner to provide electrical protection for circuit 70.

Electric circuit 70 further includes a breakout board 138 mounted to back panel 118 and a main circuit board 140 mounted to panel 84 as shown in FIG. 4. Power lines 136 are coupled to breakout board 128 via suitable electrical connectors (not shown) well-known to those skilled in the art. Board 138 includes a pair of connector banks 142 that provide a plurality of input ports for circuit 70. In the illustrative embodiment, each connector bank 142 is configured with fifteen input ports and therefore, illustrative circuit 70 includes a total of thirty input ports. In other embodiments, a different number of input ports are provided. Each input port includes two wire connection points, one for each wire of the twisted wire pairs that comprise conductors 72. Panels 114, 116 each include one or more tabs 144 that are punched out to provide corresponding apertures in panels 114, 116 through which conductors 72 are routed to reach connector banks 142.

Electric circuit 70 includes a pair of ribbon cables 146 that electrically couple breakout board 138 to main circuit board 140. Connectors 148 at the opposite ends of each ribbon cable 146 mate with corresponding connectors 150 of respective boards 138, 140. Input signals provided from the various switches of source equipment 18 on conductors 72 are communicated from board 138 to board 140 by ribbon cables 146. In addition, power is provided to board 140 from board 138 via ribbon cables 146. By having panel 84 pivot about vertical axis 110 between the closed and opened positions, rather than having panel 84 pivot downwardly about a horizontal axis at the bottom of panel 84, as is the case with some prior art alarm controllers, ribbon cables 146 do not lay across circuit 70 which reduces the risk of ribbon cable 146 short circuiting components of circuit 70.

Board 140 of circuit 70 carries a number of electrical components, including integrated circuit chips, that will be described below in connection with FIGS. 62–66. Display screen 86 and LED's 88 are coupled to board 140 and are positioned and arranged on board 140 so as to be visible through corresponding openings formed in panel 84 when board 140 is attached to the back of panel 84 as shown in FIG. 4. Board 140 includes a communication port 152. A connector 154 at an end of conductor 78 couples to port 152. Conductor 78 is routed from port 152, through interior region 120 of box 98, through one of the apertures that are created in panels 114, 116 of box 98 when tabs 144 are punched out, and to one of network hubs 44. Thus, data is provided to circuit 70 from network 14 through port 152 and data is provided from circuit 70 to network 14 through port 152.

Figure 5:
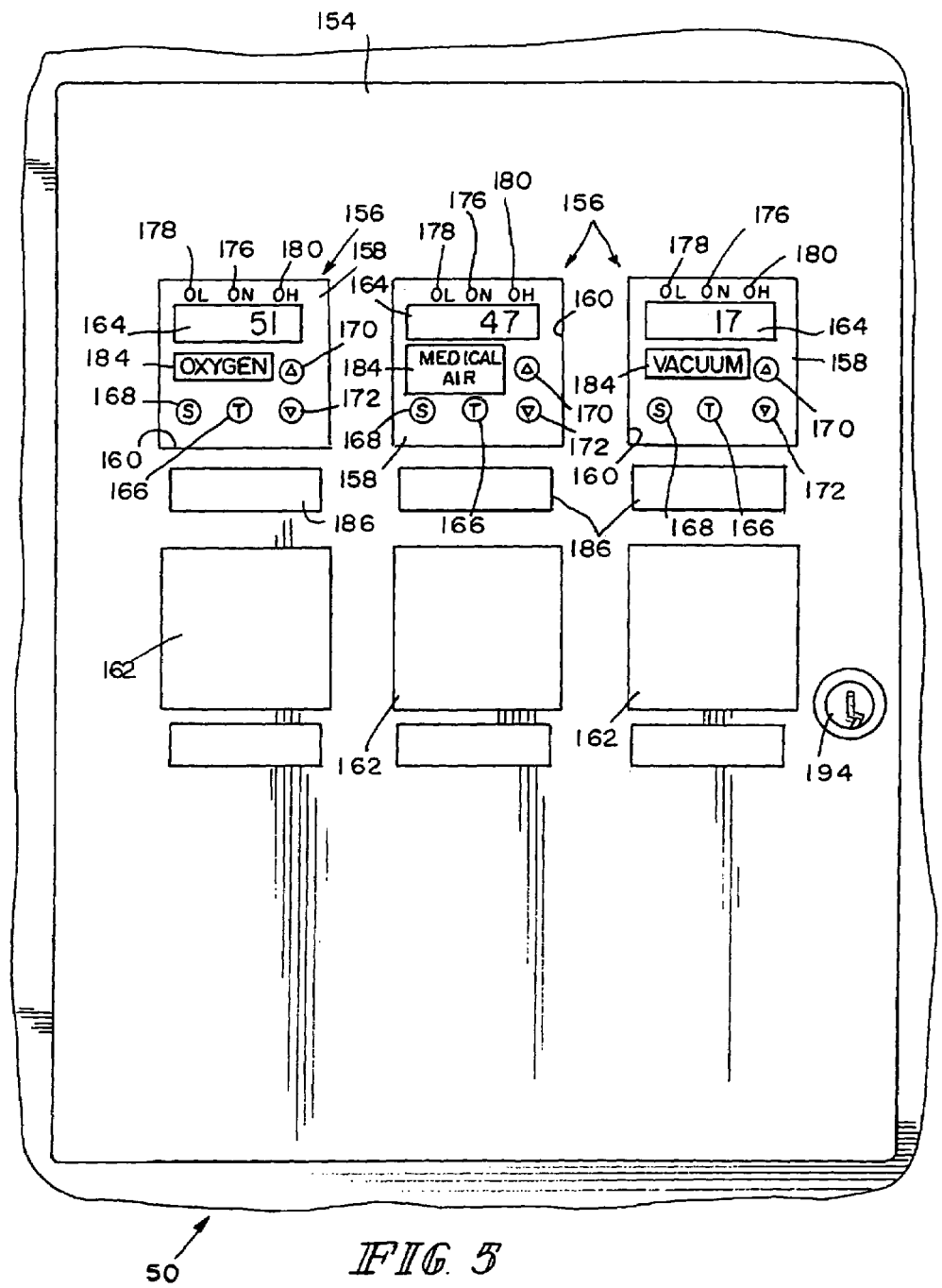
FIG. 5 is a front elevation view of a portion of one of the area alarm controllers of FIG. 2 showing three display modules, each of which displays a number indicating the gas pressure in an associated gas line of the medical gas system.
Figure 6:
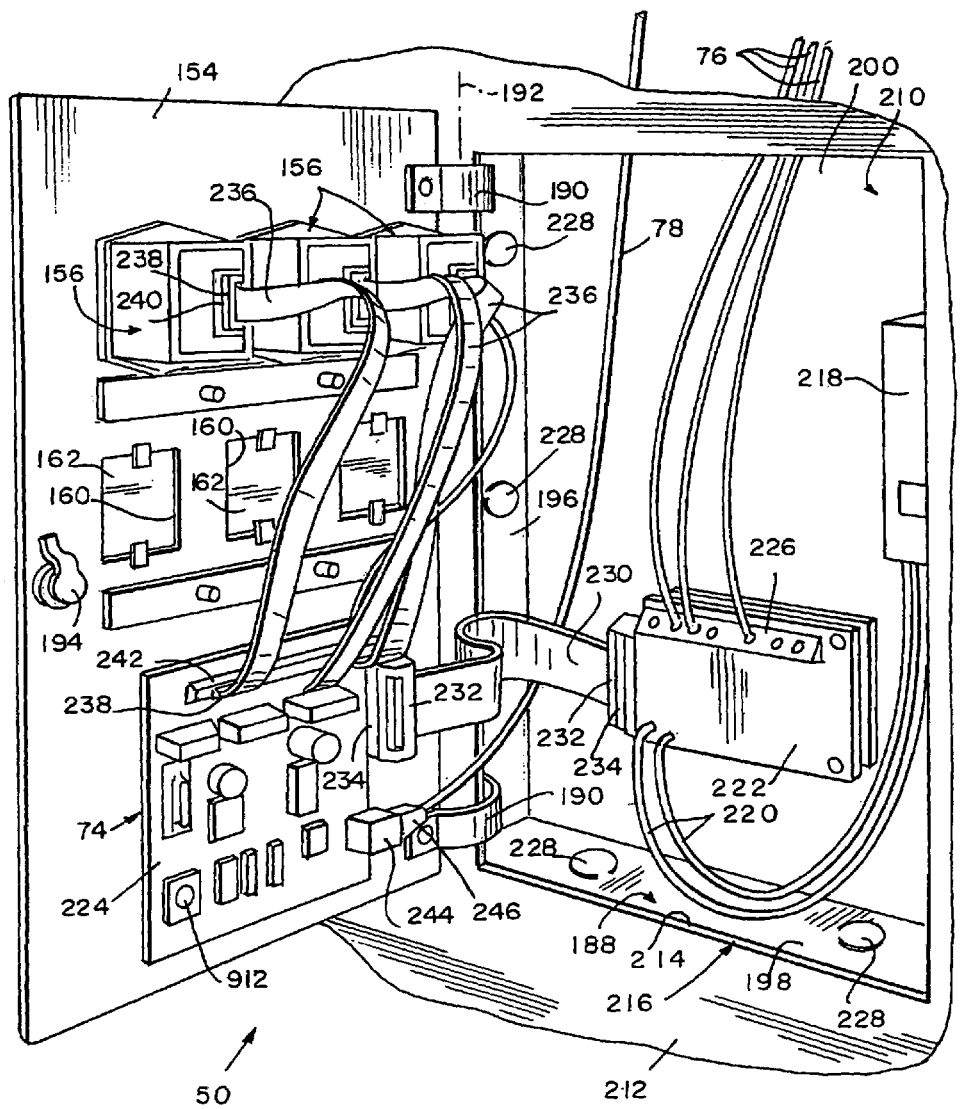
FIG. 6 is a perspective view of a portion of the area alarm controller of FIG. 4 showing a door panel of the area alarm controller moved to an opened position relative to a rough-in box of the area alarm controller to provide access to various electric circuit components of the area alarm controller.

Area alarm controller 50 includes a panel 154 and one or more display modules 156 that couple to panel 154 as shown in FIGS. 5 and 6. Each display module 156 has a front face 158 that appears in a respective opening or window 160 formed in panel 154 as shown in FIG. 5. In the illustrative embodiment, panel 154 is configured to accommodate up to six display modules 156. If less than six display modules 156 are included in illustrative alarm controller 50, then an appropriate number of filler plates 162 are coupled to panel 154 to block associated openings 160. For example, the controller 50 shown FIG. 5 has three modules 156 and three filler plates 162.

Each display module 156 is associated with a respective sensor module 54 and includes a display screen 164 on which numeric pressure readings are displayed. The pressure readings correspond to the gas pressures existing in the respective lines 16 to which modules 54 are coupled. The units of pressure measurement, such as pounds per square inch (psi), inches of mercury (in Hg) or the like, are indicated, in some embodiments, by a label or other suitable indicia (not shown) on front face 158 adjacent screen 164 and, in other embodiments, by text (not shown) that appears on screen 164 alongside the pressure readings.

Each display module 156 includes a test button 166, an alarm silence button 168, an up arrow button 170, and a down arrow button 172 as shown in FIG. 5. Each of buttons 166, 168, 170, 172 are coupled to the front face 158 of the respective module 156 and are accessible in window 160. Each display module 156 includes a "normal" LED 176 that shines green when the gas pressure in the associated line 16 is within an acceptable range, a "low" LED 178 that shines red when the gas pressure in the associated line 16 is below a minimum acceptable pressure, and a "high" LED 180 that shines red when the gas pressure in the associated line 16 is above a maximum acceptable pressure.

Each display module 156 includes an electric circuit, an example of which is shown in FIGS. 67 and 68, that is programmed for a specific gas or gas-related service. That is, depending upon what type of gas or gas-related service of gas system 12 is to be monitored by a particular display module 156, certain parameters, such as gas type, units of measure, high alarm point, and low alarm point, are stored in memory devices included in the electric circuit of the associated display module 156. By way of example, the standards set by the NFPA for the nominal pressure in lines 16 for each of the oxygen, medical air, nitrous oxide, oxygen/carbon dioxide mixture, carbon dioxide, and helium subsystems of gas system 12 is 50 psi (345 kPa) with a tolerance of +5 psi, −0 psi (+35 kPa, −0 kPa), the high alarm point is set 20% above the nominal pressure, and the low alarm point is set 20% below the nominal pressure. Standards for the nominal pressures and alarm points for other subsystems of gas system 12, such as for the nitrogen, vacuum, and WAGD subsystems, are also established by the NFPA.

The electric circuit of each display module 156 or, alternatively, circuit 74 includes a speaker (not shown) or other suitable sound-producing device that provides an audible alarm when any one or more of the input signals from sensor modules 54 indicates that the pressure existing in the respective line 16 is outside an acceptable range of pressures. To determine the range of acceptable pressures, a user may press up arrow button 170 to cause the numerical value of the pressure associated with the high alarm point to be displayed on screen 164 and the user may press the down arrow button 172 to cause the numerical value of the pressure associated with the low alarm point to be displayed on screen 164. Buttons 166, 168, 170, 172, LED's 176, 178, 180, and display screen 164 of each module 156 are some of the components included in the electric circuit of the respective module 156.

When an alarm condition occurs in one of lines 16, the electric circuit of the associated display module 156 operates to turn off "normal" LED 176, to turn on the appropriate one of "low" and "high" LED's 178, 180 thereby providing a visual alarm of the corresponding alarm condition, and to activate the associated speaker thereby providing an audible alarm of an occurring alarm condition. Alarm silence button 168 is pressed to turn off the audible alarm. In some embodiments, electric circuit 74 is programmed so that the audible alarm resounds within a predetermined period of time after being silenced, assuming the associated alarm condition is still occurring.

Test button 166 is pressed to cause the electric circuit of the associated module 156 to run a self-diagnostic test routine. During the self-diagnostic test routine of any of modules 156, the associated electric circuit determines whether the respective display screen 164, LED's 176, 178, 180, and audible alarm are functioning properly. During this same self-diagnostic test routine, the electric circuit operates to display certain indicia on screen 164 to prompt a user to press each of buttons 166, 168, 170, 172 to assure the proper operation of buttons 166, 168, 170, 172. If any portion of module 156 fails the self-diagnostic test, then an appropriate failure code is displayed on screen 164. Of course, if screen 164 fails the diagnostic test and is unable to display any information at all, this will be readily apparent since screen 164 will be blank.

At any time during the operation of modules 156, the electric circuit of each display module 156 operates to display various error codes on the associated display 164 if certain error conditions are detected. For example, in one embodiment, screen 164 displays "A 01" to indicate transducer pressure below sensor range, screen 164 displays "A 02" to indicate transducer pressure above sensor range, screen 164 displays "A 03" to indicate transducer communication time out, screen 164 displays "A 04" to indicate RAM error, screen 164 displays "A 05" to indicate ROM error, screen 164 displays "A 06" to indicate transducer status fault, screen 164 displays "A 07" to indicate incorrect transducer module connected to display module, screen 164 displays "A 08" to indicate display module programmed as vacuum but units are not inches of mercury or millimeters of mercury, screen 164 displays "A 09" to indicate display module programmed as pressure but units are not in psi or kPa, screen 164 displays "A 10" to indicate transducer programmed as invalid gas type, and screen 164 displays "A 11" to indicate transducer power short circuit detected. It will be appreciated that codes A 01 through A 11 are arbitrarily assigned and therefore, other error codes or text messages are within the scope of this disclosure.

Each display module 156 includes a label 184 or other suitable indicia that indicates the type of service for which the module 156 has been programmed. For example, labels 184 of the three modules 156 included in the controller 50 of FIG. 5 indicate that a first of the three modules 156 is programmed for use with the oxygen subsystem of gas system 12, a second of the three modules 156 is programmed for use with the medical air subsystem of gas system 12, and a third of the three modules 156 is programmed for use with the vacuum subsystem of gas system 12. In addition, controller 50 includes a set of labels 186 or other suitable indicia on panel 154 adjacent to respective modules 156 to indicate a location in the healthcare facility associated with the pressure reading displayed by the respective module 156. One example of information that may appear on label 186 is "ICU 2 EAST FLOOR 4." Of course, there are essentially an unlimited number of possibilities for the text that may appear on labels 186 to indicate various locations throughout a healthcare facility.

Area alarm controller 50 includes a box 188 and a pair of hinge mechanisms 190 that couple panel 154 to box 188 for pivoting movement about a vertical axis 192 as shown in FIG. 6. Box 188 cooperates with panel 154 to provide a housing 154, 188 of controller 50. A locking device 194 is coupled to panel 154 and is operable to lock panel 154 in a closed position relative to box 188 and to unlock panel 154 for movement about axis 192 between the closed position and an opened position. Thus, panel 154 serves as a door of alarm controller 50.

Box 188 includes side panels 196, end panels 198, and a back panel 200. Panels 196, 198, 200 define an interior region 210 of box 188. Box 188 includes a front panel 212 that is parallel with back panel 200. Panel 212 includes a rectangular edge 214 that defines an opening 216 through which interior region 210 of box 188 is accessed when panel 154 is in the opened position. Panels 196, 198 extend perpendicularly between panels 200, 212. Box 188 is configured so that panels 196, 198, 200 are receivable in an appropriately sized cavity or recess formed in a wall of a facility and so that portions of panel 212 extending perpendicularly outwardly from panels 114, 116 abut the wall of the facility to which alarm controller 50 is mounted.

Electric circuit 74 of area alarm controller 48 includes a power supply 218 that is mounted to back panel 200. Power supply 218 is the same or substantially similar to power supply 128 of master alarm controller 48. Thus, power supply 218 includes a transformer, a fuse holder, and an ON/OFF switch that function the same as transformer 130, fuse holder 132, and ON/OFF switch 134, respectively, of controller 48. Power supply 218 receives standard 110 Volt, 60 Hertz power from the healthcare facility and operates in a conventional manner to provide electrical power to the rest of circuit 74 via power lines 220.

Electric circuit 74 further includes a breakout board 222 mounted to back panel 200 and a main circuit board 224 mounted to panel 154 as shown in FIG. 6. Power lines 220 are coupled to breakout board 222 via suitable electrical connectors (not shown) well-known to those skilled in the art. Board 222 includes a connector bank 226 that provides a plurality of input ports for circuit 74. In the illustrative embodiment, connector bank 226 is configured with six input ports. In other embodiments, a different number of input ports are provided in circuit 74. Each input port provided by bank 226 includes three wire connection points, two of which are for respective wires of the twisted pair of the associated conductor 76 and one of which is for the shielding of the associated conductor 76. Panels 196, 198 each include one or more tabs 228 that are punched out to provide corresponding apertures in panels 196, 198 through which conductors 76 are routed to reach sensor modules 54.

Electric circuit 74 includes a ribbon cable 230 that electrically couples breakout board 222 to main circuit board 224. Connectors 232 at the opposite ends of ribbon cable 230 mate with corresponding connectors 234 of respective boards 222, 224. Input signals provided from sensor modules 54 on conductors 76 are communicated from board 222 to board 224 by ribbon cable 230. In addition, power is provided to board 224 from board 222 via ribbon cable 230. Electric circuit 74 further includes a set of ribbon cables 236 that electrically couple respective display modules 156 to board 224. Connectors 238 are provided at the opposite ends of each ribbon cable 236. One of connectors 238 of each ribbon cable 236 mates with a corresponding connector 240 of the respective module 156 and the other of connectors 238 of each ribbon cable mates with a corresponding connector 242 of board 224. In addition, power is provided to modules 156 from board 224 via respective ribbon cables 236.

Board 224 of circuit 74 carries a number of electrical components, including integrated circuit chips, that will be described below in connection with FIGS. 62–71. Board 224 includes a communication port 244. A connector 246 at an end of conductor 78 couples to port 244. Conductor 78 is routed from port 244, through interior region 210 of box 188, through one of the apertures that are created in panels 196, 198 of box 188 when tabs 228 are punched out, and to one of network hubs 44. Thus, data is provided to circuit 74 from network 14 through port 244 and data is provided from circuit 74 to network 14 through port 244.

Local alarm annunciator 52 includes a panel 248 and a plurality of LED's 250 that are coupled to panel 248 as shown in FIG. 7. In the illustrative embodiment, annunciator 52 includes sixteen LED's 250 that are grouped into two side-by-side vertical columns of eight LED's 250. Other embodiments have different numbers and arrangements of LED's 250. Each LED 250 provides a visual indicator, such as by turning from green to red, of a corresponding alarm condition occurring in source equipment 18. Annunciator 52 also includes a plurality of labels 252 or other suitable indicia, each of which is positioned on panel 248 adjacent a respective LED 250 and each of which includes text identifying the alarm condition associated with the respective LED 250.

Annunciator 52 includes an electric circuit 254 having a speaker (not shown) or other sound-producing device that is activated to provide an audible alarm when input signals to annunciator 52 indicate an alarm condition is occurring in source equipment 18. Circuit 254 includes an alarm silence button 256 on panel 248 that, when pressed, silences the audible alarm. In some embodiments, LED's 250 flash red upon the occurrence of associated alarm conditions and LED's 250 will be steadily lit red when alarm silence button 256 is pressed. The occurrence of a new or additional alarm condition causes circuit 254 to resound the audible alarm. In addition, in some embodiments, circuit 254 causes the audible alarm to resound if a predetermined period of time passes after button 256 is pressed, assuming an alarm condition is still occurring after the predetermined period of time. Circuit 254 also includes a test button 258 that, when pressed, starts a self-diagnostic routine to check whether LED's 250 and the audible alarm are operating properly.

Annunciator 52 includes a box 260, shown in FIG. 8, to which panel 248 couples with suitable fasteners, such as screws 262. Box 260 cooperates with panel 248 to provide a housing 248, 260 of annunciator 52. Box 260 includes side panels 264, end panels 266, and a back panel 268. Panels 264, 266, 268 define an interior region 270 of box 260. Box 260 includes a front panel 272 that is parallel with back panel 268. Panel 272 includes a rectangular edge 274 that defines an opening through which interior region 270 of box 260 is accessed when panel 248 is decoupled from box 260. Panels 264, 266 extend perpendicularly between panels 268, 272.

Electric circuit 254 of annunciator 254 includes a power supply 276 that is mounted to back panel 268. Power supply 276 is the same as or substantially similar to power supplies 128, 218 of alarm controllers 48, 50. Thus, power supply 276 provides electrical power to the rest of circuit 254 via power lines 278. Electric circuit 254 further includes a circuit board 280 mounted to panel 248. Power lines 278 are coupled to board 280 via suitable electrical connectors (not shown). Board 280 includes a pair of connector banks 282 that provides a plurality of input ports for circuit 254. In the illustrative embodiment, each connector bank 282 is configured with eight input ports. In other embodiments, a different number of input ports are provided in circuit 254. Each input port of bank 282 includes two wire connection points, one for each wire of the twisted wire pairs that comprise conductors 79. One of panels 266 includes an opening through which conductors 79 are routed as shown in FIG. 8.

Board 280 of circuit 254 carries a number of electrical components, including integrated circuit chips, that will be described below in connection with FIG. 66. LED's 250 are included as part of circuit 254 and are positioned and arranged on board 280 so as to be visible through corresponding openings formed in panel 248 when board 280 is attached to the back of panel 254 as shown in FIG. 8. Circuit 254 includes output ports that, in some embodiments, are coupled to associated input ports of one or more master alarm controllers 48. That is, instead of having conductors extending from the switches of source equipment 18 to each master alarm controller 48 and to each local alarm annunciator 52, as is shown diagrammatically in FIG. 2, a first set of conductors may extend from the switches of source equipment 18 to annunciator 52 and then a second set of conductors may extend from annunciator 52 to one or more master alarm controllers 48.

If desired, two separate input signals that are coupled to annunciator 52 by respective conductors 79 to provide annunciator 52 with two separate alarms may be combined in circuit 254 into a single output signal that is then coupled to a single input port of one or more of master alarm controllers 48. For example, if one of the input signals to annunciator 52 indicates "high line pressure" and another of the input signals to annunciator 52 indicates "low line pressure," then these two input signals may be combined into a single output signal that is fed to one or more master alarm controllers 48 as an input signal that indicates "improper line pressure."

Sensor module 54 includes a housing 284, a transducer 286 carried by housing 284, and an electric circuit 288 carried by housing 284 as shown in FIG. 9. Housing 284 includes a box 290 having an interior region 292 and a cover plate 294 that couples to a top edge 296 of box 290 with suitable coupling mechanisms, such as screws 298. Circuit 288 and transducer 286 are situated in interior region 292 of box 290 and are fastened in place with suitable fastening mechanisms. For example, in the illustrative embodiment, circuit 288 includes a circuit board 300 that mounts to rails 310 of box 290 with screws 312 and transducer 286 includes a threaded inlet 314 that extends through an opening (not shown) formed in box 290 into threaded engagement with a nut 316 such that a portion of box 290 is clamped between transducer 286 and nut 316.

A T-connector 318 is included in each line 16 at each of the points in lines 16 where the pressure is to be monitored by alarm system 10. A check valve assembly 320 extends between each T-connector 318 and the respective sensor module 54 as shown in FIG. 9. Check valve assembly 320 includes an upper connector 322 having a threaded tip 324 that threads into a bore (not shown) of threaded inlet 314 of transducer 286. Check valve assembly 320 also includes a lower connector 326 having a threaded tip 328 that threads into a bore 330 of T-connector 318. Check valve assembly 320 further includes a check valve unit 332 and a nut 334 that are interposed between connectors 322, 326.

Check valve assembly 320 operates to pneumatically couple sensor module 54 to line 16 so that transducer 286 is exposed to the pressure in line 16 when sensor module 54 is coupled to assembly 320. When module 54 is decoupled from assembly 320, check valve unit 332 closes so that, in the case of services having pressures above atmospheric pressure, the associated service in line 16 does not leak to atmosphere and so that, in the case of services having pressures below atmospheric pressure, air from the atmosphere does not enter into line 16. In preferred embodiments, check valve assembly 320 is constructed in accordance with the Diameter Index Safety System (DISS) protocol, which specifies the diameters that pneumatic connectors should have when being used with different types of services.

Transducer 286 operates in a conventional manner to produce an analog pressure signal that indicates the pressure to which transducer 286 is exposed. The analog pressure signal is communicated to circuit 288 on conductors 336. Circuit 288 is a microprocessor-based circuit that processes the pressure signal, such as by performing analog-to-digital conversion, and that transmits digital pressure data on the respective conductor 76 to the associated area alarm controller 50. Circuit 288 also transmits a host of other data to the associated alarm controller 50 in addition to transmitting data indicative of the pressure in the respective line 16.

Other types of data transmitted by circuit 288 to alarm controller 50 include, for example, serial number data, gas type data, software data, characteristic data, and status data. Serial number data indicates the serial number of the sensor module 54 transmitting the data. Gas type data indicates the type of service for which sensor module 54 is configured. Software data indicates the software revision number of software with which circuit 288 is programmed. Characteristic data indicates the characteristic, such as pressure or flow rate, being monitored by sensor module 54. Status data indicates whether sensor module 54 is operating properly or whether a fault condition has occurred. If a fault condition has occurred, then circuit 288 also transmits fault data which indicates the type of failure that occurred. Some of the fault data received by controller 50 causes the appropriate one of error codes A 01–A 11 to be displayed on screen 164 of the display module 156 associated with the sensor module 54 sending the fault data.

Circuit 288 includes one or more LED's 338 that provides a visual indicator of whether sensor module 54 is operating properly or whether a fault condition has occurred. If sensor module 54 is operating properly, then circuit 288 causes LED 338 to flash or strobe with a low frequency. If a fault condition occurs in sensor module 54, then circuit 288 causes LED 338 to flash or strobe with a high frequency. Housing 284 of sensor module 54 is made of a transparent or semitransparent material, such as, for example, a smoky plexiglass material, which enables observers to see the light that emanates from LED 338. Thus, LED 338 provides a visual "heartbeat" signal that an observer is able to see to quickly determine the status of sensor module 54.

Each of alarm controllers 48, 50, each display module 156, and each sensor module 54 includes its own microcontroller or microprocessor as mentioned above. The microcontrollers of one or more of these devices is configured to monitor the various electrical connections to the respective devices, 58, 50, 54, 156. If an electrical connection is lost or broken, a fault condition will be detected by the one or more microcontrollers that are configured to detect such conditions.

As mentioned previously, alarm controllers 48, 50 are each programmed to host or serve one or more websites. To access the websites of alarm controllers 48, 50 a user simply enters the network address of the desired website in a designated field, such as an address bar, shown on the monitor screen of any of computers 46, 82 that are linked to or included in network 14 and that are programmed with conventional web browser software. Once the websites of alarm controllers 48, 50 are accessed, various pages of the websites are navigated to view output data from alarm controllers 48, 50 and to provide input data to alarm controllers 48, 50 to configure alarm controllers 48, 50 with operating parameters. In the description below, when it is stated that a particular web page "appears on the user's computer screen," "is displayed on the user's computer screen," or the like, such statements mean that the associated alarm controller(s) 48 or alarm controller(s) 50 are transmitting data to the user's computer to cause the web page to appear on the user's computer screen.

Figure 10:
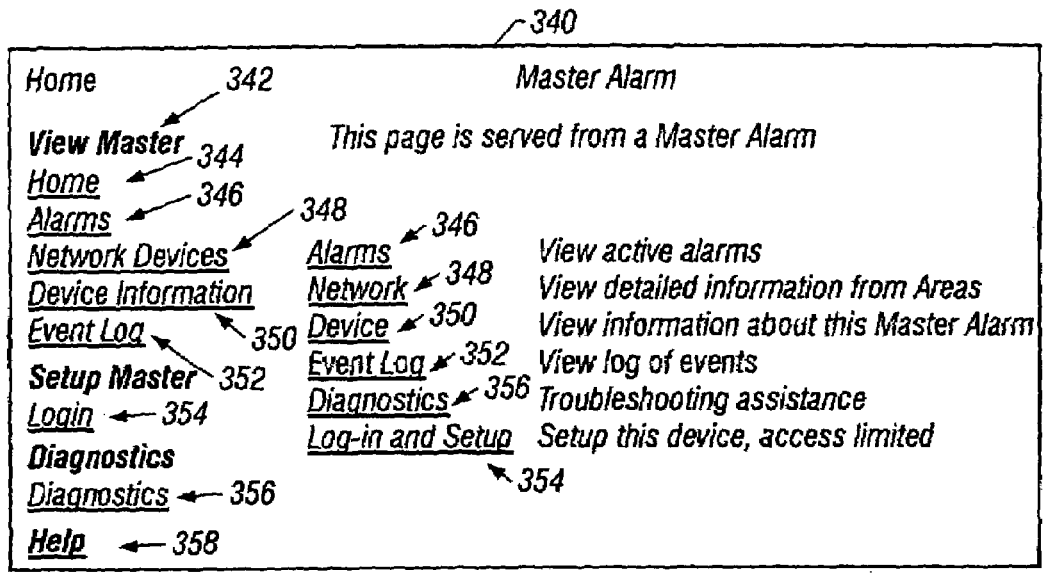

FIGS. 10–61 show examples of web pages of the websites hosted by controllers 48, 50. A large amount of textual information is shown in FIGS. 10–61 and this textual information, in certain instances, includes terms and acronyms that are used in the fields of computer programming and information technology and that are well known to those skilled in the art in these fields. Such terms and acronyms that are related to the fields of computer programming and information technology, that appear in FIGS. 10–61 and that are used to described FIGS. 10–61, are intended to have the meanings ascribed to such terms by those skilled in the art. Many of such terms are defined in Microsoft Press, Computer Dictionary, Third Edition, Microsoft Corporation, 1997.

After a user enters the network address that identifies one or more master alarm controllers 48 into the appropriate field on the screen of one of computers 46, 82, a Master Alarm Home page 340 appears on the user's computer screen as shown, for example, in FIG. 10. Page 340 includes a menu list 342 having a set of icons that are selected to hyperlink to pages of the website associated with the icons. Menu list 342 includes the following icons: Home icon 344, Alarms icon 346, Network Devices icon 348, Device Information icon 350, Event Log icon 352, Login icon 354, Diagnostics icon 356, and Help icon 358. Some of these icons are duplicated in larger text to the right of menu list 342. Identical reference numerals are used to denote icons from menu list 342 that are duplicated on page 340. The duplicated icons do not necessarily have the exact same wording as the icons of menu list 342. Page 340 includes text to the right of each duplicated icon to summarize for the user the type of information that the user will see on the pages associated with the respective icons.

The description below refers to various graphical or textual images, such as icons, buttons, or dialog boxes that appear on various web pages, as being "selected." This disclosure is intended to cover all methods for selecting graphical or textual images appearing on a computer screen. Selection of such graphical or textual images may be accomplished, for example, by moving a computer mouse to cause a cursor to overlap a portion of the image to be selected and then clicking (or double clicking) a button on the computer mouse; by using left, right, up, and down arrow keys on a computer keyboard to highlight various images and then pressing an "Enter" key of the keyboard when the desired image is highlighted; by using a "Tab" key on a computer keyboard to highlight various images and then pressing an "Enter" key of the keyboard when the desired image is highlighted; by touching a computer screen with a light pen on the portion of the screen having the desired image; and, if the computer screen is a touch screen, touching the portion of the touch screen having the desired image.

Figure 11:
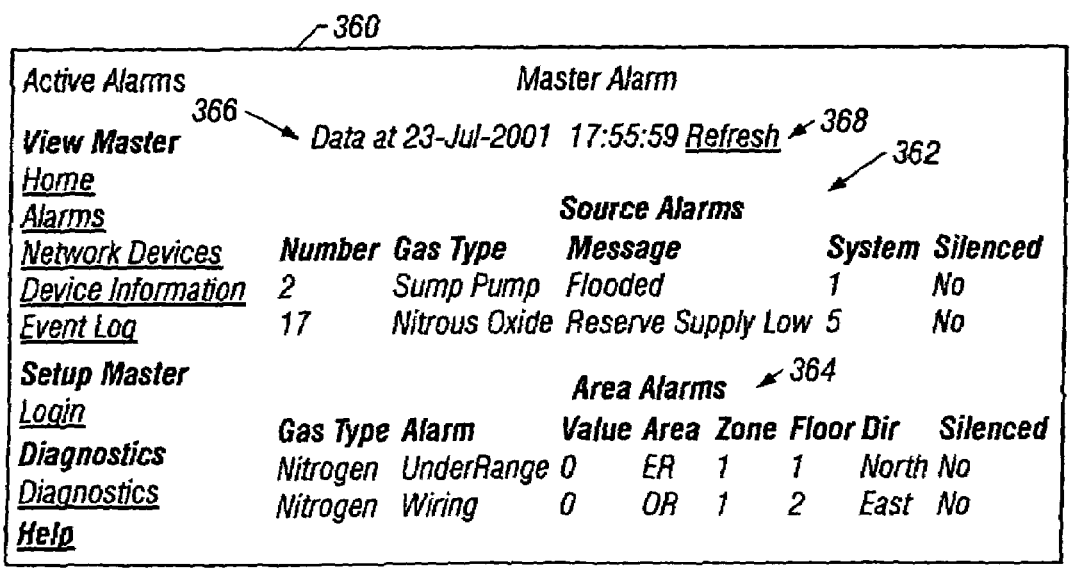

If Alarms icon 346 is selected, a Master Alarm Active Alarms page 360, an example of which is shown in FIG. 11, appears on the user's computer screen. Page 360 includes a Source Alarms table 362 that displays output data from alarm controllers 48 and an Area Alarms table 364 that displays output data from alarm controllers 50. The data shown on tables 362, 364 is a snapshot of the condition of system 12 at the time that page 360 is opened. A text line 366 near the top of page 360 indicates the date and time that the snapshot is taken. Page 360 includes a Refresh icon 368 that, when selected, updates the information on tables 362, 364 if the conditions in system 12 have changed since the previous snapshot.

Table 362 has a Number column which indicates the input port number of controllers 48 that are receiving the respective input signals which indicate the occurrence of alarm conditions in system 12. Table 362 has a Gas Type column that contains information regarding the type of service associated with the occurring alarm conditions. As can be seen in the Gas Type column of FIG. 11, one alarm condition is associated with a sump pump, which is not a gas type at all but is nonetheless able to provide an input signal to alarm controller 48, and another alarm condition is associated with the nitrous oxide subsystem of gas system 12. Table 362 has a Message column that contains the messages which are programmed to appear on display screen 86 of alarm controllers 48 for the corresponding alarm conditions. Table 362 also includes a System column that contains the system number in which the alarm conditions are occurring. These system numbers are assigned by facility personnel to the subsystems of gas system 12. Table 362 further includes a Silenced column that contains, for each alarm condition, either a "No" if alarm silence button 92 has not been pressed to silence the audible alarm that sounds when the respective alarm condition occurs, or a "Yes" if alarm silence button 92 has been pressed to silence the respective audible alarm.

Table 364 includes a Gas Type column that contains information regarding the type of service associated with the occurring alarm conditions detected by the associated area alarm controllers 50. Table 364 also includes an Alarm column that contains information about the nature of the occurring alarm conditions. In the example shown in FIG. 11, "UnderRange" is displayed in the first data line of the Alarm column of table 364 to indicate that the associated sensor module 54 is unable to read the pressure in the respective line 16 of gas system 12 because the pressure in that particular line 16 is below the range of pressures that the associated transducer 286 is capable of reading. Also in the example shown in FIG. 11, "Wiring" is displayed in the second data line of the Alarm column of table 364 to indicate that there is something wrong with the wiring of the associated portion of alarm controller 50 or with the wiring of the associated sensor module 54. Other examples of text that might appear in the Alarm column of table 364 include "High Pressure" and "Low Pressure," which correspond to the pressure in the associated line 16 being too high or too low, respectively.

Table 364 includes a Value column which contains pressure readings from the lines 16 in which the alarm conditions are occurring, assuming pressure readings are available from the respective sensor modules 54. The pressure readings are the pressure values that appear on the associated display modules 156 of the respective alarm controller 50 when page 360 is opened. Table 364 further includes Area, Zone, Floor, and Direction (abbreviated as "Dir" in table 364) columns that provide information as to the location in the healthcare facility at which each alarm condition is occurring. Table 364 also includes a Silenced column that contains, for each alarm condition, either a "No" if alarm silence button 168 of the respective display module 156 has not been pressed to silence the audible alarm that sounds when the respective alarm condition occurs, or a "Yes" if alarm silence button 168 of the respective display module 156 has been pressed to silence the respective audible alarm.

If Network Devices icon 348 is selected, a Master Alarm Network Devices page 370, an example of which is shown in FIG. 12A, appears on the user's computer screen. Page 370 includes output data that conveys information about all of the master alarm controllers 48 and all of the area alarm controllers 50 that are connected to network 14. Page 370 includes a Device column that contains the names selected for each of alarm controllers 48, 50. The example shown in FIG. 12A indicates that two master alarm controllers 48 and ten area alarm controllers 50 are coupled to network 14. Page 370 also includes, for each of alarm controllers 48, 50 coupled to network 14, a Type column, an SN column, an Area column, a Zone column, a Floor column, a Direction column, a Status column, and an Alarms column. The information contained in each of the columns on page 370 are self explanatory. For example, the SN column shows the serial number of each of the associated alarm controllers 48, 50 and the Area, Zone, Floor, and Direction columns show information about the location in facility 20 in which each alarm controller 48, 50 resides. The status column of page 370 indicates whether the associated alarm controller 48, 50 is "Ok" (i.e. operating properly), or whether an error has been detected in the operation of the associated alarm controller 48, 50. The Alarms column of page 370 indicates with or not an alarm condition is being detected by the associated alarm controller 48, 50.

Page 370 further includes Jump icons 372 and View icons 373 for each of alarm controllers 48, 50. Each of icons 372 is a hyperlink to the website of the associated alarm controller 48, 50. Thus, the user is able to link to the websites of any of the alarm controllers 48, 50 in network 14 from page 370. Each of icons 373 is a link to additional pages of the website hosted by alarm controller 48. For example, if icon 373 in the "This Master" row is selected, a first Master Alarm Specific Area page 375, an example of which is shown in FIG. 12B, appears on the user's computer screen. As another example, if icon 373 in the "Area39002" row is selected, a second Master Alarm Specific Area page 377, an example of which is shown in FIG. 12C, appears on the user's computer screen.

Page 375 includes a first table 379 that contains information about the serial number, location, and status of the master alarm controller 48 associated with the "This Master" row of page 370. The information in table 379 is the same as the information on page 370 that appears under the column heading of the same name. Page 375 further includes a second table 381 that contains information the alarm inputs being monitored by the alarm controller 48 identified in the first table 379. In the example shown in FIG. 12B, the master alarm controller 48 identified in table 379 is playing the roll of one of area alarm controllers 50 and is receiving input signals from sensor modules 54 instead of from the switches included in source equipment 18.

Page 377 includes a first table 383 that contains information about the serial number, location, and status of the area alarm controller 50 associated with the "Area39002" row of page 370. The information in table 383 is the same as the information on page 370 that appears under the column heading of the same name. Page 377 further includes a second table 385 having information regarding the input signals being received by the alarm controller 50 identified in table 383 (i.e. the Area39002 alarm controller 50). Table 385 includes a Gas Type column that shows the service type associated with each of the input signals to the Area39002 alarm controller 50, an SN column that shows the serial number of each display module 156 of the Area39002 alarm controller 50, a Trans SN column that shows the serial number of each of the sensor modules 54 of the Area39002 alarm controller 50, an Item column that shows the type of characteristic being monitored by each of the sensor modules 54 of the Area39002 alarm controller 50, a Value column that shows the numerical value of the characteristic being monitored by each of the sensor modules 54 of the Area39002 alarm controller 50, and a Units column that indicates the units associated with the numerical values shown in the Value column. Table 385 also includes Area, Zone, Floor, and Direction columns that indicate the location in facility 20 of the Area39002 alarm controller 50. In addition, table 385 includes an Alarm column that shows whether any of sensor modules 54 of the Area39002 alarm controller 50 is detecting an alarm condition. Furthermore, table 385 includes a Status column that indicates whether display modules 156 and sensor modules 54 of the Area39002 alarm controller 50 are "Ok" (i.e. operating properly), or whether an error has been detected in the operation of the associated display modules 156 and sensor modules 54.

The information appearing on pages 370, 375, 377 is a snapshot of the condition of system 12 at the time that page 370 is initially opened. A text line 374 near the top of page 370 indicates the date and time that the snapshot is taken. Each of pages 370, 375, 377 includes a Refresh icon 376 that, when selected, updates the information appearing on pages 370, 375, 377 if the conditions in system 12 have changed since the previous snapshot. In addition, each of pages 375, 377 includes a Back icon 387 that, when selected, causes page 370 to appear on the user's computer screen. In some embodiments, selection of back icon 387 also causes the information appearing on pages 370, 375, 377 to be updated and, in other embodiments, selection of icon 387 does not cause the information appearing on pages 370, 375, 377 to be updated.

If Device Information icon 350 or if view icon 373 associated with one master alarm controllers 48 is selected, a Master Alarm Device Information page 378, an example of which is shown in FIG. 13, appears on the user's computer screen. Page 378 contains some of the same information that page 370 contains regarding the location in the healthcare facility of the respective alarm controllers 48 and regarding the serial numbers of the respective alarm controllers 48. Page 378 also contains, for each of the alarm controllers 48 coupled to network 14, the model number, software version, software build, Internet Protocol (IP) address, and Media Access Control (MAC) address. The term "IP address" is referred to elsewhere in this disclosure as the "network address." The IP address can be assigned and changed in various ways, including being assigned and changed by systems administrators or authorized users as described below. The MAC address is a unique alphanumeric code that is given by device manufacturers to every device having a network interface card (NIC). Only devices having a NIC are able to connect to the Internet. Thus, every device that couples to the Internet will have a NIC that is identified by a unique MAC address.

Figure 14:
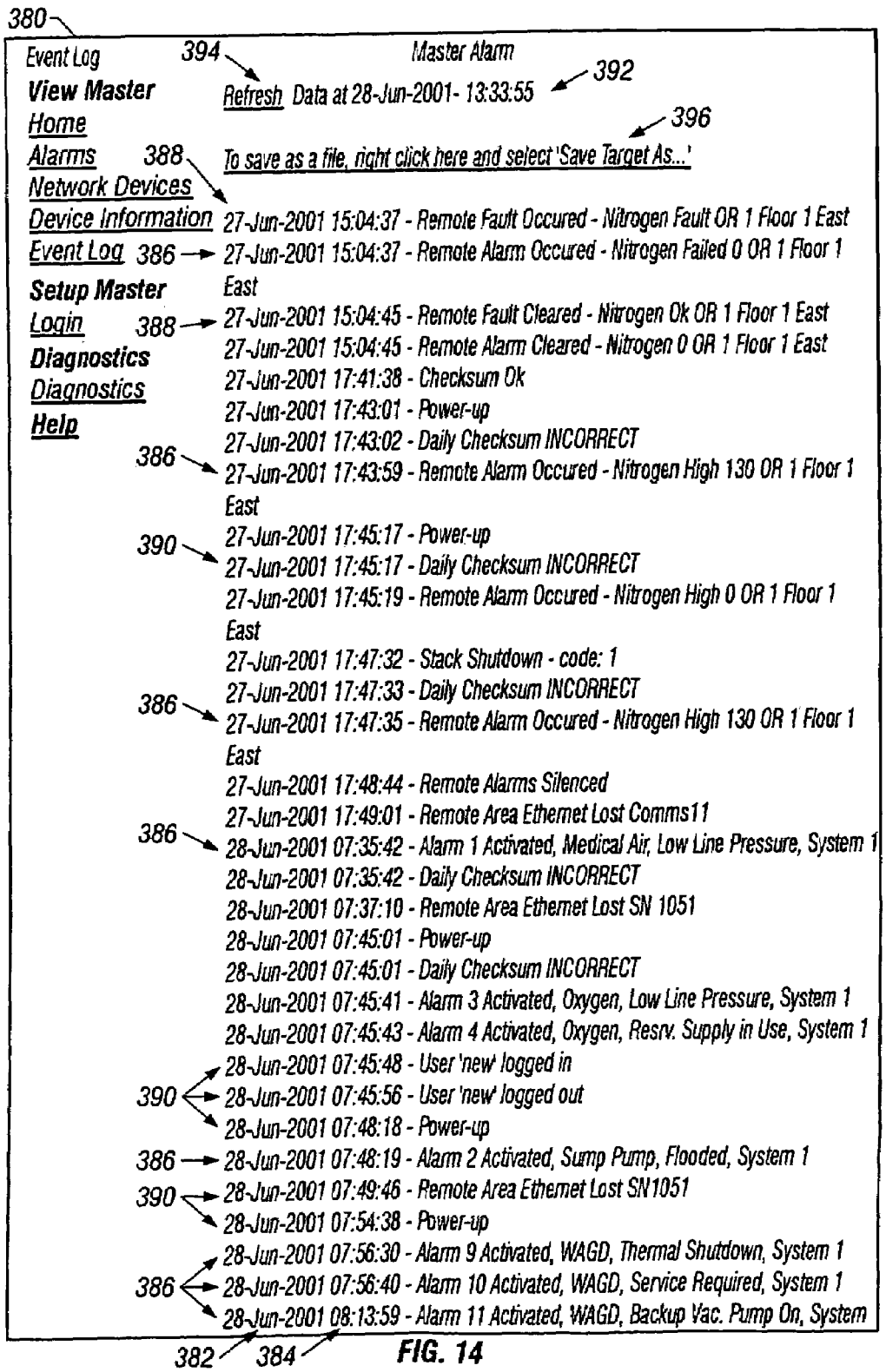

If Event Log icon 352 is selected, a Master Alarm Event Log page 380, an example of which is shown in FIG. 14, appears on the user's computer screen. Page 380 includes a list of a multitude of events that are detected by or communicated to the master alarm controllers 48 that are coupled to network 14. Only a few of these events are listed on illustrative page 380 to provide a general sense of the type of information that may appear in the event log. Each event that is logged on page 380 includes a date stamp 382 and a time stamp 384 to indicate when the event occurred. The information appearing in the event log relates, generally, to alarm conditions occurring in system 12, fault conditions occurring in the various pieces of equipment of system 10, or computer systems-related occurrences. See text lines 386 of FIG. 14 for examples of the type of information logged on page 380 when an alarm condition occurs in system 12. See text lines 388 of FIG. 14 for examples of the type of information logged on page 380 when a fault condition occurs in the equipment of system 10. See text lines 390 of FIG. 14 for examples of computer systems-related occurrences that are logged on page 380.

The data shown on page 380 is a snapshot of the event log at the time that page 380 is opened. A text line 392 near the top of page 380 indicates the date and time that page 380 is opened. Page 380 includes a Refresh icon 394 that, when selected, updates the events on page 380 if new events occur after page 380 is opened and before icon 394 is selected. Events that are listed on the event log of page 380 eventually are deleted automatically, either after a maximum number of events are listed on the event log or after a certain amount of time elapses since the occurrence of the event to be deleted. Page 380 includes a "To save as a file, right click here and select 'Save Target As . . .'" icon 396. If icon 396 is selected, then the event log is saved as a text document under a file name and in a location in the user's computer that are designated by the user. The user designates the file name and location by typing appropriate entries in file name and location bars that appear in a pop-up window on the user's computer screen when icon 396 is selected. Such pop-up windows for saving files should be well-known to anyone who has used conventional windows-based word processing software.

Figure 15:
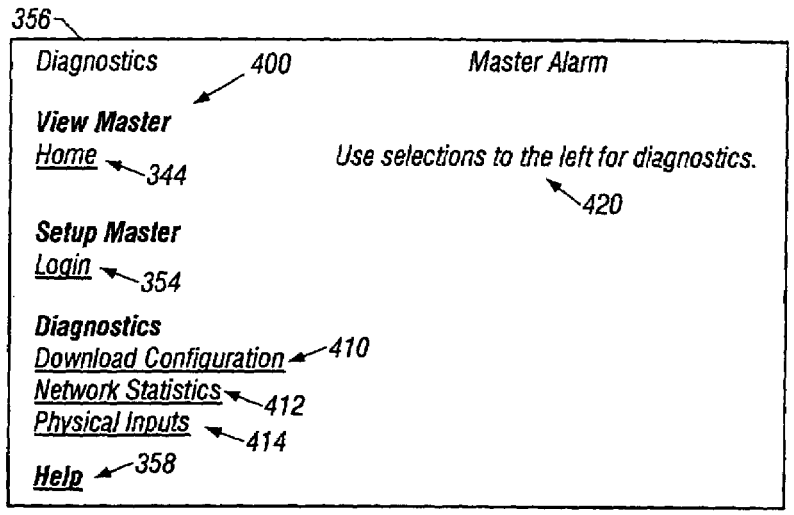

If Diagnostics icon 356 is selected, a Master Alarm Diagnostics page 398, an example of which is shown in FIG. 15, appears on the user's computer screen. Page 398 includes a menu list 400 that is different than menu list 342. Menu list 400 includes Home icon 344, Login icon 354, and Help icon 358, which are common with menu list 342, but menu list 400 includes a Download Configuration icon 410, a Network Statistics icon 412, and a Physical Inputs icon 414. Page 398 also includes a text line 420 that instructs the user to "use selections to the left for diagnostics."

Figure 16:
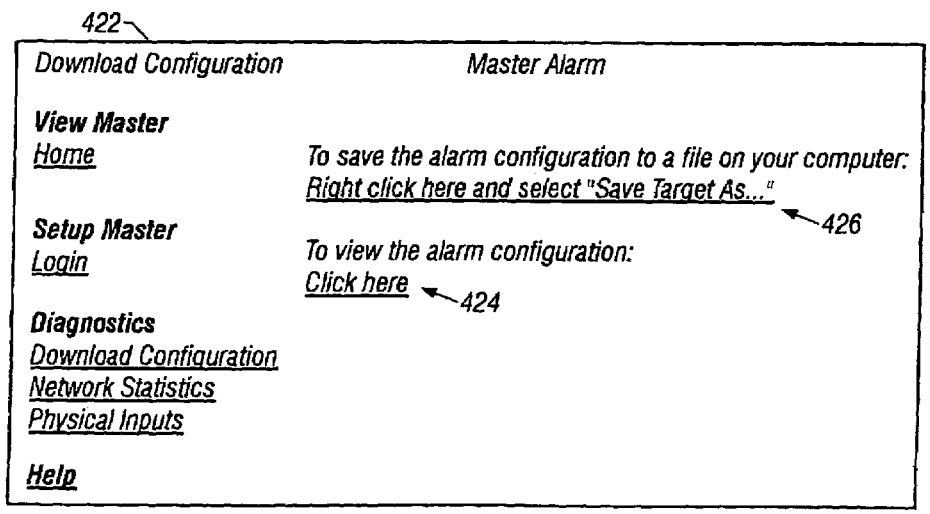

If Download Configuration icon 410 is selected, a Master Alarm Download Configuration page 422, an example of which is shown in FIG. 16, appears on the user's computer screen. Page 422 includes a Click here icon 424 that, when selected, causes a Master Alarm Device Configuration page 428 to appear on the user's computer screen. Page 422 also includes a "Right click here and select 'Save Target As . . .'" icon 426 that, when selected causes the information shown on page 428 to be saved as a text document under a file name and in a location in the user's computer that are designated by the user. The user designates the file name and location by typing appropriate entries in file name and location bars that appear in a pop-up window on the user's computer screen when icon 426 is selected.

Page 428 includes a summary list 430 of the configuration of the associated master alarm controllers 48. The list 430 shows for each alarm (i.e. each input port), numbered 1 through 30, the subsystem of system 12 associated with the respective alarm, the condition that causes the respective alarm to be activated, which of LED's 88 is assigned to the respective alarm, and which system number is associated with the respective alarm signal. For example, the text "Alarm 1-Medical Air, Low Line Pressure, led=1, system=1," shown on list 430 in FIG. 17, informs the user that the alarm signal communicated to the first input port of the associated master alarm controllers 48 on the associated conductors 72 is indicative of low line pressure in the medical air subsystem 1 of gas system 12 and that the first LED 88 of the LED's on alarm controllers 48 is assigned to this alarm signal. Other alarms shown on list 430 have similar information.

The entries for Alarms 3–6 on illustrative list 430 indicate that there are two oxygen subsystems in the associated gas system 12, Alarms 3 and 4 being associated with the first of the oxygen subsystems, as indicated by the appearance of "system=1" at the end of the corresponding text lines, and Alarms 5 and 6 being associated with the second of the oxygen subsystems, as indicated by the appearance of "system=2" at the end of the corresponding text lines. However, the second LED 88 of LED's 88 are assigned to all of Alarms 3–6 as indicated by the appearance of "led=2" in each of the corresponding text lines. It will be appreciated that master alarm controllers 48 can be configured in any desired manner and that list 430 simply shows the existing configuration. Page 428 includes a block 432 of additional information above list 430 as shown in FIG. 17. Block 432 includes information regarding device name, location, language, alarm silence, IP addressing and firmware version.

If Network Statistics icon 412 is selected, a Master Alarm Network Statistics page 434, an example of which is shown in FIG. 18, appears on the user's computer screen. Page 434 includes address information at the lines labeled IP Address, Subnet, Gateway, Fixed IP Address, Fixed Subnet, Fixed Gateway, and Mac Address. Page 434 also includes reception/transmission information at the lines labeled Receives, Unicasts, Multicasts, Broadcasts, Rx Errors, Rx Missed, Rx CRC Errors, Rx Drops, Transmits, Buffer Defers, Tx Errors, Tx Collisions, Tx Coll. Overflow, Tx FILO Efforts, and Traffic Backoffs. The data shown on page 434 is a snapshot of the network statistics at the time that page 434 is opened. Page 434 includes a Refresh icon 436 that, when selected, updates the network statistics on page 434 if the network statistics have changed after page 434 is opened and before icon 436 is selected.

Figure 19:
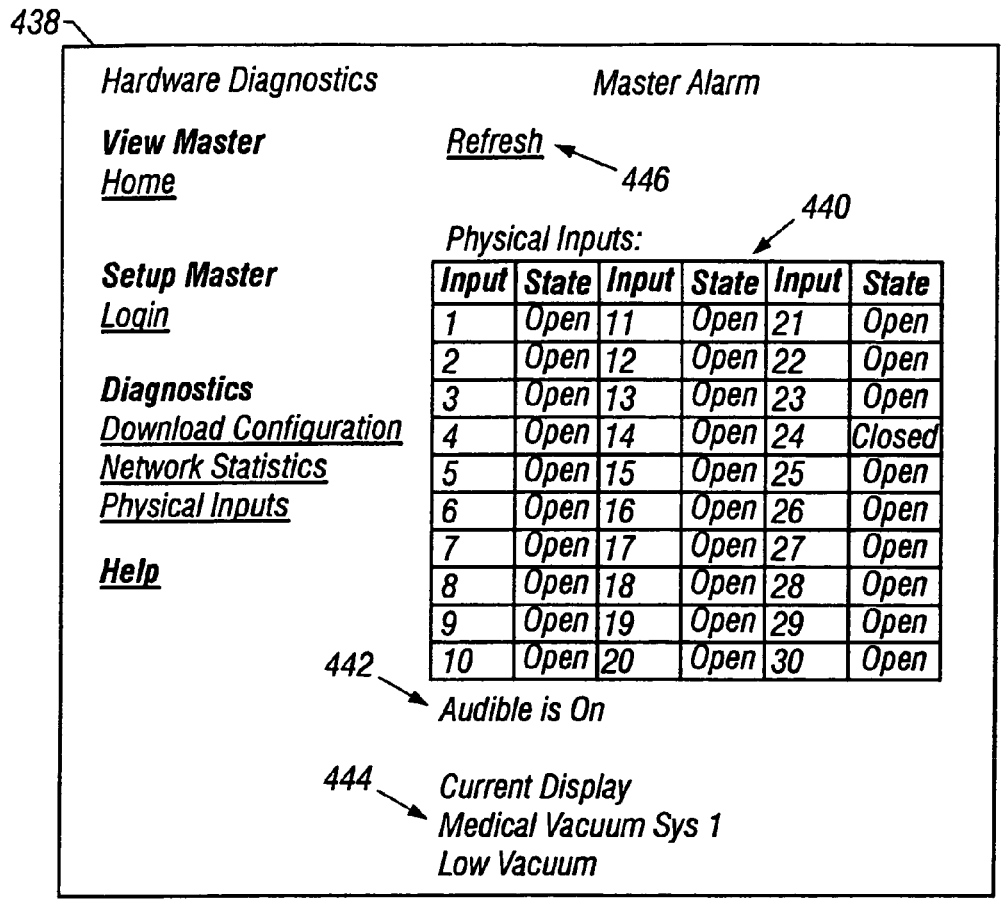

If Physical Inputs icon 414 is selected, a Master Alarm Hardware Diagnostics page 438, an example of which is shown in FIG. 19, appears on the user's computer screen. Page 438 includes a table 440 having "Input" columns that show the input port numbers of the associated master alarm controllers 48 and "State" columns that show whether the input signal received by the associated input port is in an "Open" state or a "Closed" state. In the illustrative embodiment, an Open state corresponds to no alarm condition and a Closed state corresponds to an alarm condition. In table 440 of FIG. 19, input port number 24 is indicated as being in the Closed state which means that an alarm condition is occurring in whatever portion of source equipment 18 is associated with input port number 24.

Page 438 also includes a text line 442 that indicates whether the audible alarm of the associated master alarm controllers 48 is "On" or "Off." In addition, page 438 includes a Current Display block 444 that shows any text messages that are displayed on display screens 86 of the associated alarm controllers 48 when page 438 is opened. In the example shown in FIG. 19, line 442 indicates that the audible alarm is "On" and block 444 indicates that text message "Medical Vacuum Sys 1 Low Vacuum" appeared on associated screens 86 when page 438 was opened. Since input port 24 in table 440 is the only input port in the Closed state, one can deduce from table 440 that the information shown in line 442 and block 444 refers to the alarm condition being communicated to input port 24. The data shown on page 438 is a snapshot of the state of the associated input ports, the state of the associated audible alarms, and the state of the text messages on associated screens 86 at the time that page 438 is opened. Page 438 includes a Refresh icon 446 that, when selected, updates the information on page 438.

Figure 20:
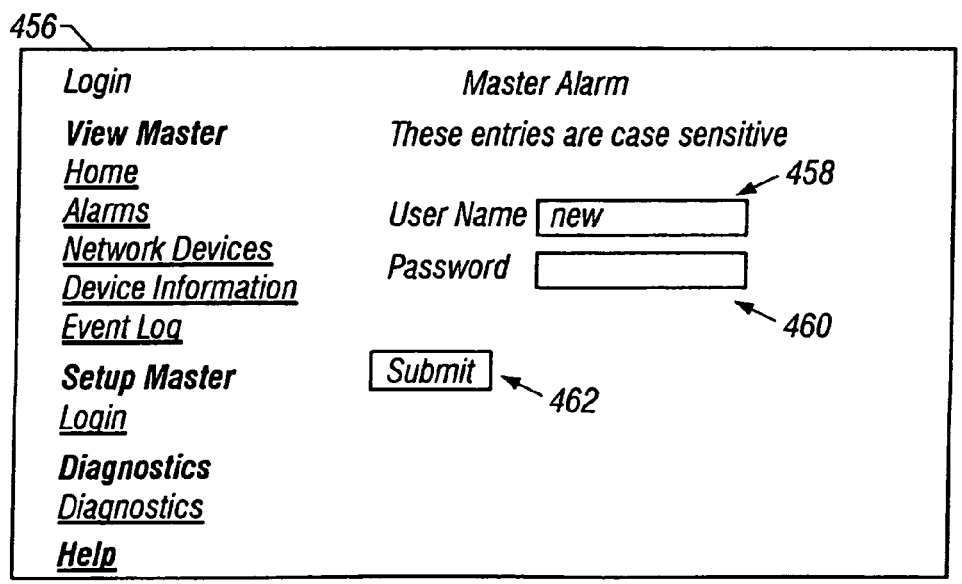
Figure 21:
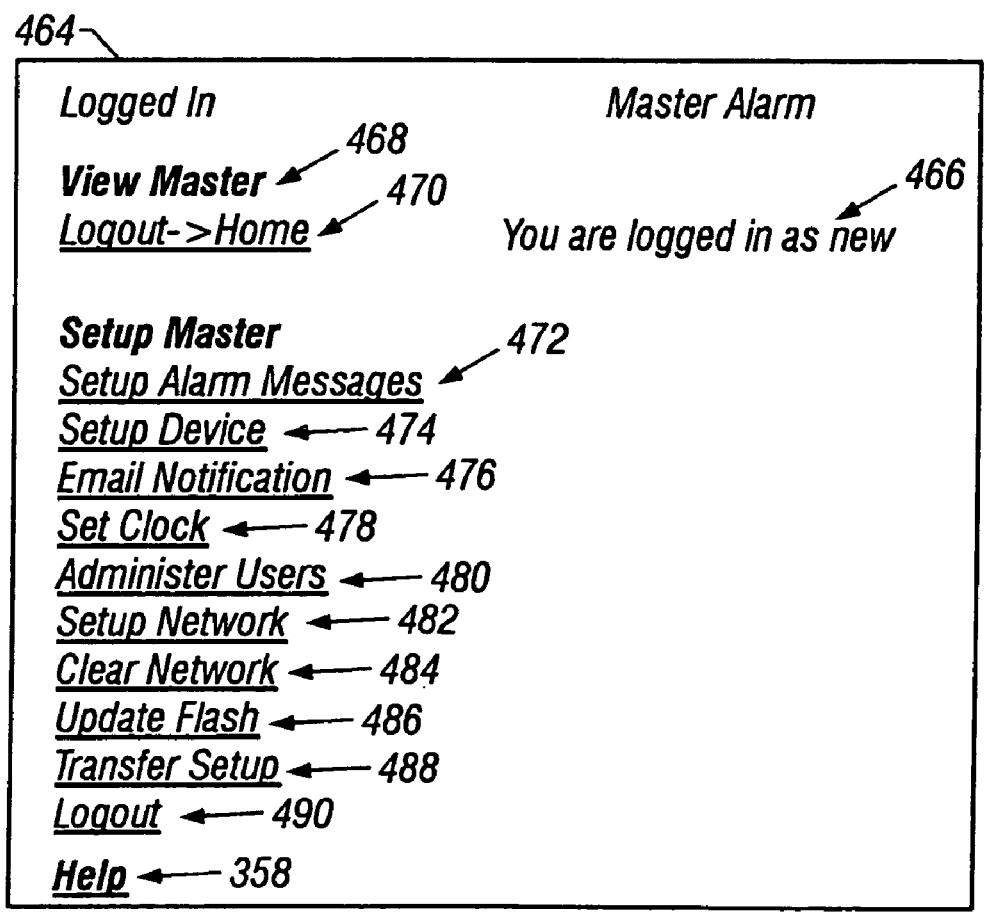

If Login icon 354 is selected, a Master Alarm Login page 456 appears on the user's computer screen as shown, for example, in FIG. 20. Page 456 includes a User Name dialog box 458 and a Password dialog box 460. Authorized users who have been assigned user names and passwords are able to type their respective user names and passwords into dialog boxes 458, 460, respectively, to access pages of the master alarm website to provide input data to alarm controllers 48 to configure the controllers 48 with operating parameters. Page 456 includes a Submit icon 462 that, when selected, causes a Master Alarm Logged In page 464, shown in FIG. 21, to appear on the user's computer screen if the user entered a valid user name and password in dialog boxes 458, 460 prior to selecting Submit icon 462. When an authorized user logs into the password protected portion of the master alarm website, this event is logged and will appear on the event log of page 380 as described above.

Page 464 includes a message 466 which indicates that the user has successfully logged in and therefore, has access to the password protected pages of the master alarm website. Page 464 also includes a menu list 468 having a set of icons that are selected to go to the password protected pages of the website associated with the icons. Menu list 468 includes the following icons: Logout>Home icon 470, Setup Alarm Messages icon 472, Setup Device icon 474, Email Notification icon 476, Set Clock icon 478, Administrate Users icon 480, Setup Network icon 482, Clear Network icon 484, Update Flash icon 486, Transfer Setup icon 488, and Logout icon 490. Menu list 468 also includes Help icon 358, as was the case with menu lists 342, 400 mentioned previously.

If Setup Alarm Messages icon 472 is selected, a Master Alarm Alarm Message Setup page 492, an example of which is shown in FIG. 22, appears on the user's computer screen. Page 492 includes an "Alarm Input" column having a set of alarm icons 494 that are numbered 1 through 30 and that correspond to the input ports of the associated master alarm controller 48. For each icon 494, page 492 shows the associated service type, the message to appear on display screen 86 when the associated alarm condition occurs, the associated LED 88 that is designated, and the associated system number.

To configure a particular alarm input, the user simply selects the desired alarm icon 494 and a Master Alarm Setup Alarm Messages Step 2 page 496 for the selected icon 494 will appear as shown in FIG. 23, for example, with reference to the alarm icon 494 associated with input port 17. Page 496 includes a Gas Type box 498, an LED box 500, and a System box 510. Each of boxes 498, 500, 510 includes a down arrow icon 512 that, when selected, causes a drop down menu to appear on page 496 with the options that are available for configuring the associated alarm input being listed in the drop down menu.

If down arrow icon 512 of box 498 is selected on page 496, the options that appear in the respective drop down menu are as follows: Unused, Nitrogen, Medical Air, Medical Vacuum, WAGD, Oxygen, Nitrous Oxide, Carbon Dioxide, Oxy./Car. Mix, Helium, Argon, Lab Air, Dental Air, Tool Air, Lab Vacuum, Dental Vacuum, and Custom. When the user then selects one of these options, the selected option will appear in box 498 and the drop down menu will disappear from the user's computer screen. Other drop down menus described below operate similarly. That is once an item is selected from a drop down menu, the drop menu disappears and the item selected appears in the dialog box associated with the drop down menu.

If down arrow icon 512 of box 500 is selected on page 496, the options that appear in the respective drop down menu are numerals 0 through 9. The user selects one of options 0 through 9 with a mouse click or with appropriate key strokes on the keyboard of the user's computer in a manner similar to that described above. Selecting option 0 means that no LED 88 will be associated with the respective alarm condition. Selecting any of options 1 through 9 designates the particular LED 88 to be associated with the respective alarm condition. If down arrow icon 512 of box 510 is selected on page 496, the options that appear in the respective drop down menu are numerals 1 through 9. The user selects one of options 1 through 9 with a mouse click or with appropriate key strokes on the keyboard of the user's computer in a manner similar to that described above. Selecting any of options 1 through 9 designates the particular system number to be associated with the respective alarm condition. The default condition for boxes 498, 500, 510 of each alarm signal are Unused, 0, 1, respectively.

Page 496 includes a Next icon 514 that is selected after the options for boxes 498, 500, 510 are selected. Selecting icon 514 causes a Master Alarm Setup Alarm Messages Step 3 page 516, an example of which is shown in FIG. 24, to be displayed on the user's computer screen. Page 516 shows the alarm number that was selected on page 492 as well as the options that were selected on page 496. Page 516 includes an "Alarm message for this input" box 518. Box 518 includes a down arrow icon 520 that, when selected, causes a drop down menu to appear on page 516 with a list of options that are available for configuring the message to be displayed on screens 86 of alarm controllers 48 when the associated alarm condition occurs. The user clicks on a desired option on the list to configure alarm controller 48 to display the desired message. Alternatively, the user may type in a message in box 518 if the user does not want to use any of the message options appearing in the drop down menu.

The list of options that appear in the drop down menu of page 516 when icon 520 is selected depends upon the type of service that was selected in connection with box 498 on page 496. For the most part, the options listed in these drop down menus correspond to alarm points of gas system 12 that are established by standards set by the NFPA. If any of Nitrogen, Oxygen, Nitrous Oxide, Carbon Dioxide, Oxy./Carb. Mix, Helium, or Argon are selected for box 498 on page 496, then the options that appear in the drop menu of page 516 when icon 520 is selected are as follows: Liquid Level Low, 2.sup.nd Supply in Use, Resrv. Supply in Use, Reserve Supply Low, High Line Pressure, and Low Line Pressure. If any of Medial Air, Lab Air, Dental Air, or Tool Air are selected for box 498 on page 496, then the options that appear in the drop menu of page 516 when icon 520 is selected are as follows: Dryer Malfunction, Dew Point High, Carbon Monoxide High, Change Filter, Receiver Water High, Separator Water High, Air Disch. Temp. High, Backup Compressor On, Compressor Malfunction, Thermal Shutdown, Service Required, High Line Pressure, and Low Line Pressure. If any of Medical Vacuum, WAGD, Lab Vacuum, or Dental Vacuum are selected for box 498 on page 496, then the options that appear in the drop menu of page 516 when icon 520 is selected are as follows: Thermal Shutdown, Service Required, Backup Vac. Pump On, and Low Vacuum.

The user selects one of the options from the drop down menu on page 516 with a mouse click or with appropriate key strokes on the keyboard of the user's computer in a manner similar to that described above. The selected option becomes the text message that appears on display screen 86 when the associated alarm condition occurs. If the user selects "Custom" as the option for box 498 on page 496, then a custom page (not shown) is presented to the user instead of page 516. The custom page includes a Custom Label dialog box in which the user types a description of the custom service associated with the respective alarm input. The custom page also includes a Custom Message dialog box in which the user types a message to be displayed on display screens 86 of the respective alarm controllers 48 when the alarm condition occurs. In FIG. 11, the words "Sump Pump" is an example of a Custom Label and the word "Flooded" is an example of a Custom Message. In the example of FIG. 11, alarm input number 2 has been custom configured with the phrases Sump Pump and Flooded. It will be appreciated there are essentially an unlimited number of ways that users are able to customize the alarm inputs, if desired.

Page 516 and the custom page each include a Next icon 522, shown in FIG. 26 with reference to page 516, that is selected either after the option for box 518 is selected or after text is typed into the Custom Label and the Custom Message dialog boxes of the custom page. Selecting icon 522 causes a Master Alarm Setup Alarm Messages Final page 524, an example of which is shown in FIG. 25, to be displayed on the user's computer screen. Page 524 indicates that the changes to the configuration of the selected alarm input are complete and shows the selections that were made by the user on the preceding couple of web pages to configure the alarm input that was selected by the user on page 492. Page 524 also includes a "Return to Alarm Messages" icon 525 that, when selected, causes page 524 to, once again, appear on the user's computer screen so that the user may select another alarm input to configure, if desired.

If the user selects Setup Device icon 474, a Master Alarm Setup Device page 526, an example of which is shown in FIG. 26, appears on the user's computer screen. Page 526 includes a Device Name box 528 in which the user types the name that the user desires to call the alarm controller 48 being configured. Page 526 also includes a Location box 530 that includes a down arrow icon 532. When icon 532 is selected a drop down menu having a list of options that are available for designating the location of the alarm controller being configured. The options that appear in the drop down menu when icon 532 is selected include OR, ICU, ER, CCU, PACU, PBX, ENG, Nurse Station, Special, and General. If the user does not wish to use one of these options, then the user can simply type a location into box 530 instead.

Page 526 also includes a Zone box 534 in which the user types a zone number or other zone designation of the healthcare facility in which the alarm controller 48 being configured is located, assuming the healthcare facility is divided into zones. Page 526 further includes a Floor box 536 in which the user types the floor number or other floor designation of the healthcare facility in which the alarm controller 48 being configured is located. In addition, page 526 includes a Direction box 538 having a down arrow icon 540 that, when selected, causes a drop down menu to appear on the user's computer screen with North, South, East, and West options being listed in the drop down menu.

Figures 27, 28:
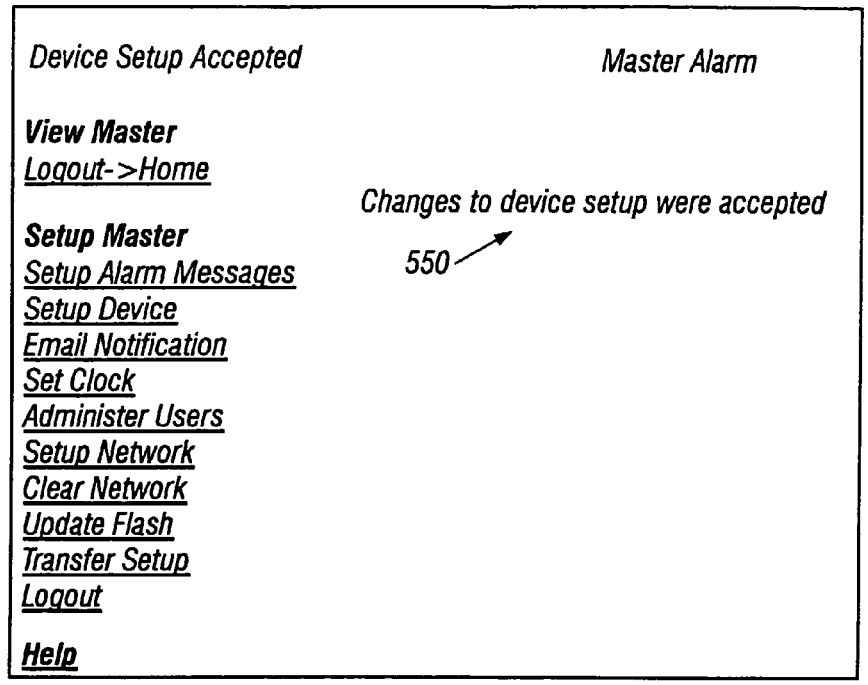

Page 526 includes a "Silenced return time" box 542 having a down arrow icon 544 that, when selected, causes a drop down menu to appear on the user's computer screen with a list of options that are available to configure alarm controllers 48 to resound the audible alarm of alarm controllers 48 after a selected period of time elapses subsequent to the silencing of the audible alarm. The options that appear in the drop down menu when icon 544 is selected include never, 30 minutes, 60 minutes, 90 minutes, and 120 minutes. Page 526 further includes a Submit icon 544 and a Reset icon 546. If the user selects icon 546, boxes 528, 530, 534, 536, 542 return to the settings that appeared in boxes 528, 530, 534, 536, 542 when page 526 was first opened. Thus, the user is able to reset boxes 528, 530, 534, 536, 542 if the user gets confused or loses track of which boxes 528, 530, 534, 536, 542 have been changed and which have not. After the user enters the desired information in boxes 528, 530, 534, 536, 542, the user selects icon 544 which causes a Master Alarm Device Setup Accepted page 548, an example of which is shown in FIG. 27, to be displayed on the user's computer screen. Page 548 includes a text line 550 which informs the user that the changes to the setup of the alarm controller 48 were accepted.

If the user selects Email Notification icon 476, a Master Alarm Email Notification page 552, an example of which is shown in FIG. 28, appears on the user's computer screen. Page 552 includes an SMTP Server Name box 554, an SMTP Server Address box 556, an Email Address 1 box 558, an Email Address 2 box 560, and an Email Address 3 box 562. Page 552 allows the user to configure the alarm controllers 48 to send an e-mail message to up to three designated e-mail addresses, to initiate a page to up to three pager numbers, or to cause any combination of up to three e-mails and pages to be sent or initiated, as the case may be, when an alarm condition occurs in gas system 12 and is sensed by alarm system 10.

To set up alarm controllers 48 with e-mail notification or pager notification, the user either types in a Simple Mail Transfer Protocol (SMTP) server name in box 554 or an SMTP address in box 556 and the user also types the appropriate e-mail addresses in one or more of boxes 558, 560, 562. Page 552 includes a text block 563 that explains to the user that the SMTP server address has priority over the SMTP server name and that if the SMTP server name is used, a Domain Name System (DNS) look-up is required. A DNS look-up resolves the SMTP server name with the SMTP server address. Text block 563 also informs the user that alarms occurring before the SMTP server name is resolved with the SMTP server address are not sent.

In FIG. 28, the e-mail address "FacilityEngineer@hospital.com" is shown in box 558 to illustrate one example of an e-mail address of a recipient to which an e-mail is sent if an alarm condition occurs in illustrative system 12. Also in FIG. 28, the e-mail address "2125554444@pager.com" is shown in box 560 to illustrate one example of an e-mail address to a pager service provider to which an e-mail is sent to initiate a page to a pager carried by a recipient if an alarm condition occurs in illustrative system 12. In this example, the number of the pager to be paged is 212-555-4444. It will be appreciated that, in alternative embodiments, alarm controllers 48 or server 42 may include dial-up software or phone emulator hardware, such as a Dial Tone Frequency Modulator (DTFM) chip, that dials a pager number to page a recipient instead of sending an e-mail to a pager service provider. In such alternative embodiments, a dialog box is provided on page 552 for the user to type in a pager number which is dialed by the dial-up software or by the phone emulator hardware if an alarm condition occurs in system 12.

In preferred embodiments of alarm system 10, any e-mails or pages that are sent by alarm system 10 to a recipient will include information identifying the alarm condition that caused the e-mail or page to be sent. For example, the e-mail or page, in some embodiments, contains text similar to lines 386 shown in FIG. 14. In alternative embodiments, less information is provided in any e-mails or pages that are sent to a recipient. Also in alternative embodiments, page 552 includes appropriate icons to permit a user to configure alarm controllers 48 so that an e-mail or page is sent to a recipient when some, but not all, alarm conditions occur. For example, if a main supply of a particular gas, such as oxygen, runs low and system 12 switches over to a back-up supply of the particular gas, thereby causing an alarm condition that is sensed by alarm system 10, then alarm controllers 48 can be configured to provide notification to a gas supplier to inform the supplier that a new supply of the particular gas should be delivered to the healthcare facility. Such notification can be in the form of an e-mailed purchase order or in the form of an e-mail having instructions to call a designated purchasing agent of the healthcare facility. It will be appreciated that a supplier of medical gases would not necessarily be interested in receiving e-mail or page notification of other alarm conditions occurring in system 12, such as high line pressure or low line pressure. If an alarm condition occurs in system 12 as a result of a particular piece of source equipment 18 needing service, then it is contemplated by this disclosure that alarm controllers 48 can be configured to send notification to a service supplier, such as the vendor of the piece of source equipment 18, of the "service required" alarm condition.

Figure 29:
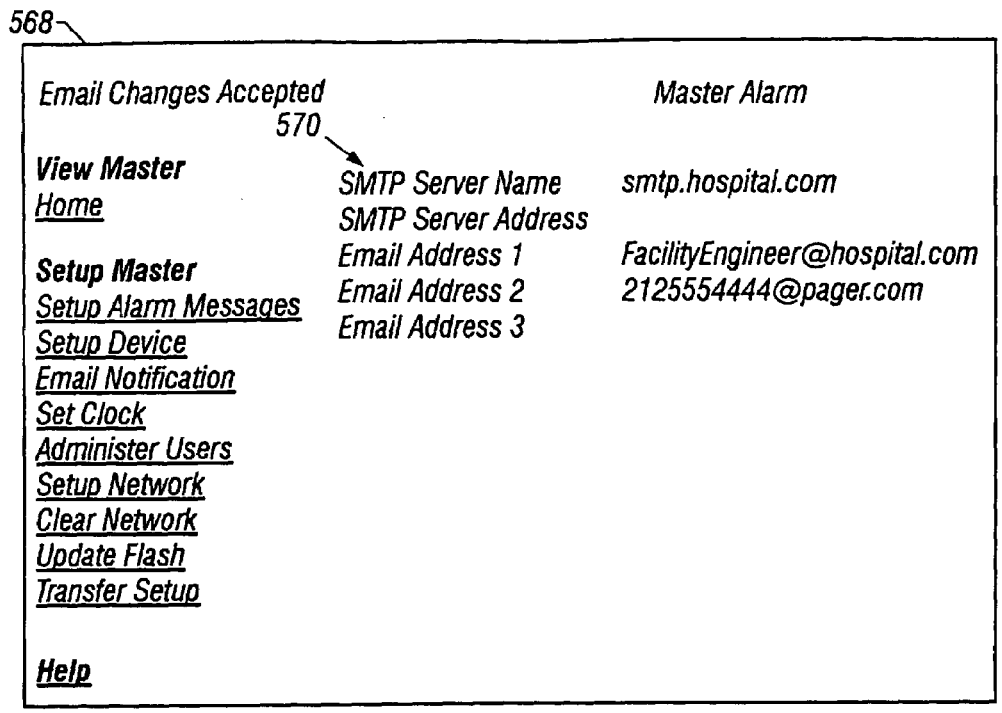

Illustrative page 552 further includes a Submit icon 564 and a Reset icon 566. If the user selects icon 566, boxes 554, 556, 558, 560, 562 return to the settings that appeared in boxes 554, 556, 558, 560, 562 when page 552 was first opened. Thus, the user is able to reset boxes 554, 556, 558, 560, 562 if the user gets confused or loses track of which boxes 554, 556, 558, 560, 562 have been changed and which have not. After the user enters the desired information in boxes 554, 556, 558, 560, 562, the user selects icon 564 which causes Master Alarm Email Changes Accepted page 568, an example of which is shown in FIG. 29, to be displayed on the user's computer screen. Page 568 includes a text block 570 which informs the user of the changes to the e-mail notification of alarm controller 48 that were accepted.

Figure 30:
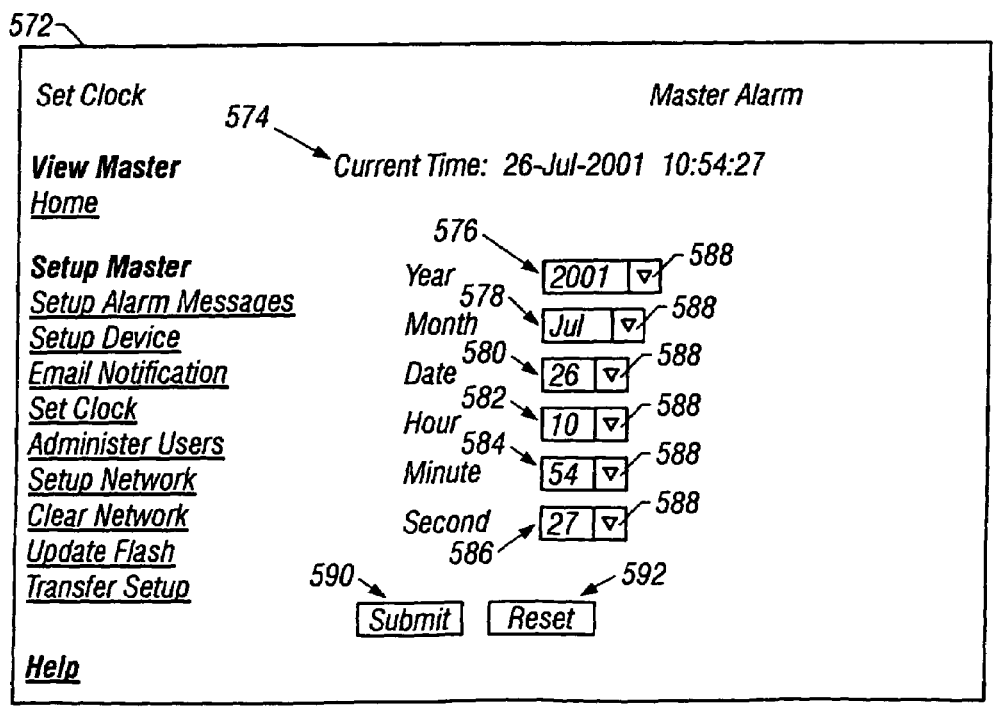

If Set Clock icon 478 is selected, a Master Alarm Set Clock page 572, an example of which is shown in FIG. 30, appears on the user's computer screen. Page 572 includes a text line 574 that indicates the date and time that the user opened page 572. Page 572 also includes a Year box 576, a Month box 578, a Date box 580, an Hour box 582, a Minute box 584, and a Second box 586. When page 572 is opened initially, boxes 576, 578, 580, 582, 584, 586 show year, month, date, hour, minute, and second information, respectively, that matches the date and time shown in line 574.

Each of boxes 576, 578, 580, 582, 584, 586 includes its own respective down arrow icon 588 that, when selected, causes an associated drop down menu to appear on page 572. The drop down menus that appear on page 572 include options that match the type of information available to be selected for associated boxes 576, 578, 580, 582, 584, 586. Specifically, the drop down menu associated with box 576 includes a list of years (e.g. 2001, 2002, 2003, and so on), the drop down menu associated with box 578 includes a list of the months (e.g. January, February, March, and so on), the drop down menu associated with box 580 includes the numbers 1 through 31 which correspond to the number of days in the longest months, the drop down menu associated with box 582 includes the numbers 00 through 23 which correspond to the hours of the day, the drop down menu associated with box 584 includes the numbers 00 through 59 which correspond to the minutes in an hour, and the drop down menu associate with box 586 includes the numbers 00 through 59 which correspond to the seconds in a minute.

Page 572 further includes a Submit icon 590 and a Reset icon 592. If the user selects icon 592, boxes 576, 578, 580, 582, 584, 586 return to the settings that appeared in boxes 576, 578, 580, 582, 584, 586 when page 572 was first opened. Thus, the user is able to reset boxes 576, 578, 580, 582, 584, 586 if the user gets confused or loses track of which boxes 576, 578, 580, 582, 584, 586 have been changed and which have not. After the user enters the desired information in boxes 576, 578, 580, 582, 584, 586, the user selects icon 590 which causes Master Alarm Clock Accepted page 594, an example of which is shown in FIG. 31, to be displayed on the user's computer screen. Page 594 includes a text block 596 which informs the user that the changes to the clock were accepted and which informs the user of the date and time that were programmed into alarm controllers 48 upon selection of icon 590.

If Administrate Users icon 480 is selected, a Master Alarm User Administration page 598, an example of which is shown in FIG. 32, appears on the user's computer screen. Page 598 includes three User Name boxes 600 that are arranged in a column on page 598 and three Password boxes 610 that are arranged in a column on page 598. Boxes 600, 610 of page 598 allow user names and passwords to be established for up to three users. Any user that opens page 598 is able to type strings of characters in boxes 600, 610, if desired, to program alarm controllers 48 with user names and associated passwords that, when later entered into boxes 458, 460, respectively, of page 456, permit the associated user to have access to those pages of the master alarm website in which input data is provided by the user to configure alarm controllers 48. Those users who know one or more valid user names and passwords are considered to be "authorized" users. That is, authorized users are able to use the master alarm website to provide input data to configure alarm controllers 48 in addition to being able to view output data provided by alarm controllers 48 on the website.

Page 598 further includes a Submit icon 612 and a Reset icon 614. If the user selects icon 614, boxes 600, 610 return to the settings that appeared in boxes 600, 610, respectively, when page 598 was first opened. Thus, the user is able to reset boxes 600, 610 if the user gets confused or loses track of which boxes 600, 610 have been changed and which have not. After the user enters the desired information in boxes 600, 610, the user selects icon 612 which causes a Master Alarm User Name Changes Accepted page 616, an example of which is shown in FIG. 33, to be displayed on the user's computer screen. Page 616 includes a line of text which informs the user that the changes to the user names and passwords were accepted. It will be appreciated that page 598 may include more or less than three each of boxes 600, 610 so that more or less, respectively, than three authorized users can be established.

Figure 34:
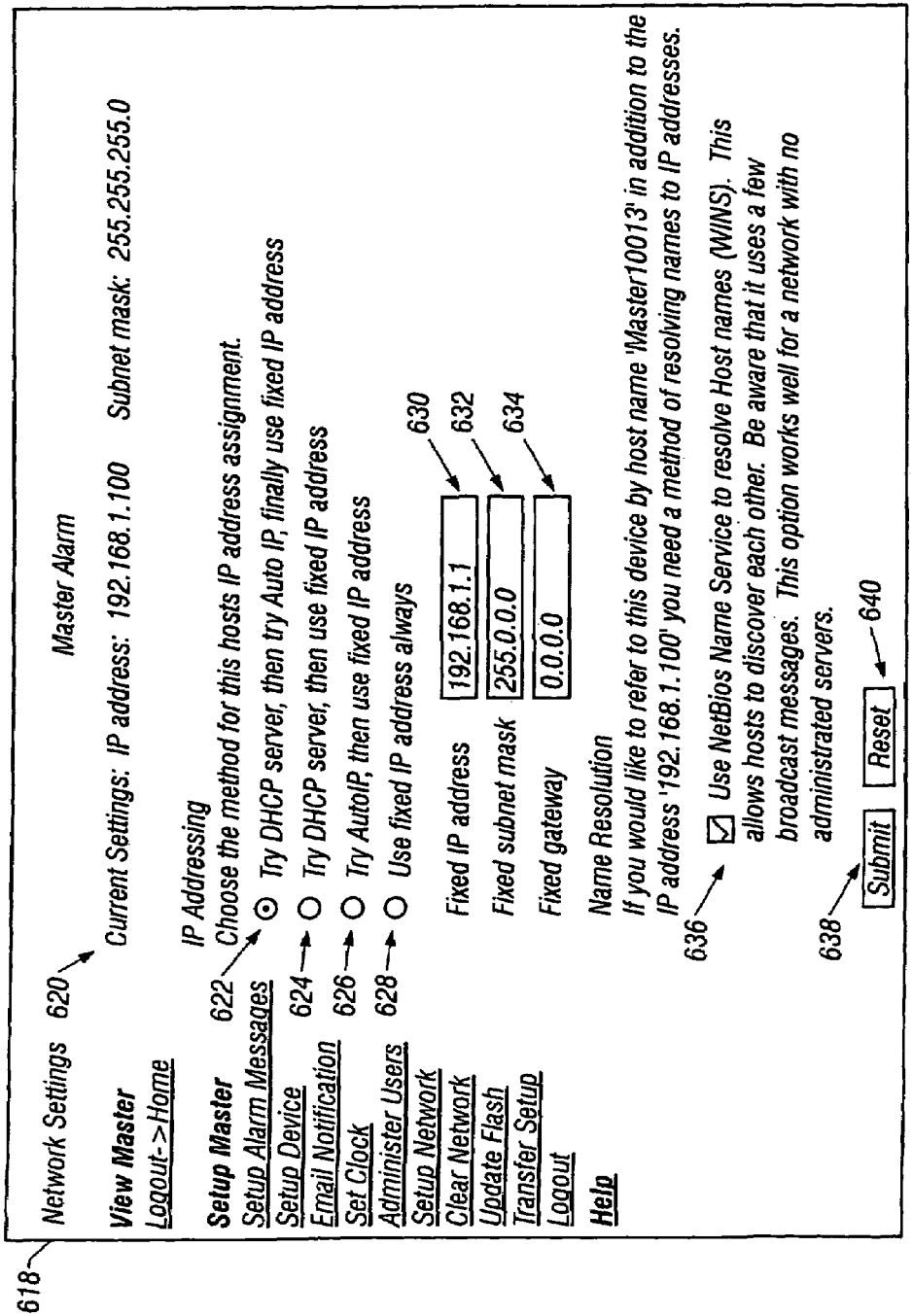

If Setup Network icon 482 is selected, a Master Alarm Network Settings page 618, an example of which is shown in FIG. 34, appears on the user's computer screen. Page 618 includes a text line 620 that indicates to the user the current settings of the IP address and the subnet mask. The IP address, as previously mentioned, is the address of the website hosted by alarm controllers 48. The subnet mask indicates the number of computer devices that are within a particular network of computers devices and that are able to communicate information to each other without having the information routed through other networks.

Figure 36:
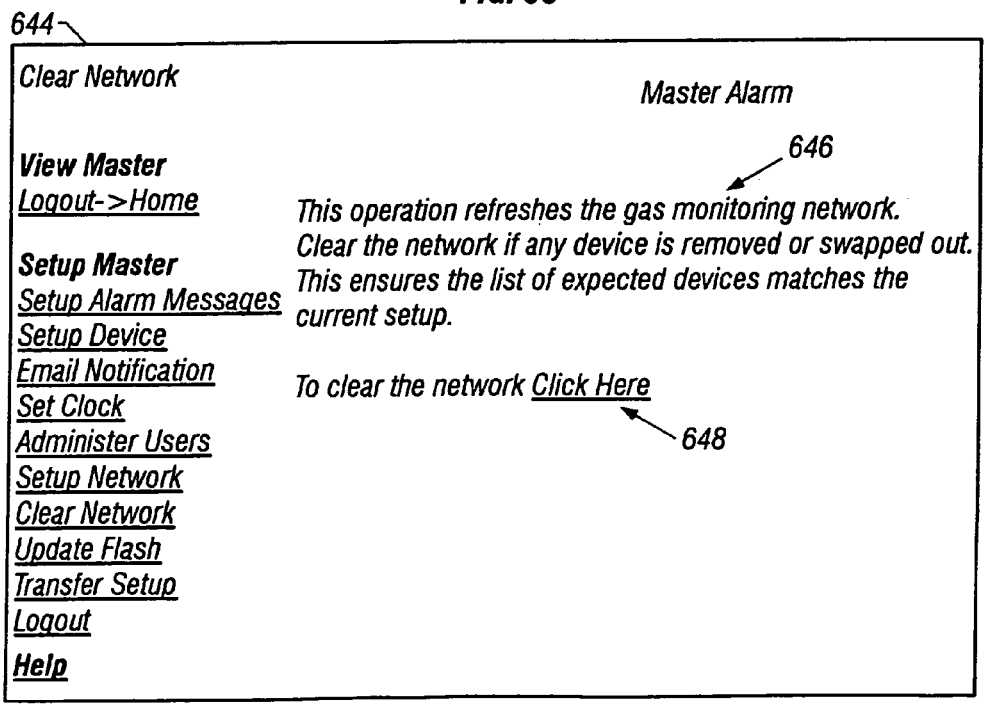

Page 618 includes first, second, third, and fourth radio buttons 622, 624, 626, 628. Only one of radio buttons 622, 624, 626, 628 can be selected at a time. Thus, for example, if button 624 is selected, then each of buttons 622, 626, 628 will be deselected automatically; if button 626 is selected, then each of buttons 622, 624, 628 will be deselected automatically; and so on. Buttons 622, 624, 626, 628 each correspond to a particular method for configuring alarm controllers 48 for IP addressing. In FIG. 36, button 622 is selected to configure the IP addressing of alarm controllers 48 by first trying a Dynamic Host Configuration Protocol (DHCP) server, then trying Auto IP, and finally using a fixed IP address.

A fixed IP address is a 32-bit (4-byte) binary number that uniquely identifies a host and that is shown in dotted quad format, where the decimal value of each of the four bytes are separated by periods. The first three bytes of an IP address are assigned by InterNIC Registration Service and the last byte identifies the host within the network, such as network 14, to which the host is connected. Auto IP refers to an IP addressing method in which a network-enabled device, such as personal computers 46, 82 and controllers 48, 50, automatically assigns itself a temporary IP address when the device connects to the Internet. A DHCP server is a server, such as server 42, that is able to assign temporary addressing designations to a host, such as controllers 48, automatically when the host connects to the network. The addressing methods associated with buttons 624, 626, 628 are subsets of the addressing methods associated with button 622.

Page 618 includes a "Fixed IP address" box 630, a "Fixed subnet mask" box 632, and a "Fixed gateway" box 634. In order for a website to be operational, it must have an IP address, a subnet mask, and a gateway. Thus, these addresses are either fixed in boxes 630, 632, 634 or they are temporarily assigned by an appropriately programmed server or web-enabled device. If button 628 is selected, then boxes 630, 632, 634 must be properly filled in for the website to be operational since no temporary addressing designations will be assigned. Thus, the selection of one of buttons 622, 624, 626, 628 is somewhat dependent upon whether the network of a particular healthcare facility has a server, or alternatively, connects to a server, having DHCP software and whether controller 48 is configured with Auto IP software. Page 618 also includes a check box 636 that, when selected (i.e. when checked), configures alarm controllers 48 to use NetBios Name Service to resolve the IP address with the device name. If a device name is resolved with an IP address, then the user is able to type the device name, instead of the network address, into the address bar on the user's computer screen to reach the website. In the example shown in FIG. 36, box 636 is checked and therefore, a user can reach the website by typing either device name "Master10013" or network address "192.168.1.100" in the address bar.

Figure 35:
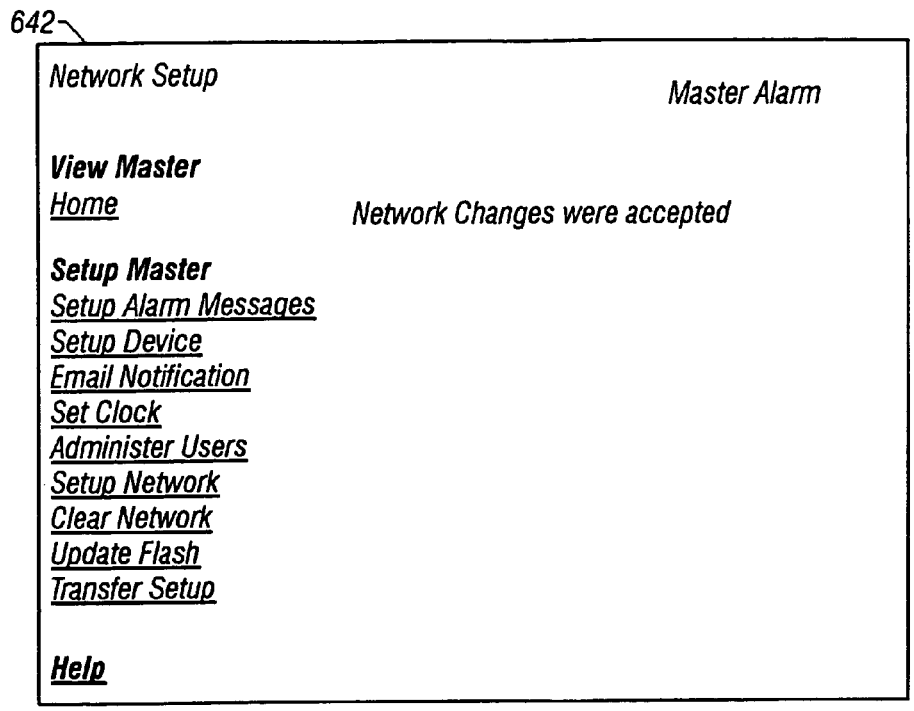

Page 618 further includes a Submit icon 638 and a Reset icon 640. If the user selects icon 640, buttons 622, 624, 626, 628 and boxes 630, 632, 634, 636 are returned to the settings that appeared in buttons 622, 624, 626, 628 and boxes 630, 632, 634, 636, respectively, when page 618 was first opened. Thus, the user is able to reset buttons 622, 624, 626, 628 and boxes 630, 632, 634, 636 if the user gets confused or loses track of which buttons 622, 624, 626, 628 and boxes 630, 632, 634, 636 have been changed and which have not. After the user makes the desired entries and selections on page 618, the user selects icon 638 which causes a Master Alarm Network Setup page 642, an example of which is shown in FIG. 35, to be displayed on the user's computer screen. Page 642 includes a line of text which informs the user that the changes to the network were accepted.

Figure 37:
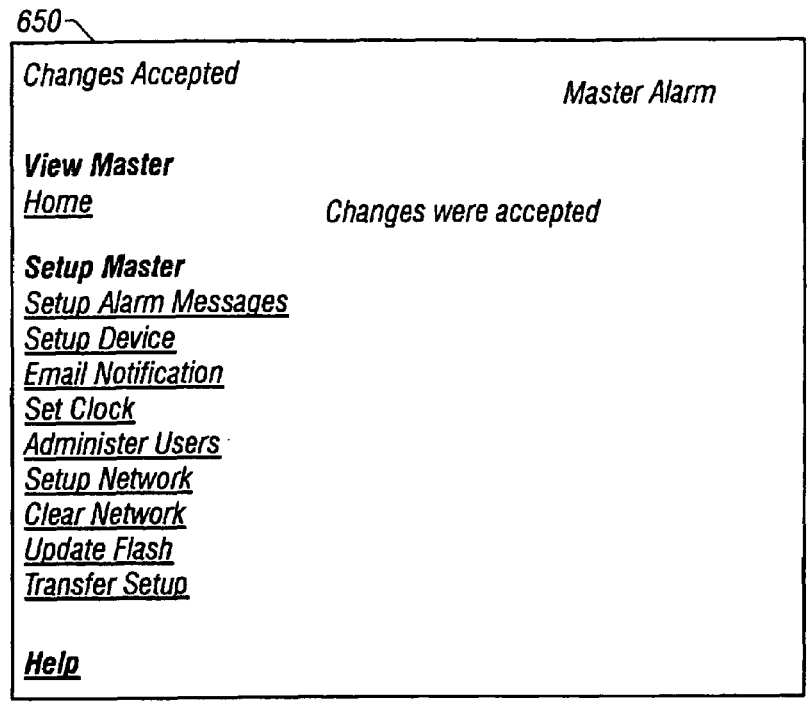

If Clear Network icon 484 is selected, a Master Alarm Clear Network page 644, an example of which is shown in FIG. 36, appears on the user's computer screen. Page 644 includes a text block 646 that instructs the user to clear the network if a device is removed or swapped out of the gas monitoring network, meaning that an input signal from source equipment 18 has been disconnected from alarm controllers 48 or that one of alarm controllers 48, 50 has been disconnected from network 14. Page 644 includes a Click Here icon 648 that, when selected, clears the network. During the process of clearing the network, alarm controllers 48 determine which device or devices have been disconnected, and then alarm controllers 48 configure themselves automatically by clearing out any setup information associated with the device or devices that have been disconnected and by retaining any setup information associated with the devices that are still connected to alarm controllers 48 either directly or via network 14. After the network is cleared, a Master Alarm Changes Accepted page 650, an example of which is shown in FIG. 37, appears on the user's computer screen to inform the user that changes to the configuration of alarm controllers 48 were accepted.

The Clear Network page 644 also permits system 10 to self-configure when system 10 is first installed in facility 20. To self-configure system 10, the user selects icon 648. Because master alarm controller 48 communicates with all of the associated area alarm controllers 50 through network 14 and because sensor modules 54 communicate gas type information, etc. to area alarm controllers 50, master alarm controller 48 is able to self-configure so that system 10 becomes operative. It will be appreciated however, that some information, such as location in facility 20 of each alarm controller 48, 50 may be missing when system 10 is self-configured. In addition, because the input signals to master alarm controller from source equipment 18 are simple, binary signals, such input signals will be self-configured as Alarm 1, Alarm 2, Alarm 3, etc., or the like. It will be appreciated that, if source equipment 18 is able to communicate serial data, then alarm controllers 48 are programmed to receive such serial data, similar to the manner in which alarm controller 50 are programmed, thereby allowing system 10 to self-configure with more information about the input signals from source equipment 18.

Figure 38:
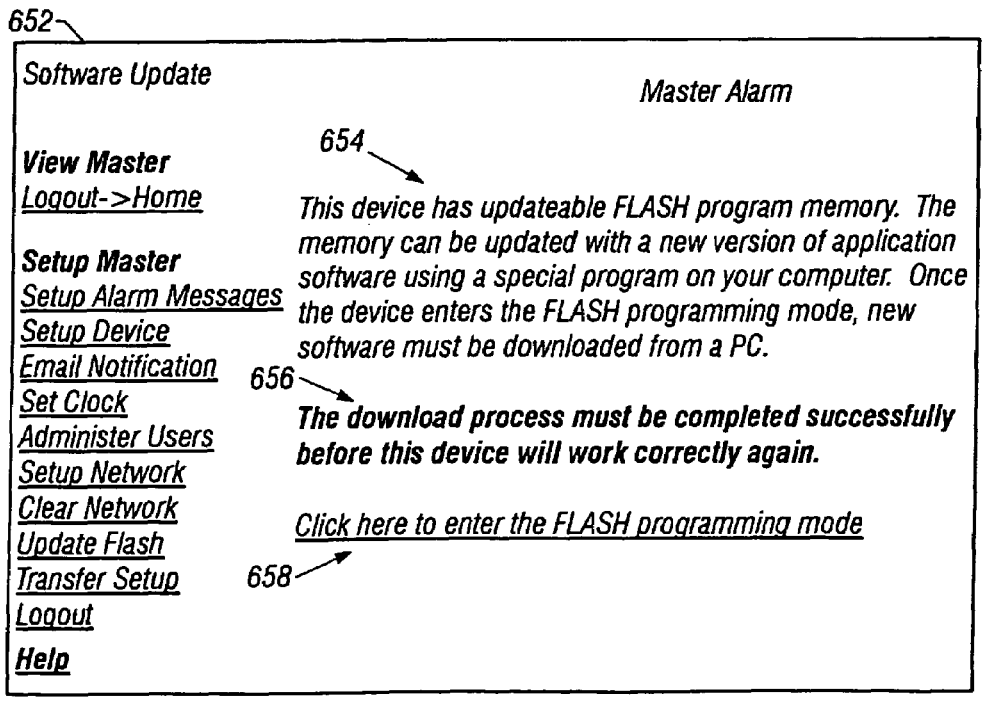
Figure 39:
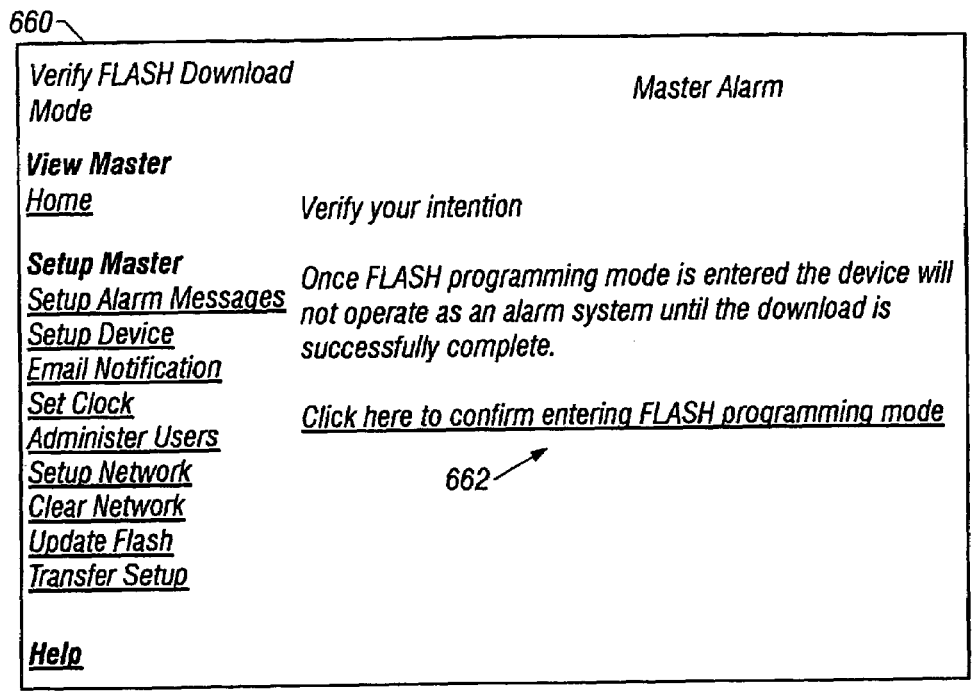

If Update Flash icon 486 is selected, a Master Alarm Software Update page 652, an example of which is shown in FIG. 38, appears on the user's computer screen. Page 652 includes a text block 654 that explains to the user that alarm controllers 48 can be programmed with updated application software by downloading the updated software to the memory of alarm controllers 48 from a personal computer. Page 652 includes a bolded text line 656 that warns the user that the download process must be completed successfully before alarm controllers 48 will work correctly again. Page 652 also includes a "Click here to enter the FLASH programming mode" icon 658 that, when selected, causes a Master Alarm Verify FLASH Download Mode page 660, an example of which is shown in FIG. 39, to appear on the user's computer screen.

Page 660 asks the user to verify the user's intention to enter the FLASH programming mode and again warns the user that the download process must be completed successfully before alarm controllers 48 will work correctly again. Page 660 includes a "Click here to confirm entering FLASH programming mode" icon 662 that, when selected, causes the FLASH programming mode to be entered. After the FLASH programming mode is entered, FLASH download software stored in the memory of the user's computer runs to transmit the updated application software to the memory of alarm controllers 48 to replace the prior application software, once the user enters the appropriate commands as dictated by the FLASH download software. After the updated application software is successfully downloaded to alarm controllers 48, the user types in the appropriate IP address into the address bar of the user's computer to access the website of alarm controllers 48, which website is controlled by the updated application software.

Figure 40:
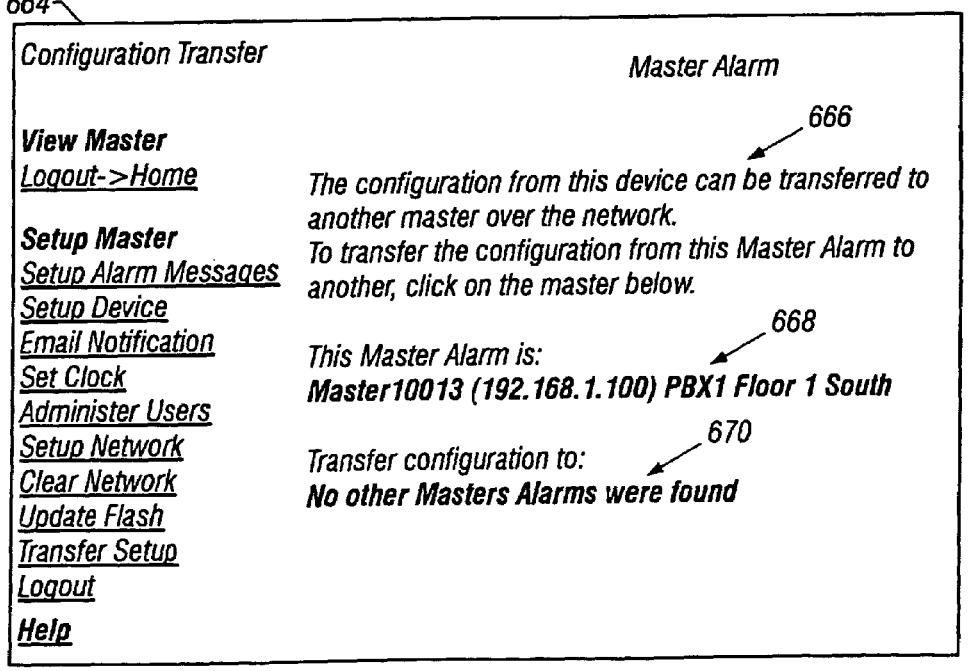

If Transfer Setup icon 488 is selected, a Master Alarm Configuration Transfer page 664, an example of which is shown in FIG. 40, appears on the user's computer screen. Page 664 includes a text block 666 that informs the user that the configuration of the host alarm controller 48 can be transferred to one or more other alarm controllers 48 that are included in network 14 and that have a network address or network addresses different than that of the host alarm controller 48. Page 664 includes a text line 668 informing the user of the name, network address, and location of the host alarm controller 48 of controllers 48 that cooperate to serve the website being viewed by the user. Page 664 further includes a list 670 of all of the other alarm controllers 48, if any, that have network addresses different than the host alarm controller 48 and that are coupled to network 14. The user then selects the alarm controllers 48 from list 670 to which the configuration of the host alarm controller 48 is to be transferred. Once the configuration transfer is completed successfully, a Master Alarm Successful Transfer page (not shown) appears on the user's computer screen to inform the user of the successful configuration transfer.

If Logout icon 490 icon is selected, a Master Alarm Logout page 672, an example of which is shown in FIG. 41, appears on the user's computer screen to inform the user that the user has logged out of the setup portion of the website. Alternatively, if Logout>Home icon 470 is selected, then page 672 is bypassed and Master Alarm Home page 340 appears on the user's computer screen instead of page 672. In addition, if Home icon 344 is selected then Home page 340 appears on the user's computer screen. If Help icon 358 is selected, then various information is provided on or is accessible from a Help page (not shown) to assist the user in using the website of alarm controllers 48. The Help page also includes a phone number and an e-mail address so that the user can call or e-mail, respectively, for help if desired.

If one of jump icons 372 is selected on page 370, shown in FIG. 12A, for one of area alarm controllers 50, then the user links to the website of the alarm controller 50 identified by the associated icon 372. Thus, the user is able to access a desired one of the websites of alarm controllers 50 by selecting the icon 372 on page 370 that is associated with the desired website. Alternatively, if the user knows the network address of the alarm controller 50 having the website that the user desires to access, then the user can type the network address into the address bar on the user's computer screen. The description below of a website associated with one of alarm controllers 50 is applicable to the websites of all of alarm controllers 50 unless specifically noted otherwise. Of course, each alarm controller 50 has its own unique output data and its own unique configuration due to the fact that each alarm controller 50 monitors different portions of gas system 12, resides at a different locations in healthcare facility 20, has its own network address, etc.

After the user either selects one of icons 372 associated with one of area alarm controllers 50 or enters the network address that identifies one of area alarm controllers 50 into the appropriate field on the screen of the user's computer, an Area Alarm Home page 680 appears on the user's computer screen as shown, for example, in FIG. 42. Page 680 includes a menu list 682 having a set of icons that are selected to hyperlink to the pages of the website associated with the icons. Menu list 682 includes the following icons: Home icon 684, Gas Readings icon 686, Device Information icon 688, Masters icon 690, Alarms icon 692, Event Log icon 694, Login icon 696, Network Statistics icon 698, and Help icon 700. Some of these icons are duplicated in larger text to the right of menu list 682. Identical reference numerals are used to denote icons from menu list 682 that are duplicated on page 680. The duplicated icons do not necessarily have the exact same wording as the icons of menu list 682.

Figure 43:
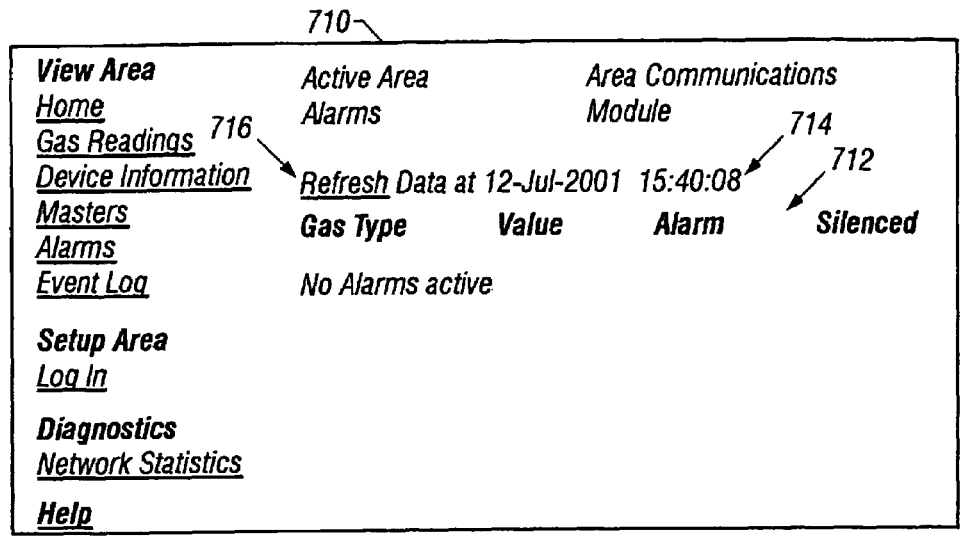

If Alarms icon 692 is selected, an Area Alarm Active Area Alarms page 710, an example of which is shown in FIG. 43, appears on the user's computer screen. Page 710 includes an Alarms table 712 that displays output data from alarm controllers 50 to show any alarm conditions sensed by sensor modules 54. The data shown on table 712 is a snapshot of the pressures in associated lines 16 at the time that page 710 is opened. A text line 714 near the top of page 710 indicates the date and time that the snapshot is taken. Page 710 includes a Refresh icon 716 that, when selected, updates the information on table 712 if the alarm conditions in the associated lines 16 have changed since the previous snapshot.

Table 712 has a Gas Type column that contains information regarding the type of service associated with the occurring alarm conditions detected by the associated alarm controller 50. In the example shown in FIG. 43, no alarm conditions are occurring in lines 16 of the associated alarm controller 50 and this is indicated by the text "No alarms active" which appears in the Gas Type column. Table 712 has a Value column which contains the pressure readings provided by the associated sensor modules 54 that are sensing alarm conditions in respective lines 16. The pressure readings are the pressure values that appear on the display screens 164 of associated display modules 156 of the respective alarm controller 50 when page 712 is opened.

Table 712 also includes an Alarm column that contains information about the nature of the occurring alarm conditions. Examples of the text that may appear in the Alarm column of table 712 include, "UnderRange" to indicate that the associated sensor module 54 is unable to read the pressure in the respective line 16 of gas system 12 because the pressure in that particular line 16 is below the range of pressures that the associated transducer 286 is capable of reading, "Wiring" to indicate that there is something wrong with the wiring of the associated portion of alarm controller 50 or with the wiring of the associated sensor module 54, "High Pressure" to indicate that the pressure in the associated line 16 is too high, and "Low Pressure" to indicate that the pressure in the associated line 16 is too low. Table 712 further includes a Silenced column that contains, for each alarm condition, either a "No" if the alarm silence button 168 of the respective display module 156 has not been pressed to silence the audible alarm that sounds when the respective alarm condition occurs, or a "Yes" if alarm silence button 168 of the respective display module 156 has been pressed to silence the respective audible alarm.

Figure 44:
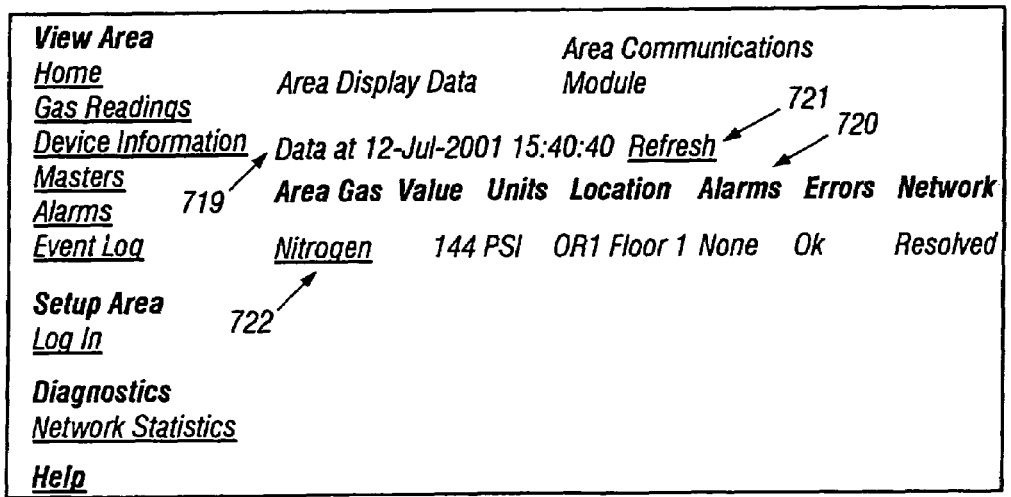

If Gas Readings icon 686 is selected, a first Area Alarm Area Display Data page 718, an example of which is shown in FIG. 44, appears on the user's computer screen. Page 718 includes a Data table 720 that shows various output data for each of the input signals provided to the associated alarm controller 50 regardless of whether any of the input signals indicate an alarm condition. The data shown on table 720 is a snapshot of the pressures in associated lines 16 at the time that page 718 is opened. A text line 719 near the top of page 718 indicates the date and time that the snapshot is taken. Page 718 includes a Refresh icon 721 that, when selected, updates the information on table 720 if the pressures in the associated lines 16 have changed since the previous snapshot.

Table 720 includes an Area Gas column that contains the name of the service being monitored by the associated sensor module 54, a Value column that contains the pressure reading being sensed by the associated sensor module 54, a Units column that indicates the units of measure of the corresponding pressure reading, a Location column that contains information about the location in the healthcare facility of the associated sensor module 54, an Alarms column that contains information indicating whether the associated sensor module 54 is sensing an alarm condition, an Errors column that contains information indicating whether an error condition is detected by the associated sensor module 54, and a Network Column that indicates whether the network connection is resolved or unresolved.

Each line item appearing in the Area Gas column of table 720 is configured as an Area Gas icon 722, that when selected, causes an associated second Area Alarm Area Display Data page 724, an example of which is shown in FIG. 45, to appear on the user's computer screen. In the illustrative example, page 724 is associated with the "Nitrogen" icon 722 of FIG. 44. Page 724 includes a text line 725 indicating the date and time that page 724 is opened. Page 724 also includes a Data table 726 which contains a host of information about the associated display module 156 and sensor module 54.

Table 726 of page 724 contains some of the same information that table 720 of page 718 contains regarding gas type (the Gas Type line of table 726 corresponds to the Area Gas column of table 720), pressure value (the Value line of table 726 corresponds to the Value and Units columns of table 720), alarm occurrence (the Alarm line of table 726 corresponds to the Alarms column of table 720), error occurrence (the Status line of table 726 corresponds to the Error column of table 720), network resolution (the Connection line of table 726 corresponds to the Network column of table 720), and location of the associated sensor module 54 (the Area, Zone, Floor, and Direction lines of table 726 correspond to the Location column of table 720).

Table 726 also contains some information not appearing on table 720. For example, table 726 includes a Measurement line 728 that indicates the type of measurement, such as pressure or flow rate, being sensed by the associated sensor module 54, an Alarm High line 730 that indicates the pressure at which a high pressure alarm condition occurs in the associated line 16, an Alarm Low line 732 that indicates the pressure at which a low pressure alarm condition occurs in the associated line 16, a Display SN line 734 that indicates the serial number of the associated display module 156, and a Transducer SN line 736 that indicates the serial number of the associated sensor module 54.

If Device Information icon 688 is selected, an Area Alarm Device Info page 738, an example of which is shown in FIG. 46, appears on the user's computer screen. Page 738 contains Area, Zone, Floor, and Direction lines items that indicate the location in the healthcare facility of the associated alarm controller 50. Page 738 also contains line items indicating the serial number, the model number, the software version, the software build, the IP address, and the MAC address of the associated alarm controller 50. Page 738 further includes line items indicating the date and time that page 738 was opened and a line item indicating that an Area Communications Module (referred to elsewhere in this disclosure as area alarm controller 50) is the type of device for which information is provided on page 738.

If Masters icon 690 is selected, an Area Alarm Masters page 740, an example of which is shown in FIG. 47, appears on the user's computer screen. Page 740 includes a table 742 having information about each of the master alarm controllers 48 that are coupled to network 14. Table 742 includes a Master column which lists the name of each alarm controller 48 that is coupled to network 14, a Location column which lists the location in the healthcare facility of each alarm controller 48 that is coupled to network 14, and a Details column that lists a host of information (not shown in the FIG. 47 example) about each alarm controller 48 that is coupled to network 14. The information appearing in the Details column of table 742 is similar to, or the same as, the information that appears in the Description column on page 370, shown in FIG. 12A, regarding master alarm controllers 48.

The names of alarm controllers 48 in the Master column of table 742 are configured as Master Alarm icons 744, each of which is a hyperlink to the website of the alarm controllers 48 identified by the associated icon 744. Thus, the user is able to link to the website of any of alarm controllers 48 from each of the websites associated with alarm controllers 50. In some embodiments, table 742 includes hyperlinks to other area alarm controllers 50 in addition to hyperlinks (i.e. icons 744) to master alarm controllers 48. In other embodiments, table 742 includes Jump icons similar to Jump icons 372 of page 370 that are hyperlinks to other area alarm controllers 48, 50.

Figure 48:
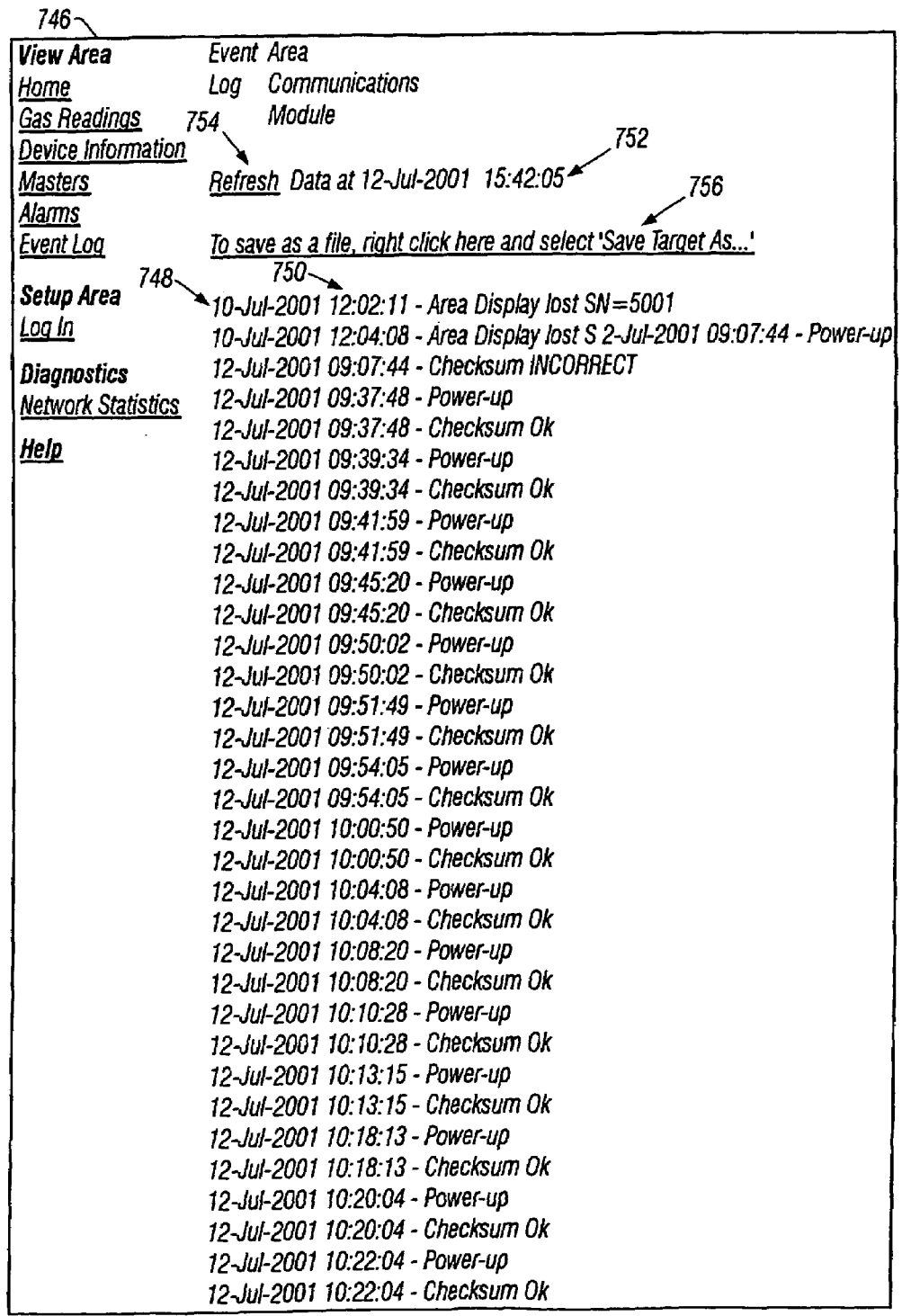

If Event Log icon 694 is selected, an Area Alarm Event Log page 746, an example of which is shown in FIG. 48, appears on the user's computer screen. Page 746 includes a list of a multitude of events that are detected by or communicated to the associated alarm controller 50. Only a few of these events are listed on illustrative page 746 to provide a general sense of the type of information that may appear in the event log. Each event that is logged on page 746 includes a date stamp 748 and a time stamp 750 to indicate when the event occurred. The information appearing in the event log relates, generally, to alarm conditions occurring in lines 16 of system 12, fault conditions occurring in the associated alarm controller 50 or the associated sensor modules 54, or computer systems-related occurrences.

The data shown on page 746 is a snapshot of the event log at the time that page 746 is opened. A text line 752 near the top of page 746 indicates the date and time that page 746 is opened. Page 746 includes a Refresh icon 754 that, when selected, updates the events on page 746 if new events occur after page 746 is opened and before icon 754 is selected. Events that are listed on the event log of page 746 eventually are deleted automatically, either after a maximum number of events are listed on the event log or after a certain amount of time elapses since the occurrence of the event to be deleted. Page 746 includes a "To save as a file, right click here and select 'Save Target As . . . '" icon 756. If icon 756 is selected, then the event log is saved as a text document under a file name and in a location in the user's computer that are designated by the user. The user designates the file name and location by typing appropriate entries in file name and location bars that appear in a pop-up window on the user's computer screen when icon 756 is selected. Such pop-up windows for saving files should be well-known to anyone who has used conventional windows-based word processing software.

Figure 49:
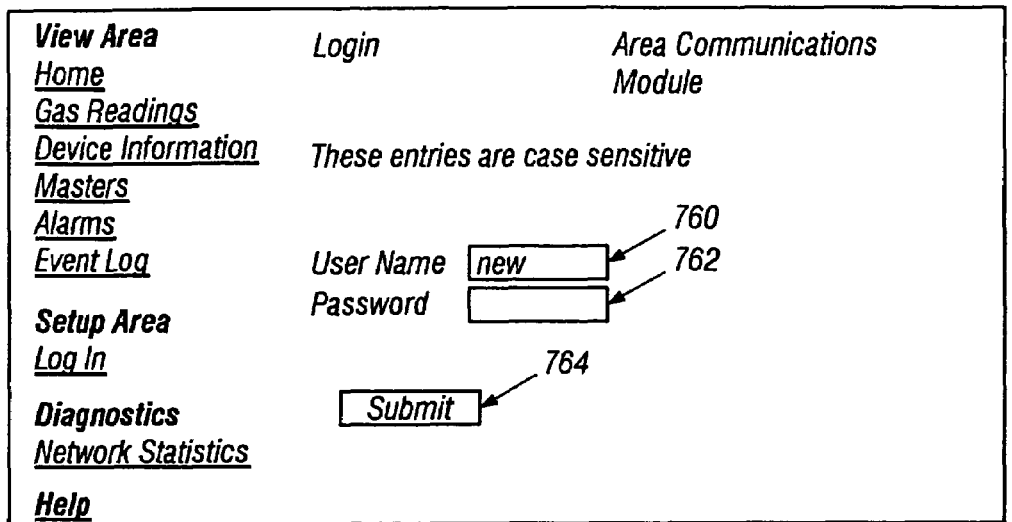
Figure 50:
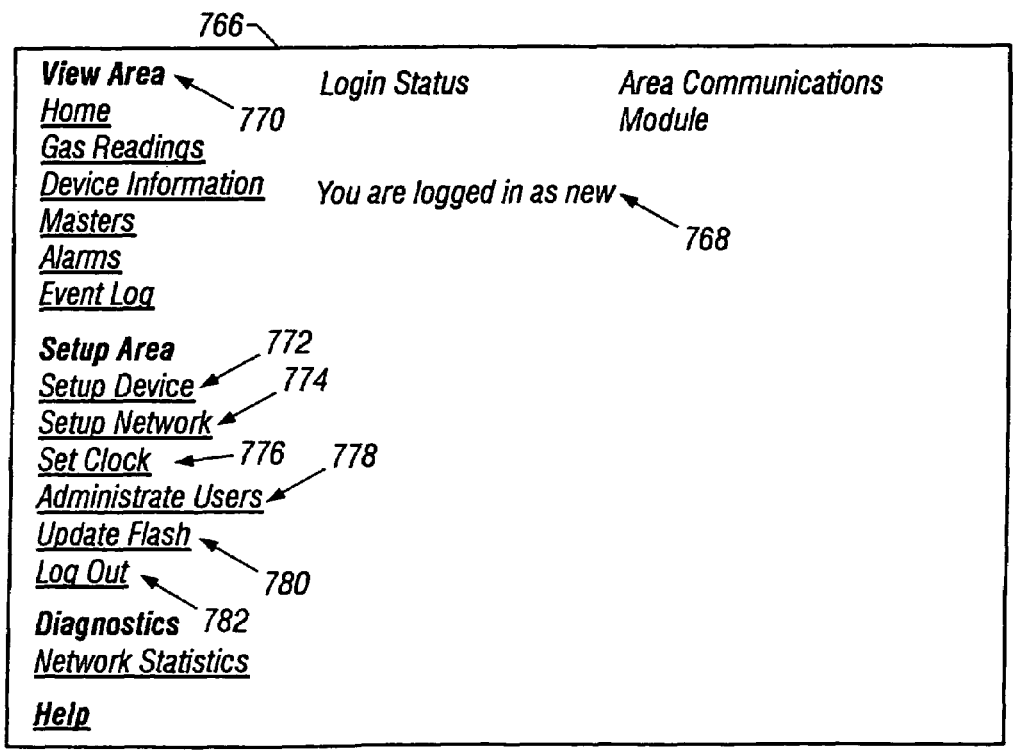

If Login icon 696 is selected, an Area Alarm Login page 758 appears on the user's computer screen as shown in FIG. 49. Page 758 includes a User Name dialog box 760 and a Password dialog box 762. Authorized users who have been assigned user names and passwords are able to type their respective user names and passwords into dialog boxes 760, 762, respectively, to access pages of the area alarm website to provide input data to the corresponding alarm controller 50 to configure the controller 50 with operating parameters. Page 758 includes a Submit icon 764 that, when selected, causes an Area Alarm Login Status page 766, shown in FIG. 50, to appear on the user's computer screen if the user entered a valid user name and password in dialog boxes 760, 762 prior to selecting Submit icon 764. When an authorized user logs into the password protected portion of the area alarm website, this event is logged and will appear on the event log of page 746 as described above.

Page 766 includes a message 768 which indicates that the user has successfully logged in and therefore, has access to the password protected pages of the area alarm website. Page 766 also includes a menu list 770 having many of the same icons that appear on menu list 682 but also having a additional icons that are selected to go to the password protected pages of the website associated with the icons. Menu list 770 includes the following additional icons: Setup Device icon 772, Setup Network icon 774, Set Clock icon 776, Administrate Users icon 778, Update Flash icon 780, and Logout icon 782.

Figure 51:
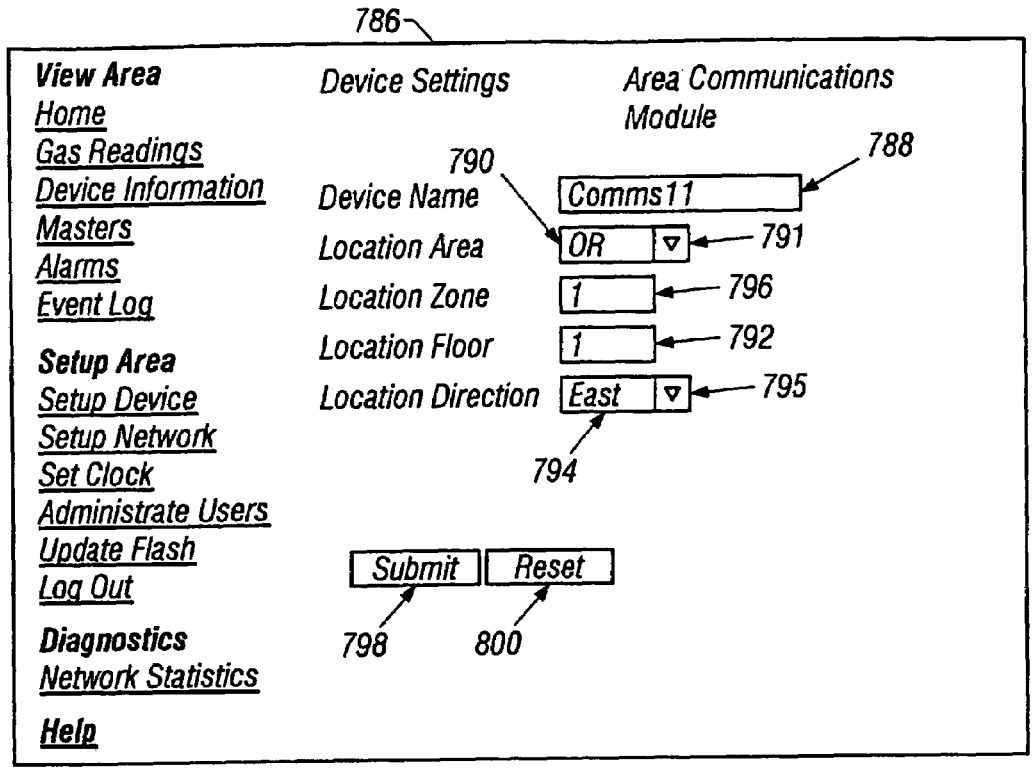

If Setup Device icon 772 is selected, an Area Alarm Device Settings page 786, an example of which is shown in FIG. 51, appears on the user's computer screen. Page 786 includes a Device Name box 788 in which the user types the name that the user desires to assign to the alarm controller 50 being configured. Page 786 also includes a Location Area box 790 that includes a down arrow icon 791. When icon 791 is selected a drop down menu having a list of options that are available for designating the location of the alarm controller 50 being configured. The options that appear in the drop down menu when icon 791 is selected include OR, ICU, ER, CCU, PACU, PBX, ENG, Nurse Station, Special, and General. If the user does not wish to use one of these options, then the user can simply type a location into box 790 instead.

Page 786 also includes a Location Zone box 796 in which the user types a zone number or other zone designation of the healthcare facility in which the alarm controller 50 being configured is located, assuming the healthcare facility is divided into zones. Page 786 further includes a Location Floor box 792 in which the user types the floor number or other floor designation of the healthcare facility in which the alarm controller 50 being configured is located. In addition, page 786 includes a Location Direction box 794 having a down arrow icon 795 that, when selected, causes a drop down menu to appear on the user's computer screen with North, South, East, and West options being listed in the drop down menu.

Figure 52:
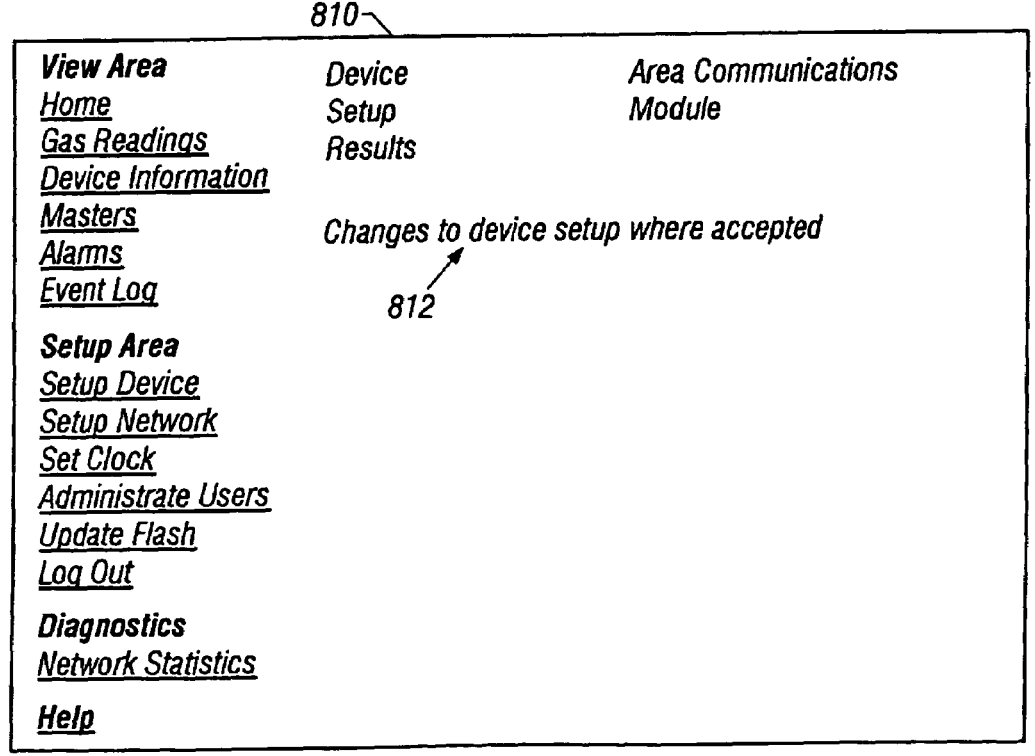

Page 786 further includes a Submit icon 798 and a Reset icon 800. If the user selects icon 800, boxes 788, 790, 792, 794, 796 return to the settings that appeared in boxes 788, 790, 792, 794, 796 when page 786 was first opened. Thus, the user is able to reset boxes 788, 790, 792, 794, 796 if the user gets confused or loses track of which boxes 788, 790, 792, 794, 796 have been changed and which have not. After the user enters the desired information in boxes 788, 790, 792, 794, 796, the user selects icon 798 which causes an Area Alarm Device Setup Results page 810, an example of which is shown in FIG. 52, to be displayed on the user's computer screen. Page 810 includes a text line 812 which informs the user that the changes to the device setup were accepted.

Figure 53:
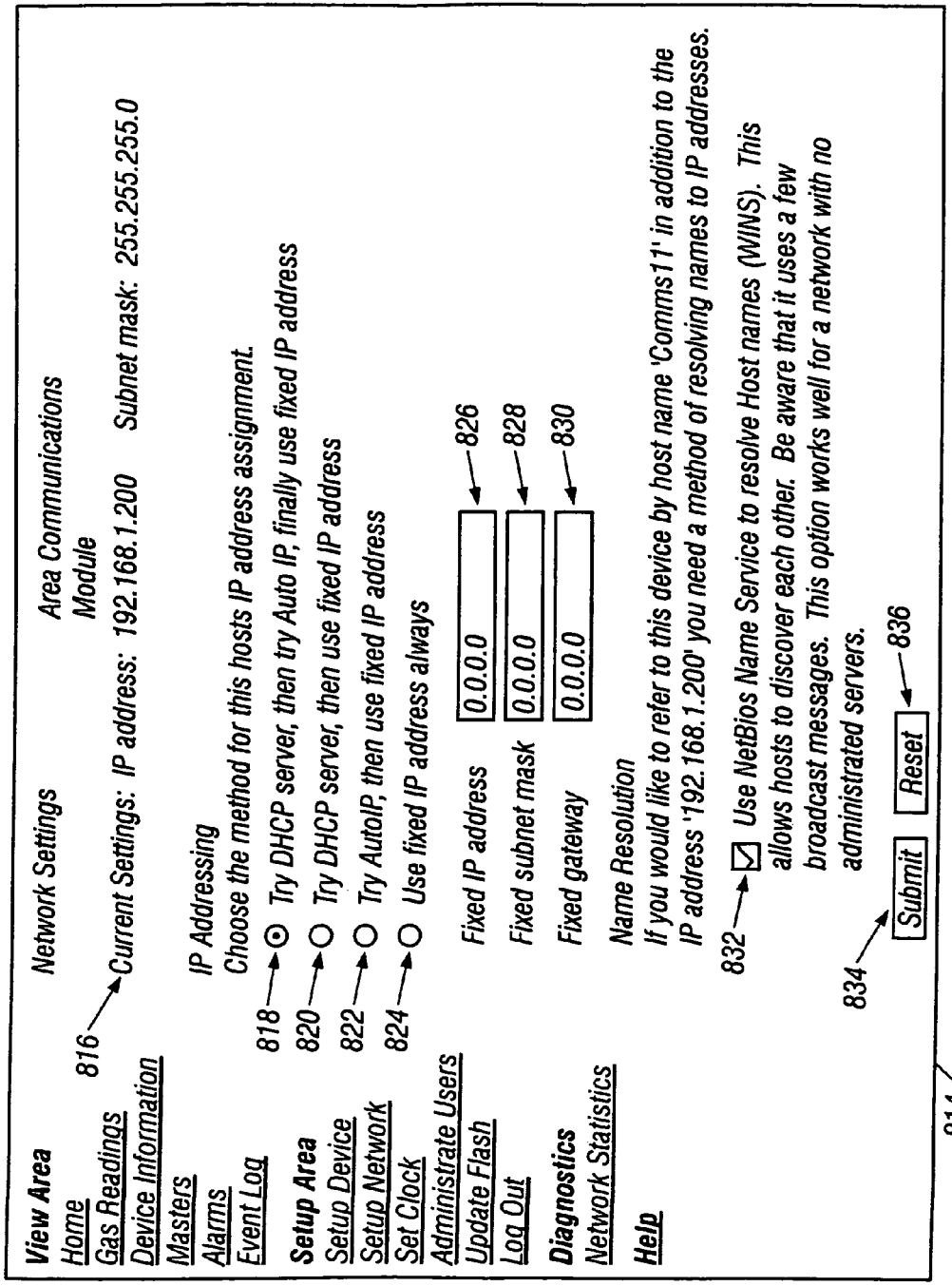

If Setup Network icon 774 is selected, an Area Alarm Network Settings page 814, an example of which is shown in FIG. 53, appears on the user's computer screen. Page 814 includes a text line 816 that indicates to the user the current settings of the IP address and the subnet mask. The IP address is the address of the website hosted by the associated alarm controller 50. In the illustrative embodiment, the IP address of each alarm controller 50 is different than the IP address of all of the other alarm controllers 50 and different than the IP address of all of the alarm controllers 48.

Figures 56, 57:
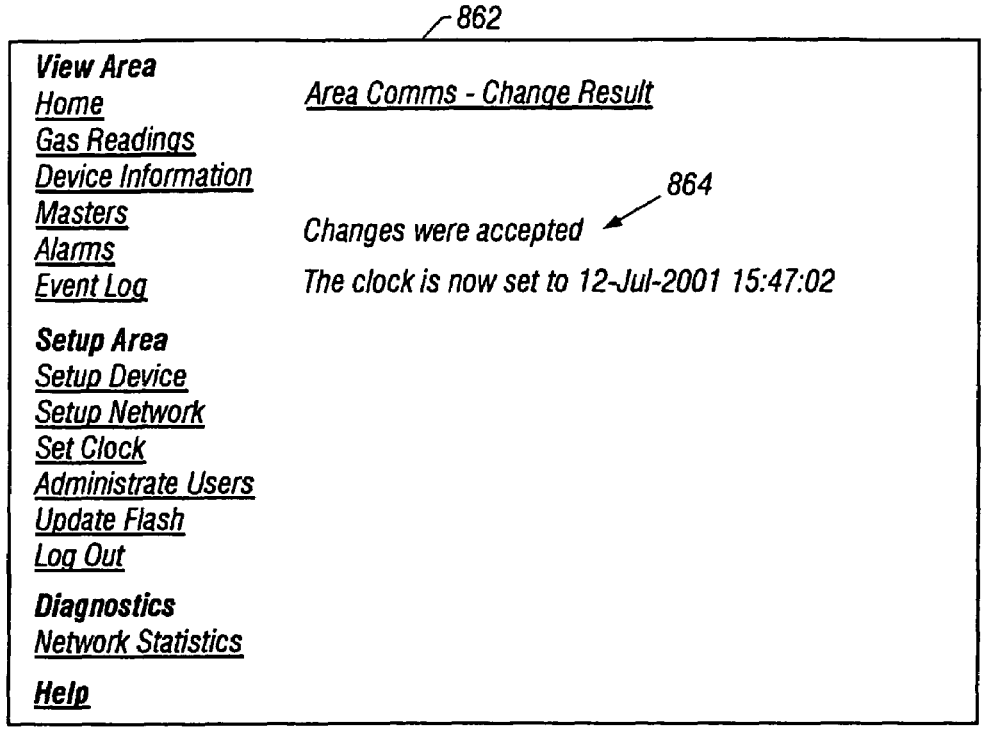

Page 814 includes first, second, third, and fourth radio buttons 818, 820, 822, 824. Only one of radio buttons 818, 820, 822, 824 can be selected at a time. Thus, for example, if button 818 is selected, then each of buttons 820, 822, 824 will be deselected automatically; if button 820 is selected, then each of buttons 818, 822, 824 will be deselected automatically; and so on. Buttons 818, 820, 822, 824 each correspond to a particular method for configuring alarm controller 50 for IP addressing. In FIG. 56, button 818 is selected to configure the IP addressing of the associated alarm controller 50 by first trying a Dynamic Host Configuration Protocol (DHCP) server, then trying Auto IP, and finally using a fixed IP address. The addressing methods associated with buttons 820, 822, 824 are subsets of the addressing methods associated with button 818.

Page 814 includes a "Fixed IP address" box 826, a "Fixed subnet mask" box 828, and a "Fixed gateway" box 830. Page 814 also includes a check box 832 that, when selected (i.e. when checked), configures the associated alarm controller 50 to use NetBios Name Service to resolve the IP address with the device name. The various types of IP addressing methods associated with buttons 818, 820, 822, 824, the purpose of the information in boxes 826, 828, 830, and the purpose of name resolution associated with check box 832 are the same as were discussed above in connection with buttons 622, 624, 626, 628, boxes 630, 632, 634, and check box 636, respectively, of FIG. 34.

Page 814 further includes a Submit icon 834 and a Reset icon 836. If the user selects icon 836, buttons 818, 820, 822, 824 and boxes 826, 828, 830, 832 return to the settings that appeared in buttons 818, 820, 822, 824 and boxes 826, 828, 830, 832, respectively, when page 814 was first opened. Thus, the user is able to reset buttons 818, 820, 822, 824 and boxes 826, 828, 830, 832 if the user gets confused or loses track of which buttons 818, 820, 822, 824 and boxes 826, 828, 830, 832 have been changed and which have not. After the user makes the desired entries and selections on page 814, the user selects icon 834 which causes an Area Alarm Network Setup Result page 838, an example of which is shown in FIG. 54, to be displayed on the user's computer screen. Page 838 includes a line of text which informs the user that the changes to the network setup were accepted.

If Set Clock icon 776 is selected, an Area Alarm Set Clock page 840, an example of which is shown in FIG. 55, appears on the user's computer screen. Page 840 includes a text line 842 that indicates the date and time that the user opened page 840. Page 840 also includes a Year box 844, a Month box 846, a Date box 848, an Hour box 850, a Minute box 852, and a Second box 854. When page 840 is opened initially, boxes 844, 846, 848, 850, 852, 854 show year, month, date, hour, minute, and second information, respectively, that matches the date and time shown in line 842. Each of boxes 844, 846, 848, 850, 852, 854 includes its own respective down arrow icon 856 that, when selected, causes an associated drop down menu to appear on page 840. Each of the drop down menus that appear on page 840 when icon 856 of associated boxes 844, 846, 848, 850, 852, 854 is selected are the same as the drop down menus that appear on page 572 when icon 588 of associated boxes 576, 578, 580, 582, 584, 586 is selected, respectively, as described above.

Page 840 further includes a Submit icon 858 and a Reset icon 860. If the user selects icon 860, boxes 844, 846, 848, 850, 852, 854 return to the settings that appeared in boxes 844, 846, 848, 850, 852, 854 when page 840 was first opened. Thus, the user is able to reset boxes 844, 846, 848, 850, 852, 854 if the user gets confused or loses track of which boxes 844, 846, 848, 850, 852, 854 have been changed and which have not. After the user enters the desired information in boxes 844, 846, 848, 850, 852, 854, the user selects icon 858 which causes an Area Alarm Change Result page 862, an example of which is shown in FIG. 56, to be displayed on the user's computer screen. Page 862 includes a text block 864 which informs the user that the changes to the clock were accepted and which informs the user of the date and time that were programmed into the associated alarm controller 50 upon selection of icon 858.

If Administrate Users icon 778 is selected, an Area Alarm User Administration page 866, an example of which is shown in FIG. 57, appears on the user's computer screen. Page 866 includes three User Name boxes 868 that are arranged in a column on page 866 and three Password boxes 870 that are arranged in a column on page 866. Boxes 868, 870 of page 866 allow user names and passwords to be established for up to three users. Any user that opens page 866 is able to type strings of characters in boxes 868, 870, if desired, to program the associated alarm controller 50 with user names and associated passwords that, when later entered into boxes 868, 870, respectively, of page 866, permit the associated user to have access to those pages of the area alarm website in which input data is provided by the user to configure the associated alarm controller 50. It will be appreciated that alarm controllers 48, 50 can be programmed to have different authorized users. That is, the authorized users established for each of controllers 48, 50 need not be the same.

Figure 58:
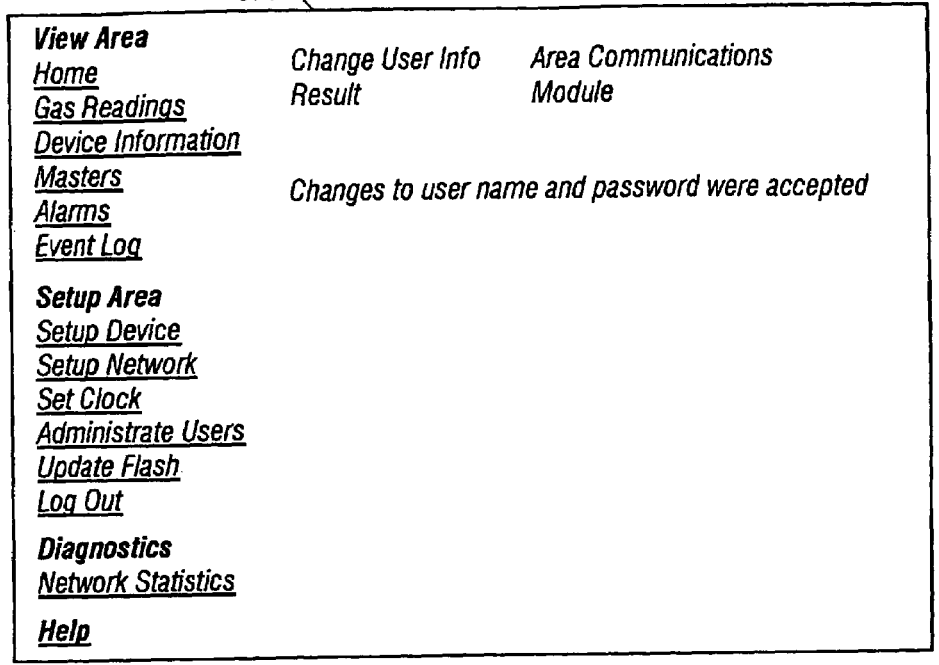

Page 862 further includes a Submit icon 872 and a Reset icon 874. If the user selects icon 874, boxes 868, 870 return to the settings that appeared in boxes 868, 870, respectively, when page 862 was first opened. Thus, the user is able to reset boxes 868, 870 if the user gets confused or loses track of which boxes 868, 870 have been changed and which have not. After the user enters the desired information in boxes 868, 870, the user selects icon 872 which causes an Area Alarm Change User Info Result page 876, an example of which is shown in FIG. 58, to be displayed on the user's computer screen. Page 876 includes a line of text which informs the user that the changes to the user names and passwords were accepted. It will be appreciated that page 866 may include more or less than three each of boxes 868, 870, as was the case with page 598.

Figure 59:
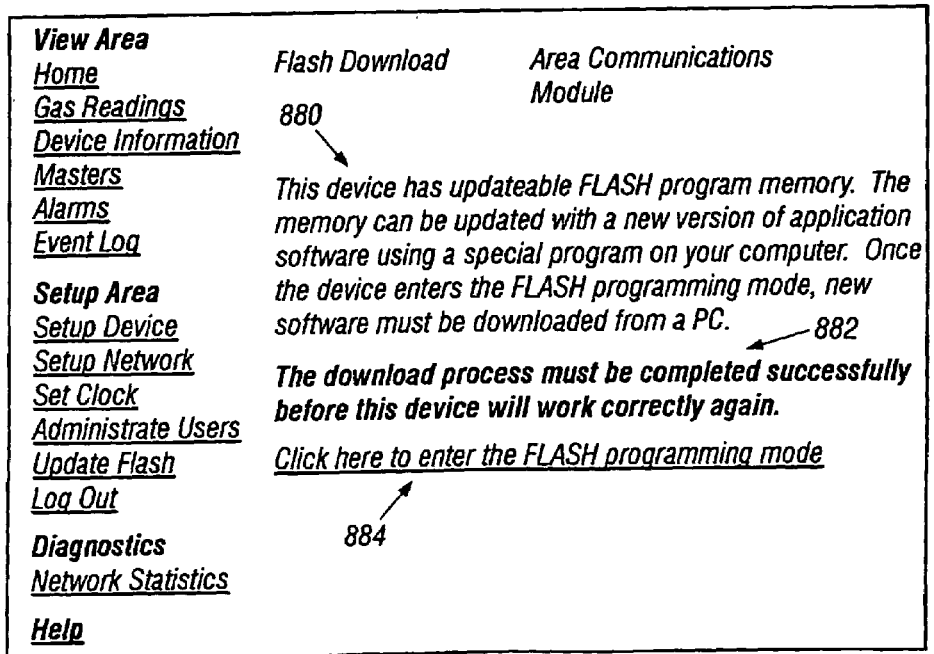

If Update Flash icon 780 is selected, an Area Alarm Flash Download page 878, an example of which is shown in FIG. 59, appears on the user's computer screen. Page 878 includes a text block 880 that explains to the user that the alarm controller 50 can be programmed with updated application software by downloading the updated software to the memory of the alarm controller 50 from a personal computer. Page 878 includes a bolded text line 882 that warns the user that the download process must be completed successfully before the alarm controller 50 will work correctly again. Page 878 also includes a "Click here to enter the FLASH programming mode" icon 884 that, when selected, causes an Area Alarm Confirm Download page 886, an example of which is shown in FIG. 60, to appear on the user's computer screen.

Page 886 asks the user to verify the user's intention to enter the FLASH programming mode and again warns the user that the download process must be completed successfully before the alarm controller 50 will work correctly again. Page 886 includes a "Click here to confirm entering FLASH programming mode" icon 888 that, when selected, causes the FLASH programming mode to be entered. After the FLASH programming mode is entered, FLASH download software stored in the memory of the user's computer runs to transmit the updated application software to the memory of alarm controller 50 to replace the prior application software, once the user enters the appropriate commands as dictated by the FLASH download software. After the updated application software is successfully downloaded to alarm controller 50, the user types in the appropriate IP address into the address bar of the user's computer to access the website of alarm controllers 50, which website is controlled by the updated application software.

If Network Statistics icon 698 is selected, an Area Alarm Communications Statistics page 890, an example of which is shown in FIG. 61, appears on the user's computer screen. Page 890 includes an Ethernet table 892 and a Serial Communications table 894. Table 892 includes address information at the lines labeled IP Address, Subnet, Gateway, Fixed IP Address, Fixed Subnet, Fixed Gateway, and Mac Address. Table 892 also includes reception/transmission information at the lines labeled Receives, Unicasts, Multicasts, Broadcasts, Rx Errors, Rx Missed, Rx CRC Errors, Rx Drops, Transmits, Buffer Defers, Tx Errors, Tx Collisions, Tx Coll. Overflow, Tx FILO Effors, and Traffic Backoffs. Table 894 includes serial communication information at the lines labeled Receives, Transmits, Bad CRC, Missed End, and Packet Too Long. The data shown on page 890 in tables 892, 894 is a snapshot of the communications statistics for the associated alarm controller 50 at the time that page 890 is opened. Page 890 includes a Refresh icon 896 that, when selected, updates the communications statistics on page 890 if the communications statistics have changed after page 890 is opened and before icon 896 is selected.

If Logout icon 782 icon is selected, an Area Alarm Logout page (not shown) appears on the user's computer screen to inform the user that the user has logged out of the password protected portion of the area alarm website. The Area Alarm Logout page is essentially the same as page 672 shown in FIG. 41 except that "Area Alarm" or "Area Communications Module" appears in the upper right corner of the page instead of "Master Alarm" and menu list 682 appears on the left side of the page instead of menu list 342. Alternatively, if Home icon 684 is selected when the user is logged into the password protected portion of the area alarm website, then the user is automatically logged out of the password protected pages and Home page 680 appears on the user's computer screen. In addition, if Home icon 684 is selected when the user is on any of the non-password protected pages of the area alarm website, then Home page 680 appears on the user's computer screen. If Help icon 700 is selected, then various information is provided on or is accessible from a Help page (not shown) to assist the user in using the website of the associated alarm controller 50. The Help page also includes a phone number and an e-mail address so that the user can call or e-mail, respectively, for help if desired.

It should be readily apparent from the above description that the websites associated with alarm controllers 48, 50 permit a large amount of output data to be viewed and retrieved from alarm controllers 48, 50 and permit alarm controllers 48, 50 to be quickly and easily configured with input data for operation. Because alarm controllers 48, 50 each are programmed with the software necessary to host their respective websites, it is not necessary to install separate software on one or more of personal computers 46 in network 14 (or personal computers 82 that couple to network 14 via Internet 80) in order for personal computers 46, 82 to communicate with alarm controllers 48, 50. Any of personal computers 46 in network 14 and any remote personal computers 82 that couple to network 14 via Internet 80 are able to receive output data from and provide input data to alarm controllers 48, 50, assuming the users of personal computers 46, 82 know the appropriate IP addresses and have been set up with user names and passwords.

It will be appreciated that, because the gas pressures in lines 16 are sensed by sensor modules 54 and communicated to alarm controllers 48, 50 and because the gas pressure information is accessible to computers 46, 82 via network 14 and the Internet 80, data trending of the gas pressures in lines 16 is possible, as is data trending of any type of information that is detected by system 10. Such data trending may uncover persistent or recurring problems in system 12, thereby enabling modifications or redesigns in system 12 to be made. In addition, such data trending may enhance supply management capabilities by showing how often particular gas supplies need replenished.

As mentioned above, alarm controllers 48, 50 communicate with one another via network 14 and sensor modules 54 communicate serial data to alarm controllers 50. Each master alarm controller 48 sends advertisement, request, configuration, and clear network messages through network 14 to other alarm controllers 48, 50 at different times either automatically or when prompted to do so by a user, as the case may be. Each of the messages from master alarm controllers 48 is formatted in extensible markup language (XML) and is linked to network 14 via a User Datagram Protocol (UDP) having data channel 55987.

The advertisement and clear network messages from alarm controllers 48 are broadcast messages, whereas the request and configuration messages from alarm controllers 48 are unicast messages. The advertisement messages are sent regularly by each alarm controller 48 to inform the other network devices that the alarm controller 48 sending the advertisement message is present on network 14. The request messages are sent by alarm controllers 48 to specific alarm controllers 50 to request gas readings from the specific alarm controller 50 being queried. The configuration message is sent from one master alarm controller 48 to another to configure the receiving alarm controller 48 like the sending alarm controller 48. The clear network message is a user initiated message that clears alarm controllers 48, 50 of the setup information contained therein.

Each area alarm controller 50 sends advertisement and gas reading messages through network 14 to other alarm controllers 48, 50 at different times either automatically or when prompted to do so by a particular alarm controller 48, as the case may be. Each of the messages from area alarm controllers 50 is formatted in extensible markup language (XML) and is linked to network 14 via a User Datagram Protocol (UDP) having data channel 55987. The advertisement messages from alarm controllers 50 are broadcast messages, whereas the gas reading messages from alarm controllers 50 are unicast messages. The advertisement messages are sent regularly by each alarm controller 50 to inform the other network devices that the alarm controller 50 sending the advertisement message is present on network 14. The gas reading messages are sent by alarm controllers 50 to specific alarm controllers 48 when gas readings are requested by the specific alarm controllers 48.

Circuits 74 of each area alarm controller 50 sends query unknown devices, network connect, and data request messages to the associated display modules 156. Display modules 156 send new response, connection response, and data response messages to circuit 74 of the associated area alarm controller 50. Each of the messages between circuits 74 of area alarm controllers 50 and display modules 156 is formatted in extensible markup language (XML) and is provided at a rate of 38400 baud under an RS-485 protocol. The query unknown devices messages from circuits 74 of alarm controllers 50 are broadcast messages, whereas the new response, network connect, connection response, data request, and data response messages are unicast messages.

The query unknown devices messages are sent by circuits 74 to find out what devices are coupled to circuit 74. The new response messages are sent by display modules 156 in response to receiving a query unknown devices message to inform the associated area alarm controller 50 of the serial number of the queried display module 156. The network connect messages are sent by alarm controllers 50 to notify a particular display module 156 that the particular display module 156 is recognized and that it need not respond to further query unknown device messages. The connection response messages are sent by display modules 156 to notify the associated circuit 74 that the display module is ready to provide data to the associated circuit 74. The data request messages are sent by alarm controllers 48 to display modules 156 to request data from the display modules 156. The data response messages are sent by display modules 156 to the associated circuit 74 and include the data available from display modules 156.

According to this disclosure, alarm controllers 48, 50 are each able to be configured for operation without the use of a personal computer, such as personal computers 46, 82. Circuit 70 of each master alarm controller 48 includes a button 910 on circuit board 140 that is accessible when door panel 84 is unlocked and moved to the opened position. When button 910 is engaged or operated, the associated alarm controller 48 enters into a manual programming mode. Similarly, circuit 74 of each area alarm controller 50 includes a button 912 on circuit board 224 that is accessible when door panel 156 is unlocked and moved to the opened position. When button 912 is engaged or operated, the associated alarm controller 50 enters into a manual programming mode.

During the manual programming mode of each alarm controller 48, the user operates respective buttons 90, 92 to scroll through various programming options that appear on display screen 86 and to select desired programming options appearing on display screen 86. For example, in one embodiment, button 90 is pressed to scroll through the various programming options and button 92 is pressed to select the programming option appearing on screen 86. In general, the programming options that appear on display screen 86 correspond to the various programming options mentioned above in connection with FIGS. 22–27.

During the manual programming mode of each alarm controller 50, the user operates one or more of respective buttons 166, 168, 170, 172 to scroll through various programming options that appear on display screen 164 of associated display modules 156 and to select desired programming options appearing on respective display screens 164. For example, in one embodiment, button 166 is pressed to scroll through the various programming options and button 168 is pressed to select the programming option appearing on screen 164. In some embodiments, when either the high alarm point or the low alarm point is to be set manually on a particular display module 156, the associated buttons 170, 172 are pressed to either raise or lower, respectively, the number appearing on screen 164 until the displayed number matches the desired alarm point. It will be appreciated that, in other embodiments, the high alarm points and low alarm points of each display module 156 are programmed during their manufacture and cannot be changed by personnel at a healthcare facility. In general, the programming options that appear on display screen 86 correspond to the various programming options mentioned above in connection with FIG. 51.

Buttons 90, 92, 910, therefore, serve as user inputs that are operable to manually program alarm controllers 48 and buttons 166, 168, 170, 172, 912 serve as user inputs that are operable to manually program alarm controllers 50. It will be appreciated that other types of user inputs, such as knobs, levers, switches, keys, and the like that are operable to manually configure alarm controllers 48, 50 are within the scope of this disclosure. It will be appreciated that configuring the operating parameters of alarm controllers 48, 50 manually is more cumbersome and is more time consuming than using a personal computer to program these alarm controllers 48, 50 via the websites hosted by alarm controllers 48, 50. However, those that prefer manual programming of alarm controllers 48, 50 are able to do so. In addition, when manual programming of alarm controllers 48, 50 becomes necessary, such as if network 14 ceases to operate properly, then such manual programming is possible.

In the detailed descriptions that follow with regard to FIGS. 62–72, several integrated circuits and other components are identified, with particular circuit types and sources. In many cases, terminal names and pin numbers for these specifically identified circuit types and sources are noted. This should not be interpreted to mean that the identified circuits are the only circuits available from the same, or any other, sources that will perform the described functions. Other circuits are typically available from the same, and other, sources which will perform the described functions. The terminal names and pin numbers of such other circuits may or may not be the same as those indicated for the specific circuits identified in this application.

The description below of circuit 70 of one of master alarm controllers 48, shown in the corresponding lettered sheets of the maps of FIGS. 62–66, applies to all master alarm controllers 48 unless specifically noted otherwise. Arrow boxes having therein either SH1, SH2, SH3, SH4, or SH5 appear throughout FIGS. 62A–62U, 63A–63L, 64A–64Q, 65A–65L, and 66A–66X. SH1 corresponds to the circuit schematic of FIGS. 62A–62U, SH2 corresponds to the circuit schematic of FIGS. 63A–63L, SH3 corresponds to the circuit schematic of FIGS. 64A–64Q, SH4 corresponds to the circuit schematic of FIGS. 65A–65L, and SH5 corresponds to the circuit schematic of FIGS. 66A–66X. Adjacent to each arrow box is a line name. The line names and the SH designations associated with each arrow box appearing in FIGS. 62–66 are used to connect up the various lines from each of FIGS. 62–66 to the appropriate lines of the other FIGS. 62–66 in a manner well-known to those skilled in the art.

As shown in FIG. 62, circuit 70 includes a Model No. 68331 microcontroller (.mu.C) made by Motorola Inc. Pins 1, 7, 10, 14, 15, 16, 17, 18, 21, 27, 34, 36, 38, 53, 55, 59, 73, 88, 90, 104, 105, 106, 108, 111, 123, 126, 129 of the 68331 .mu.C are open as shown in FIGS. 62H and 62I. Pins 2, 12, 20, 26, 35, 48, 54, 62, 74, 82, 91, 107, 128, 134 of the 68331 .mu.C are each coupled to digital ground (DGND) as shown in FIG. 62I. Pins 11, 19, 25, 37, 47, 61, 72, 86, 89, 109, 121, 135, 144 of the 68331 .mu.C are each coupled to plus five volts digital (+5 VD) and are each coupled through respective 1 .mu.F capacitors to DGND as shown in FIGS. 62D, 62G, and 62J.

Figure 62A:
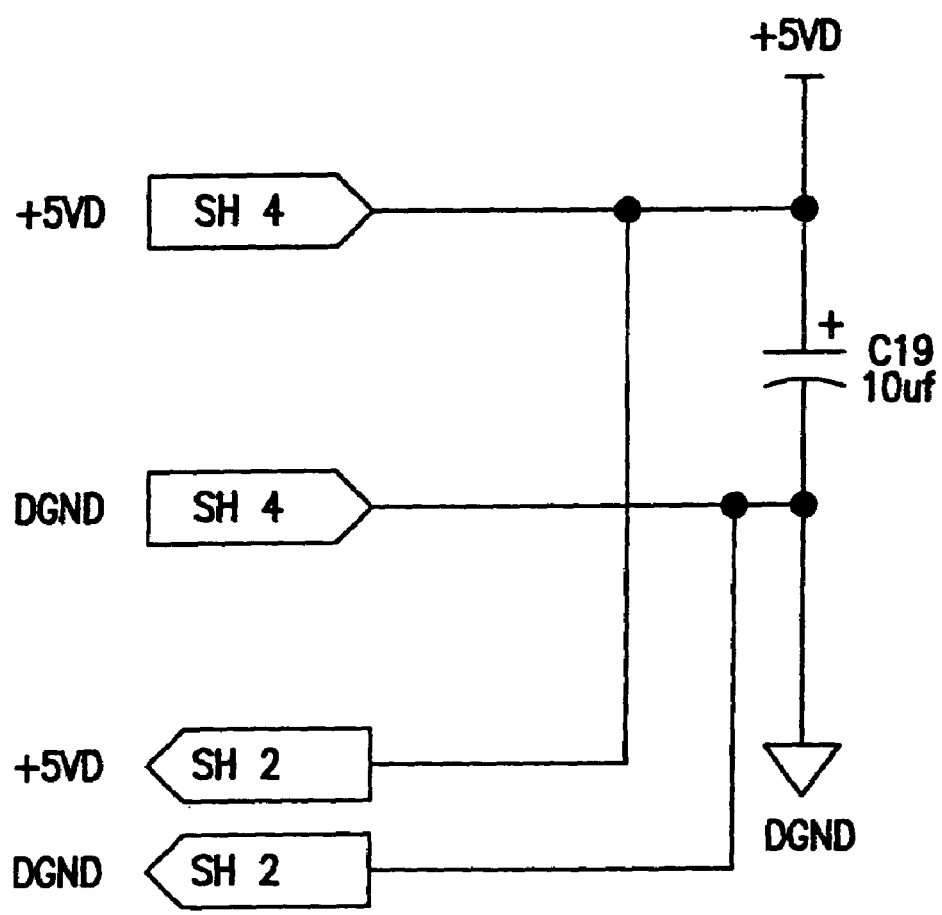
FIG. 62 is a circuit schematic map showing how to lay out FIGS. 62A–62U to form an electric circuit schematic of a first portion of an electric circuit of one of the master alarm controllers.
Figure 62B:
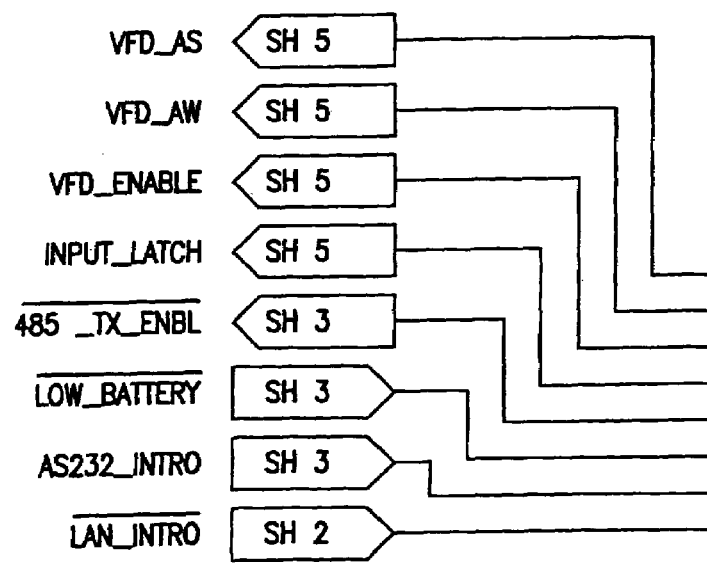
Figure 62C:
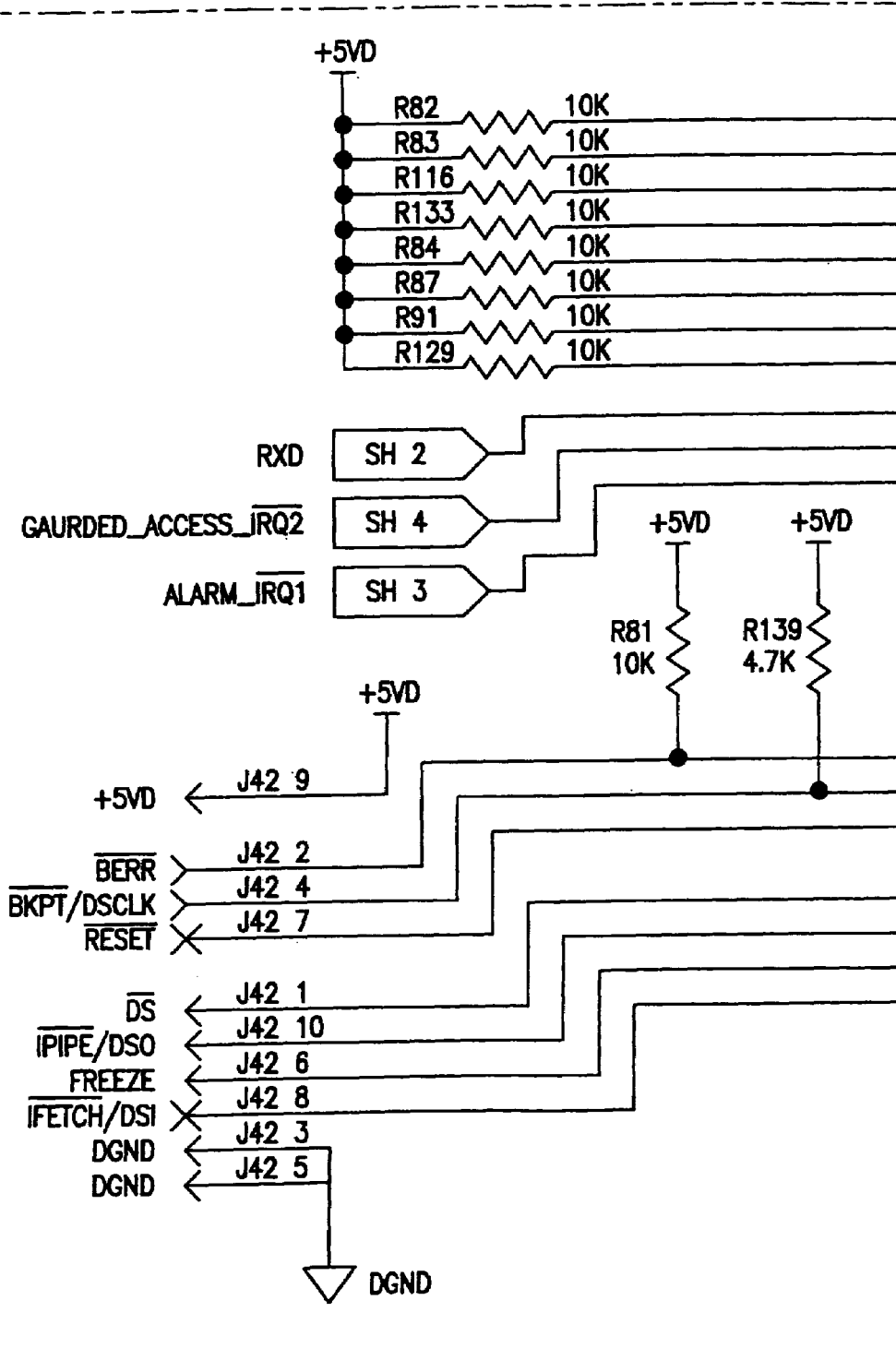
Figure 62D:
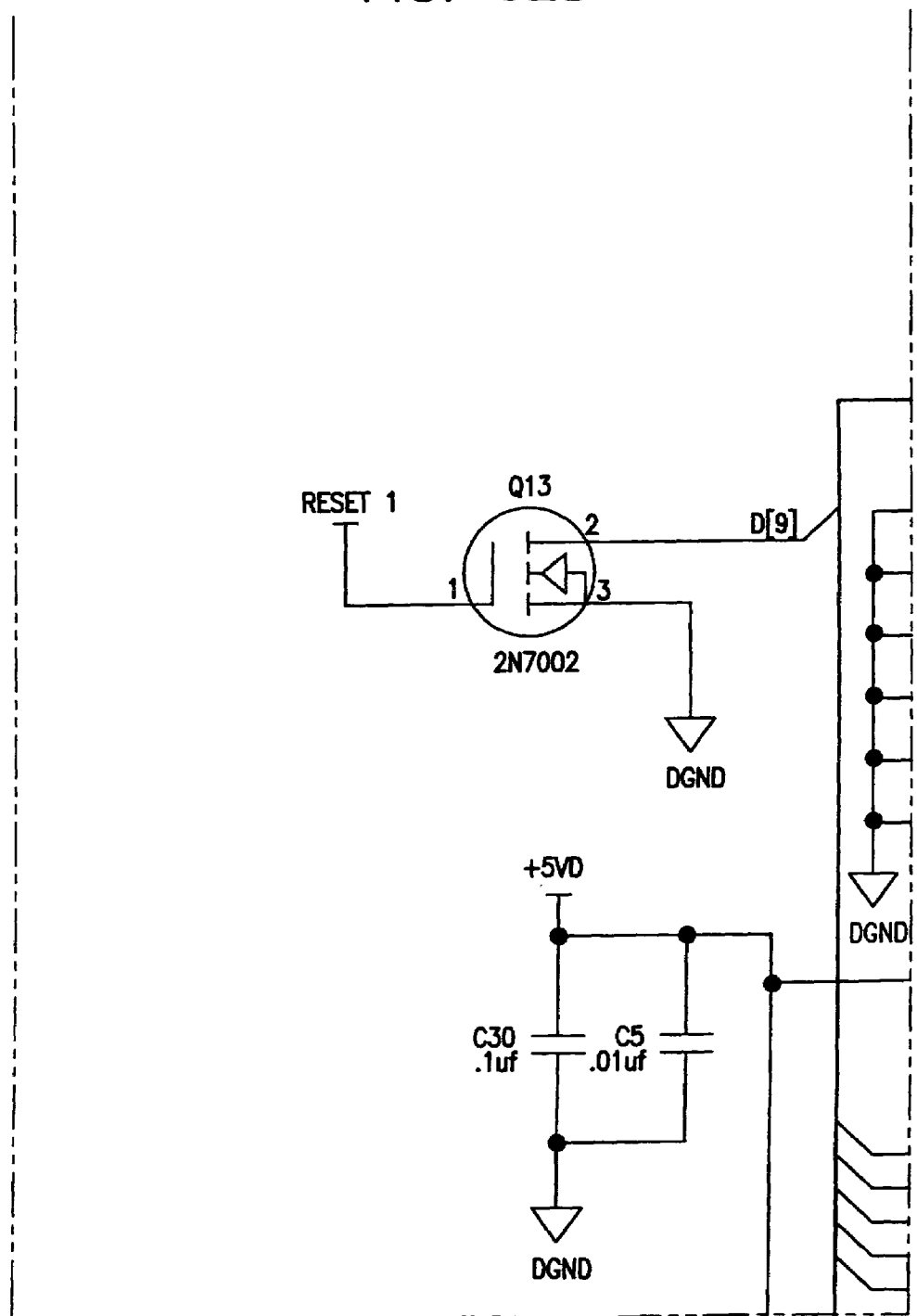
Figure 62E:
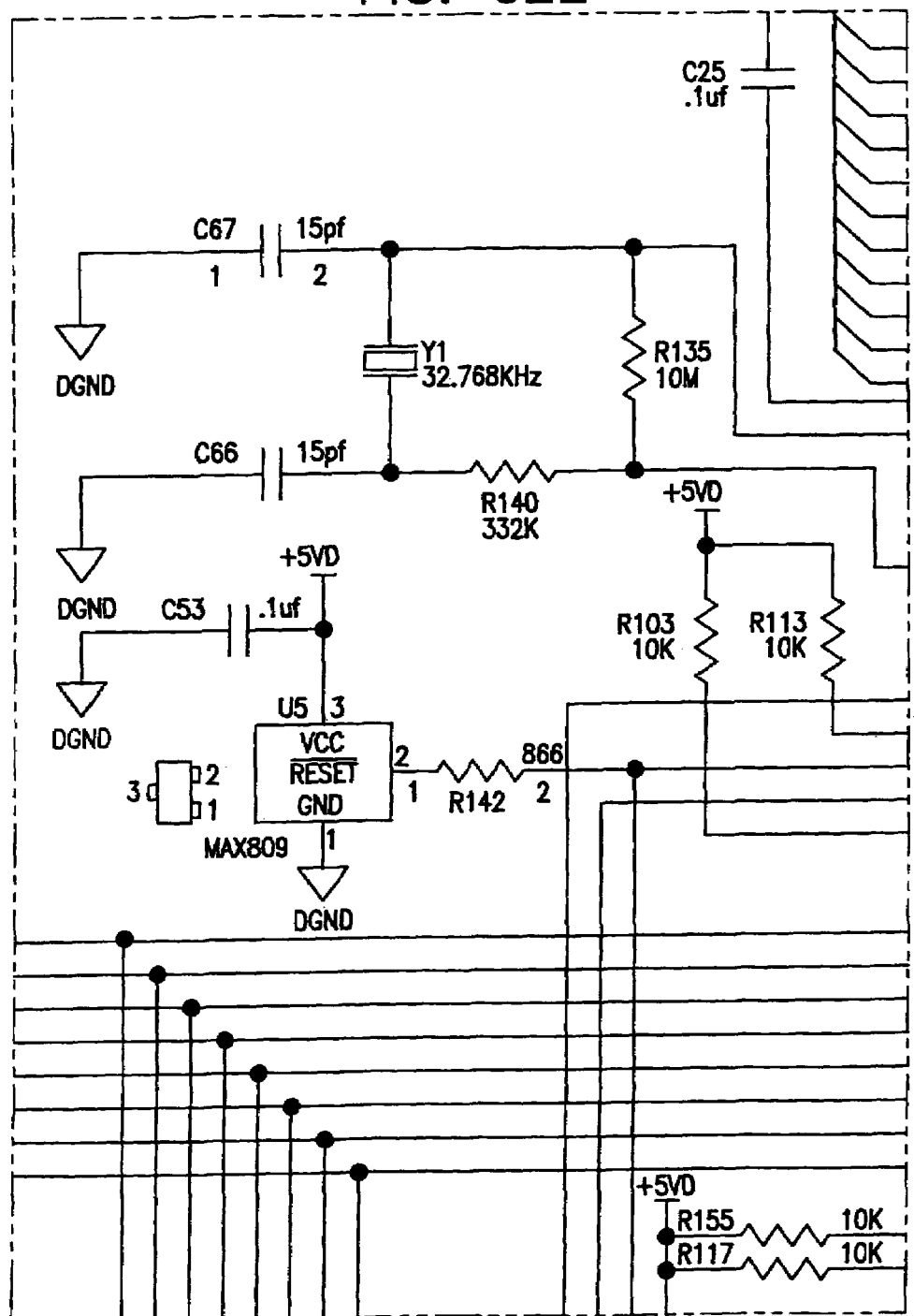
Figure 62F:
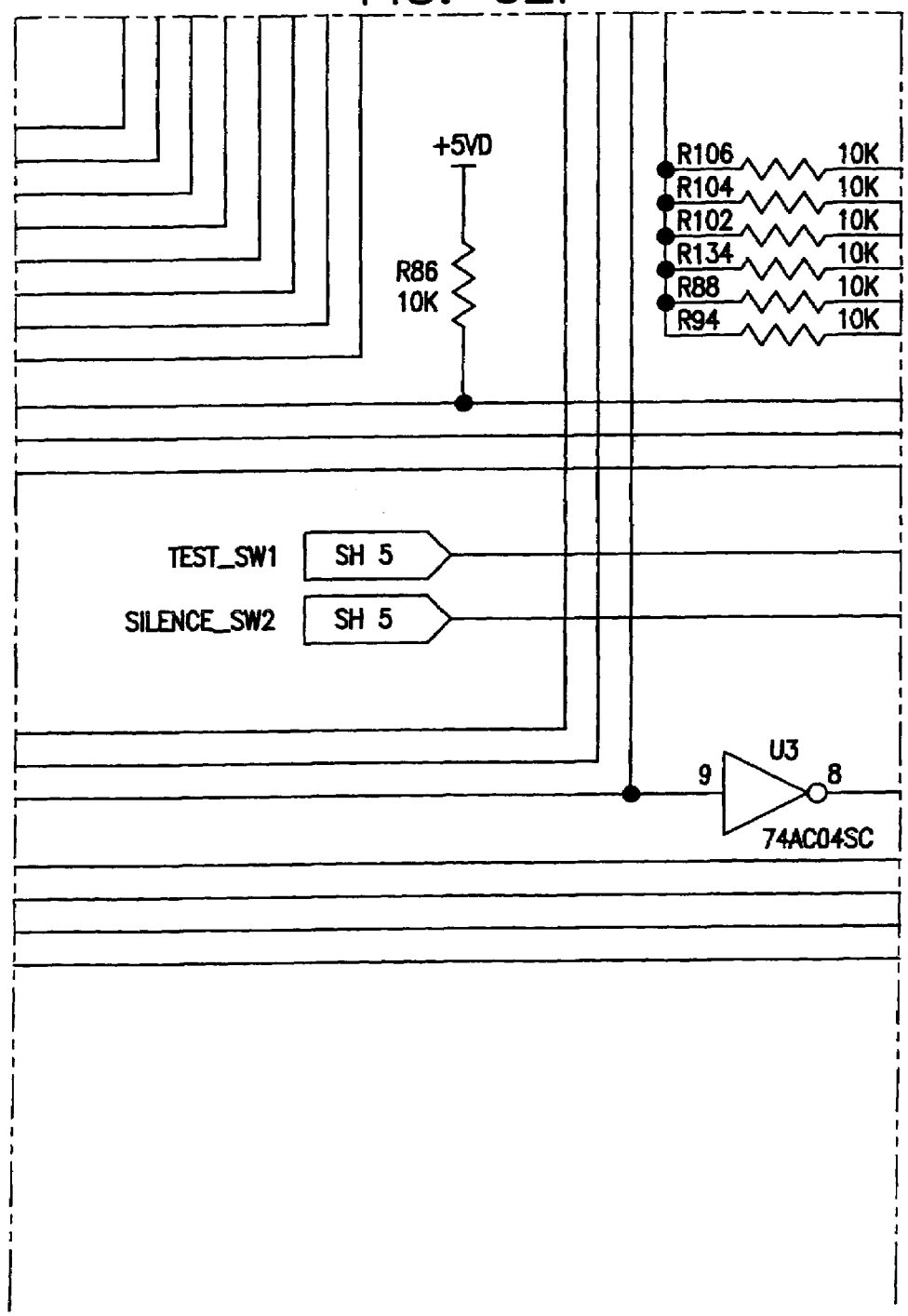
Figure 62G:
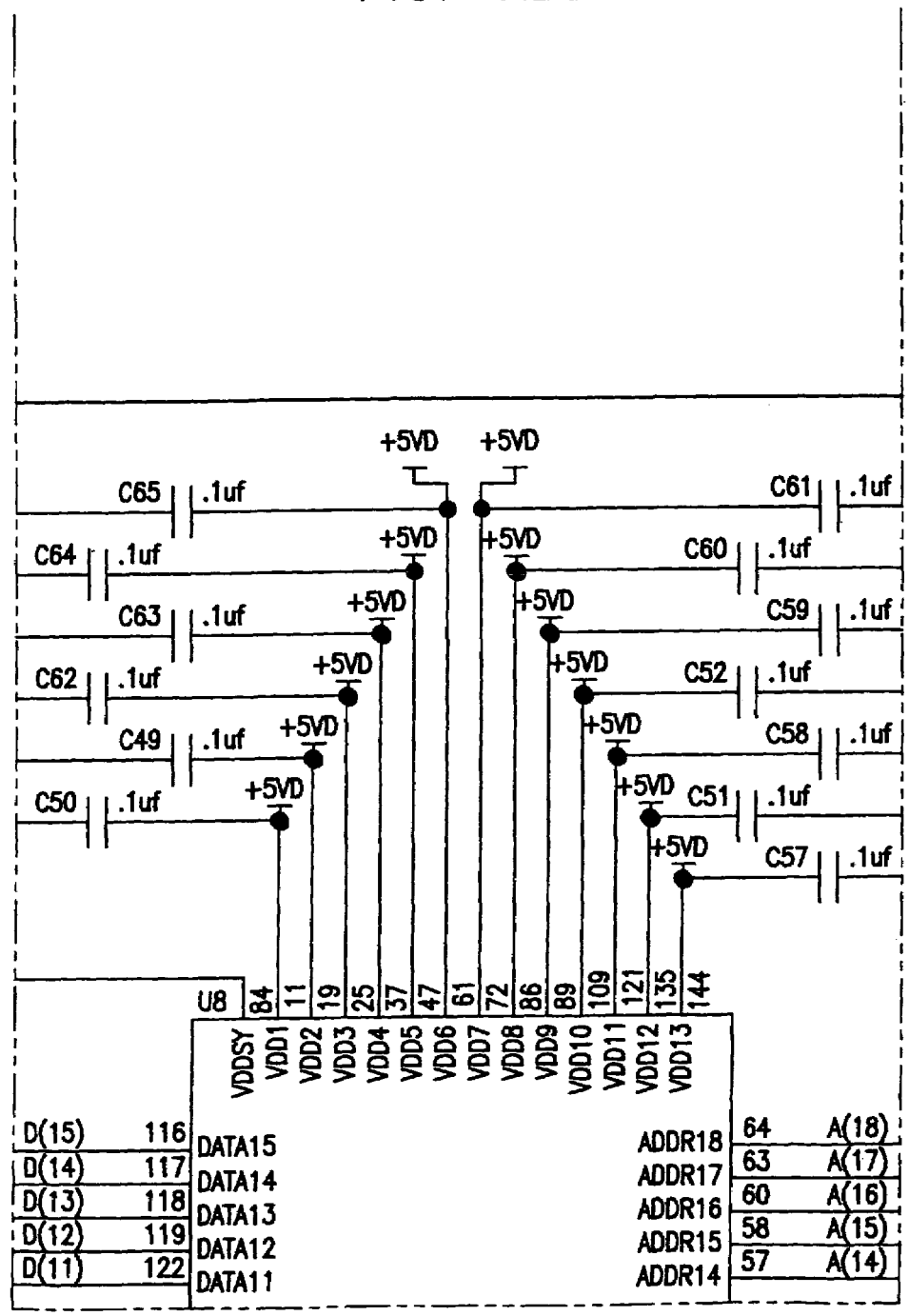
Figure 621:
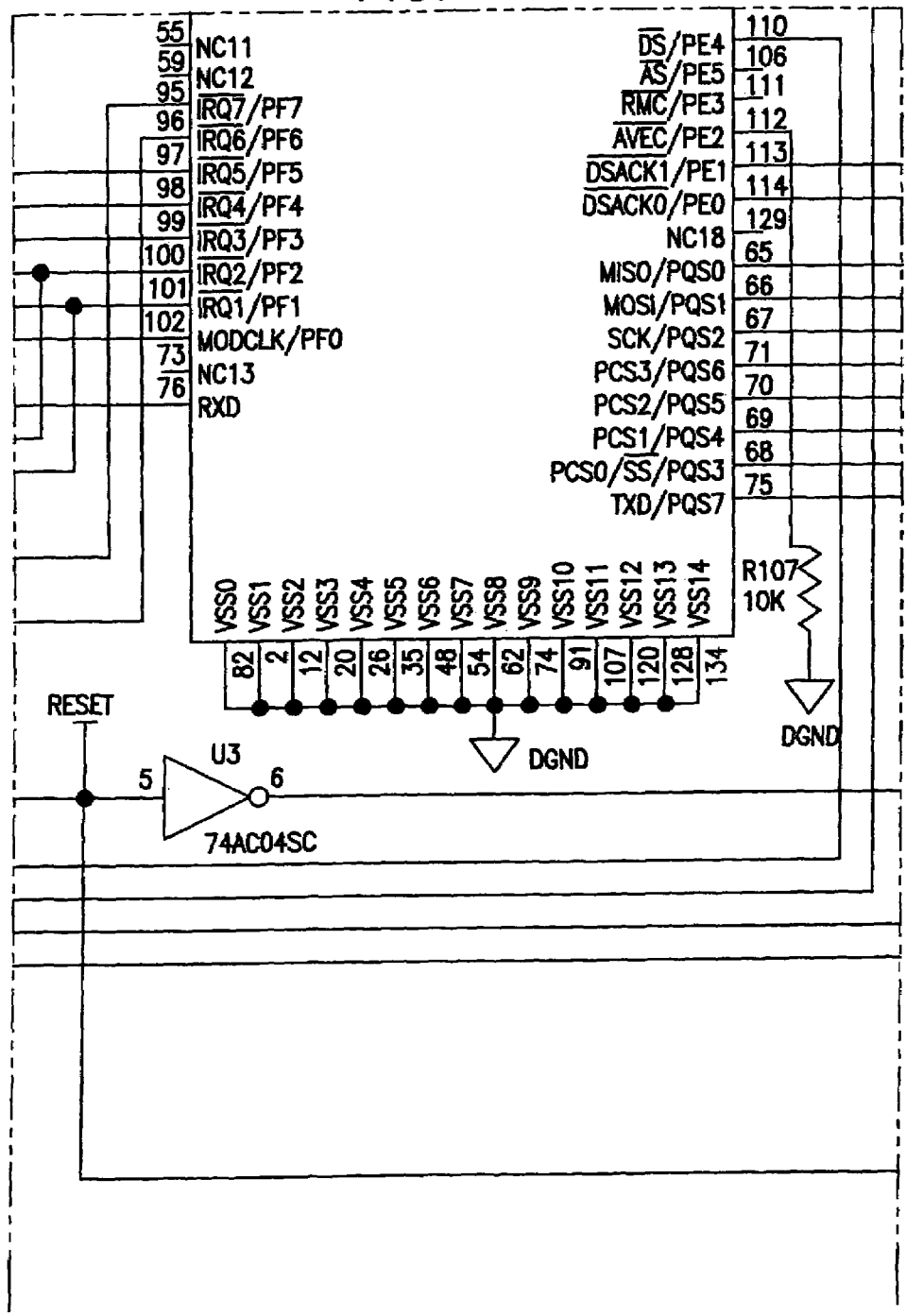

Pin 84 of the 68331 .mu.C is coupled directly to +5 VD and is also coupled to DGND through a parallel combination of a 1 .mu.F capacitor and a 0.01 .mu.F capacitor as shown in FIGS. 62D, 62E, and 62G. In addition, pin 84 of the 68331 .mu.C is coupled to pin 87 of the 68331 .mu.C through a 0.1 microfarad capacitor as shown in FIGS. 62D, 62E, 62G and 62H. Pin 83 of the 68331 .mu.C is coupled to one terminal of a 10 M.OMEGA. resistor and pin 85 of the 68331 .mu.C is coupled to the other terminal of the 10 M.OMEGA. resistor as shown in FIGS. 62E and 62H. Pin 83 of the 68331 .mu.C is also coupled to one terminal of a 32768 kHz oscillator or clock through a 332 k.OMEGA.

resistor and pin 85 is coupled to the other terminal of the 32768 kHz clock. The two terminals of the 32768 kHz clock are each coupled to DGND through respective 15 pF capacitors.

Pin 94 of the 68331 .mu.C is coupled to +5 VD through a 10 k.OMEGA. resistor and pin 94 is also coupled to a notBERR line as shown in FIGS. 62C, 62E, 62F, and 62H. Pin 80 and pin 92 of the 68331 .mu.C are each coupled to +5 VD through respective 10 k.OMEGA. resistors as shown in FIGS. 62E and 62H. Pin 92 of the 68331 .mu.C is coupled to a notRESET line which is, in turn, coupled to pin 9 of a 74AC04SC Hex Inverter, such as that made by National Semiconductor. Pin 8 of the 74AC04SC Hex Inverter is coupled to pin 5 of the 74AC04SC Hex Inverter by a RESET line. RESET line is also coupled to circuitry shown in the schematic of FIGS. 63A–63L as will be described in further detail below.

Figure 62J:
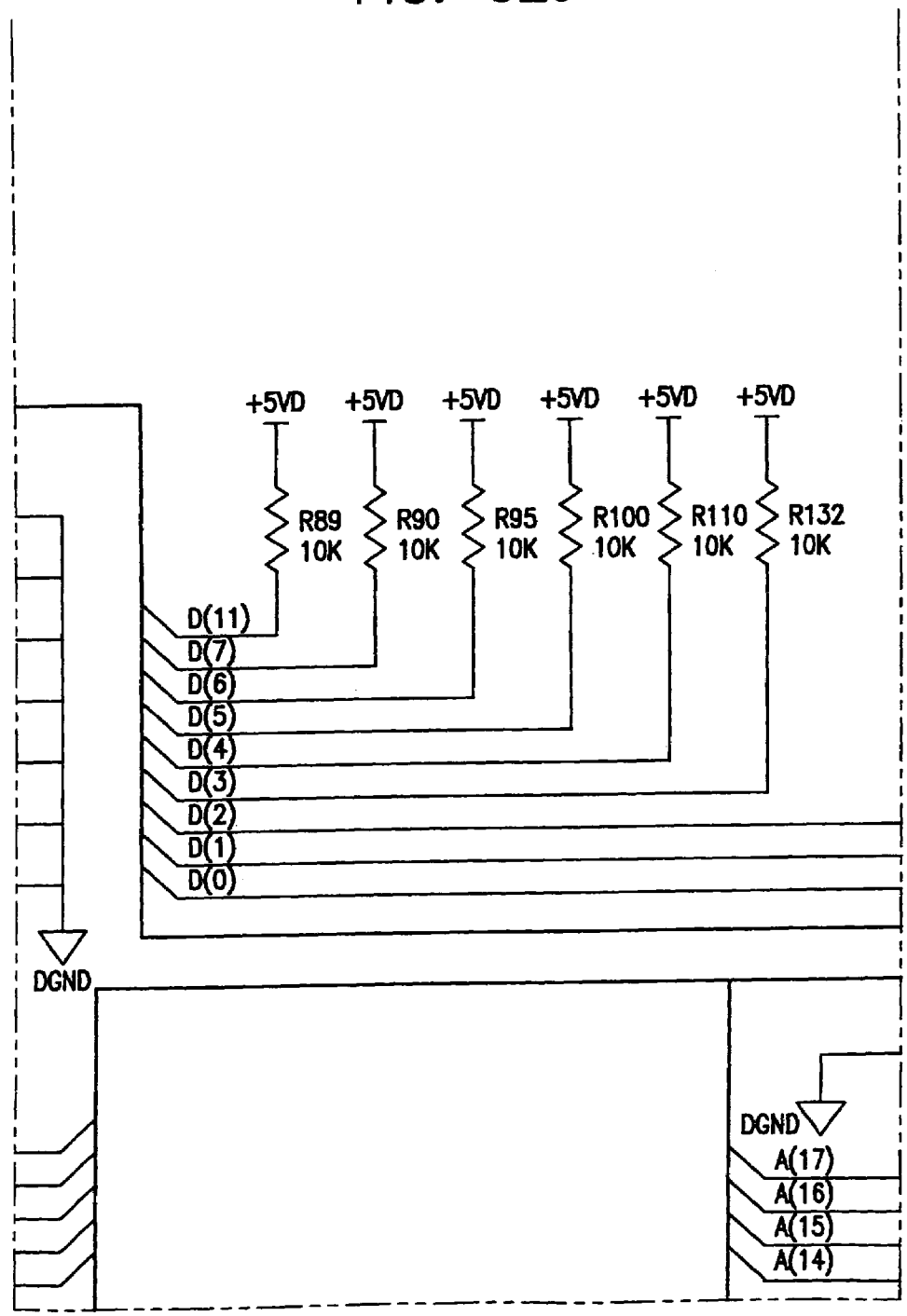

As shown in FIG. 62E, circuit 70 includes a MAX809 reset chip which is made by Maxim Integrated Products. Pin 92 of the 68331 .mu.C is coupled to pin 2 of the MAX809 reset chip through an 866.OMEGA. resistor as shown in FIGS. 62E and 62H. Pin 1 of the MAX809 reset chip is coupled to DGND as shown in FIG. 62E. Pin 3 of the MAX809 reset chip is coupled directly to +5 VD and is also coupled to DGND through a 1 .mu.F capacitor as shown in FIG. 62E. The 74AC04SC hex inverter is designated as circuit component "U3" in circuit 70 and, as can be seen in FIG. 62R, pin 7 of the 74AC04SC hex inverter is coupled to DGND, pin 14 of the 74AC04SC hex inverter is coupled to +5 VD, and pin 14 of the 74AC04SC hex inverter is coupled to pin 7 thereof through a 0.1 .mu.F capacitor.

Pin 79 of the 68331 .mu.C is coupled directly to a notBKPT/DSCLK line and is coupled to +5 VD through a 4.7 k.OMEGA. resistor as shown in FIGS. 66C, 62E, 62F, and 62H. Pins 23, 24, 28, 29, 30, 31, 32, and 33 of the 68331 .mu.C are each coupled to +5 VD through respective 10 k.OMEGA. resistors as shown in FIGS. 62C, 62E, 62F, and 62H. In addition, pins 23, 24, 28, 29, 30, 31, 32, and 33 of the 68331 .mu.C are coupled to a VFD_AS line, a VFD_notAW line, a VFD_ENABLE line, an INPUT_LATCH line, a not485_TX_ENBL line, a notLOW_BATTERY line, an RS232_INTRO line, and a notLAN_INTRO line, respectively, as shown in FIGS. 62B, 62E, and 62H. The VFD_AS, VFD_notAW, VFD_ENABLE, and INPUT_LATCH lines are each coupled to circuitry shown in the schematic of FIGS. 66A–66X as will be described in further detail below. In addition, the not485_TX_ENBL, notLOW_BATTERY, and RS232_INTRO lines are each coupled to circuitry shown in the schematic of FIGS. 64A–64Q, whereas the notLAN_INTRO line is coupled to circuitry shown in the schematic of FIGS. 63A–63L, as will be described in further detail below.

Pins 13, 22, 97, 98, 99, 100, 101, and 102 of the 68331 .mu.C are each coupled to +5 VD through respective 10 k.OMEGA. resistors as shown in FIGS. 62C, 62E, 62F, 62H, and 62I. In addition, pin of the 68331 .mu.C is coupled to a GAURDED_ACCESS_notIRQ2 line and pin 101 of the 68331 .mu.C is coupled to an ALARM_notIRQ1 line as shown in FIGS. 62C, 62F, and 62I. Pin 95 of the 68331 .mu.C is coupled to a TEST_SW1 line and pin 96 of the 68331 .mu.C is coupled to a SILENCE_SW2 line as shown in FIGS. 62F and 62I. Pin 76 of the 68331 .mu.C is coupled to an RXD line as shown in FIGS. 62C, 62F, and 62I and pin 76 of the 68331 .mu.C is also coupled to +5 VD through a 10 k.OMEGA. resistor as shown in FIGS. 62F and 62I. As will be described in further detail below, the RXD line is coupled to circuitry shown in the schematic of FIGS. 63A–63L, the ALARM_notIRQ1 line is coupled to circuitry shown in the schematic of FIGS. 64A–64Q, the GAURDED_ACCESS_notIRQ2 line is coupled to circuitry shown in the schematic of FIGS. 65A–65L, and the TEST_SW1 and SILENCE_SW2 lines are coupled to circuitry shown in the schematic of FIGS. 66A–66X.

Figure 62K:
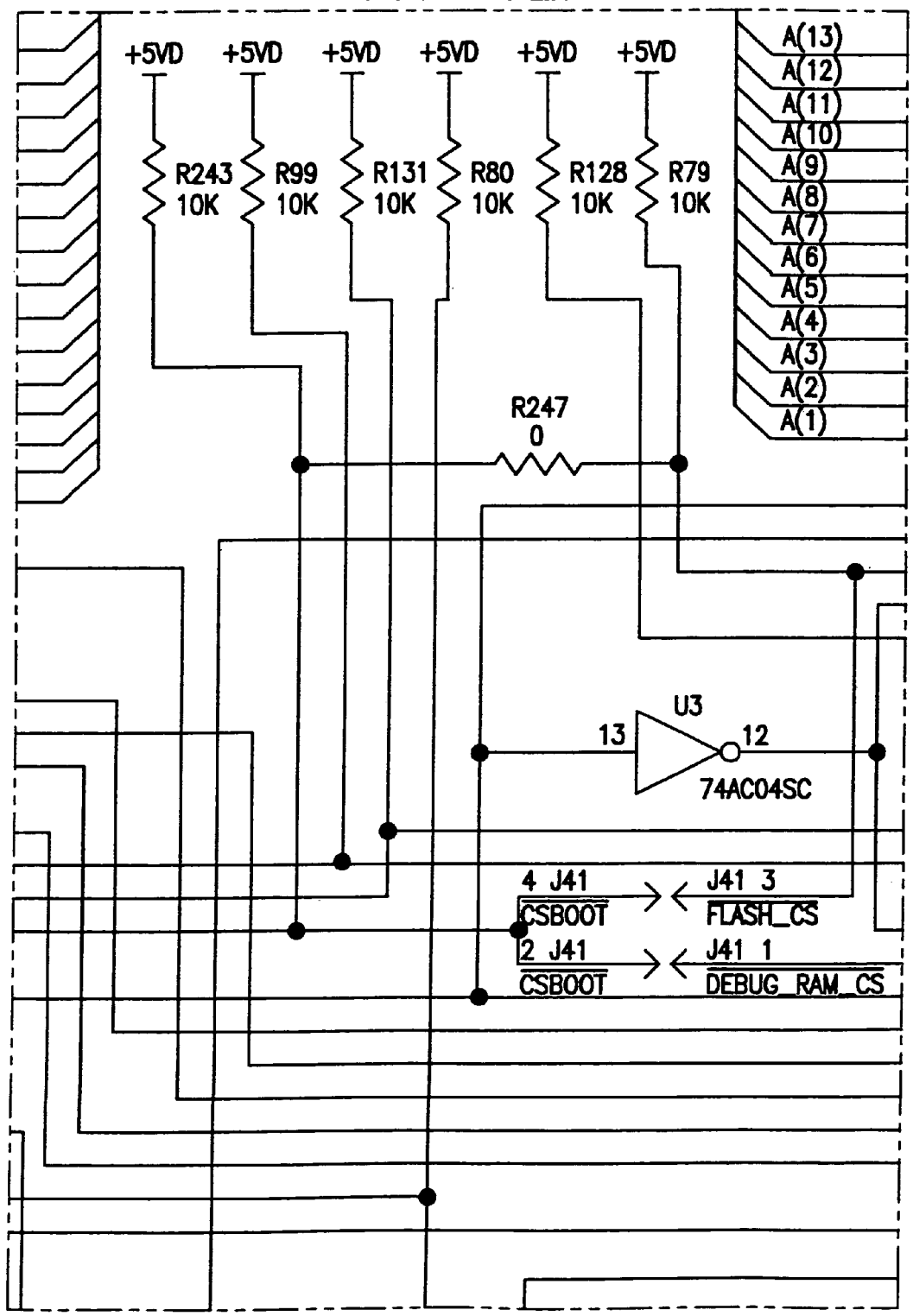
Figure 62L:
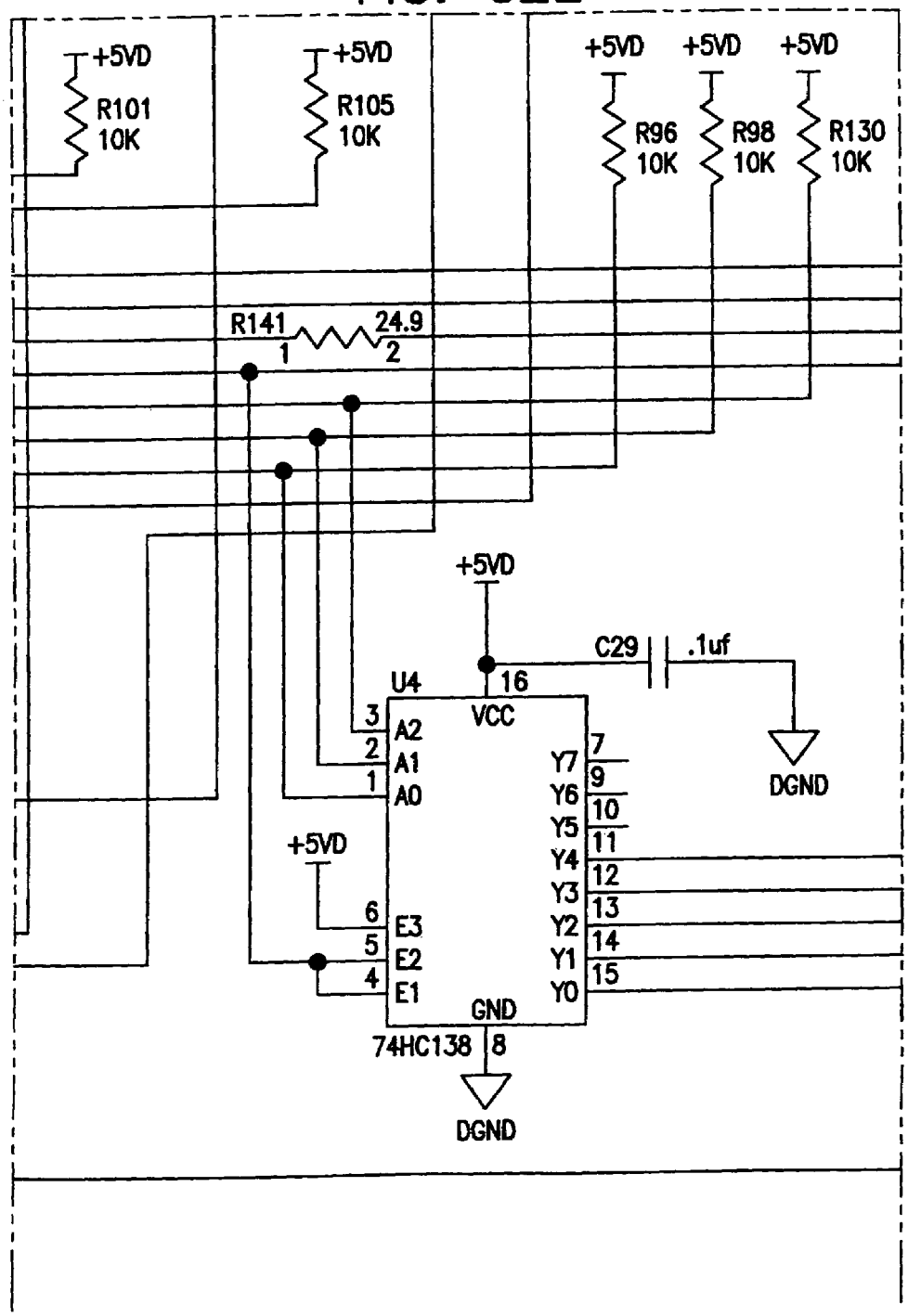

Pin 75 of the 68331 .mu.C is coupled to a TXD line as shown in FIGS. 62I, 62K, 62L, 62N, 62Q, 62T, and 62U and the TXD line is coupled to circuitry shown in the schematic of FIGS. 64A–64Q as will be described in further detail below. Pins 65, 66, 68, 69, 70, and 71 of the 68331 .mu.C are each coupled to +5 VD through respective 10 k.OMEGA. resistors as shown in FIGS. 62I, 62L, and 62O. In addition, pins 65, 66 of the 68331 .mu.C are coupled to MISO and MOSI lines, respectively, as shown in FIGS. 62I, 62L, 62O, and 62R. Pin 67 of the 68331 .mu.C is coupled to an SPI_CLK line through a 24.9.OMEGA. resistor as shown in FIGS. 62I, 62L, 62O, and 62R. The SPI_CLK line is coupled to +5 VD through a 10 k.OMEGA. resistor as shown in FIGS. 62O and 62R. The MISO line, the MOSI line and the SPI_CLK line are each coupled to circuitry shown in the schematic of FIGS. 64A–64Q and are each coupled to circuitry shown in the schematic of FIGS. 66A–66X, as will be described in further detail below. In addition, +5 VD and DGND is coupled from the circuitry shown in the schematic of FIGS. 62A–62U to the circuitry shown in the schematic of FIGS. 66A–66X as shown in FIG. 62R.

Pins 68, 69, and 70 of the 68331 .mu.C are coupled to pins 1, 2, and 3, respectively, of a 74HC138 3-to-8 line decoder, such as that manufactured by Fairchild Semiconductor Corporation, as shown in FIGS. 62I and 62L. Pin 71 of the 68331 .mu.C is coupled to pins 4 and 5 of the 74HC138 3-to-8 line decoder (hereinafter "74HC138 decoder") as also shown in FIGS. 62I and 62L. Pin 6 of the 74HC138 decoder is coupled to +5 VD as shown in FIG. 62L. Pins 7, 9, 10, and 11 of the 74HC138 decoder are open as also shown in FIG. 62L. Pin 8 of the 74HC138 decoder is coupled to DGND. Pin 16 of the 74HC138 decoder is directly coupled to +5 VD and is coupled to DGND through a 0.1 .mu.f capacitor as shown in FIG. 62L. Pins 11, 12, and 13 of the 74HC138 decoder are coupled to a notLOCAL_ALARM_CS line, a notLED_DISPLAY_CS line, and a notSEEPROM1_CS line, respectively, as shown in FIGS. 62L and 62O. Pin 14 of the 74HC138 decoder is coupled to pin 11 of the 74AC04SC hex inverter and pin 10 of the 74AC04SC hex inverter is coupled to a RTC_SELECT line as also shown in FIGS. 62L and 62O. Pin 15 of the 74HC138 decoder is coupled to pin 3 of the 74AC04SC hex inverter and pin 4 of the 74AC04SC hex inverter is coupled to a notVFD_CE line. The notVFD_CE line, the notLOCAL_ALARM_CS line, and the notLED_DISPLAY_CS line are each coupled to the circuitry shown in the schematic of FIGS. 66A–66X as will be described in further detail below. In addition, the notSEEPROM1_CS line and the RTC_SELECT line are coupled to the circuitry shown in the schematic of FIGS. 63A–63L as will also be described in further detail below.

Pins 113 and 114 of the 68331 .mu.C are each coupled to +5 VD through respective 10 k.OMEGA. resistors as shown in FIGS. 62I and 62L. Pin 112 of the 68331 .mu.C is coupled to DGND through a 10 k.OMEGA. resistor as shown in FIG. 62I. Pins 77, 81, and 110 of the 68331 .mu.C are coupled to a notIPIPE/DSO line, a notDS line, and a FREEZE line, respectively, as shown in FIGS. 62C, 62F, 62H, 62I, 62K, and 62L. Pin 78 of the 68331 .mu.C is coupled to a notIFETCH/DSI line as shown in FIGS. 62C, 62F, 62H, and 62K. In addition, pin 78 of the 68331 .mu.C is coupled to +5

VD through a 10 k.OMEGA. resistor as shown in FIGS. 62H and 62K. The notBERR, notBKPT/DSCLK, notRESET, notDS, notIPIPE/DSO, FREEZE, and notIFETCH/DSI lines are coupled to pins 2, 4, 7, 1, 10, 6, and 8, respectively, of a connector J42 as shown in FIG. 62C. Pin 9 of the connector J42 is coupled to +5 VD and pins 3 and 5 of the connector J42 are coupled to DGND as also shown in FIG. 62C. The connector J42 provides circuit 70 with a background debug port to which a debugger. The debugger permits the application software to be executed and viewed, line-by-line, in order to debug and analyze any problems associated with the application software.

Pins 3, 4, 8, 9, and 143 of the 68331 .mu.C are coupled to a notLAN_CS_W line, a notUART line, an AUX_CS8, and ALARM_BUZZER line, and a notLAN_CS_R line, respectively, as shown in FIGS. 62K, 62N, 62Q, 62T, and 62U. The notLAN_CS_W and notLAN_CS_R lines are coupled to the circuitry shown in the schematic of FIGS. 63A–63L, the notUART line is coupled to the circuitry shown in the schematic of FIGS. 64A–64Q, the ALARM_BUZZER line is coupled to the circuitry shown in the schematic of FIGS. 65A–65L, and the AUX_CS8 line is coupled to the circuitry shown in the schematic of FIGS. 66A–66X, all of which will be described in further detail below.

Figure 62M:
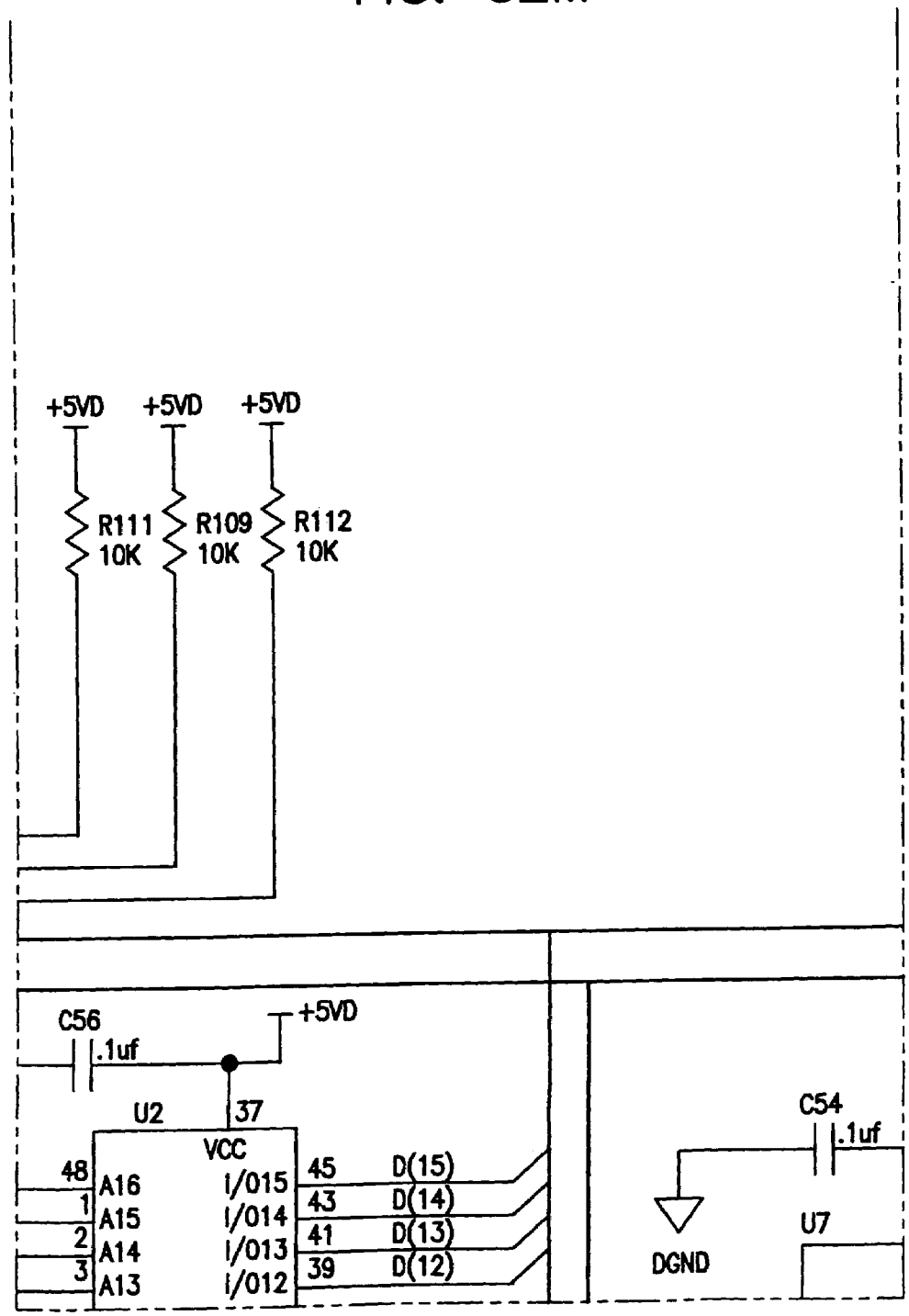
Figure 62N:
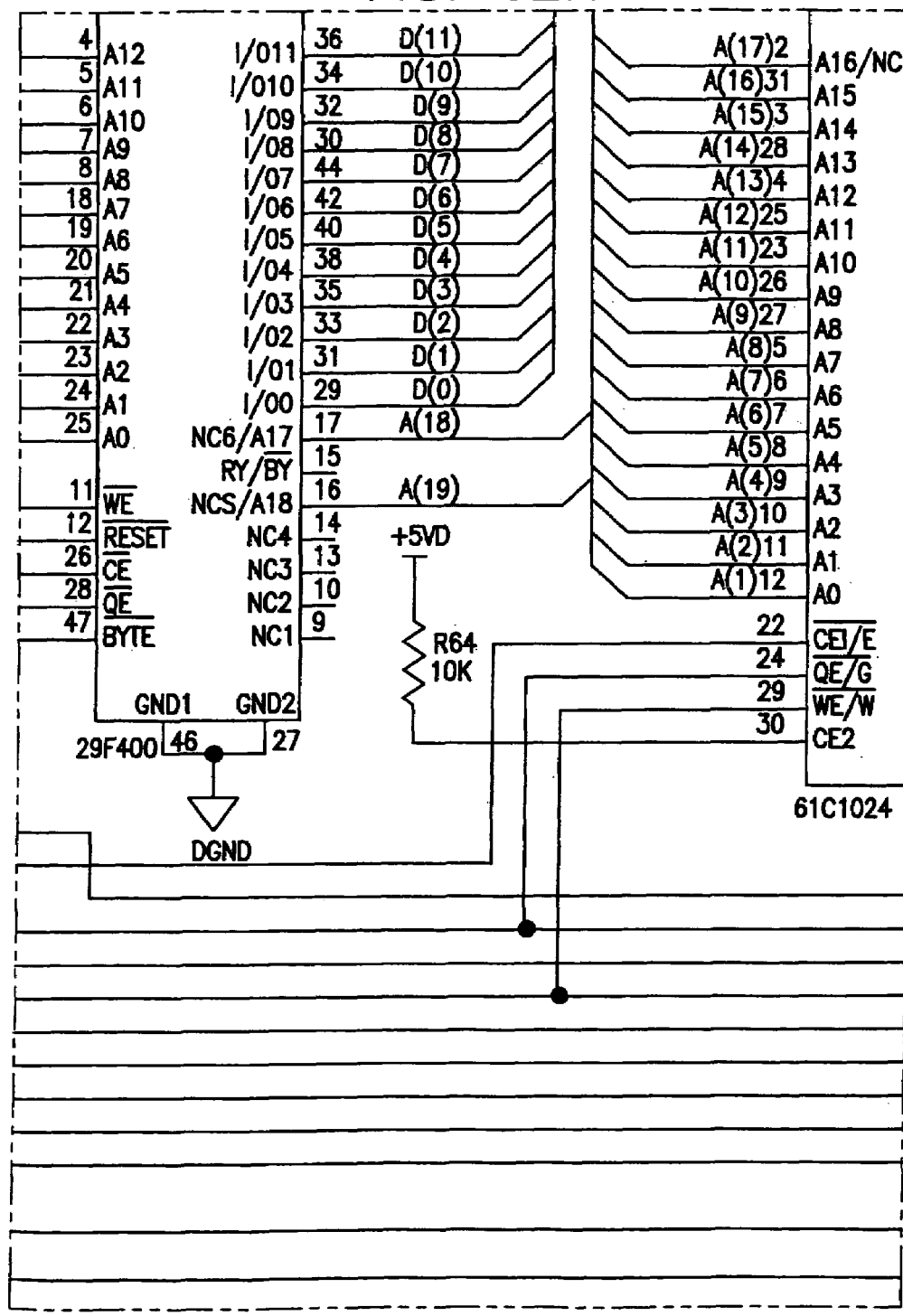
Figure 620:
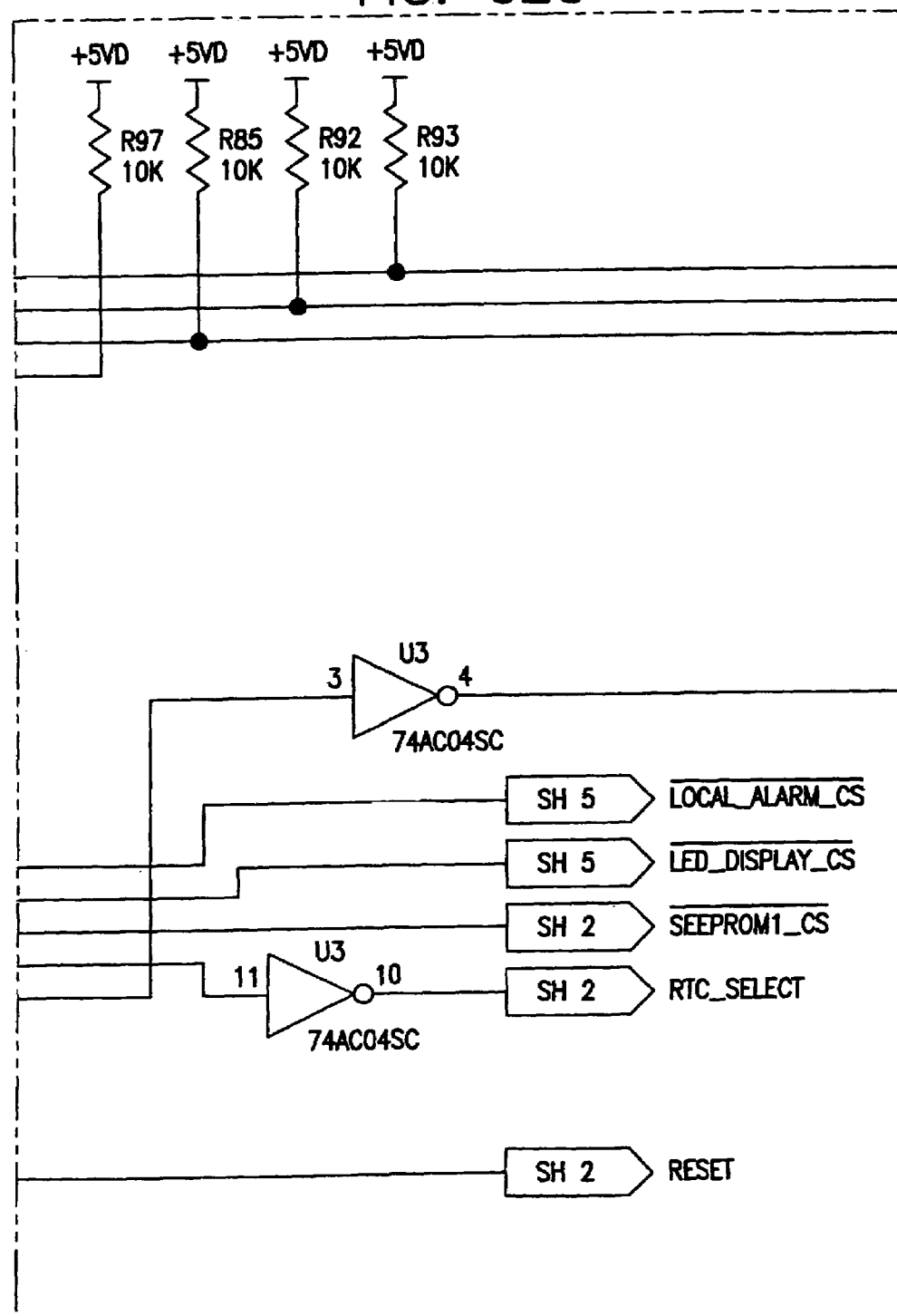
Figure 62P:
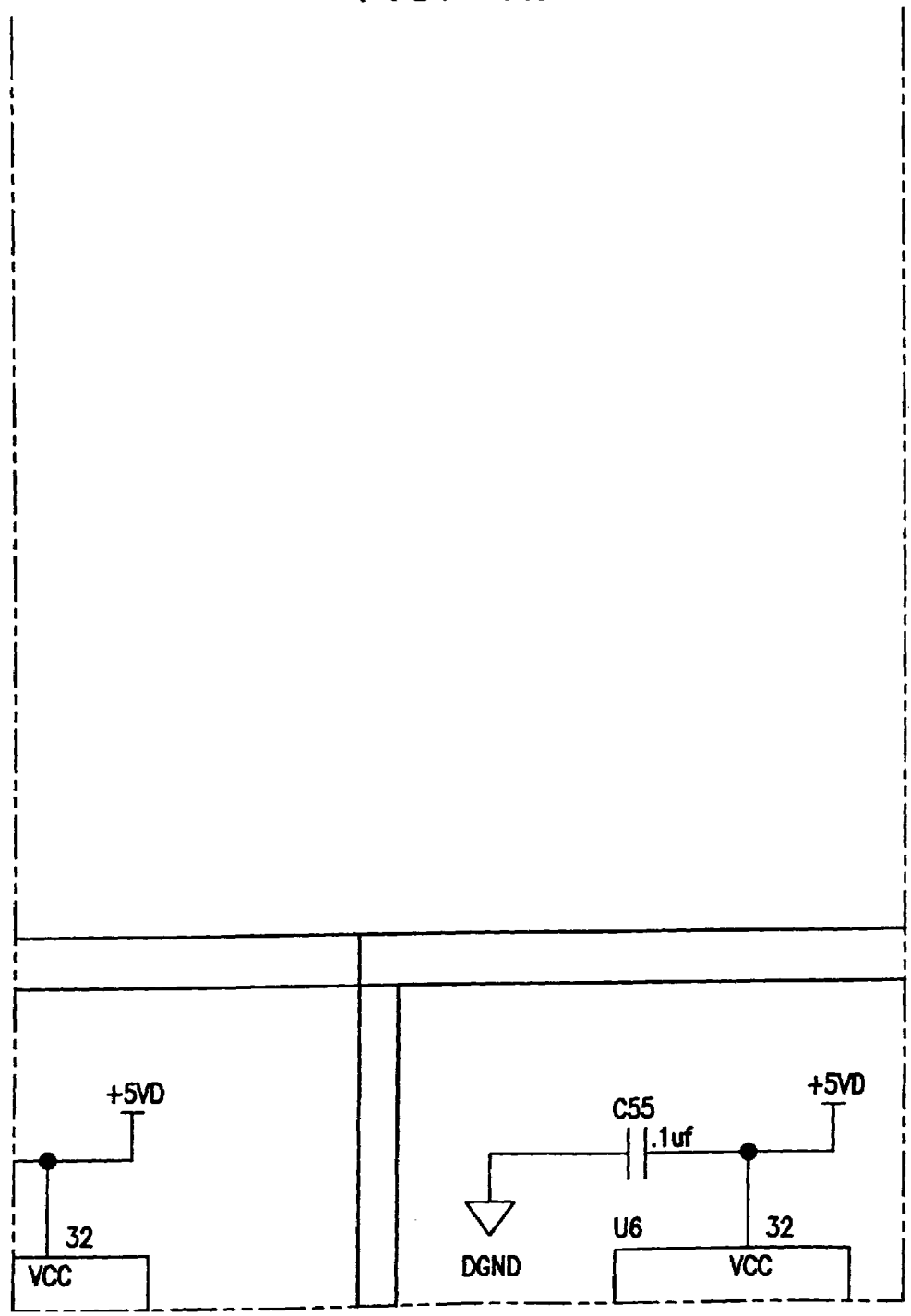
Figure 62Q:
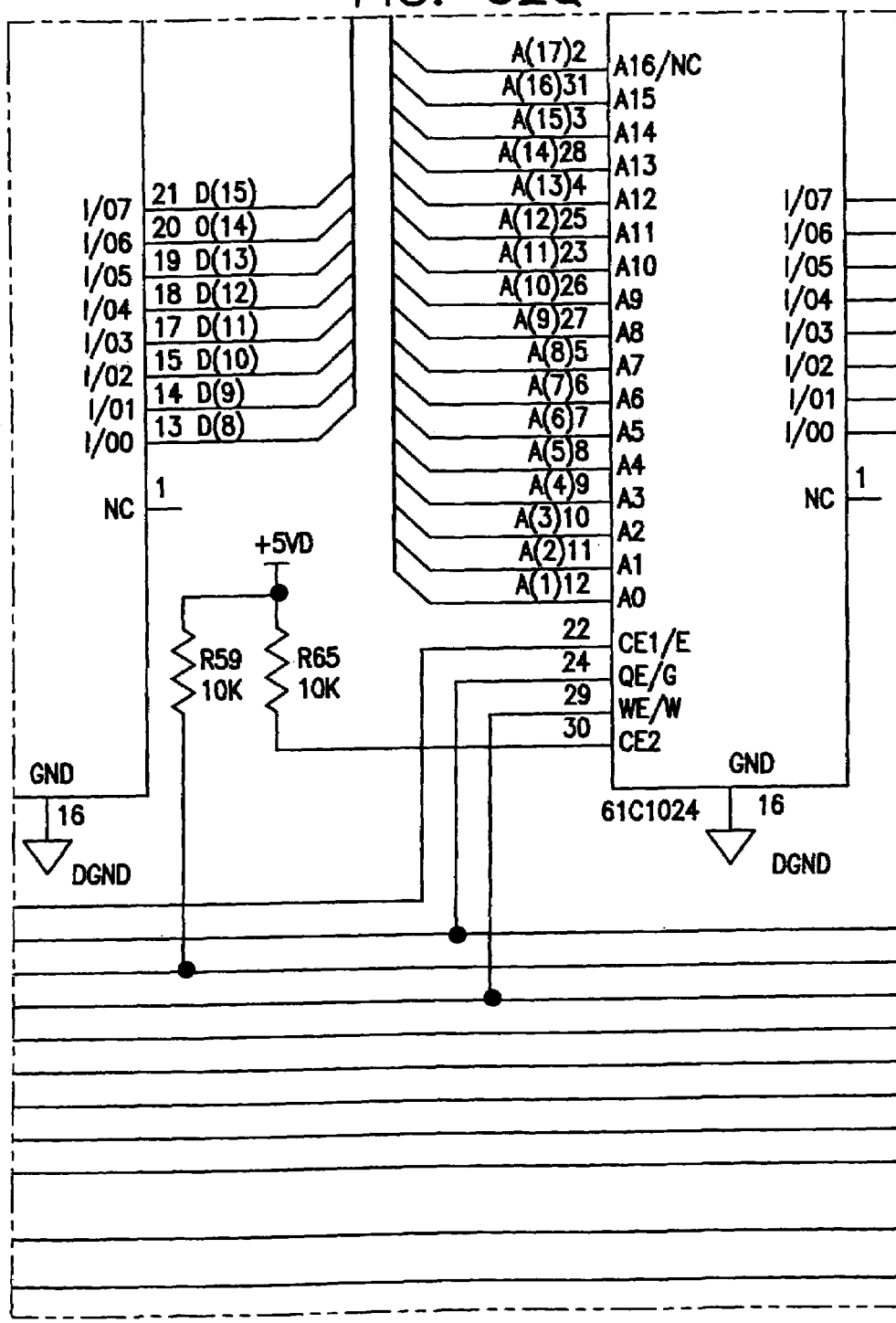
Figure 62R:
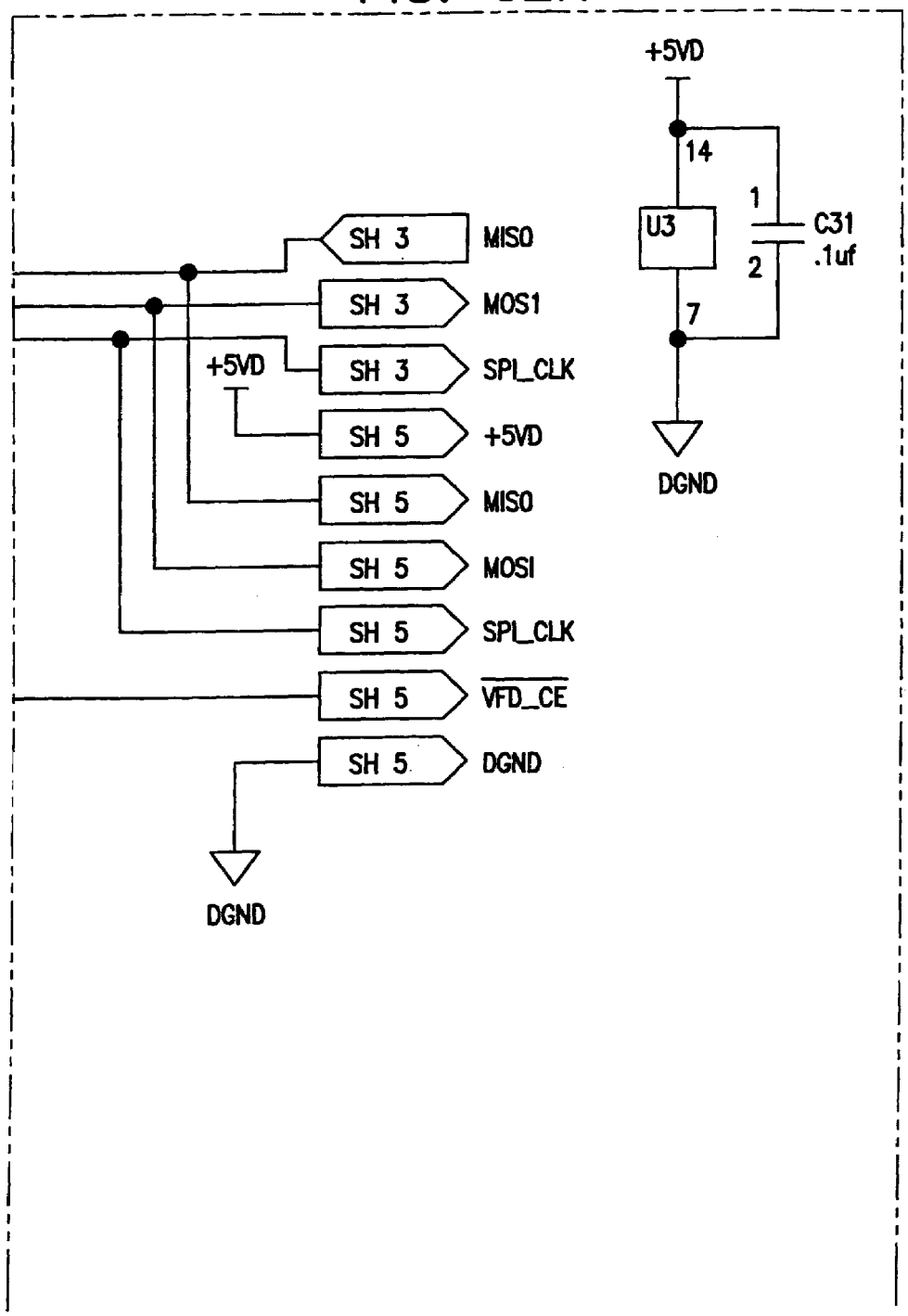
Figure 62S:
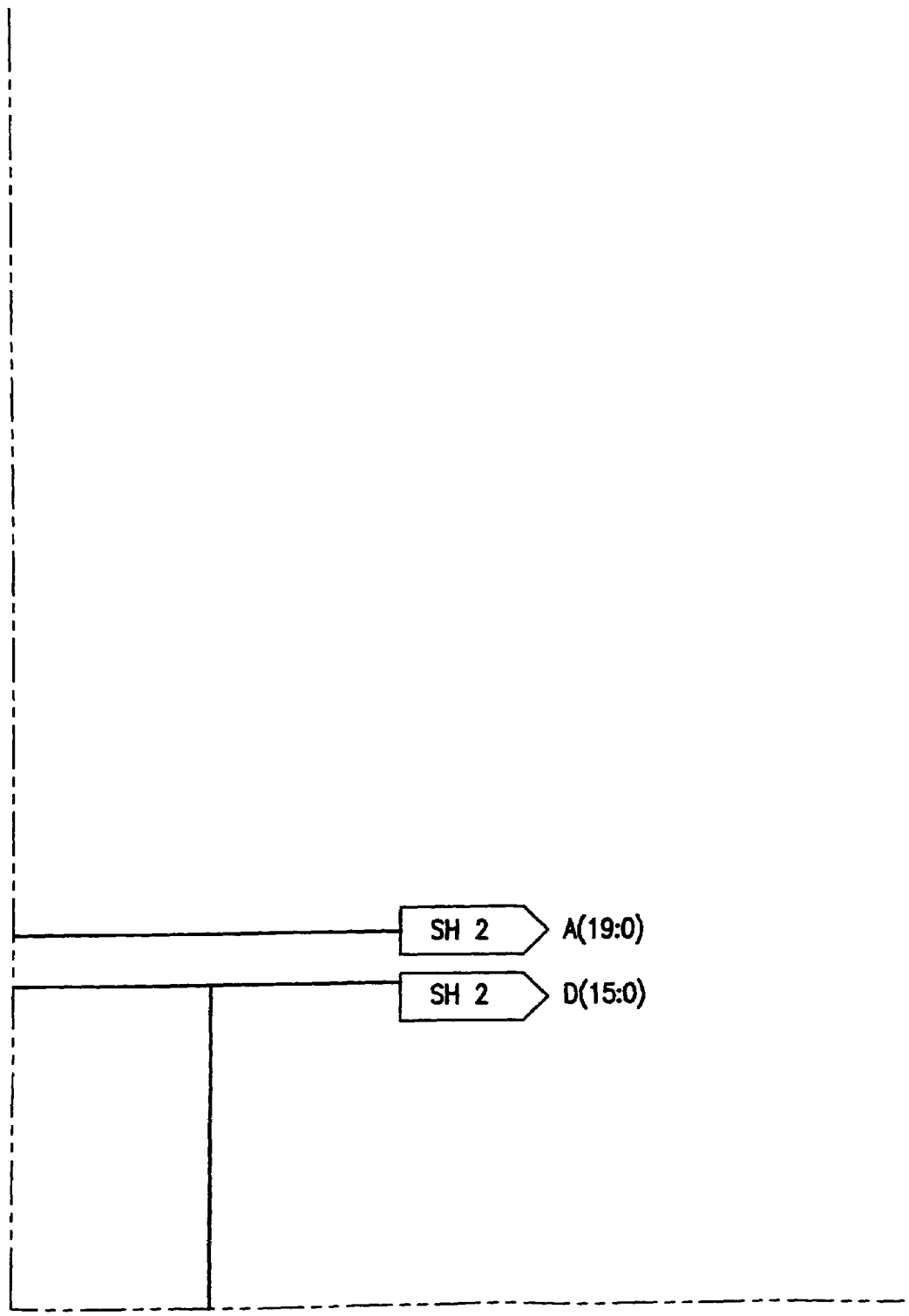
Figure 62T:
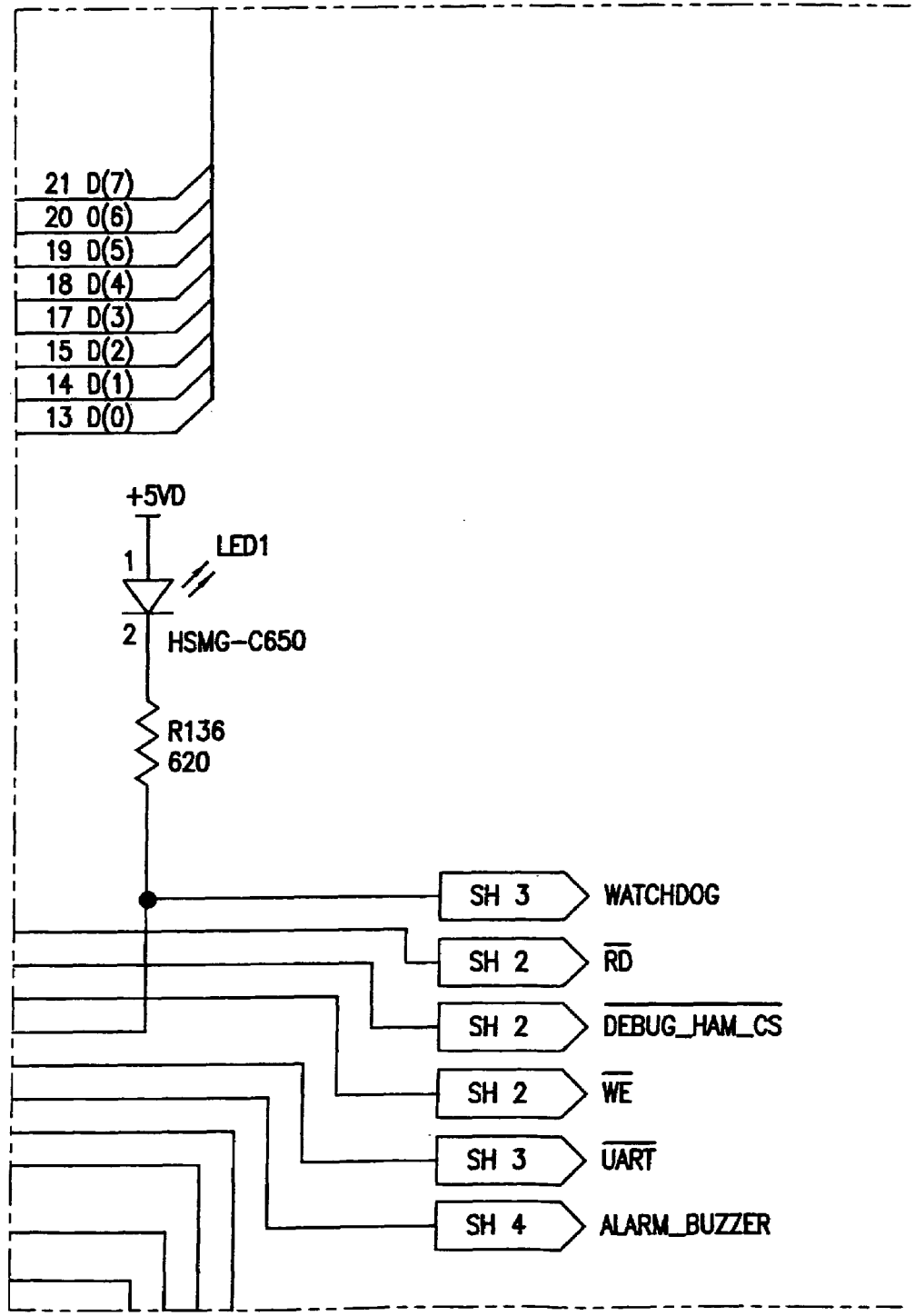

Pin 5 of the 68331 .mu.C is coupled directly to a WATCHDOG line and is coupled to +5 VD through a series combination of a 620.OMEGA. resistor and a first HSMG-C650 light emitting diode (LED) as shown in FIGS. 62H, 62K, 62N, 62Q, and 62T. The first HSMG-C650 LED is arranged so that its cathode couples to +5 VD and so that its anode couples to the 650.OMEGA. resistor as shown in FIG. 62T. As also shown in FIG. 62T, the WATCHDOG line is coupled to the circuitry shown in the schematic of FIGS. 64A–64Q as will be described in further detail below.

Circuit 70 includes a 29F400 Flash Memory chip, shown in FIGS. 62M and 62N, which is manufactured by Advanced Micro Devices, Inc. and in which application software is stored. Circuit 70 also includes first and second 61C1024 Static Random Access Memory (SRAM) chips, shown in FIGS. 62M, 62N, 62P, and 62Q, which are manufactured by Integrated Silicon Solution, Inc., and in which various input data and output data of alarm system 10 is stored. The first 61C1024 chip is indicated by a "U6" designation and the second 61C1024 chip is indicated by a "U7" designation.

Pin 103 of the 68331 .mu.C is coupled to a notWE line that, in turn, is coupled to pin 11 of the 29F400 chip and to pin 29 of each of the first and second 61C1024 chips as shown in FIGS. 62H, 62K, 62M, 62N, 62P, and 62Q. In addition and as also shown in FIGS. 62H, 62K, 62M, 62N, 62P, and 62Q, pin 103 of the 68331 .mu.C is coupled to pin 13 of the 74AC04SC hex inverter and pin 12 of the 74AC04SC hex inverter is coupled to a notRD line which, in turn, is coupled to each of the following: pin 28 of the 29F400 chip and pin 24 of each of the first and second 61C1024 chips. The notWE line and the notRD line are coupled to circuitry shown in the schematic of FIGS. 63A–63L as will be described in further detail below.

Pin 140 of the 68331 mu.C is coupled to +5 VD through a 10 k.OMEGA. resistor as shown in FIGS. 62H and 62K. Pin 140 splits into a pair of notCSBOOT lines, one of which couples to a notDEBUG_RAM_CS line and the other of which couples to a notFLASH_CS line as shown in FIG. 62K. The notDEBUG_RAM_CS line is coupled to pin 30 of the first 61C1024 chip through the series combination of a first 10 k.OMEGA. resistor and a second 10 k.OMEGA. resistor as shown in FIGS. 62K, 62N, and 62Q. The common terminal of the first and second 10 k.OMEGA. resistors is coupled to +5 VD as shown in FIG. 62Q. Pin 30 of the second 61C1024 chip is coupled to +5 VD through a 10 k.OMEGA. resistor as shown in FIG. 62N. The notDEBUG_RAN_CS line is also coupled to circuitry shown in the schematic of FIGS. 63A–63L as will be described in further detail below. Pin 26 of the 29F400 chip is coupled to +5 VD through a 10 k.OMEGA. resistor as shown in FIGS. 62K and 62N. In addition, pin 26 of the 29F400 chip is coupled to pin 140 of the 68331 .mu.C and to the notFLASH_CS line as shown in FIGS. 62H, 62K, and 62N.

Pins 141 and 142 of the 68331 .mu.C are each coupled to +5 VD through a respective 10 k.OMEGA. resistor as shown in FIGS. 62H and 62K. Pin 141 of the 68331 .mu.C is also coupled to pin 22 of the first 61C1024 chip as shown in FIGS. 62H, 62K, 62N, and 62Q. Pin 142 of the 68331 mu.C is also coupled to pin 22 of the second 61C1024 chip as shown in FIGS. 62H, 62K, and 62N. Pin 32 of each of the first and second 61C1024 chips is coupled directly to +5 VD and is coupled to DGND through respective 0.1 .mu.F capacitors as shown in FIGS. 62M and 62P. Pin 16 of each of the first and second 61C1024 chips is coupled to DGND as shown in FIG. 62Q. Pin 1 of each of the first and second 61C1024 chips is open as also shown in FIG. 62Q. Pin 37 of the 29F400 chip is coupled directly to +5 VD and is coupled to DGND through a 0.1 .mu.F capacitor as shown in FIGS. 62J and 62M. Pins 27 and 46 of the 29F400 chip are each coupled to DGND as shown in FIG. 62N. Pins 9, 10, 13, 14, and 15 of the 29F400 chip are open as also shown in FIG. 62N. Pin 12 of the 29F400 chip is coupled to pin 6 of the 74AC04SC hex inverter as shown in FIGS. 62I, 62K, 62L, and 62N.

Pins 115, 39, 40, 41, 42, 43, 44, 45, 46, 49, 50, 51, 52, 56, 57, 58, 60, 63, 63, and 6 of the 68331 mu.C form an address bus having A(0), A(1), . . . , A(19) lines, respectively, as shown in FIGS. 62G and 62H. The A(1) through A(19) lines couple to pins 25, 24, 23, 22, 21, 20, 19, 18, 8, 7, 6, 5, 4, 3, 2, 1, 48, 17, and 16, respectively, of the 29F400 chip as shown in FIGS. 62J, 62K, 62M, and 62N. The A(1) through A(17) lines couple to pins 12, 11, 10, 9, 8, 7, 6, 5, 27, 26, 23, 25, 4, 28, 3, 31, and 2, respectively, of each of the first and second 61C1024 chips as shown in FIGS. 62N and 62Q. As shown in FIG. 62S, the A(0) through A(19) lines are coupled to circuitry shown in the schematic of FIGS. 63A–63L as will be described in further detail below.

Pins 139, 138, 137, 136, 133, 132, 131, 130, 127, 125, 124, 122, 119, 118, 117, and 116 of the 68331 .mu.C form a data bus having D(0), D(1), . . . D(15) lines, respectively, as shown in FIGS. 62G and 62H. The D(9) line is coupled to a drain terminal of a 2N7002 N-channel enhancement mode field-effect transistor as shown in FIG. 62D. A source terminal of the 2N7002 transistor is coupled to DGND and a gate terminal of the 2N7002 transistor is coupled to the RESET line as also shown in FIG. 62D. The D(0) through D(7) lines and the D(11) line are each coupled to +5 VD through respective 10 k.OMEGA. resistors as shown in FIG. 62J. The D(0) through D(15) lines are coupled to pins 29, 31, 33, 35, 38, 40, 42, 44, 30, 32, 34, 36, 39, 41, 43, and 45, respectively, of the 29F400 chip as shown in FIGS. 62M and 62N. In addition, the D(0) through D(7) lines are coupled to pins 13, 14, 15, 17, 18, 19, 20, 21, respectively, of the first 61C1024 chip as shown in FIGS. 62Q and 62T. Furthermore, the D(8) through D(15) lines are coupled to pins 13, 14, 15, 17, 18, 19, 20, 21, respectively, of the second 61C1024 chip as shown in FIG. 62Q. As shown in FIG. 62S, the D(0) through D(15) lines are coupled to circuitry shown in the schematic of FIGS. 63A–63L as will be described in further detail below.

Figure 62U:
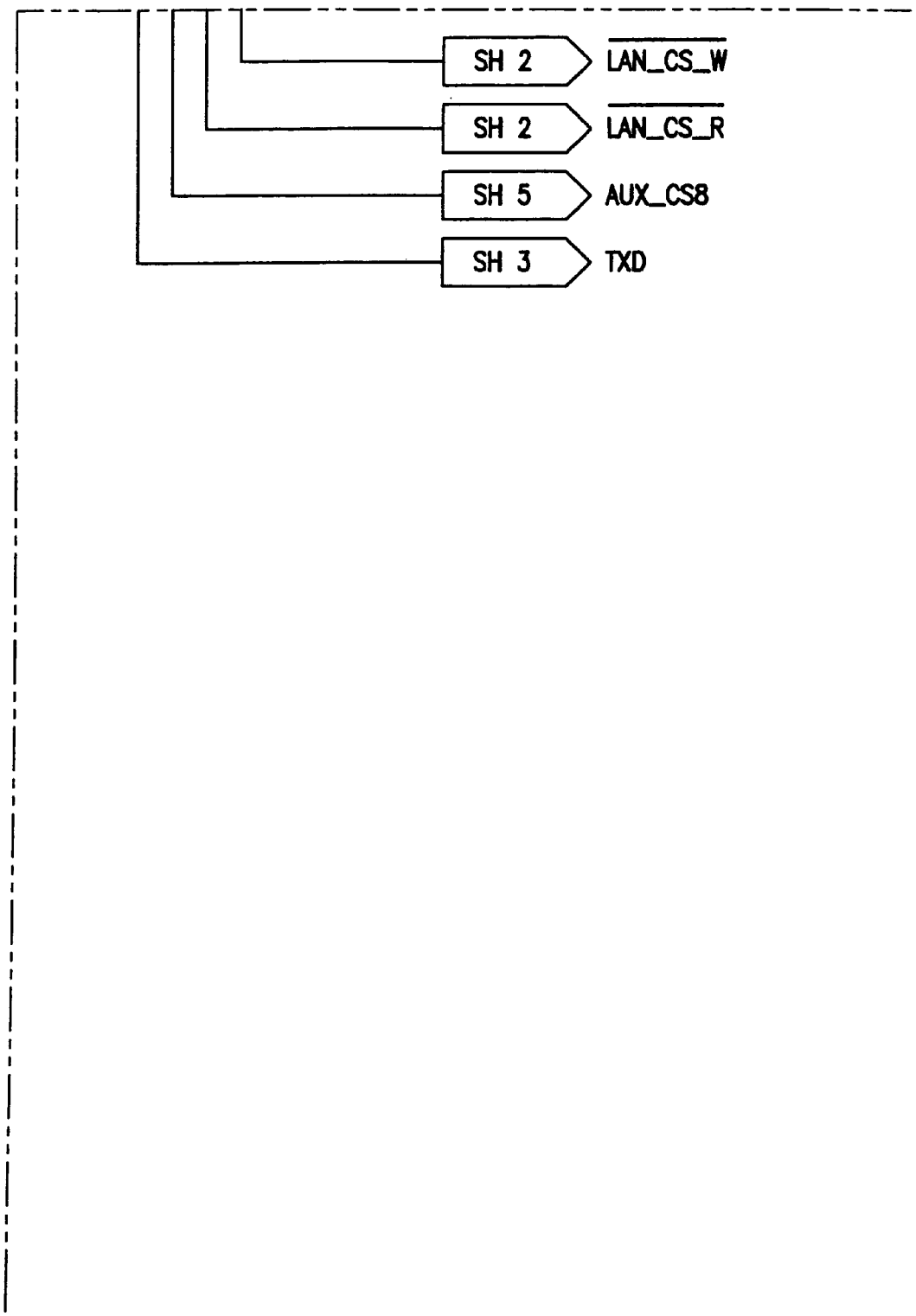

As shown in FIG. 62A, a +5 VD line and a DGND line from SH4 (i.e. FIGS. 65A–65L) provide +5 VD and DGND, respectively, for the circuitry of FIGS. 62A–62U. The +5 VD line is coupled to the DGND line through a 10 .mu.F capacitor as also shown in FIG. 62A. The +5 VD line and the DGND line are each coupled to circuitry shown in the schematic of FIGS. 63A–63L as will be described in further detail below.

Figure 63A:
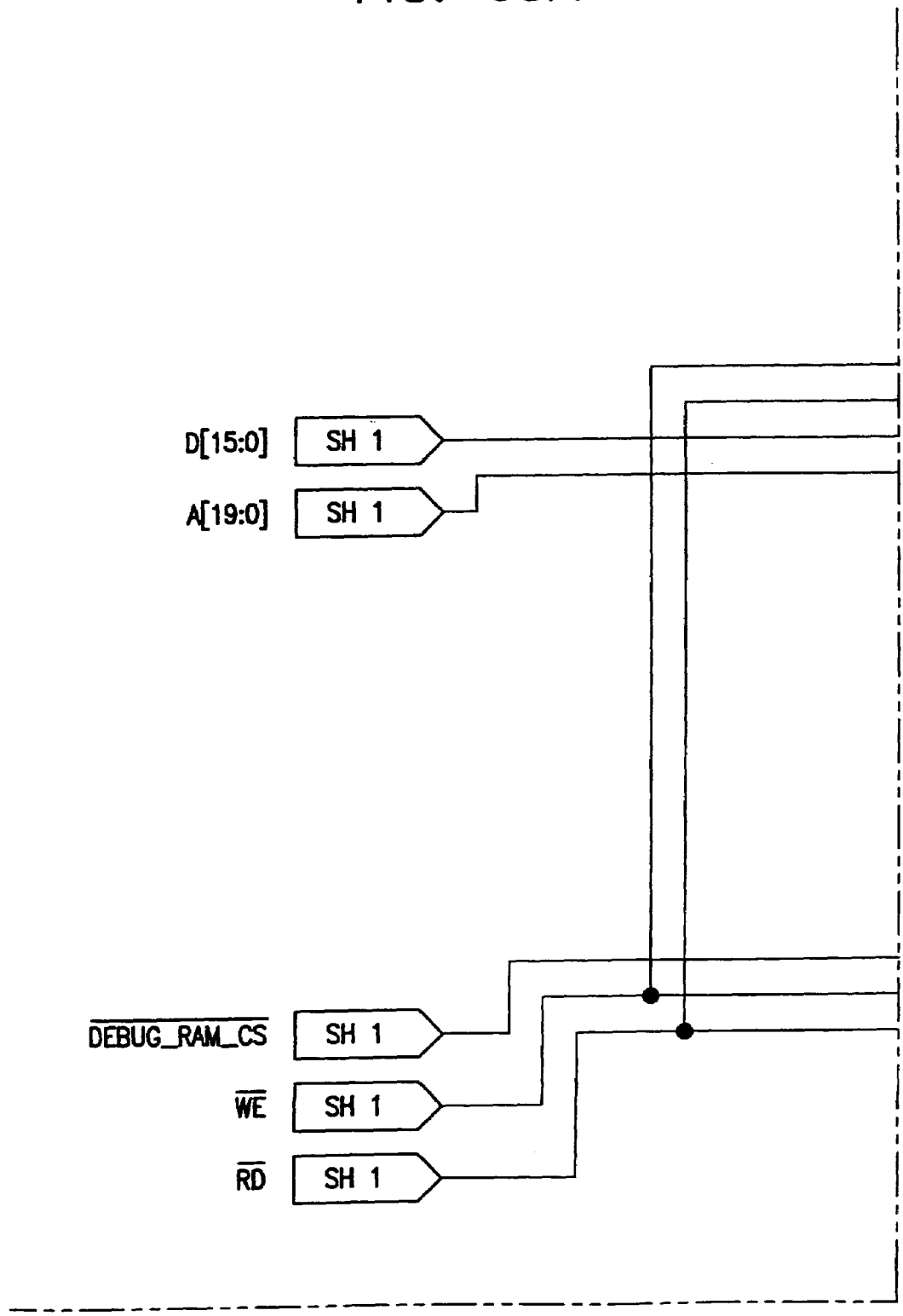
FIG. 63 is a circuit schematic map showing how to lay out FIGS. 63A–63L to form an electric circuit schematic of a second portion of the electric circuit of one of the master alarm controllers.
Figure 63C:
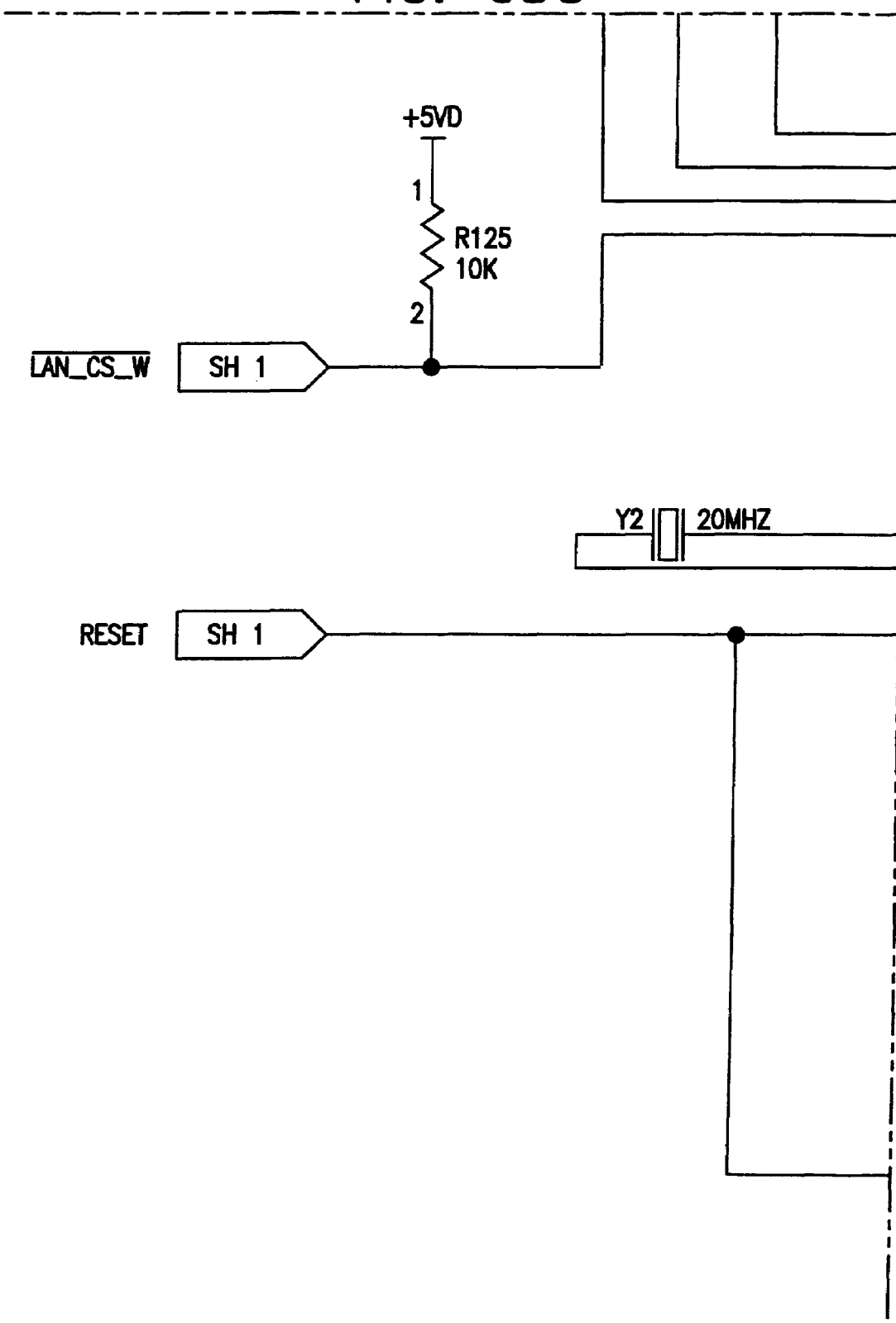
Figure 63D:
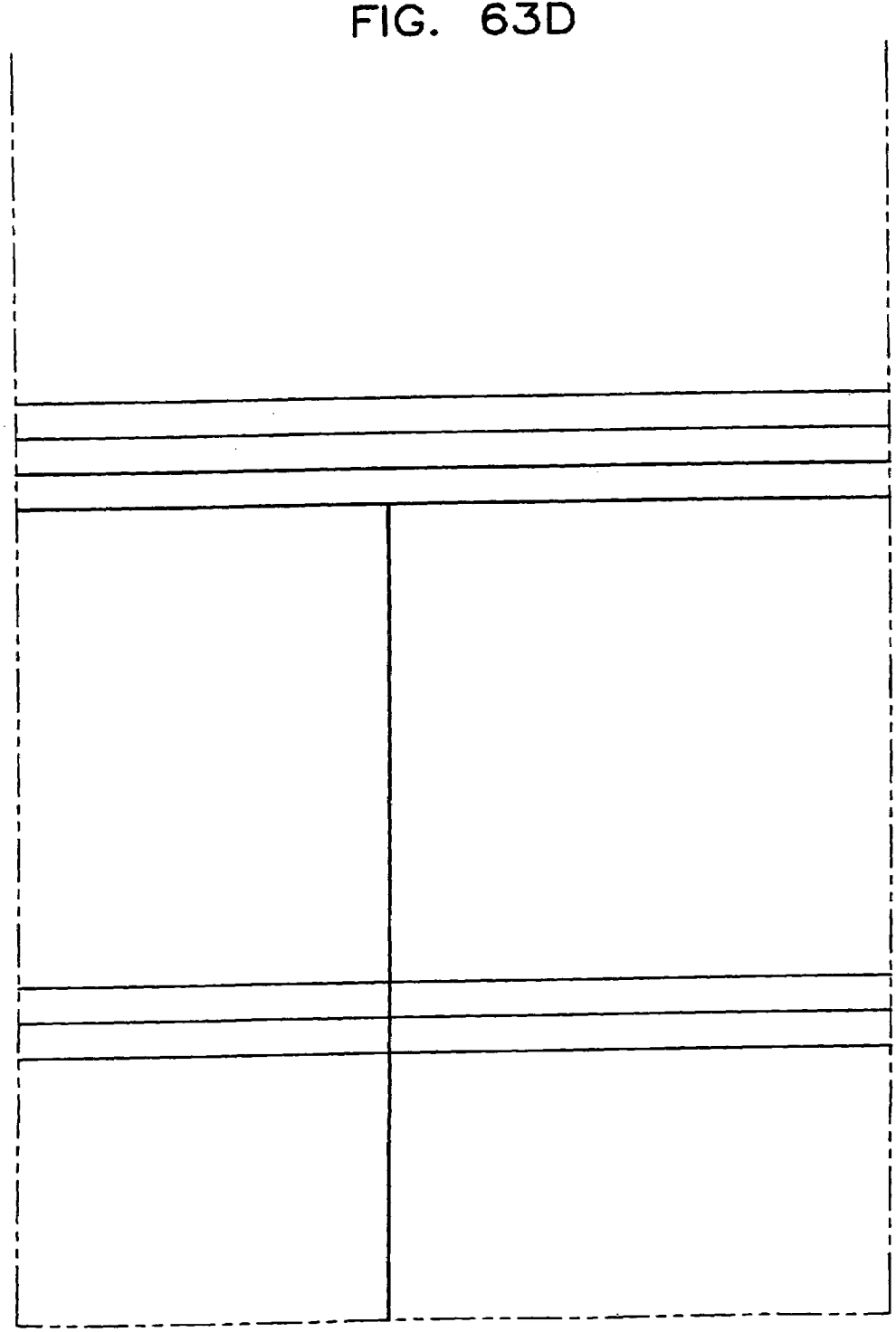
Figure 63F:
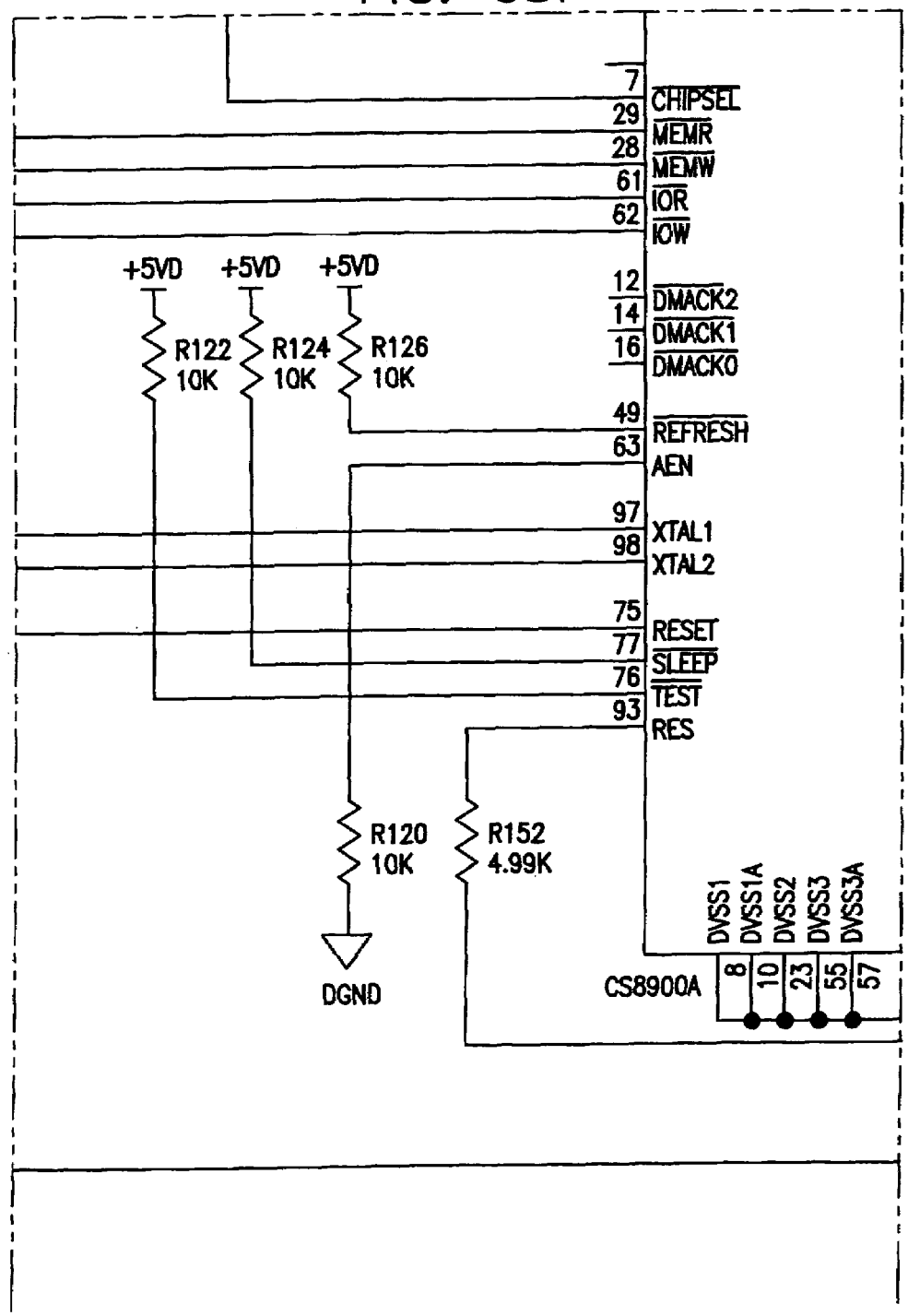
Figure 63G:
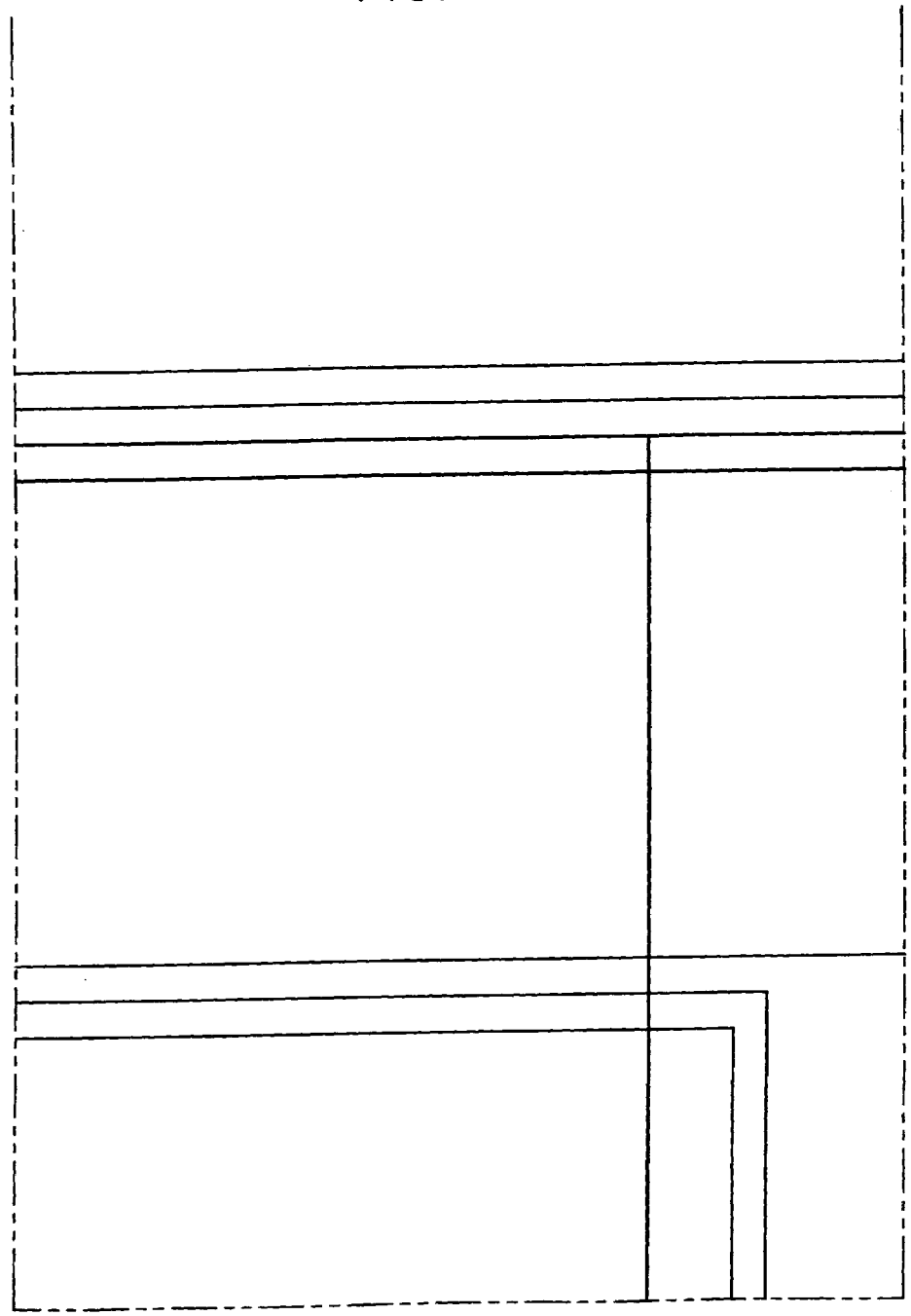
Figure 63H:
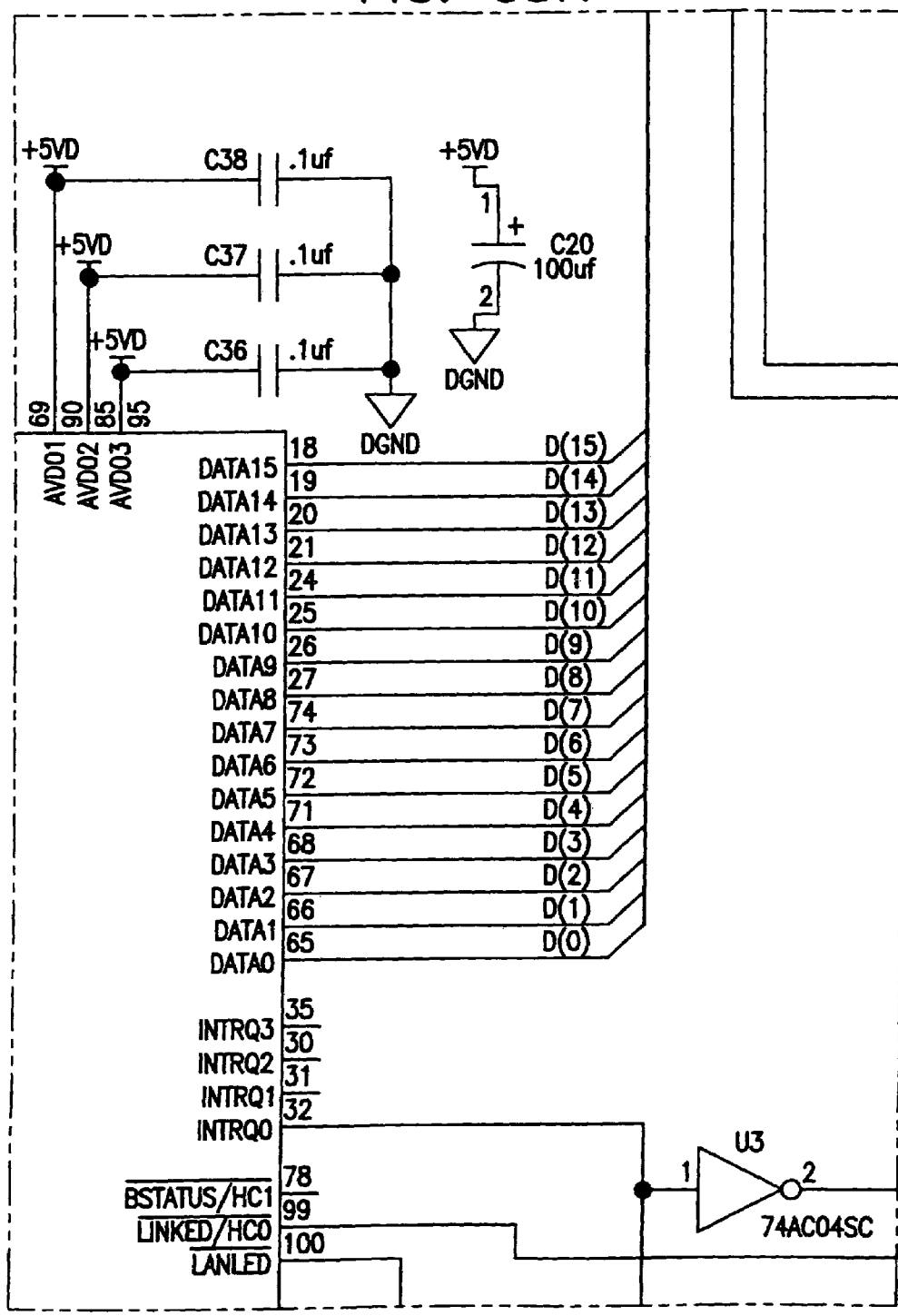
Figure 631:
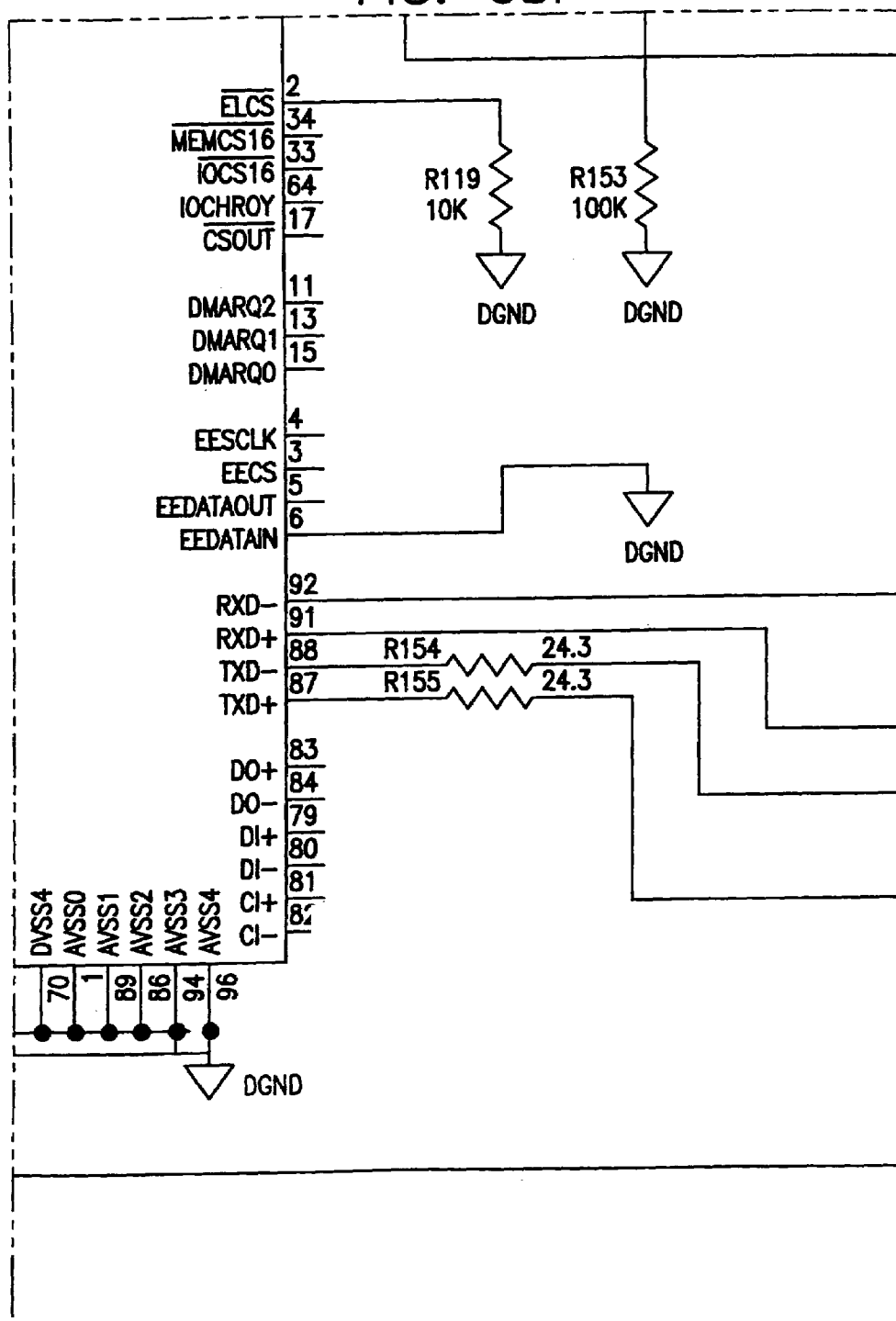

Referring now to the schematic of FIGS. 63A–63L, circuit 70 includes a CS8900A Ethernet LAN Controller chip made by Cirrus Logic, Inc. Pins 3, 4, 5, 11, 12, 13, 14, 15, 16, 17, 30, 31, 33, 34, 35, 64, 78, 79, 80, 81, 82, 83, and 84 of the CS8900A chip are open as shown in FIGS. 63F, 63H, and 63I. Pins 1, 8, 10, 23, 55, 57, 70, 89, 86, 94, and 96 of the CS8900A chip are each coupled to DGND as shown in FIGS. 63F and 63I. Pin 93 of the CS8900A chip is coupled to DGND through a 4.99 k.OMEGA. resistor as also shown in FIGS. 63F and 63I. Pins 9, 22, 56, 69, 85, 90, and 95 are each coupled directly to +5 VD and are each coupled to DGND through respective 0.1 .mu.F capacitors as shown in FIGS. 63E and 63H. Pin 6 of the CS8900A chip is coupled to DGND as shown in FIG. 63I and pin 60 of the CS8900A chip is coupled to DGND as shown in FIG. 63E.

A 100 .mu.F capacitor is coupled to +5 VD and to DGND as shown in FIG. 63H. As shown in FIG. 63B, the +5 VD line and the DGND line from SHI (i.e. FIGS. 62A–62U) provide +5 VD and DGND, respectively, for the circuitry of FIGS. 63A–63L. The +5 VD line and the DGND line are each coupled to circuitry shown in the schematic of FIGS. 64A–64Q as will be described in further detail below.

Pin 7 of the CS8900A chip is coupled to DGND through a 10 k.OMEGA. resistor as shown in FIGS. 63E and 63F. Pins 28 and 29 of the CS8900A chip are each coupled to +5 VD through respective 10 k.OMEGA. resistors as shown in FIGS. 63B, 63C, and 63F. Pin 2 of the CS8900A chip is coupled to DGND through a 10 k.OMEGA. resistor as shown in FIG. 63I. The notLAN_CS_R line is routed from the circuity of FIGS. 62A–62U to pin 61 of the CS8900A chip and the notLAN_CS_W line is routed from the circuity of FIGS. 62A–62U to pin 62 of the CS8900A chip as shown in FIGS. 63B, 63C, and 63F. In addition, pins 61 and 62 of the CS8900A chip are coupled to +5 VD through respective 10 k.OMEGA. resistors as also shown in FIGS. 63B, 63C, and 63F. Pins 49, 76, and 77 of the CS8900A chip are each coupled to +5 VD through a respective 10 k.OMEGA. resistor as shown in FIG. 63F. Pin 63 of the CS8900A chip is coupled to DGND through a 10 k.OMEGA. resistor as also shown in FIG. 63F.

Pin 97 of the CS8900A chip is coupled to one terminal of a 20 MHz clock and pin 98 of the CS8900A chip is coupled to the other terminal of the 20 MHz clock as shown in FIGS. 63C and 63F. The RESET line is routed from the circuitry of FIGS. 62A–62U and is coupled to pin 75 of the CS8900A chip as also shown in FIGS. 63C and 63F. A shown in FIG. 63L, the RESET line is coupled to circuitry shown in the schematic of FIGS. 64A–64Q as will be described in further detail below.

Figure 63J:
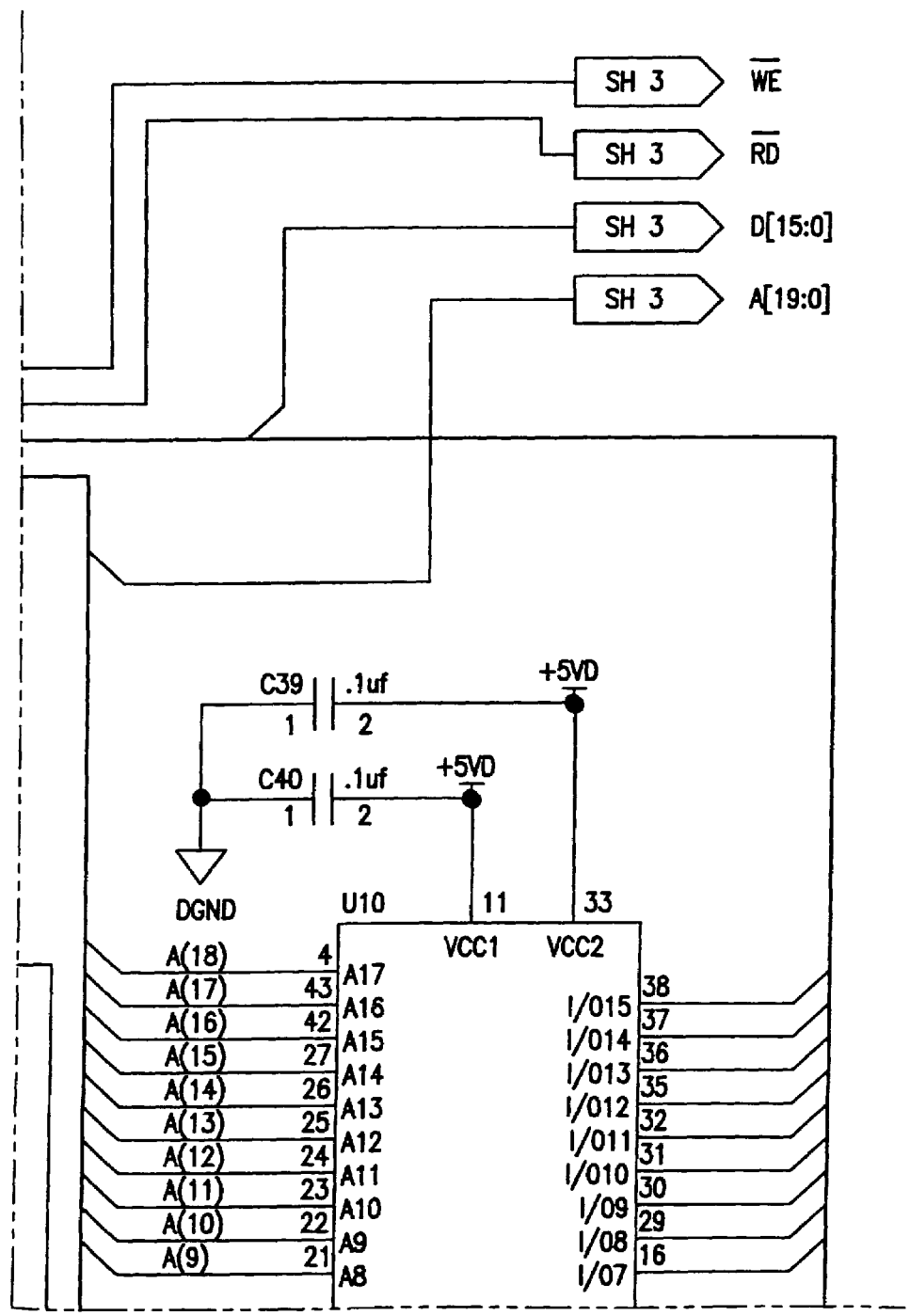
Figure 63K:
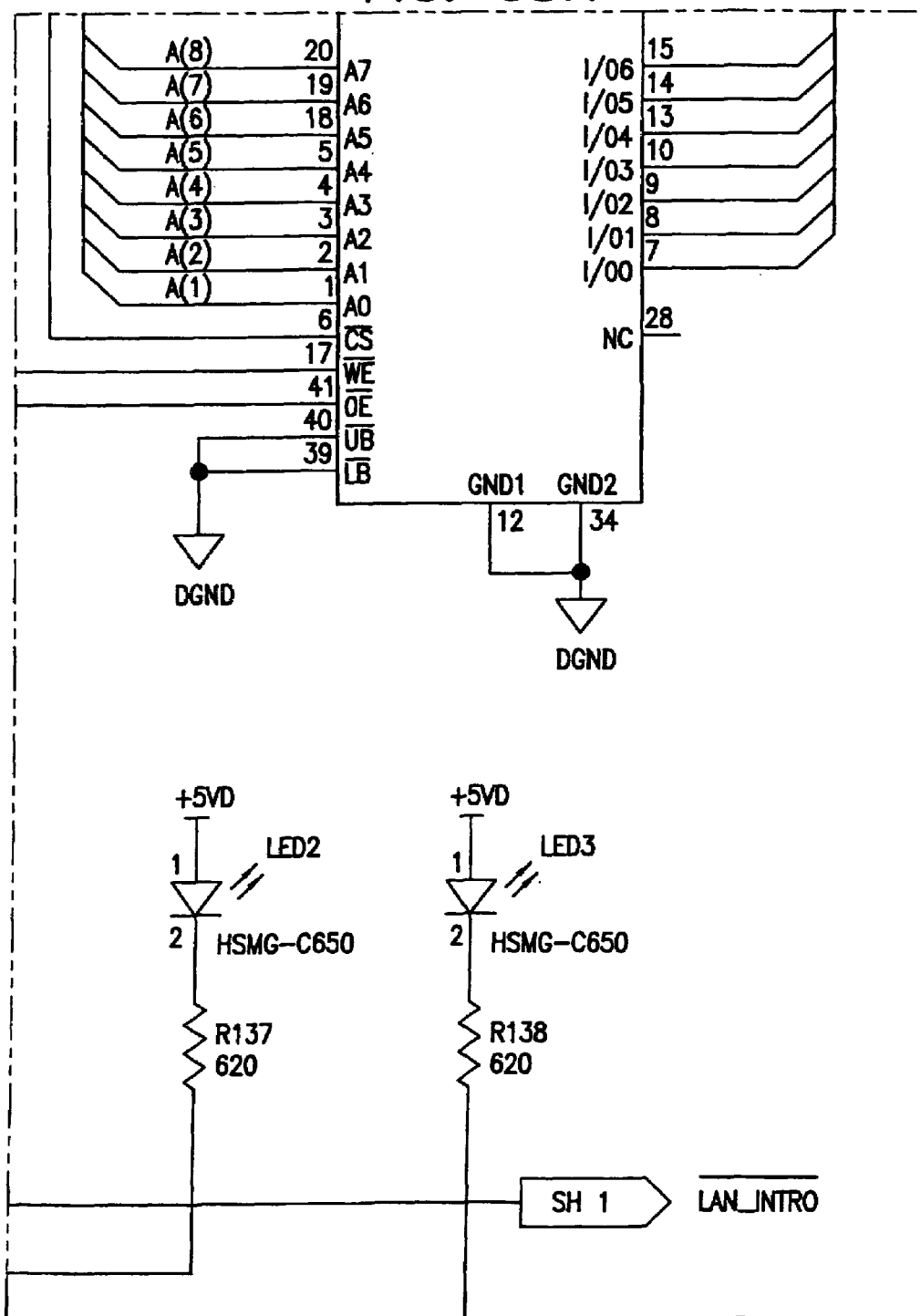
Figure 63L:
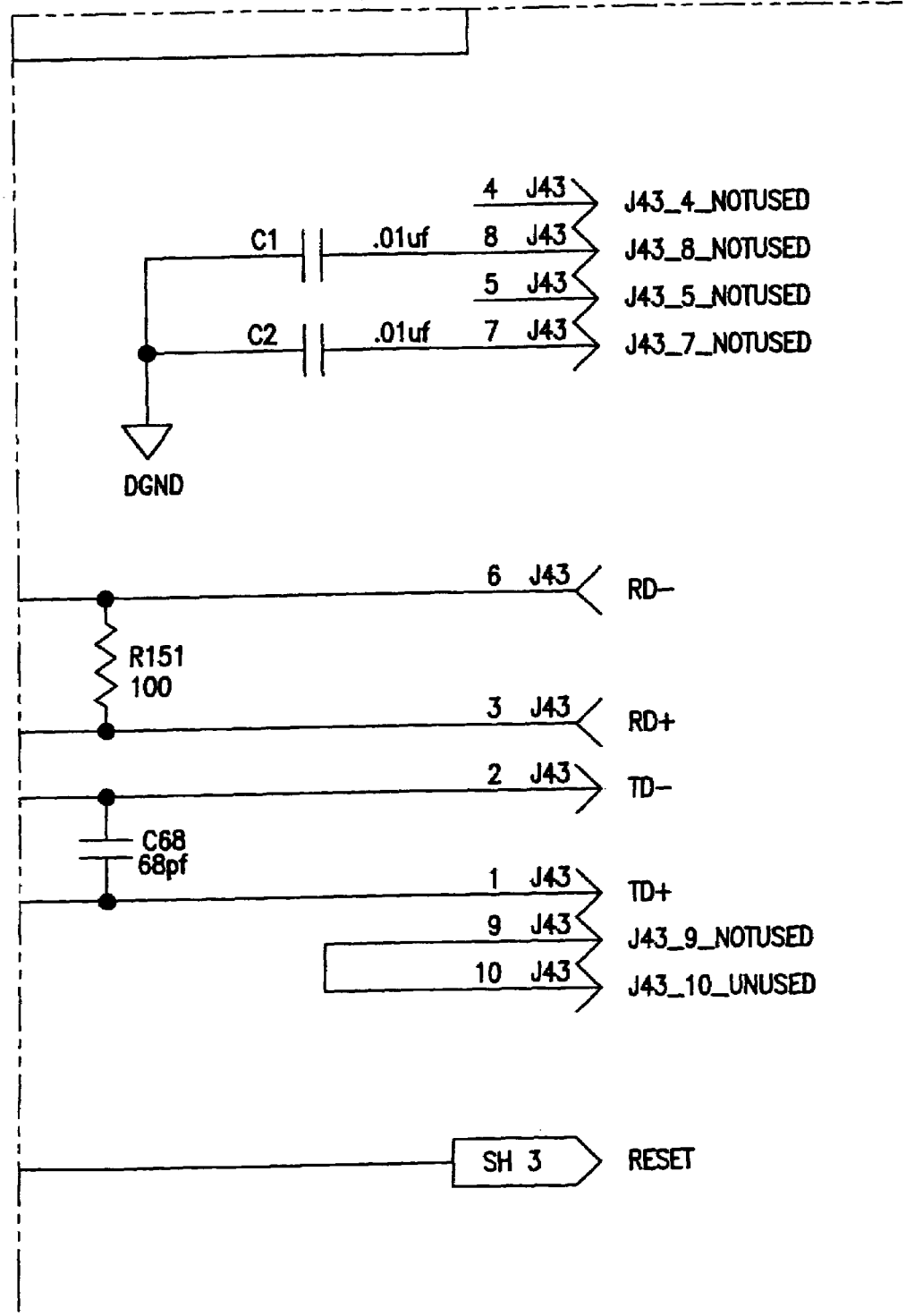

Pin 91 of the CS8900A chip is coupled to an RD+ line and pin 92 of the CS8900A chip is coupled to an RD− line as shown in FIGS. 63I and 63L. The RD+ line is coupled to the RD− line by a 100.OMEGA. resistor as shown in FIG. 63L. Pin 87 of the CS8900A chip is coupled to a TD+ line through a 24.3.OMEGA. resistor and pin 88 of the CS8900A chip is coupled to a TD− line through a 24.3.OMEGA. resistor as shown in FIGS. 63I and 63L. The TD+ line is coupled to the TD− line by a 68 pF capacitor as shown in FIG. 63L. The RD+, RD−, TD+, and TD− lines are coupled to pins 3, 6, 1, and 2, respectively, of a connector J43 as shown in FIG. 63L. Pins 4, 5, 7, 8, 9, and 10 of the connector J43 are not used. However, pins 9 and 10 of the connector J43 are shorted together and pins 7 and 8 of the connector J43 are each coupled to DGND through respective 0.01 .mu.F capacitors as shown in FIG. 63L. The connector J43 provides circuit 70 with communication port 152 through which data is transmitted by circuit 70 to network 14 and through which data is received by circuit 70 from network 14.

Pin 99 of the CS8900A chip is coupled to +5 VD through the series combination of a 620.OMEGA. resistor and a second HSMG-C650 LED as shown in FIGS. 63H and 63K. Pin 100 of the CS8900A chip is coupled to +5 VD through the series combination of a 620.OMEGA. resistor and a third HSMG-C650 LED as shown in FIGS. 63H, 63I, 63K, and 63L. The anode of each of the second and third HSMG-C650 LED's is coupled to +5 VD and the cathode of each of the second and third HSMG-C650 LED's is coupled to respective 620.OMEGA. resistors. Pin 32 of the CS8900A chip is coupled to pin 1 of the 74AC04SC hex inverter and is also coupled to DGND through a 100 k.OMEGA. resistor as shown in FIGS. 63H and 63I. Pin 2 of the 74AC04SC hex inverter is coupled to the notLAN_INTRO line which is, in turn, coupled to circuitry shown in the schematic of FIGS. 62A–62U.

The A(0) through A(18) lines from the circuitry of FIGS. 62A–62U are coupled to pins 37, 38, 39, 40, 41, 42, 43, 44, 45, 46, 47, 48, 50, 51, 52, 53, 54, 58, and 59, respectively, of the CS8900A chip as shown in FIGS. 63A, 63D, and 63E. In addition, the A(0) line is also coupled to pin 36 of the CS8900A chip as shown in FIG. 63E. The D(0) through D(15) lines from the circuitry of FIGS. 62A–62U are coupled to pins 65, 66, 67, 68, 71, 72, 73, 74, 27, 26, 25, 24, 21, 20, 19, and 18, respectively, of the CS8900A chip as shown in FIGS. 63A, 63D, 63G, and 63H.

Circuit 70 includes a K6R4016C1C SRAM chip made by Samsung Semiconductor, Inc. Pin 28 of the K6R4016C1C chip is open as shown in FIG. 63K. Pins 12, 34, 39, and 40 of the K6R4016C1C chip are each coupled to DGND as also shown in FIG. 63K. Pins 11 and 33 of the K6R4016C1C chip are each coupled directly to +5 VD and are each coupled to DGND through respective 0.1 .mu.F capacitors as shown in FIG. 63J. The A(1) through A(18) lines are coupled to pins 1, 2, 3, 4, 5, 18, 19, 20, 21, 22, 23, 24, 25, 26, 27, 42, 43, and 4, respectively, of the K6R4016C1C chip as shown in FIGS. 63J and 63K. The D(0) through D(15) lines are coupled to pins 7, 8, 9, 10, 13, 14, 15, 16, 29, 30, 31, 32, 35, 36, 37, and 38, respectively, of the K6R4016C1C chip as also shown in FIGS. 63J and 63K. The notDEBUG_RAM_CS, the notWE, and the notRD lines from the circuitry of FIGS. 62A–62U are coupled to pins 6, 17, and 41, respectively, of the K6R4016C1C chip as shown in FIGS. 63A, 63D, 63G, 63J, and 63K. Each of the A(0) through A(19) lines, the D(0) through D(15) lines, the notWE line, and the notRD line are coupled to circuitry shown in the schematic of FIGS. 64A–64Q as will be described in further detail below.

Figure 64A:
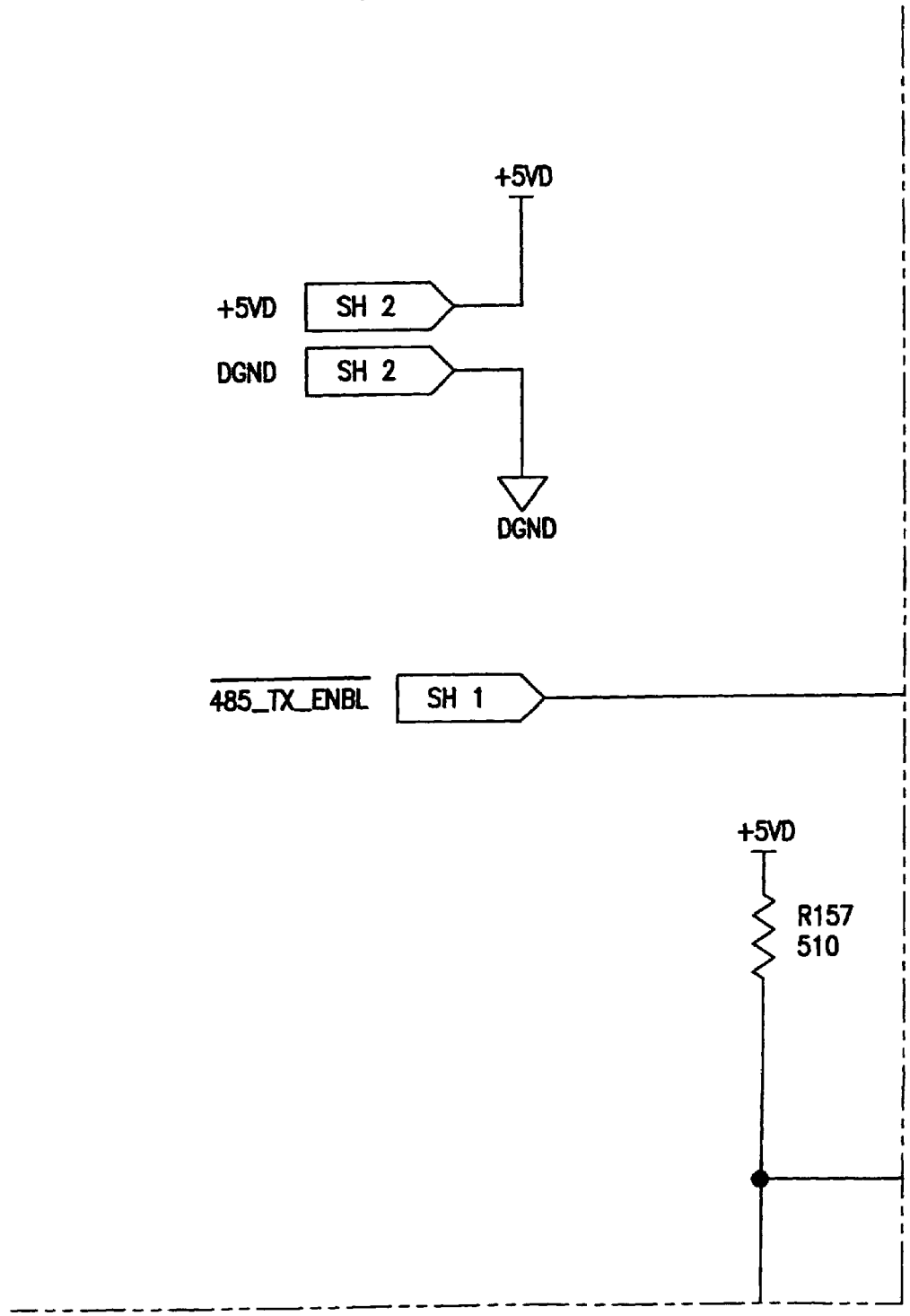
FIG. 64 is a circuit schematic map showing how to lay out FIGS. 64A–64Q to form an electric circuit schematic of a third portion of the electric circuit of one of the master alarm controllers.
Figure 64B:
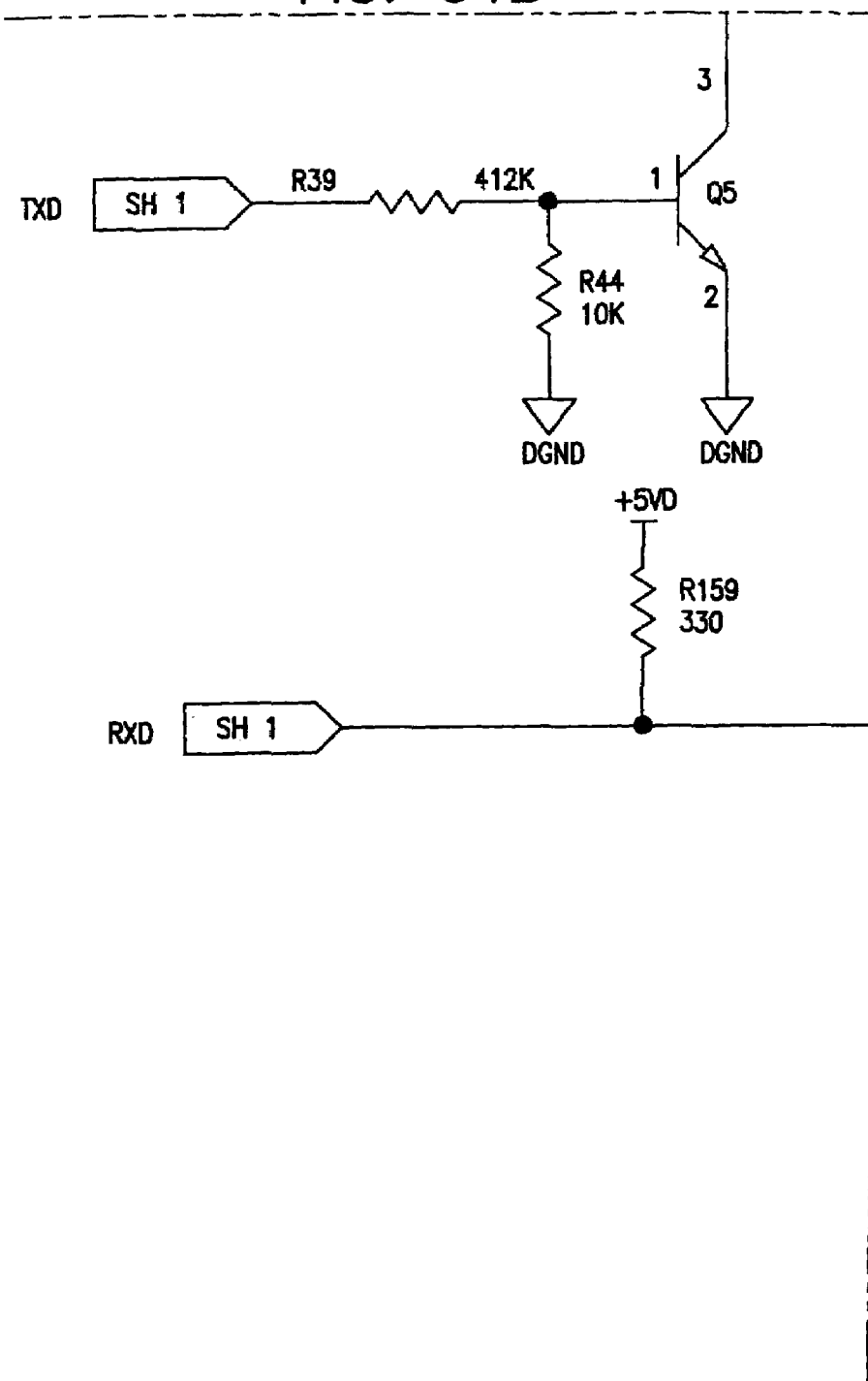
Figure 64C:
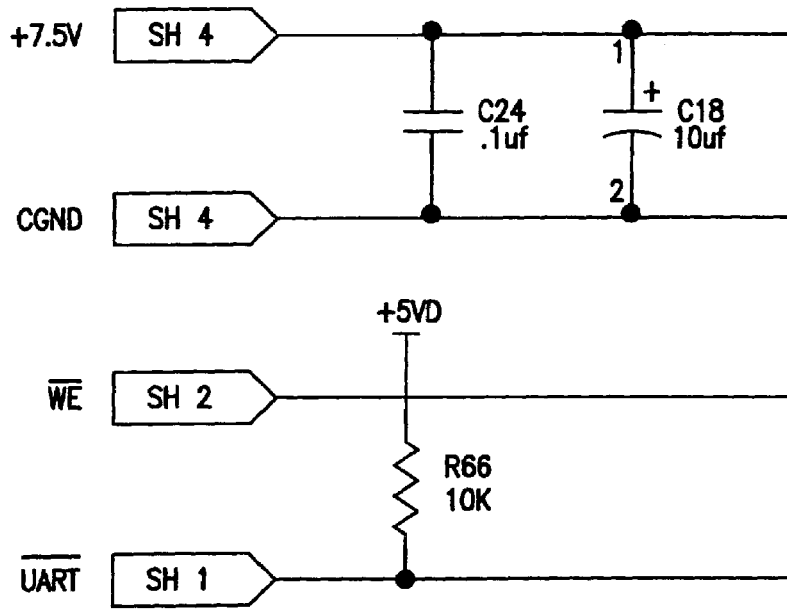
Figure 64D:
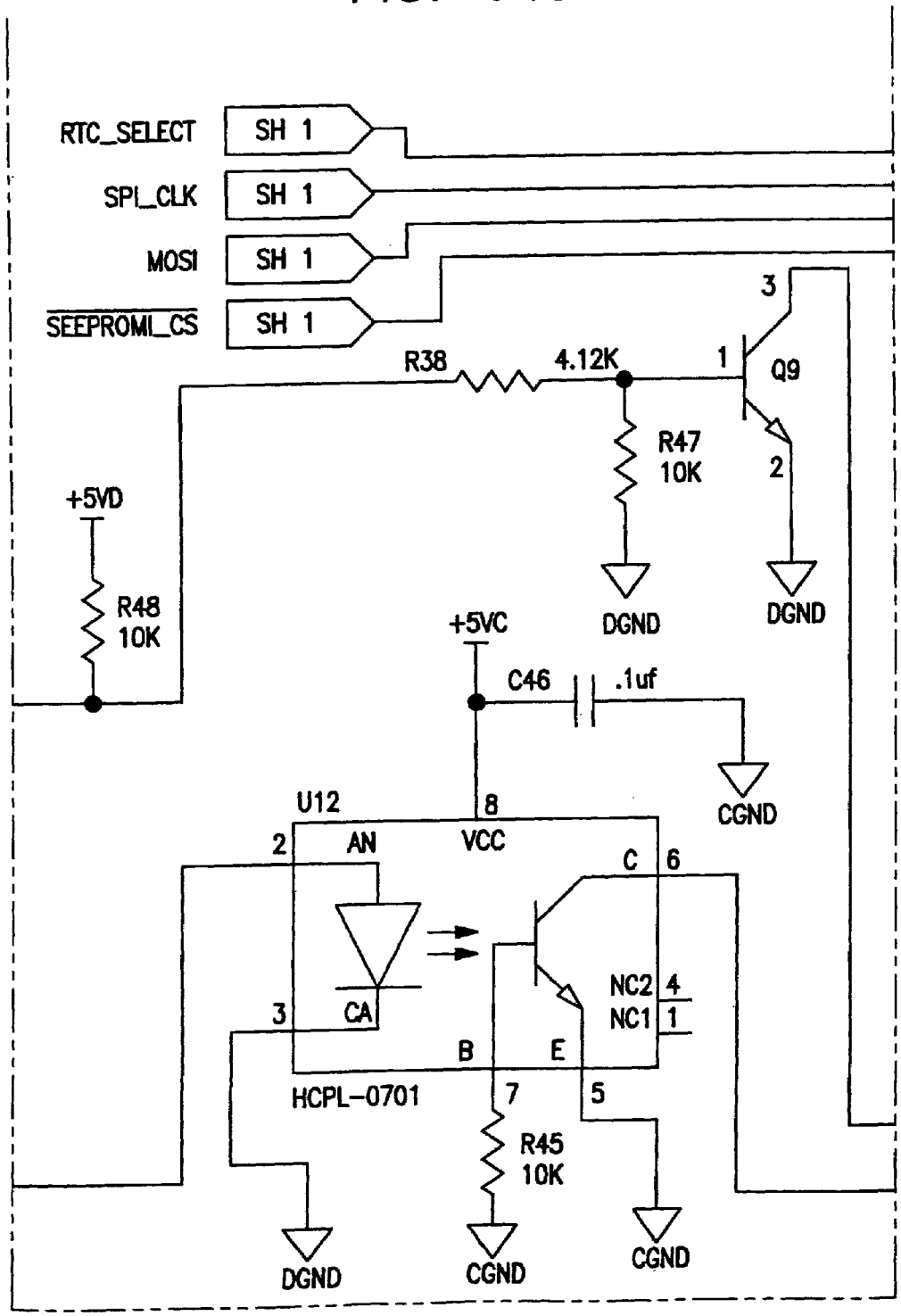
Figure 64E:
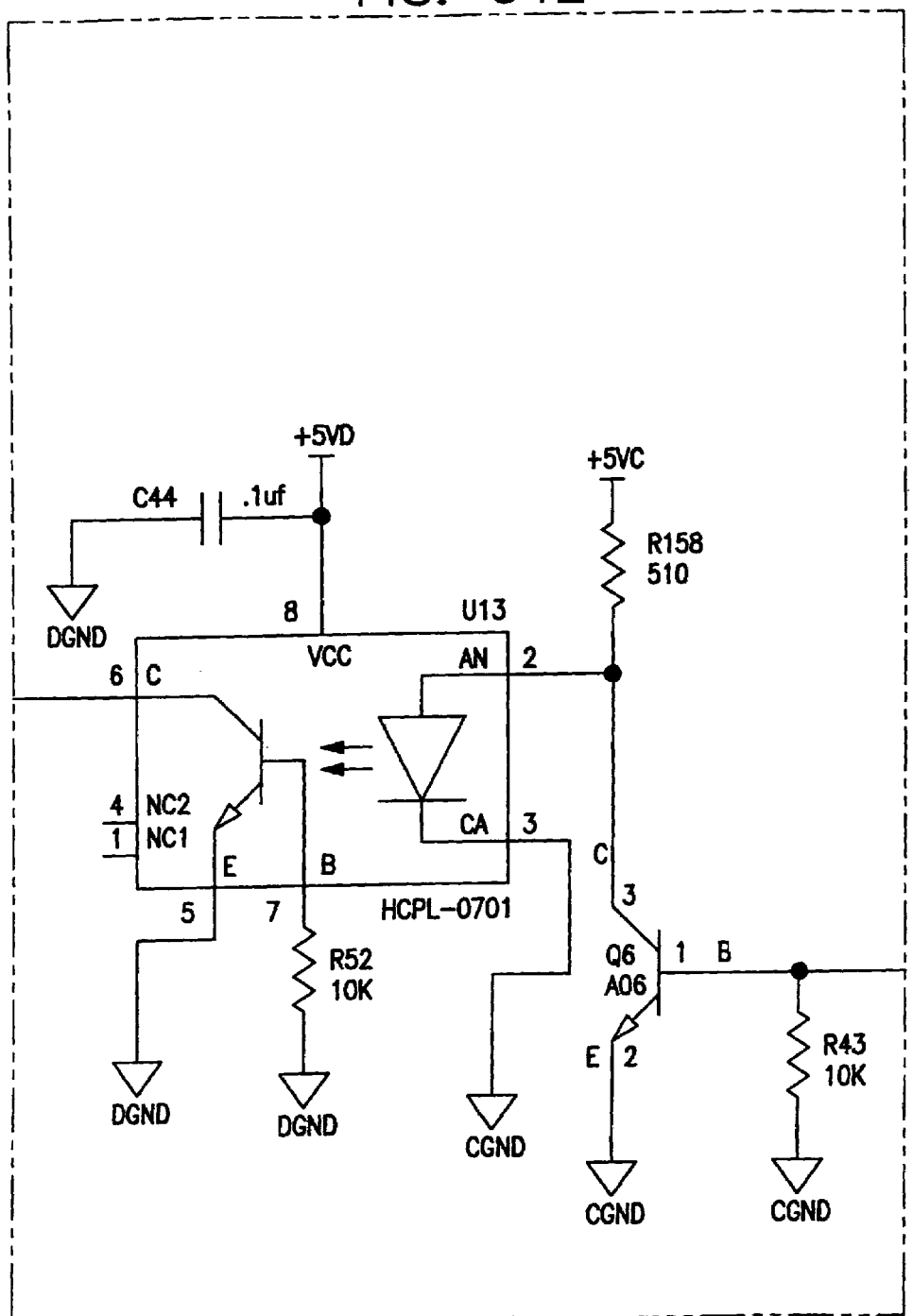
Figure 64F:
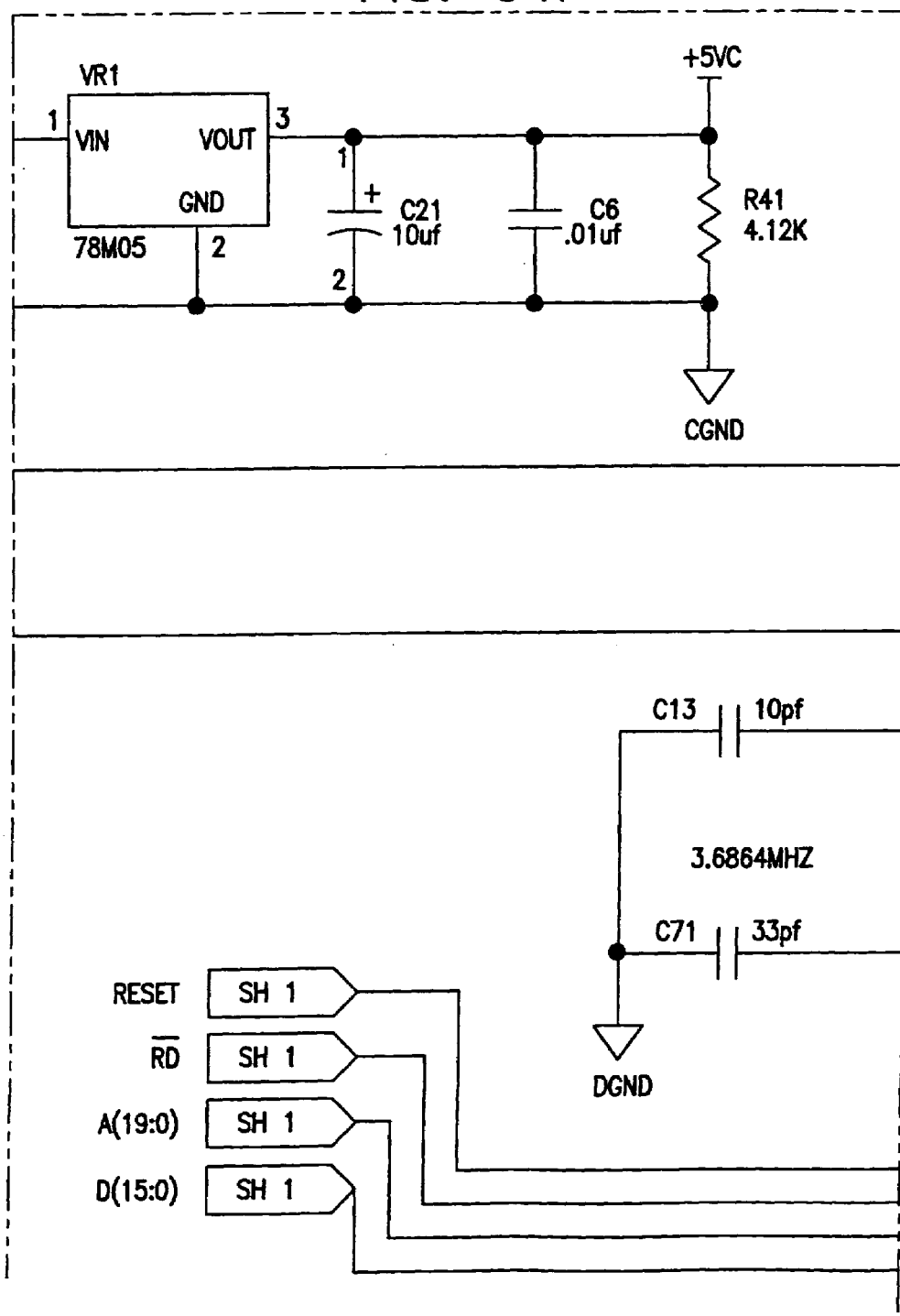
Figure 64G:
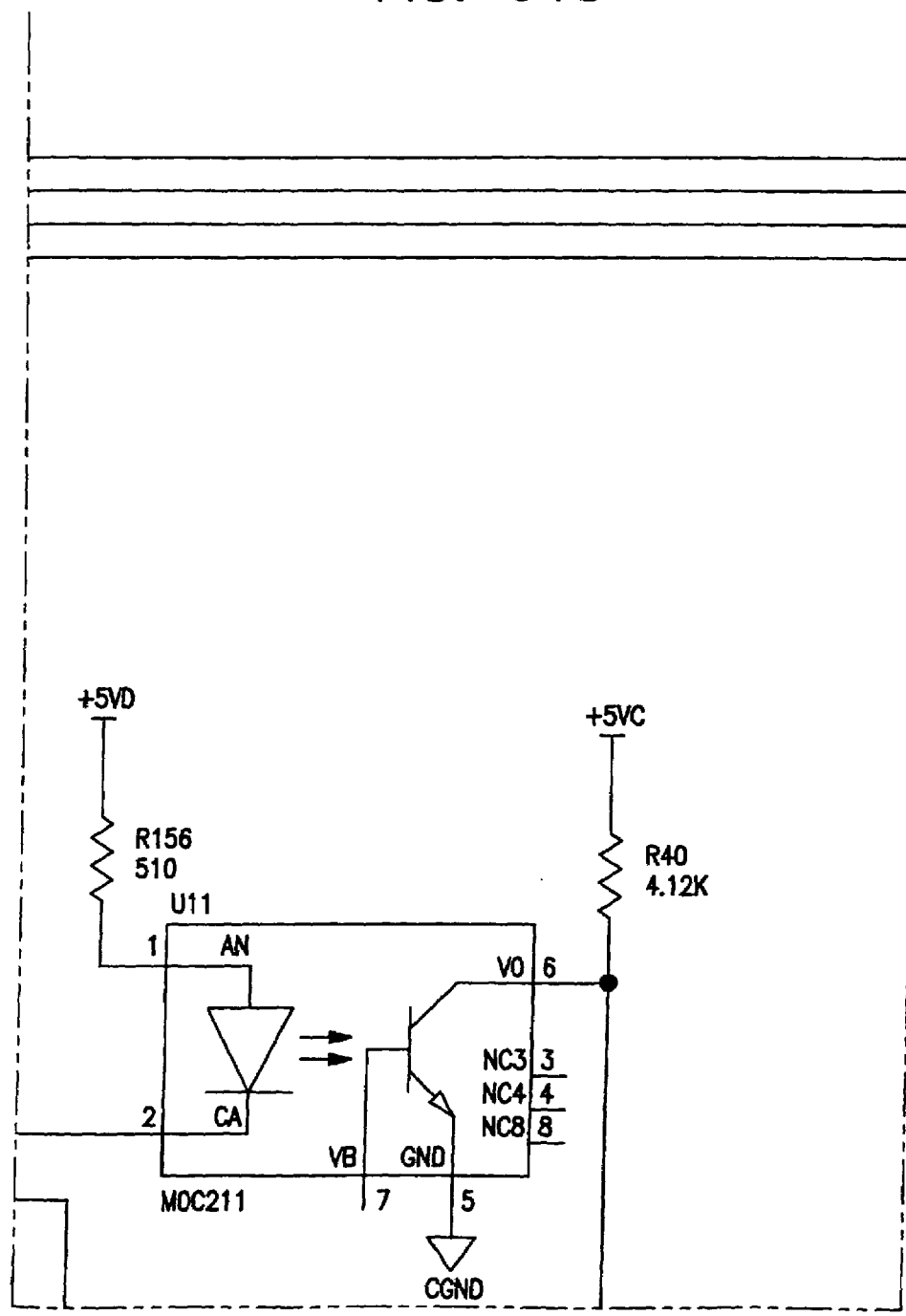
Figure 64H:
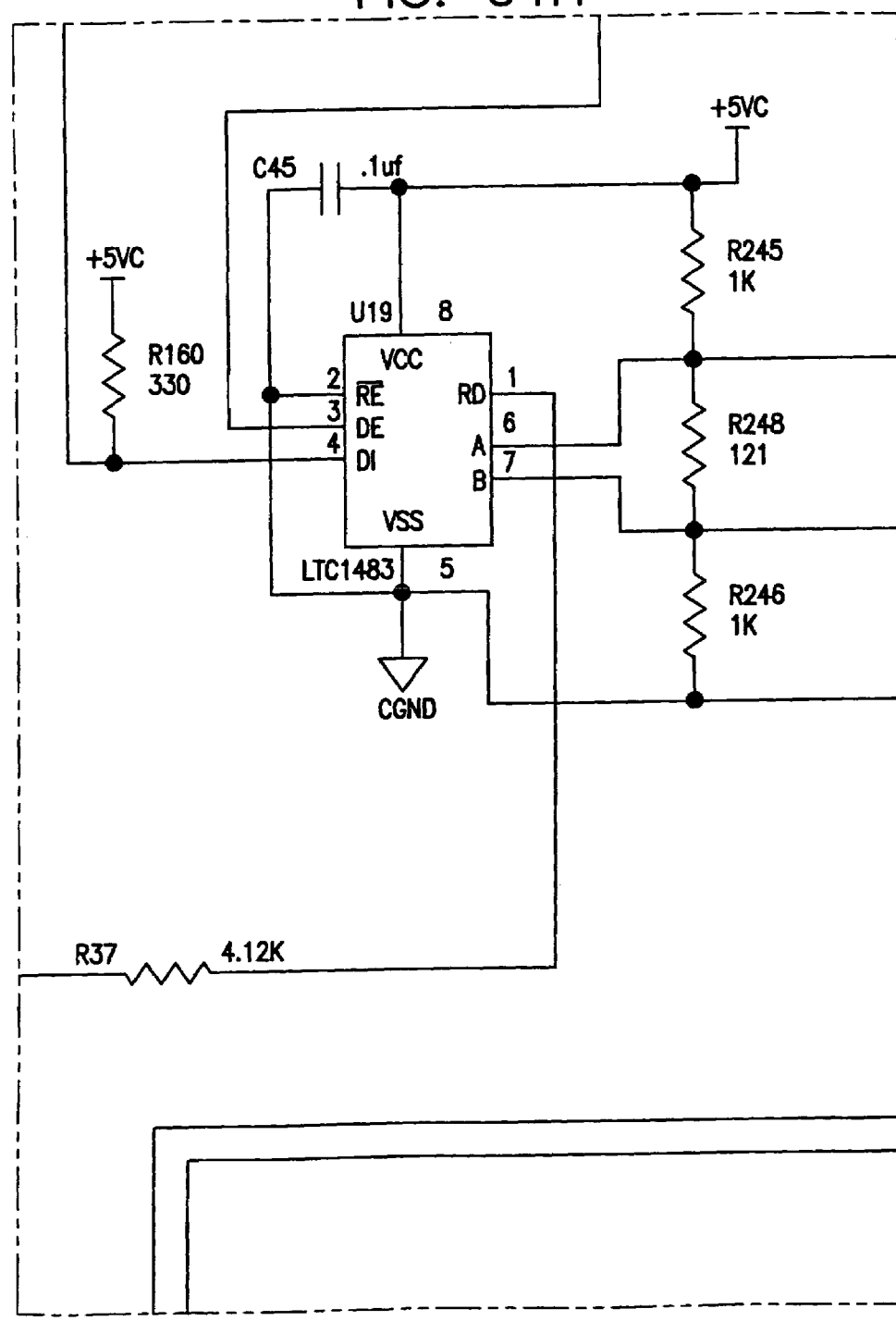
Figure 641:
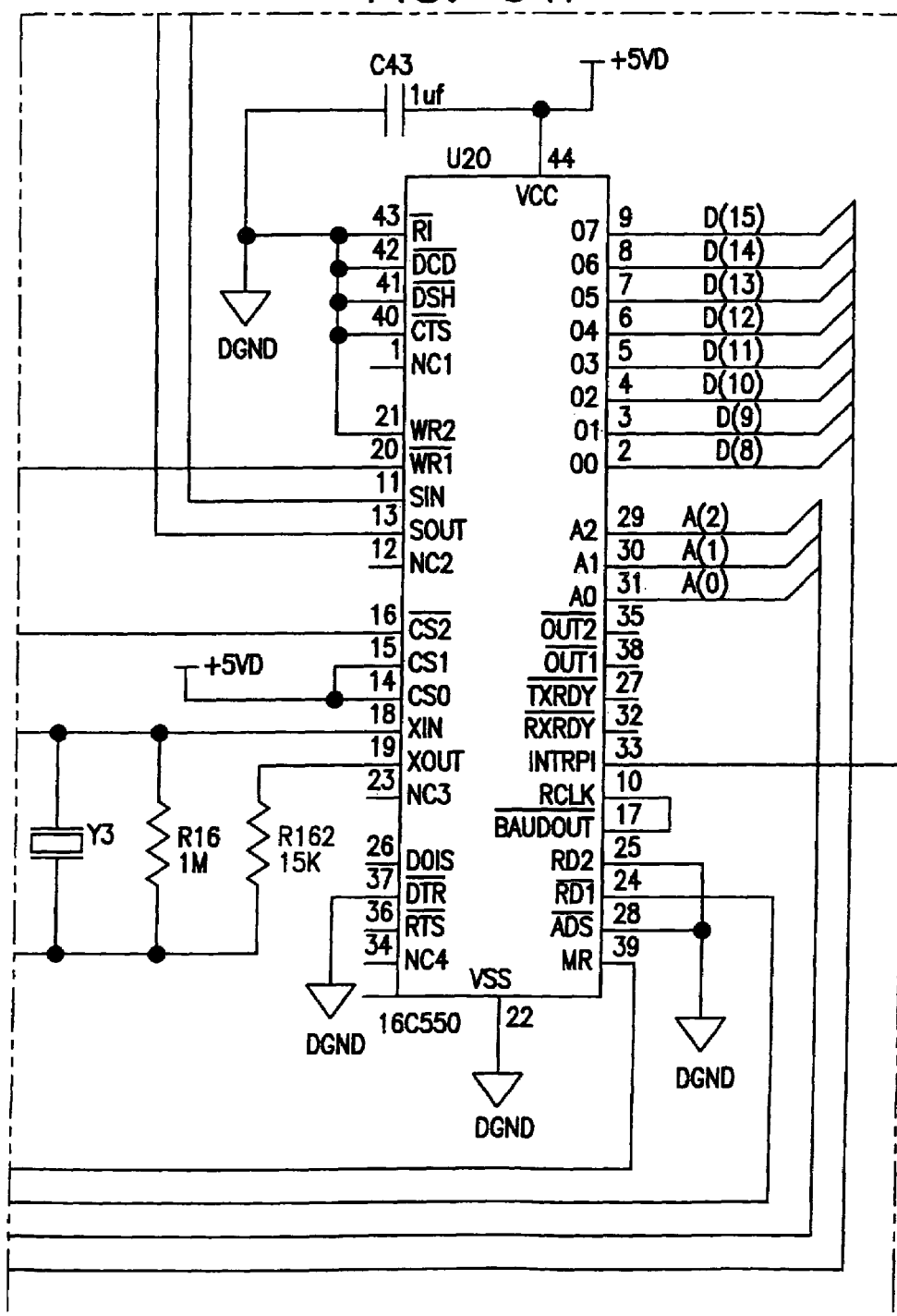
Figure 64J:
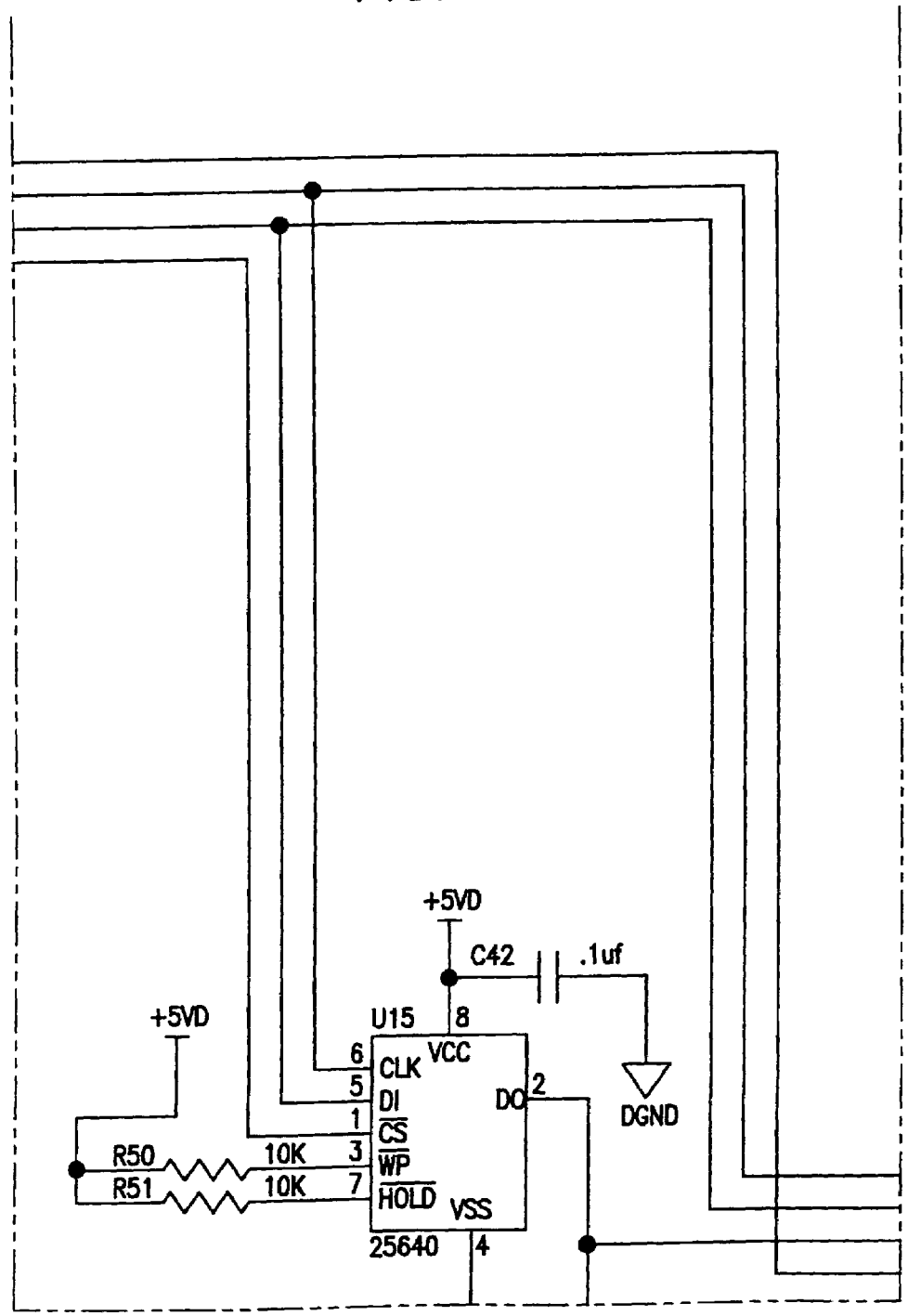
Figure 64K:
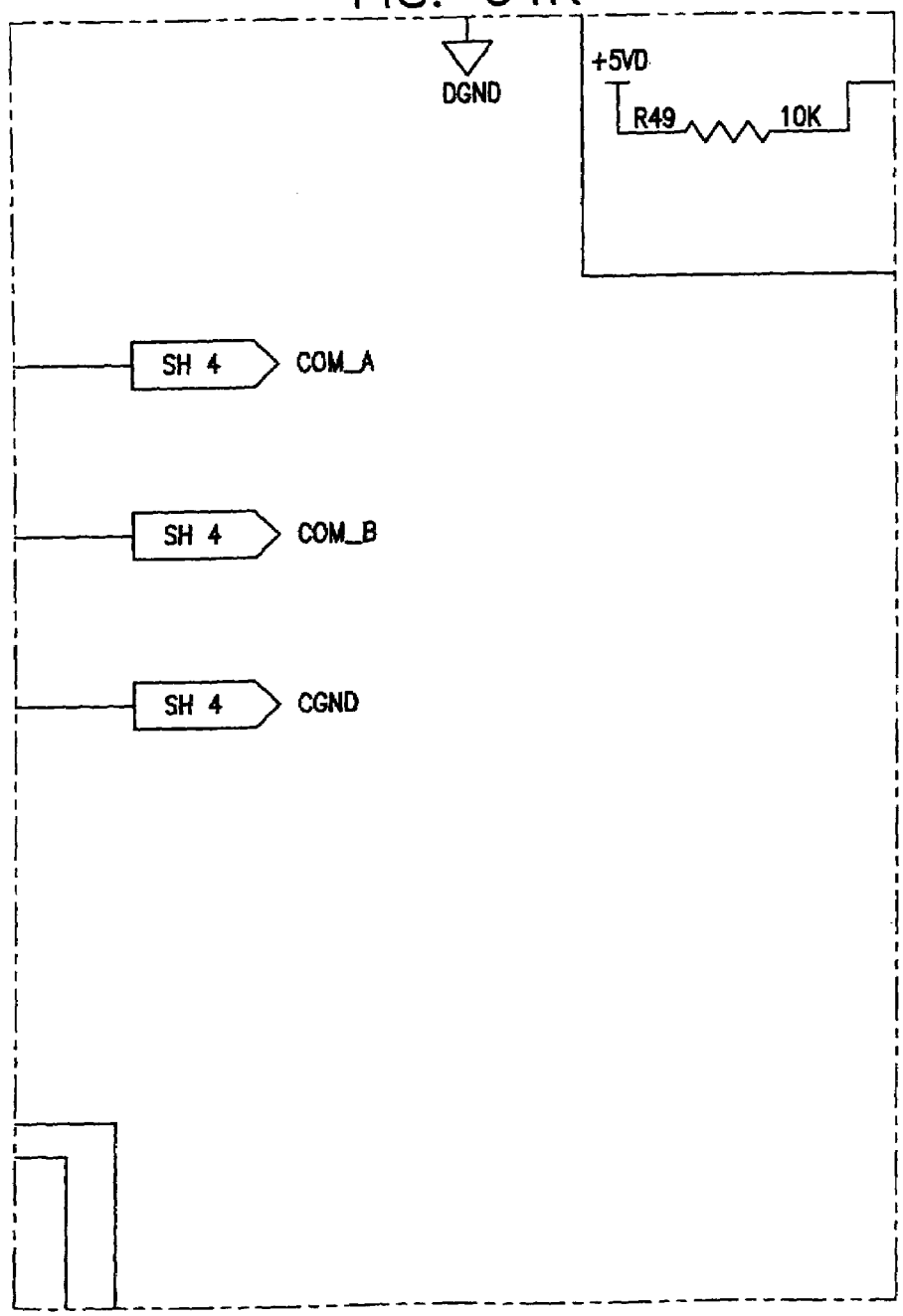
Figure 64L:
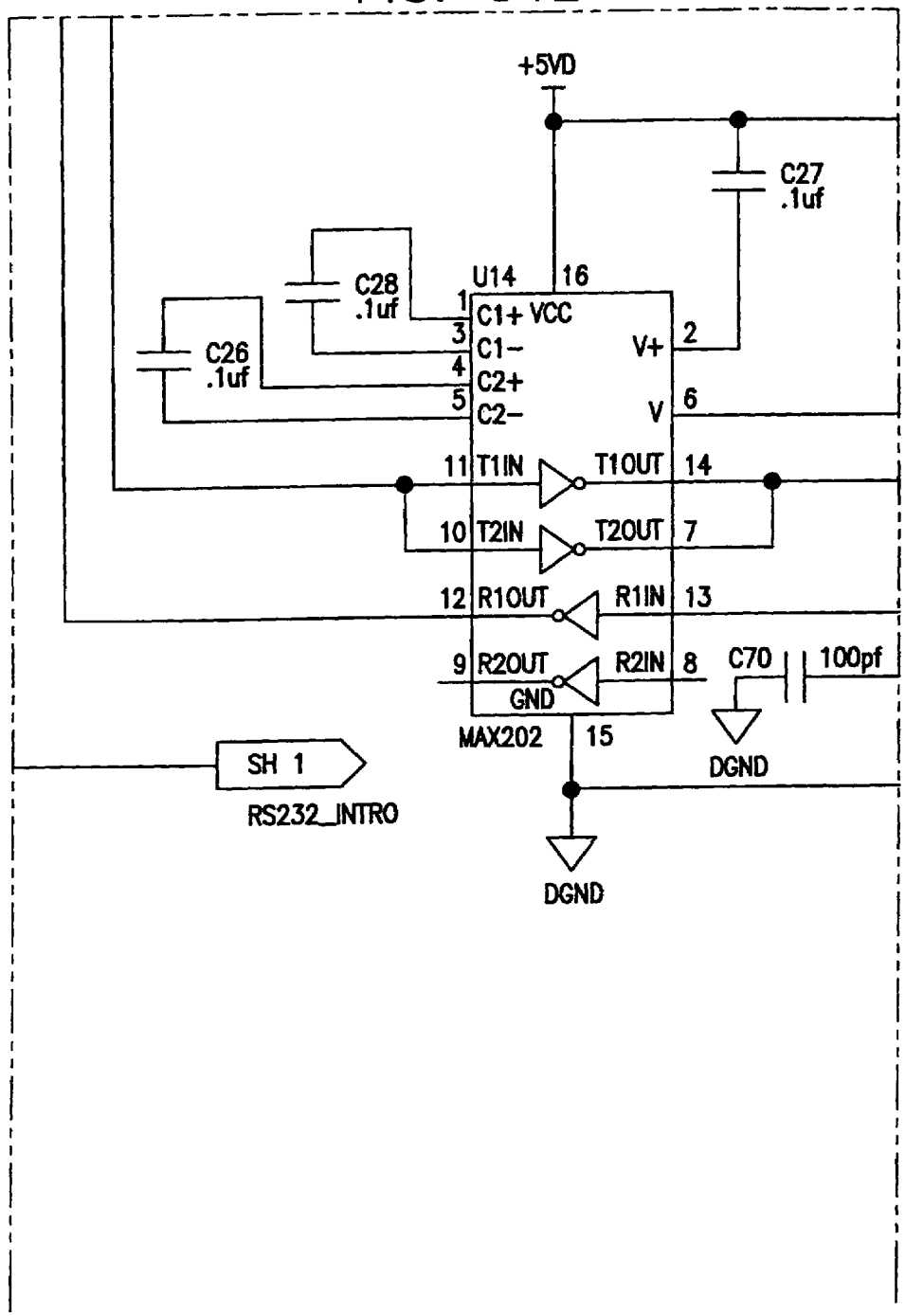
Figure 64M:
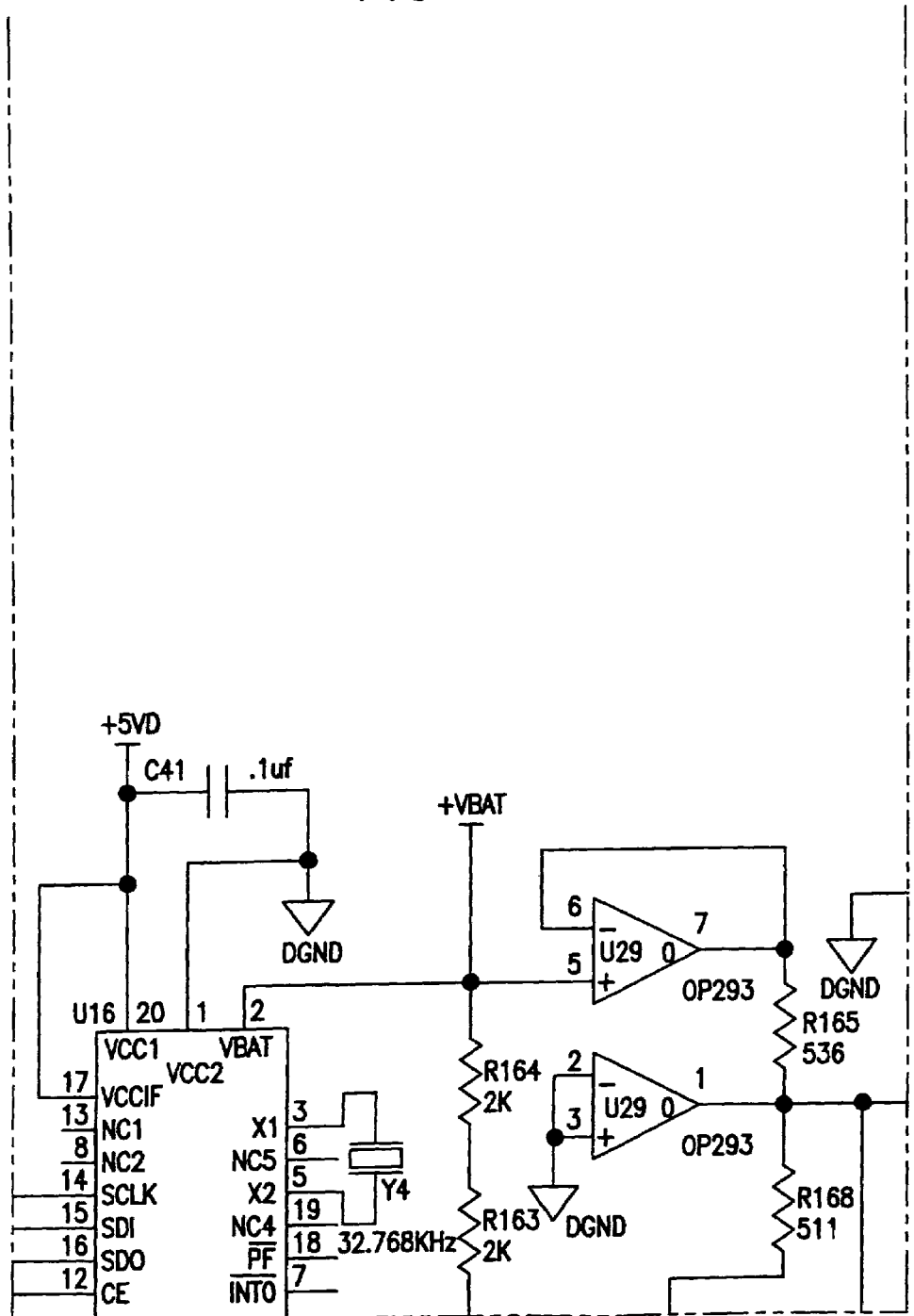
Figure 64N:
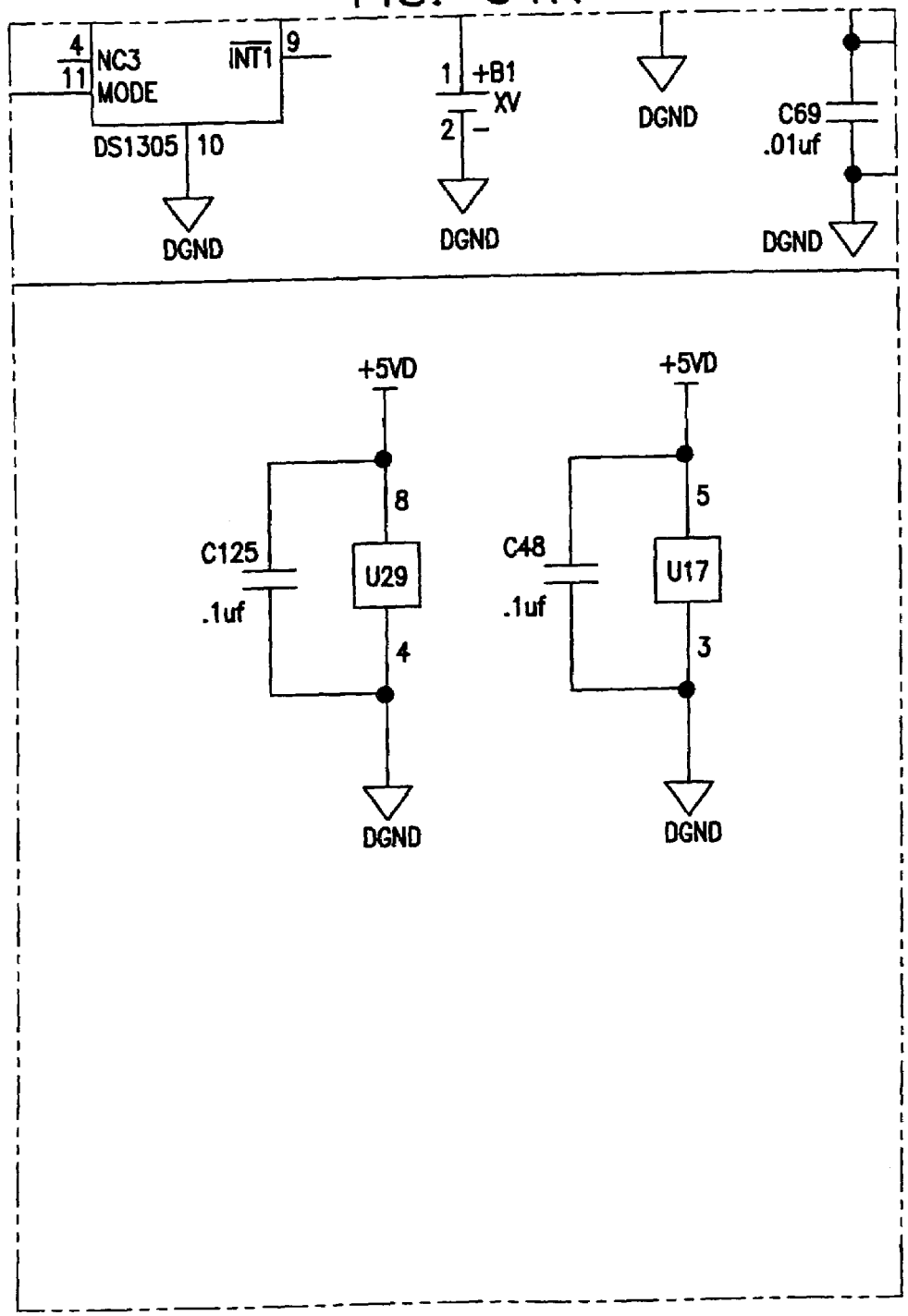
Figure 640:
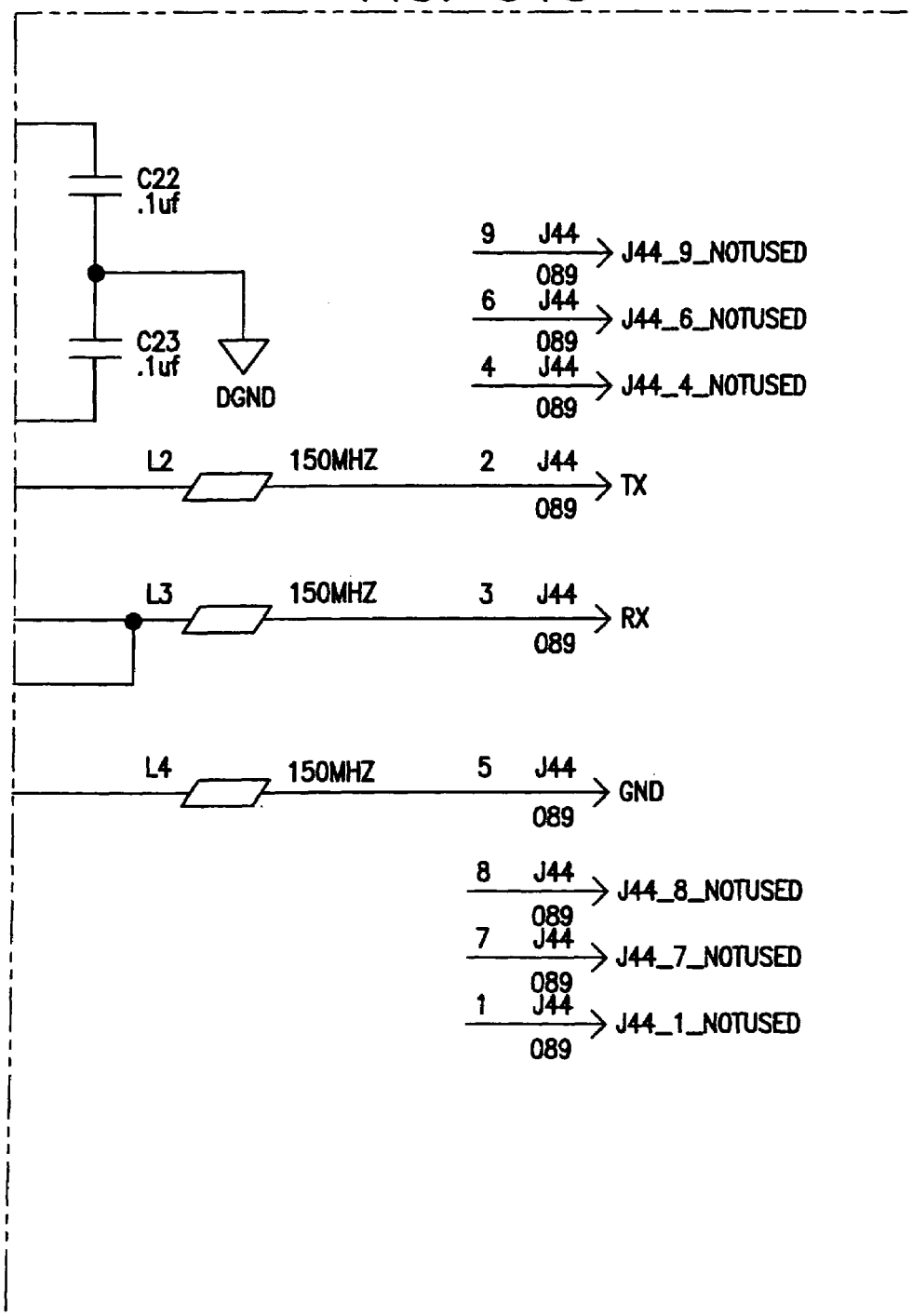
Figure 64P:
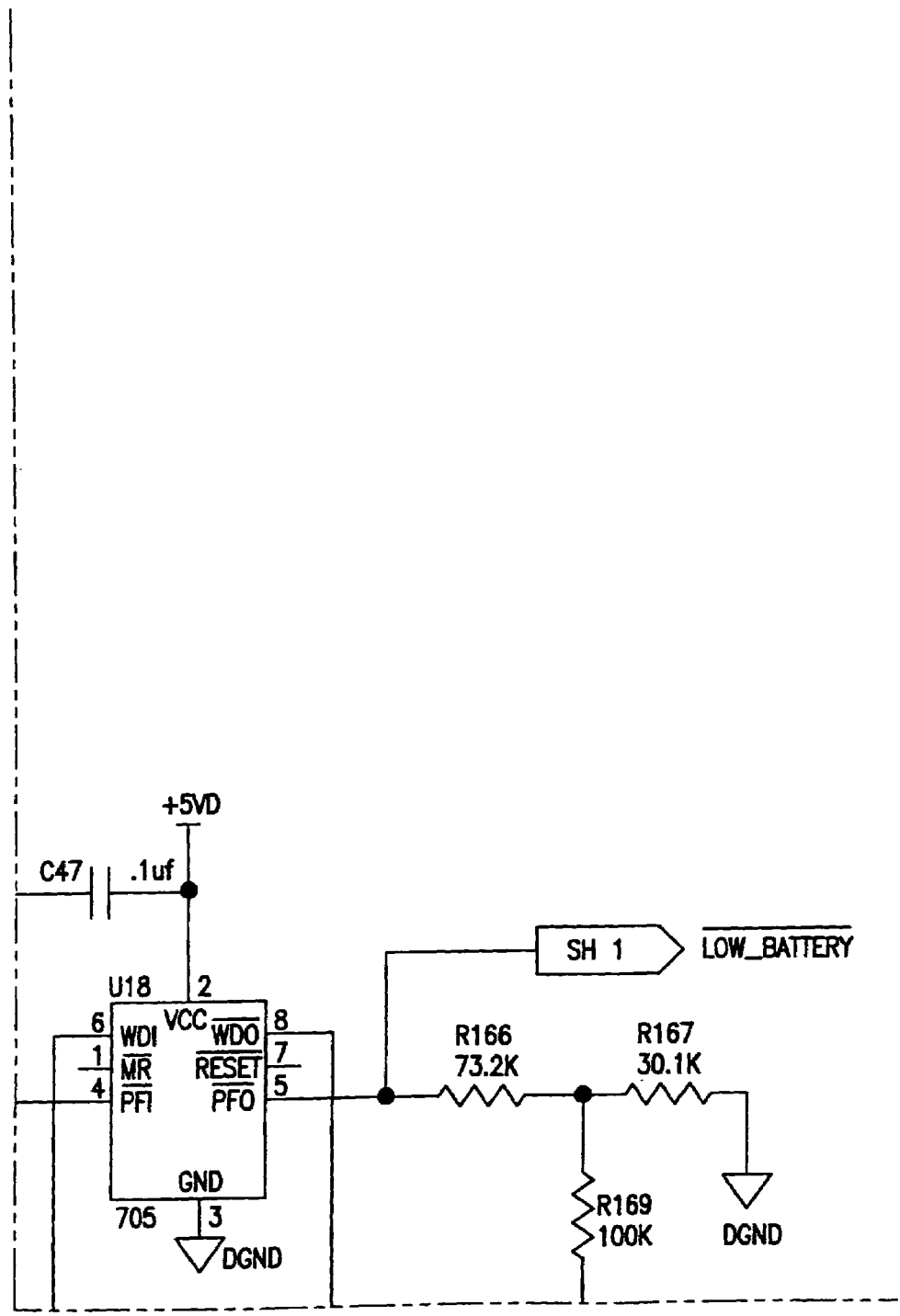
Figure 64Q:
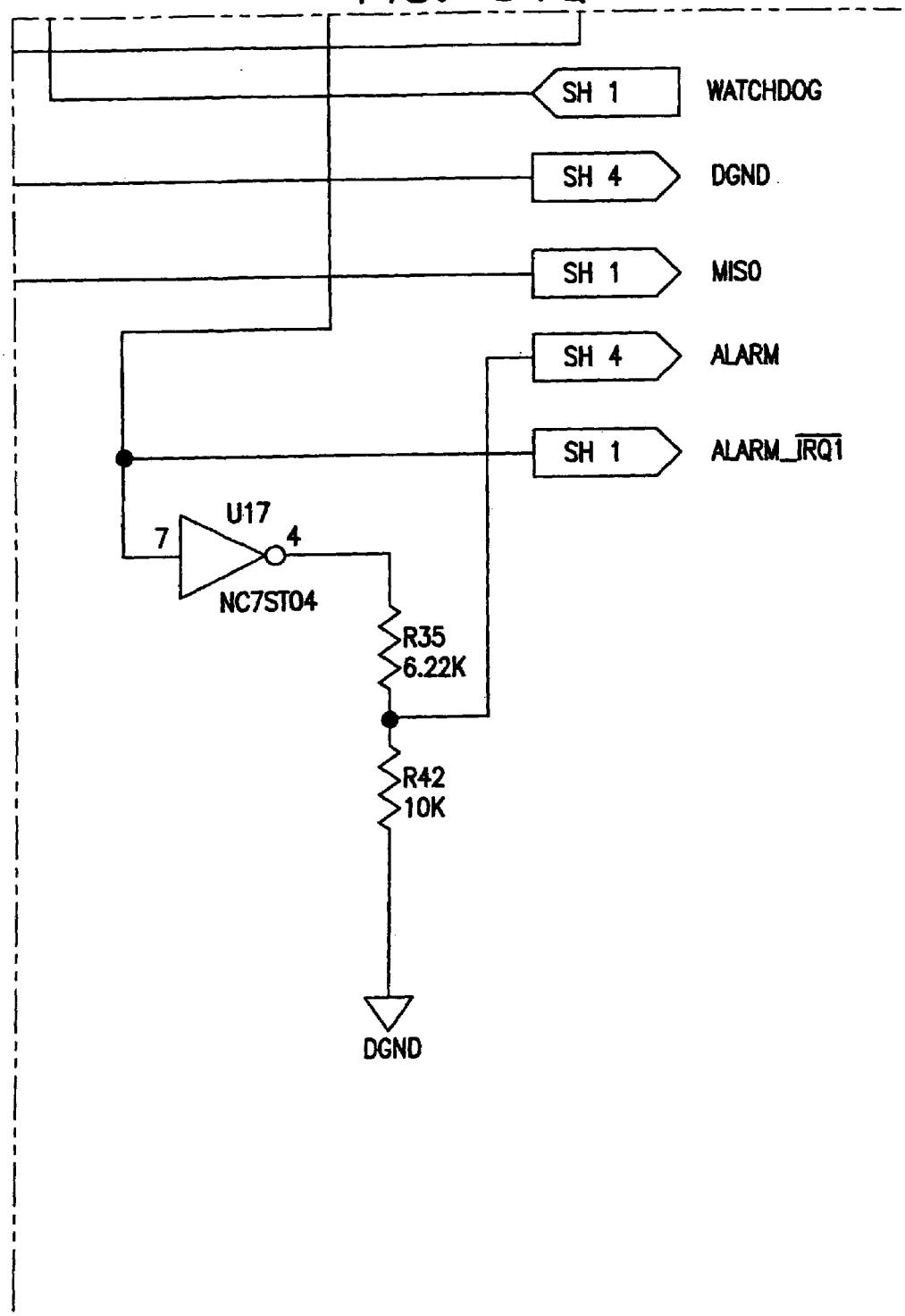

Referring now to FIGS. 64A–64Q, circuit 70 includes a 44-pin, 16C550 universal asynchronous receiver and transmitter (UART) chip, such as that manufactured by Exar Corporation. Pins 1, 12, 23, 26, 27, 32, 34, 35, 36, and 38 of the 16C550 chip are open as shown in FIG. 64I. Pins 21, 22, 25, 28, 37, 40, 41, 42, and 43 of the 16C550 chip are each coupled to DGND as also shown in FIG. 64I. Pin 10 of the 16C550 chip is short circuited to pin 17 of the 16C550 chip. Pins 14 and 15 of the 16C550 chip are each coupled to +5 VD. Pin 44 of the 16C550 chip is coupled directly to +5 VD and is also coupled to DGND through a 1 .mu.F capaciator as shown in FIG. 64I. Pin 18 of the 16C550 chip is coupled to one terminal of a 1 M.OMEGA. resistor and pin 19 of the 16C550 chip is coupled to the other terminal of the 1 M.OMEGA. resistor through a 15 k.OMEGA. resistor as shown in FIG. 64I. A first terminal of a 3.6864 MHz oscillator or clock is coupled to pin 18 of the 16C550 chip and a second terminal of the 3.6864 MHz clock is coupled to pin 19 of the 16C550 chip through the 15 k.OMEGA. resistor such that the 3.6864 MHz clock is in parallel with the 1 M.OMEGA. resistor. The first terminal of the 3.6864 MHz clock is coupled to DGND through a 10 pF capacitor and the second terminal of the 3.6864 MHz clock is coupled to DGND through a 33 pF capacitor as shown in FIGS. 64F and 64I.

The notUART line from the circuitry of FIGS. 62A–62U is coupled to pin 16 of the 16C550 chip and is also coupled to +5 VD through a 10 k.OMEGA. resistor as shown in FIGS. 64C, 64F, and 64I. The notWE line from the circuitry of FIGS. 63A–63L is coupled to pin 20 of the 16C550 chip as also shown in FIGS. 64C, 64F, and 64I. The notRD and RESET lines from the circuitry of FIGS. 62A–62U are coupled to pins 24 and 39, respectively, of the 16C550 chip as shown in FIGS. 64F and 64I. As shown in FIGS. 62I and 62L, pin 33 of the 16C550 chip is coupled to the RS232_INTRO line which is, in turn, coupled to the circuitry of FIGS. 62A–62U as described above. The A(0) through A(2) lines are coupled to pins 31, 30, and 29, respectively, of the 16C550 chip as shown in FIGS. 64F and 64I. The D(8) through D(15) lines are coupled to pins 2, 3, 4, 5, 6, 7, 8, and 9, respectively, of the 16C550 chip as also shown in FIGS. 64F and 64I.

Circuit 70 includes a MAX202 line driver/receiver (aka transceiver) chip which is shown in FIG. 64L and which is manufactured by Maxim Integrated Products. Pin 11 of the 16C550 chip is coupled to pin 12 of the MAX202 chip as shown in FIGS. 64H, 64I, 64K, and 64L. Pin 13 of the 16C550 chip is coupled to each of pins 10 and 11 of the MAX202 chip as also shown in FIGS. 64H, 64I, 64K, and 64L. Pin 8 of the MAX202 chip is open as shown in FIG. 64L. Pin 1 of the MAX202 chip is coupled to pin 3 of the MAX202 chip by a 0.1 .mu.F capacitor as also shown in FIG. 64L. Similarly, pin 4 of the MAX202 chip is coupled to pin 5 of the MAX202 chip by a 0.1 .mu.F capacitor. Pin 16 of the MAX202 chip is coupled directly to +5 VD and is coupled to DGND through a 0.1 .mu.F capacitor as shown in FIGS. 64L and 64O. Pin 2 of the MAX202 chip is coupled to +5 VD through a 0.1 .mu.F capacitor and pin 6 of the MAX202 chip is coupled to DGND through a 0.1 .mu.F capacitor as also shown in FIGS. 64L and 64O.

Pins 7 and 14 of the MAX202 chip are coupled to a TX line through a first 150 MHz ferrite bead high frequency filter as shown in FIGS. 64L and 64O. Pin 13 is coupled to an RX line through a second 150 MHz ferrite bead high frequency filter and is coupled to DGND through a 100 pF capacitor as also shown in FIGS. 64L and 64O. Pin 15 of the MAX202 chip is coupled directly to DGND and is also coupled to a GND line through a third 150 MHz ferrite bead high frequency filter. The TX, RX, and GND lines are coupled to pins 2, 3, and 5, respectively, of a connector J44 as shown in FIG. 64O. Pins 1, 4, 6, 7, 8, and 9 of the connector J44 are not used. The connector J44 provides circuit 70 with an RS-232 communication port to which a user can couple a personal computer that is not otherwise connected to network 14 to configure the master alarm controller 48 through the RS-232 port. In other words, the connector J44 allows a user to couple a personal computer directly to the master alarm controller 48 to obtain output data therefrom and to provide input data thereto.

Circuit 70 includes a MOC211 optoisolator chip which is made, for example, by Fairchild Semicondutor and which is shown in FIG. 64G. Circuit 70 also includes an LTC1483 differential line transceiver chip which is available from Linear Technology Corporation and which is shown in FIG. 64H. Circuit 70 further includes a first HCPL-0701 low input current, high gain optocoupler chip, shown in FIG. 64D, and a second HCPL-0701 low input current, high gain optocoupler chip, shown in FIG. 64E, both of which are manufactured by Agilent Technologies.

The not485_TX_ENBL line from the circuitry of FIGS. 62A–62U is coupled to the base of an NPN transistor (identified as circuit element Q9) through a 4.12 k.OMEGA. resistor as shown in FIGS. 64A and 64D. The not485_TX_ENBL line is also coupled to +5 VD through a 10 k.OMEGA. resistor. The base of the Q9 transistor is coupled to DGND through a 10 k.OMEGA. resistor and the emitter of the Q9 transistor is coupled directly to DGND as shown in FIG. 64D. The collector of the Q9 transistor is coupled to pin 2 of the MOC211 chip as shown in FIGS. 64D and 64G. Pins 3, 4, 7, and 8 of the MOC211 chip are open as shown in FIG. 64G. Pin 1 of the MOC211 chip is coupled to +5 VD through a 510.OMEGA. resistor and pin 5 of the MOC211 chip is coupled to CGND as also shown in FIG. 64G. Pin 6 of the MOC211 chip is coupled to +5 VC through a 4.12 k.OMEGA. resistor and is also coupled directly to pin 3 of the LTC1483 chip as shown in FIGS. 64G and 64H.

Pin 2 of the LTC1483 chip is coupled directly to CGND and is coupled to +5 VC through a 0.1 .mu.F capacitor as shown in FIG. H. Pin 5 of the LTC1483 chip is coupled to CGND and pin 8 of the LTC1483 chip is coupled to +5 VC as also shown in FIG. H. As shown in FIGS. 64H and 64K, pin 5 is also coupled to a CGND line, which is, in turn, coupled to circuitry shown in the schematic of FIGS. 65A–65L as will be described in further detail below. As shown in FIGS. 64H and 64K, pin 6 of the LTC1483 chip is coupled to a COM_A line, which is coupled to circuitry shown in the schematic of FIGS. 65A–65L as will be described in further detail below, and pin 7 of the LTC1483 chip is coupled to a COM_B line, which is coupled to circuitry shown in the schematic of FIGS. 65A–65L as will be described in further detail below. The COM_A line is coupled to +5 VC through a 1 k.OMEGA. resistor and is coupled to the COM_B line through a 121.OMEGA. resistor. The COM_B line is coupled to the CGND line through a 1 k.OMEGA. resistor.

Pin 4 of the LTC1483 chip is coupled to pin 6 of the first HCPL-0701 chip and is coupled to +5 VC through a 330.OMEGA. resistor as shown in FIGS. 64D, 64G, and 64H. Pins 1 and 4 of the first HCPL-0701 chip are open as shown in FIG. 64D. Pin 5 of the first HCPL-0701 chip is coupled directly to CGND and pin 7 of the first HCPL-0701 chip is coupled to CGND through a 10 k.OMEGA. resistor as also shown in FIG. 64D. Pin 8 of the first HCPL-0701 chip is coupled directly to +5 VC and is coupled to CGND through a 0.1 .mu.F capacitor. Pin 3 of the first HCPL-0701 chip if coupled to DGND. Pin 2 of the first HCPL-0701 chip is coupled to the collector of an NPN transistor (identified as circuit element Q5) and is coupled to +5 VD through a 510.OMEGA. resistor as shown in FIGS. 64A, 64B, and 64D. The emitter of the Q5 transistor is coupled directly to DGND and the base of the Q5 transistor is coupled to DGND through a 10 k.OMEGA. resistor as shown in FIG. 64B. The TXD line from the circuitry of FIGS. 62A–62U is coupled to the base of the Q5 transistor through a 4.12 k.OMEGA. resistor as also shown in FIG. 64B.

Pin 1 of the LTC1483 chip is coupled to the base of an NPN transistor (identified as circuit element Q6) through a 4.12 k.OMEGA. resistor as shown in FIGS. 64E and 64H. In addition, the base of the Q6 transistor is coupled to CGND through a 10 k.OMEGA. resistor as shown in FIG. 64E. The emitter of the Q6 transistor is coupled to CGND and the collector of the Q6 transistor is coupled to +5 VC through a 510.OMEGA. resistor as also shown in FIG. 64E. The collector of the Q6 transistor is also coupled to pin 2 of the second HCPL-0701 chip. Pins 1 and 4 of the second HCPL-0701 chip are open. Pin 3 of the second HCPL-0701 chip is coupled to CGND and pin 5 of the second HCPL-0701 chip is coupled to DGND as shown in FIG. 64E. Pin 7 of the second HCPL-0701 chip is coupled to DGND through a 10 k.OMEGA. resistor. Pin 8 of the second HCPL-0701 chip is coupled directly to +5 VD and is coupled to DGND through a 0.1 .mu.F capacitor as shown in FIG. 64E. As shown in FIGS. 64B and 64E, pin 6 of the second HCPL-0701 chip is coupled to +5 VD through a 330.OMEGA. resistor and is also coupled to the RXD line from the circuitry of FIGS. 62A–62U.

Circuit 70 includes a 25640 Serial CMOS EEPROM chip (Serial Peripheral Interface (SPI) Synchronous Bus) which is manufactured, for example, by Fairchild Semiconductor Corporation and which is shown in FIG. 64J. Circuit 70 also includes a 20-pin, DS1305 Serial Alarm Real Time Clock chip which is manufactured by Dallas Semiconductor and which is shown in FIGS. 64M and 64N. The MOSI line from the circuitry of FIGS. 62A–62U is coupled to pin 5 of the 25640 chip and is coupled to pin 15 of the DS1305 chip as shown in FIGS. 64D, 64G, 64J, and 64M. The SPI_CLK line from the circuitry of FIGS. 62A–62U is coupled to pin 6 of the 25640 chip and is coupled to pin 14 of the DS1305 chip as also shown in FIGS. 64D, 64G, 64J, and 64M.

The notSEEPROM1_CS line from the circuitry of FIGS. 62A–62U is coupled to pin 1 of the 25640 chip as shown in FIGS. 64D, 64G, and 64J. Pins 3 and 7 of the 25640 chip are each coupled to +5 VD through respective 10 k.OMEGA. resistors as shown in FIG. 64J. Pin 4 of the 25640 chip is coupled to DGND. Pin 8 of the 25640 chip is coupled directly to +5 VD and is coupled to DGND through a 0.1 .mu.F capacitor as shown in FIG. 64J. As shown in FIGS. 64J, 64K, 64M, 64N, and 64Q, pin 2 of the 25640 chip is coupled to pin 16 of the DS1305 chip and is also coupled to the MISO line, which is, in turn, coupled to the circuitry of FIGS. 62A–62U. The RTC_SELECT line from the circuitry of FIGS. 62A–62U is coupled to pin 12 of the of the DS1305 chip as shown in FIGS. 64D, 64G, 64J, and 64M. Pins 4, 6, 7, 8, 9, 13, 18, and 19 of the DS1305 chip are open as shown in FIGS. 64M and 64N. Pin 10 of the DS1305 chip is coupled to DGND as shown in FIG. 64N. Pin 11 of the DS1305 chip is coupled to +5 VD through a 10 k.OMEGA. resistor as shown in FIGS. 64K and 64N. Pins 17 and 20 of the DS1305 chip are each coupled directly to +5 VD, which is, in turn, coupled to DGND through a 0.1 .mu.F capacitor as shown in FIG. 64M. Pin 1 of the DS1305 chip is coupled directly to DGND as also shown in FIG. 64M.

Pin 3 of the DS1305 chip is coupled to a first terminal of a 32.768 kHz oscillator or clock and pin 5 of the DS1305 chip is coupled to the second terminal of the 32.768 kHz clock as shown in FIG. 64M. Circuit 70 includes an OP293 operational amplifier, such as that made by Analog Devices, Inc., as also shown in FIG. 64M. Pin 2 of the DS1305 chip is coupled to pin 5 of the OP293 chip and to +VBAT. In addition, pin 2 of the DS1305 is coupled to the positive terminal of a 3-volt lithium battery through a pair of 2 k.OMEGA. resistors as shown in FIGS. 64M and 64N. The negative terminal of the 3-volt lithium battery is coupled to DGND as shown in FIG. 64N.

Pins 6 and 7 of the OP293 chip are coupled together in unity gain buffer configuration as shown in FIG. 64M. In addition, pins 2 and 3 of the OP293 chip are coupled to DGND and pin 1 of the OP293 chip is open. As shown in FIG. 64P, circuit 70 includes a 705 supervisory circuit chip, such as a MAX705 supervisory circuit chip made by Maxim Integrated Products. Pin 7 of the OP293 chip is coupled to pin 4 of the 705 chip through a 536.OMEGA. resistor as shown in FIGS. 64M and 64P. Pin 4 of the 705 chip is also coupled to DGND through a 511.OMEGA. resistor as shown in FIGS. 64M, 64N, and 64P. Pins 1 and 7 of the 705 chip are open as shown in FIG. 64P. Pin 3 of the 705 chip is coupled to DGND. Pin 2 of the 705 chip is coupled directly to +5 VD and is coupled to DGND through a 0.1 .mu.F capacitor as shown in FIGS. 64M and 64P.

The WATCHDOG line from the circuitry of FIGS. 62A–62U is coupled to pin 6 of the 705 chip as shown in FIGS. 64P and 64Q. Pin 5 of the 705 chip is coupled to the notLOW BATTERY line of the circuitry of FIGS. 62A–62U and is also coupled to DGND through the series combination of a 73.2 k.OMEGA. resistor and a 30.1 k.OMEGA. resistor as shown in FIG. 64P. The common terminal of the 73.2 k.OMEGA. resistor and a 30.1 k.OMEGA. resistor is coupled to pin 4 of the 705 chip as shown in FIGS. 64M, 64N, 64P, and 64Q. As shown in FIGS. 64M, 64N, 64P, and 64Q, pin 4 of the 705 chip is also coupled through a 0.01 .mu.F capacitor to DGND and to the DGND line which, in turn, couples to the circuitry of FIGS. 65A–65L as will be described in further detail below.

Pin 8 of the 705 chip is coupled to the ALARM_notIRQ1 line which, in turn, couples to the circuitry of FIGS. 62A–62U as described above. As shown in FIGS. 64P and 64Q, pin 8 of the 705 chip also couples to pin 2 of a NC7ST04 HST inverter chip, such as that manufactured by Fairchild Semiconductor Corporation. Pin 4 of the NC7ST04 chip couples through a 4.12 k.OMEGA. resistor to an ALARM line which, in turn, couples to the circuitry of FIGS. 65A–65L as will be described in further detail below. The ALARM line is coupled to DGND through a 10 k.OMEGA. resistor as shown in FIG. 64Q. The NC7ST04 chip is designated as circuit component "U7" in circuit 70 and, as can be seen in FIG. 64N, pin 3 of the NC7ST04 chip is coupled to DGND, pin 5 of the NC7ST04 chip is coupled to +5 VD, and pin 5 of the NC7ST04 chip is coupled to pin 3 thereof through a 0.1 .mu.F capacitor. Similarly, the OP293 chip is designated as circuit component "U29" in circuit 70 and, as also can be seen in FIG. 64N, pin 4 of the OP293 chip is coupled to DGND, pin 8 of the OP293 chip is coupled to +5 VD, and pin 8 of the OP293 chip is coupled to pin 4 thereof through a 0.1 .mu.F capacitor.

Circuit 70 includes a 78M05 3-pin positive voltage regulator chip, such as that available from National Semiconductor Corporation, as shown in FIG. 64F. As shown in FIGS. 64C and 64F, pin 1 of the 78M05 chip is coupled to a +7.5V line which is coupled to the circuitry shown in the schematic of FIGS. 65A–65L as will be described in further detail below. Pin 2 of the 78M05 chip is coupled to a CGND line which is also coupled to the circuitry shown in the schematic of FIGS. 65A–65L as will be described in further detail below. Pin 3 of the 78M05 chip is coupled to +5 VC as shown in FIG. 64F. Pin 3 of the 78M05 chip is coupled to CGND through the parallel combination of a 10 .mu.F capacitor, a 0.01 .mu.F capacitor, and a 4.12 k.OMEGA. resistor as also shown in FIG. 64F. Pin 2 of the 78M05 chip is coupled to CGND through the parallel combination of a 10 .mu.F capacitor and a 0.1 .mu.F capacitor as shown in FIGS. 64C and 64F. As shown in FIG. 64A, the +5 VD line and the DGND line from SH2 (i.e. FIGS. 63A–63L) provide +5 VD and DGND, respectively, for the circuitry of FIGS. 64A–64Q.

Figure 65A:
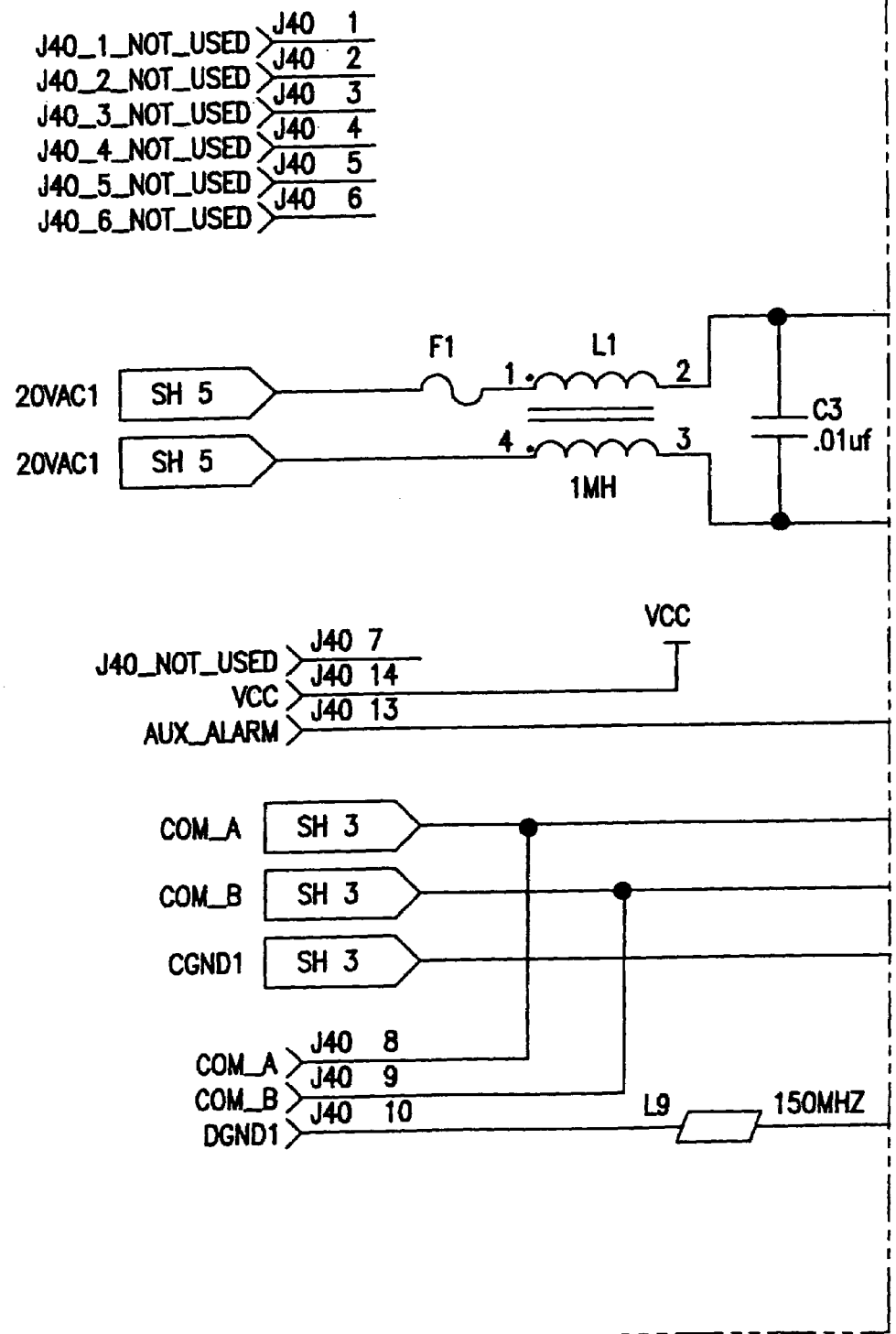
FIG. 65 is a circuit schematic map showing how to lay out FIGS. 65A–65L to form an electric circuit schematic of a fourth portion of the electric circuit of one of the master alarm controllers.
Figure 65B:
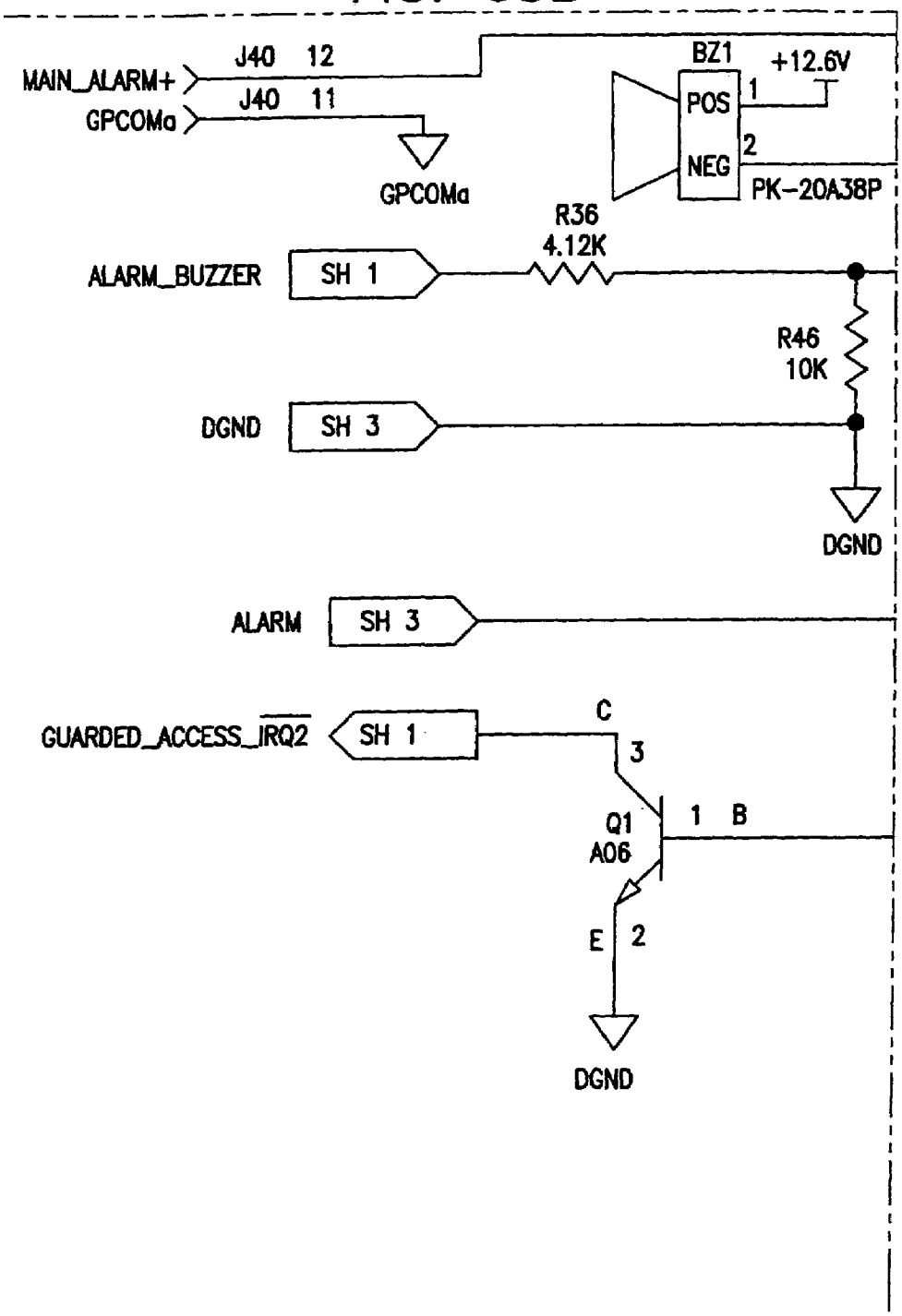
Figure 65C:
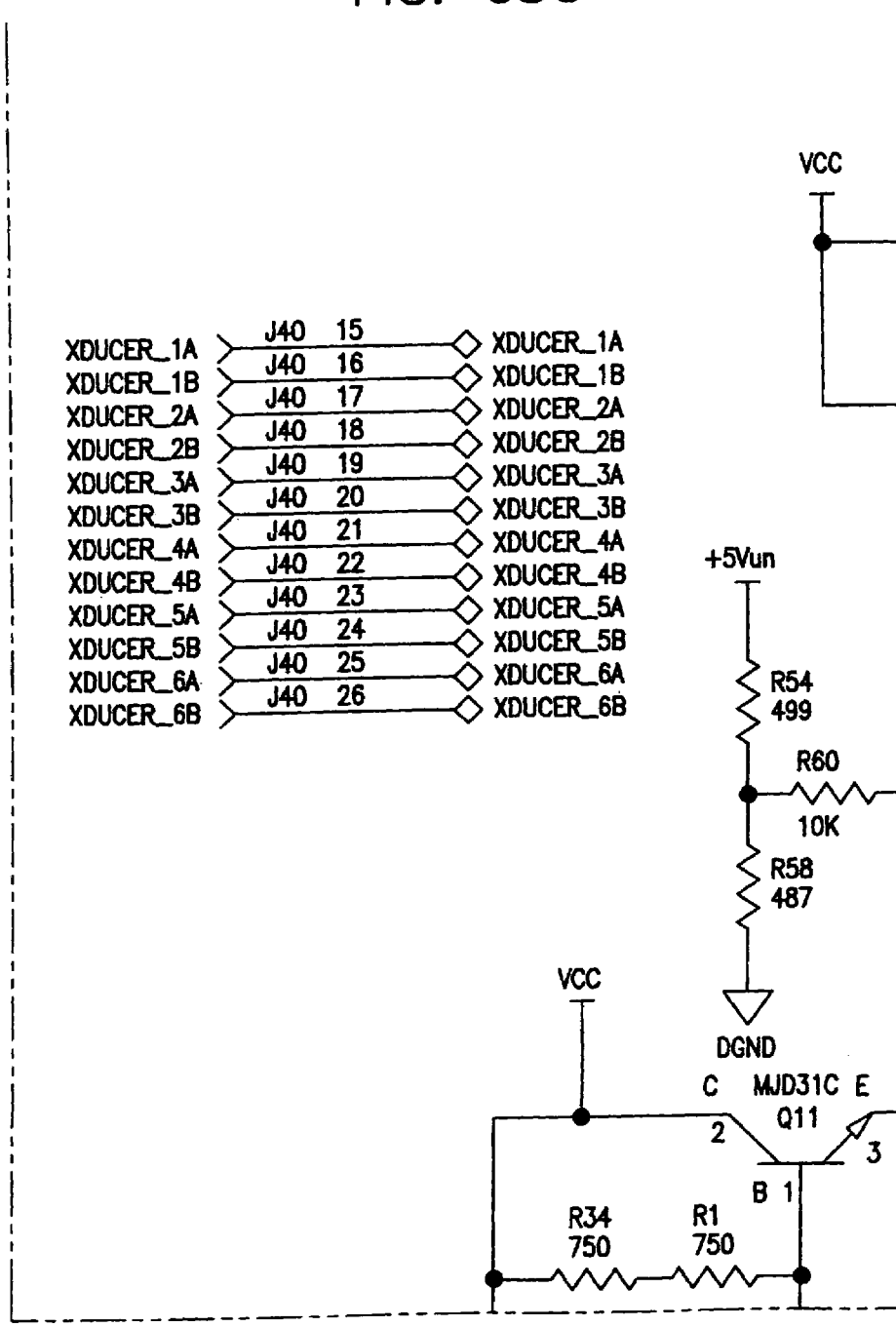
Figure 65D:
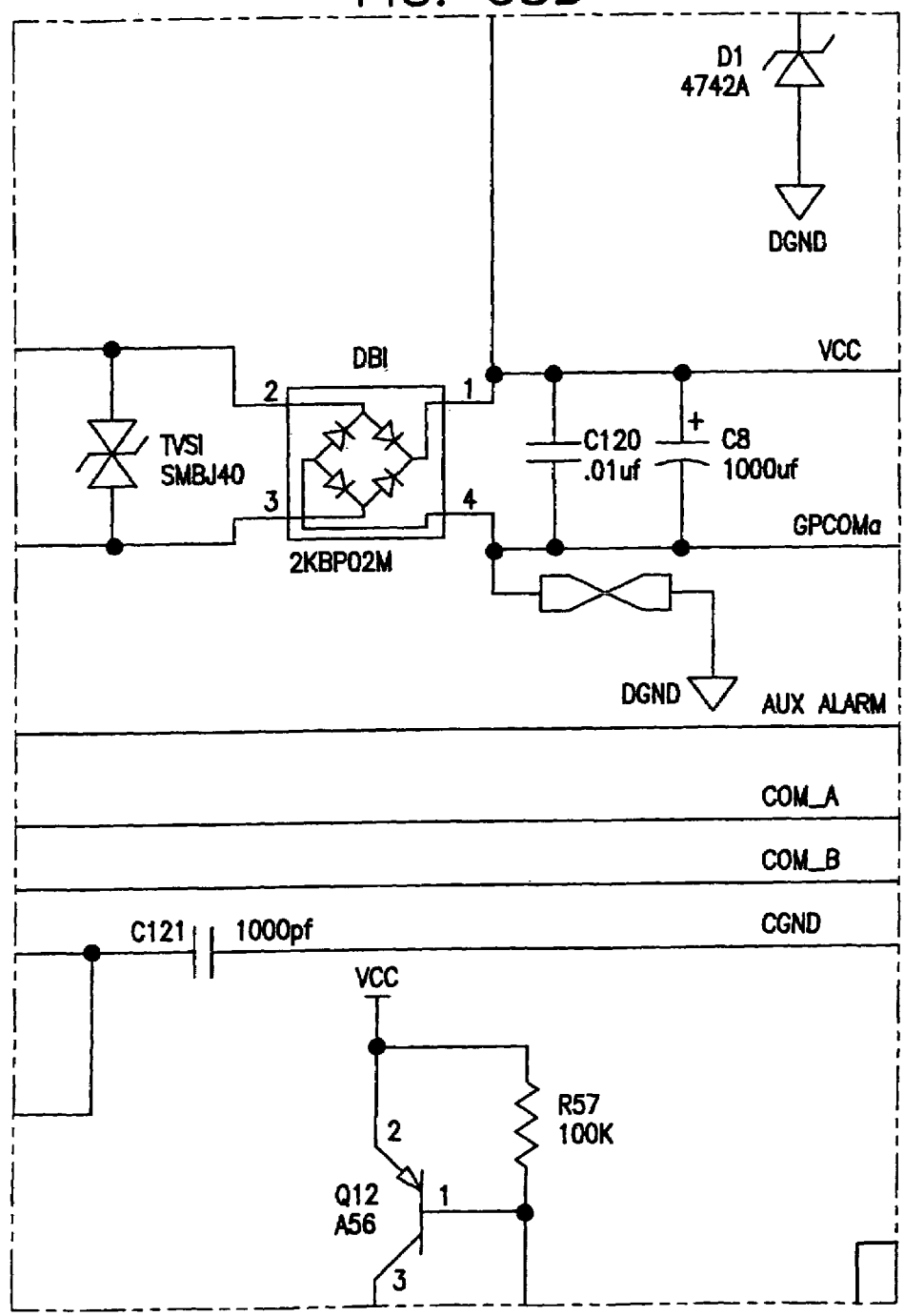

Referring now to FIGS. 65A–65L, a 20VAC1 line, shown in FIG. 65A, is coupled through the series combination of a fuse and one coil of a 1 mH pulse suppression transformer to pin 2 of a 2 KBP02M 2.0 Ampere bridge rectifier which is shown in FIG. 65D and which is available from Fairchild Semiconductor Corporation. A 20VAC2 line is coupled through the other coil of the 1 mH transformer to pin 3 of the 2 KBP02M rectifier as shown in FIGS. 65A and 65D. The 20VAC1 and 20VAC2 lines are each coupled to circuitry shown in the schematic of FIGS. 66A–66X as will be described in further detail below. Pin 2 of the 2 KBP02M rectifier is coupled to pin 3 of the 2 KBP02M rectifier by the parallel combination of a 0.01 .mu.F capacitor and an SMBJ40 bidirectional diode as shown in FIGS. 65A and 65D. Pin 4 of the 2 KBP02M rectifier is coupled to DGND as shown in FIG. 65D. Pin 4 of the 2 KBP02M rectifier is also coupled to a GPCOMa line. Pin 1 of the 2 KBP02M rectifier is coupled to a VCC line as shown in FIG. 65D. Pin 1 of the 2 KBP02M rectifier is coupled to pin 4 of the 2 KBP02M rectifier by the parallel combination of a 0.01 .mu.F capacitor and a 1000 .mu.F capacitor as also shown in FIG. 65D.

Figure 65E:
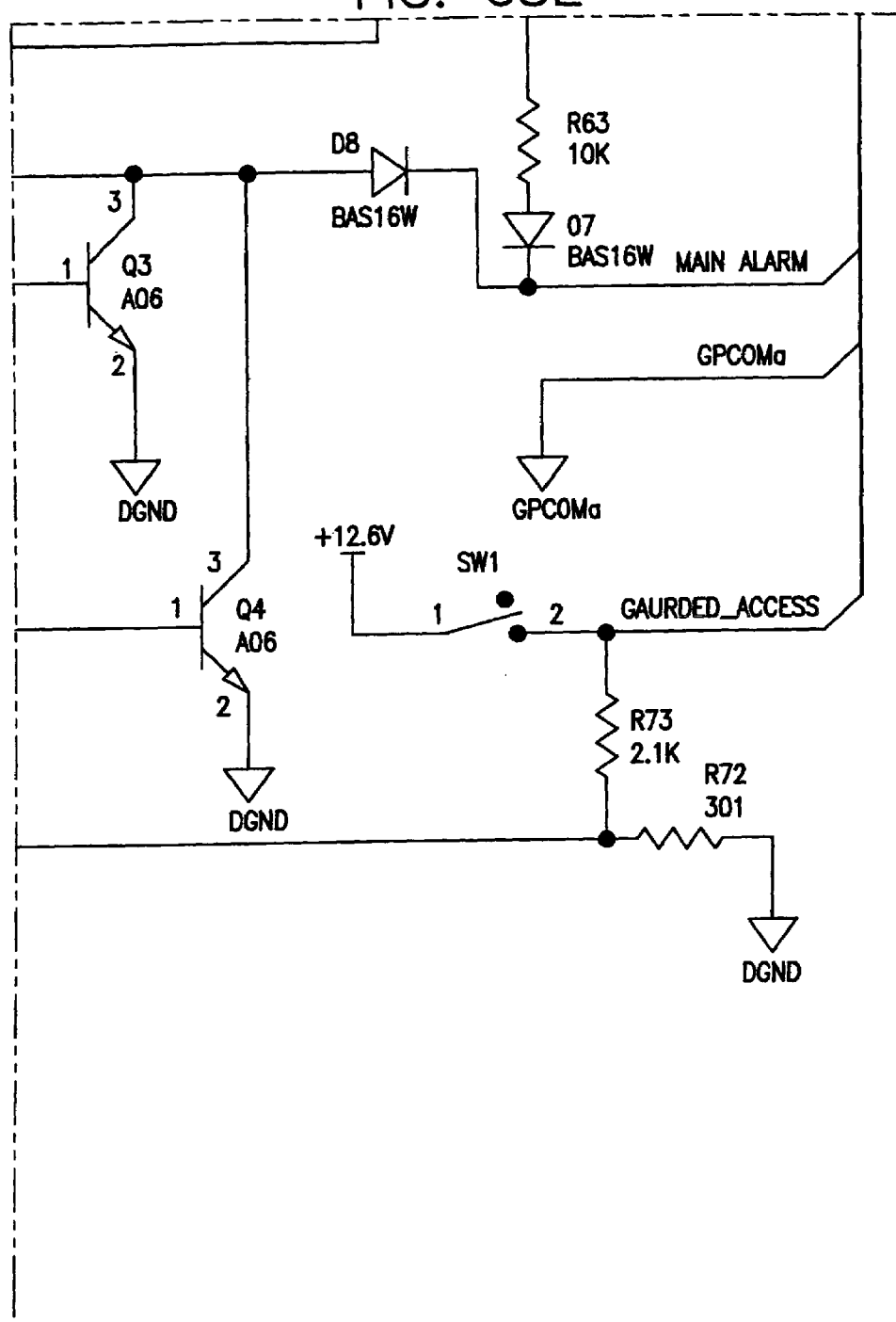
Figure 65F:
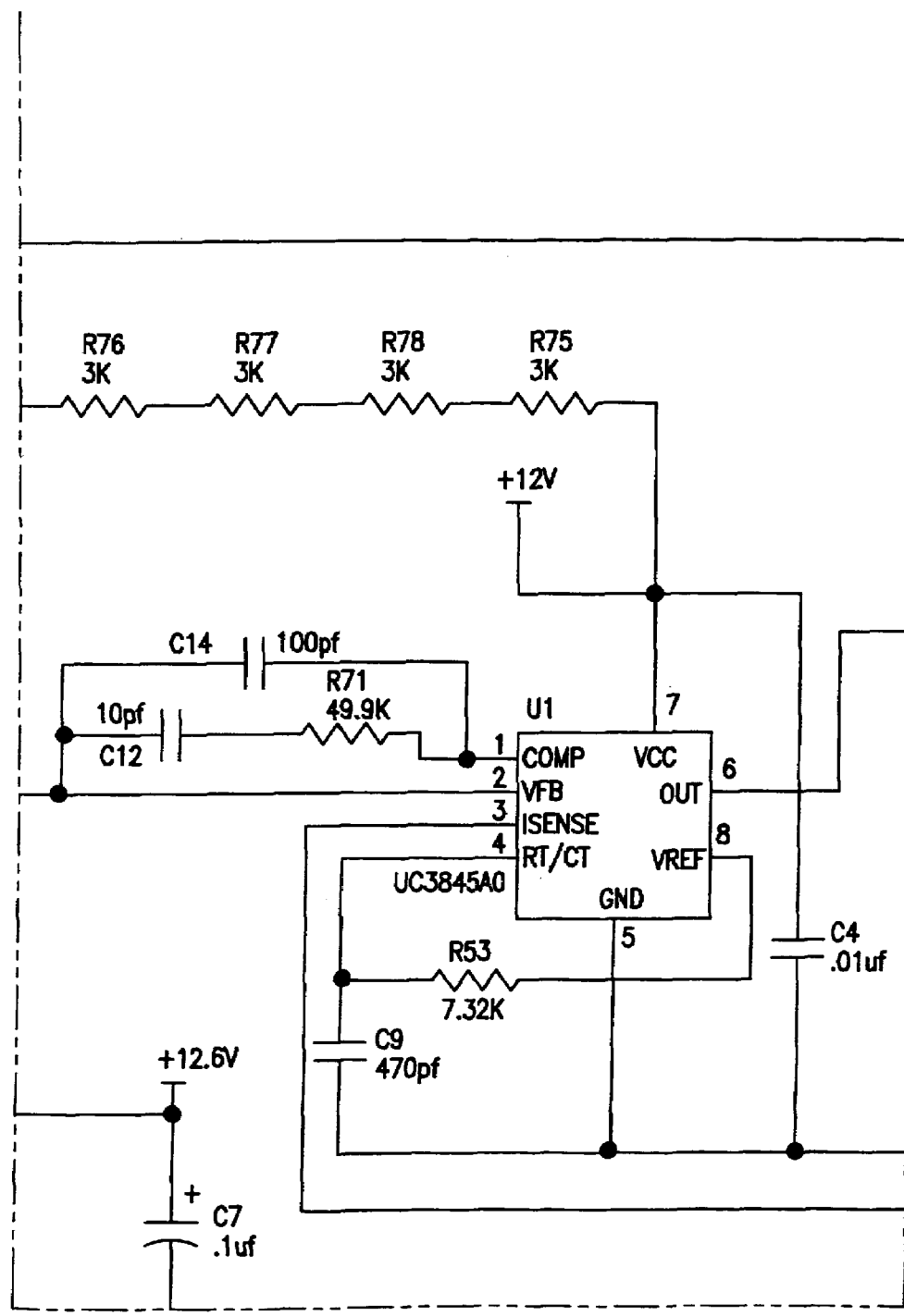
Figure 65G:
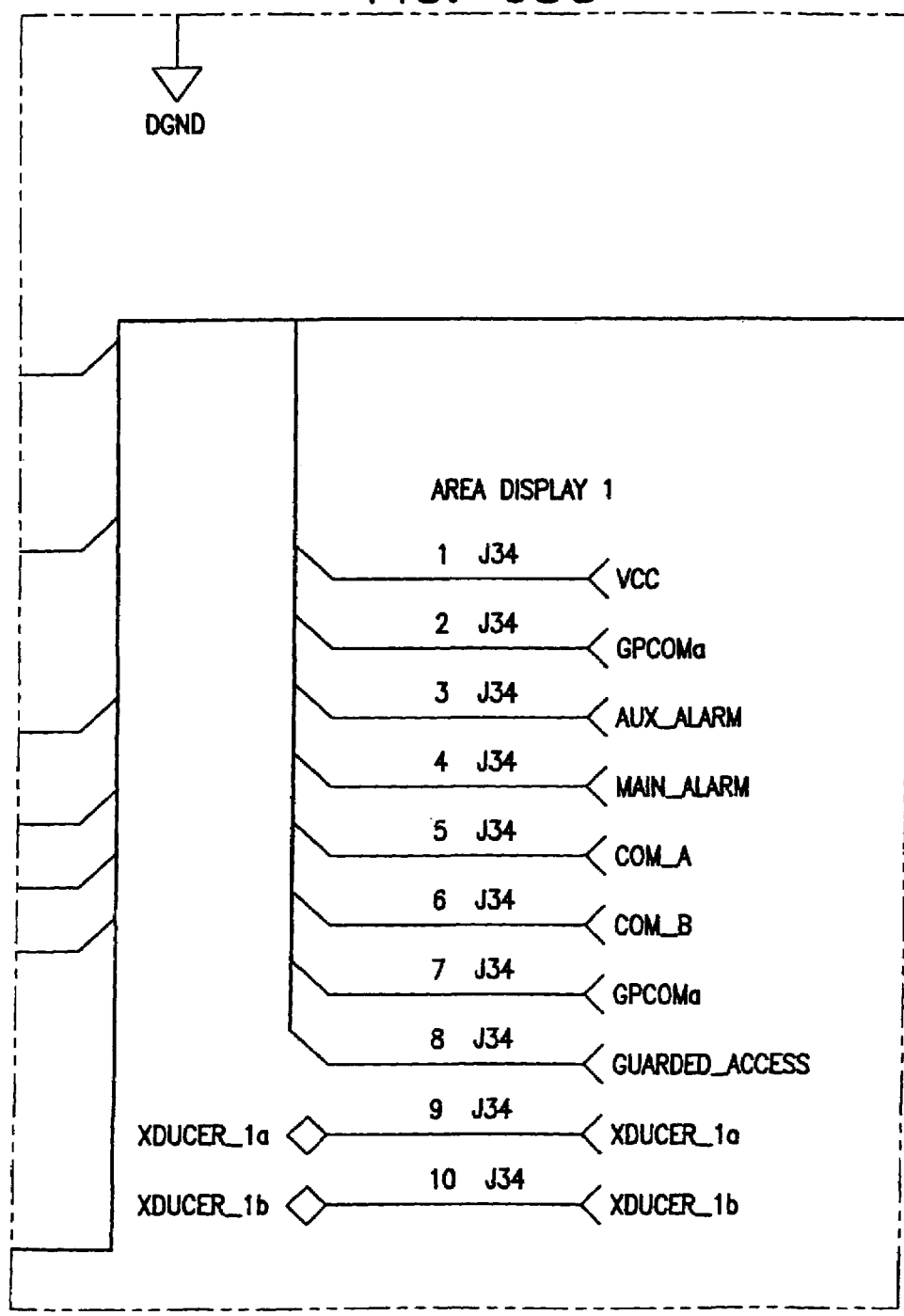

Pin 1 of the 2 KBP02M rectifier is coupled to the collector of an MJD31C NPN epitaxial silicon transistor, such as that available from Fairchild Semiconductor Corporation, as shown in FIGS. 65C and 65D. The collector of the MJD31C transistor is also coupled to VCC as shown in FIG. 65C. Pin 1 of the 2 KBP02M rectifier is coupled to the base of the MJD31C transistor through a series pair of 750.OMEGA. resistors as shown in FIGS. 65C and 65D. In addition, the base of the MJD31C transistor is coupled to the cathode of a 4742A diode and the anode of the 4742A diode is coupled to DGND as also shown in FIGS. 65C and 65D. The emitter of the MJD31C transistor is coupled directly to +12.6V and is coupled to DGND through a 1 .mu.F capacitor as shown in FIGS. 65C, 65F, and 65G.

Circuit 70 includes a connector J40, various pins of which are shown in FIGS. 65A, 65B, and 65C. Pins 1–7 of the connector J40 are not used. The COM_A and COM_B lines from the circuitry of FIGS. 64A–64Q are coupled to pins 8 and 9 of the connector J40, respectively, as shown in FIG. 65A. The CGND line from the circuitry of FIGS. 64A–64Q is coupled to pin 10 of the connector J40 through a 150 MHz ferrite bead high frequency filter as also shown in FIG. 65A. A 1000 pF capacitor is inserted in the CGND line as shown in FIG. 65D. Pin 13 of the connector J40 is coupled to an AUX_ALARM line and pin 14 of the connector J40 is coupled to VCC as shown in FIG. 65A. Pins 15, 16, 17, 18, 19, 20, 21, 22, 23, 24, 25, and 26 coupled to XDUCER__1A, XDUCER__1B, XDUCER__2A, XDUCER__2B, XDUCER__3A, XDUCER__3B, XDUCER__4A, XDUCER__4B, XDUCER__5A, XDUCER__5B, XDUCER__6A, and XDUCER__6B lines, respectively, as shown in FIG. 65C.

Pin 11 of the connector J40 is coupled to the GPCOMa line as shown in FIG. 65B. Pin 12 of the connector J40 is coupled to a MAIN_ALARM+ line which is, in turn, coupled to the collector of a transistor (identified as circuit component Q12) as shown in FIGS. 64B, 64D, and 64E. The emitter of the Q12 transistor is coupled directly to VCC and is coupled to the base of the Q12 transistor through a 100 k.OMEGA. resistor as shown in FIG. 65D. The base of the Q12 transistor is coupled to the anode of a first BAS16W diode and the cathode of the first BAS16W diode is coupled to a MAIN_ALARM line as shown in FIGS. 65D and 65E. The MAIN_ALARM line is coupled to the cathode of a second BAS16W diode and the anode of the second BAS16W diode is coupled to pin 2 of a PK-20A38P piezoelectric buzzer (i.e. speaker 94) as shown in FIGS. 65B and 65E. Pin 1 of the PK-20A38P buzzer is coupled to +12.6V as shown in FIG. 65B.

Pin 2 of the PK-20A38P buzzer is coupled to the collector of a first NPN transistor (identified as circuit component Q3) and is coupled to the collector of a second NPN transistor (identified as circuit component Q4) as shown in FIGS. 65B and 65E. The ALARM line from the circuitry of FIGS. 64A–64Q is coupled to the base of the Q4 transistor and the emitter of the Q4 transistor is coupled to DGND as shown in FIGS. 65B and 65E. The ALARM_BUZZER line from the circuitry of FIGS. 62A–62U is coupled to the base of the Q3 transistor through a 4.12 k.OMEGA. resistor as also shown in FIGS. 65B and 65E. The base of the Q3 transistor is coupled through a 10 k.OMEGA. resistor to both DGND and the DGND line from the circuitry of FIGS. 64A–64Q. The emitter of the Q3 transistor is coupled to DGND as shown in FIG. 65E.

The collector of an NPN transistor (identified as circuit component Q1), shown in FIG. 65B, is coupled to the GUARDED_ACCESS_notIRQ2 line which is, in turn, coupled to the circuitry of FIGS. 62A-62Q as described above. The emitter of the Q1 transistor is coupled to DGND as shown in FIG. 65B. The base of the Q1 transistor is coupled to DGND through a 301.OMEGA. resistor as shown in FIGS. 65B and 65E. The base of the Q1 transistor is also coupled to a GUARDED_ACCESS line through a 2.1 k.OMEGA. resistor as also shown in FIGS. 65B and 65E. The first terminal of a switch (i.e. button 910) is coupled to +12.6V and the second terminal of the switch is coupled to the GUARDED_ACCESS line as shown in FIG. 65E. The GPCOMa line is coupled to DGND as also shown in FIG. 65E.

Figure 65H:
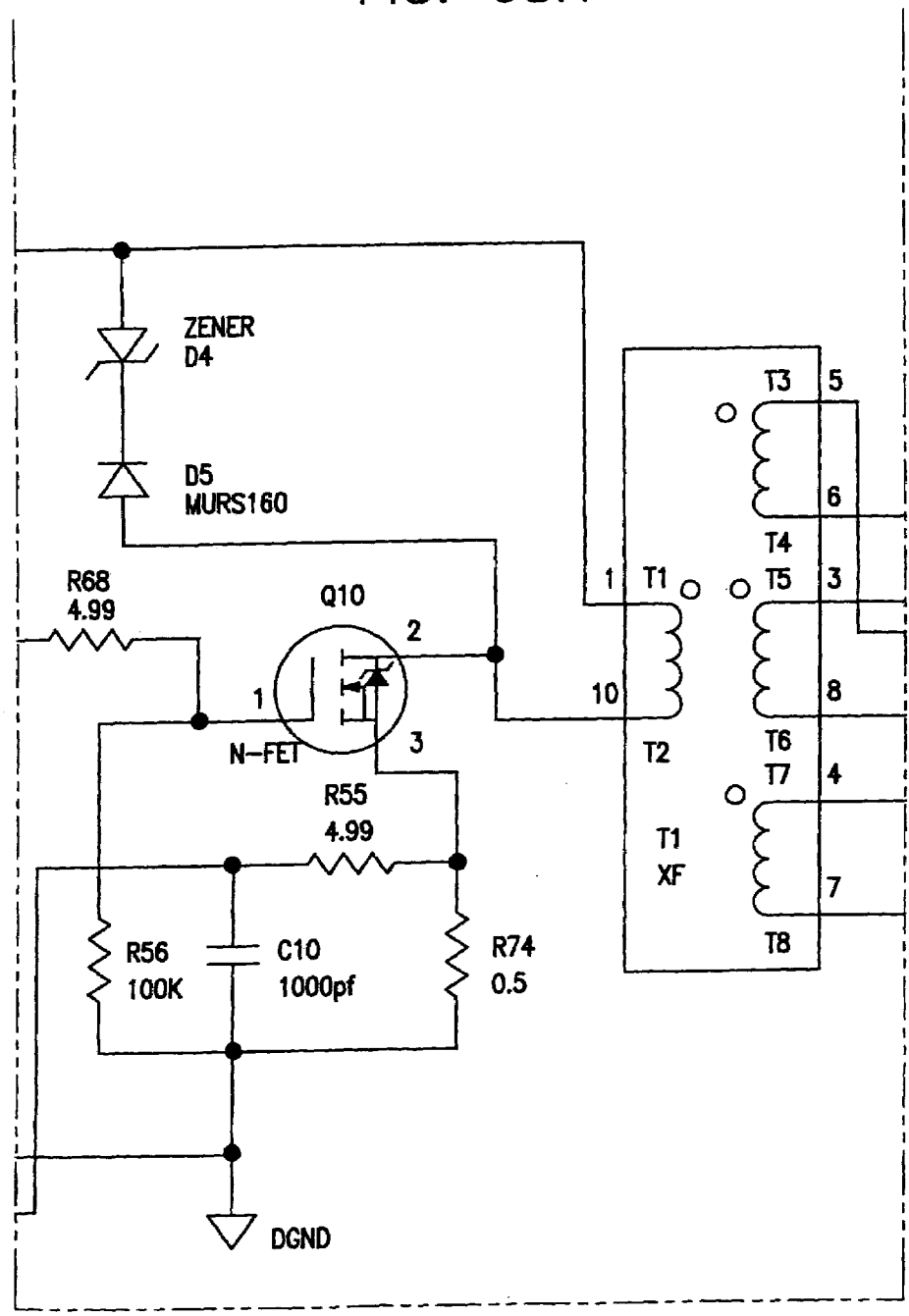
Figure 651:
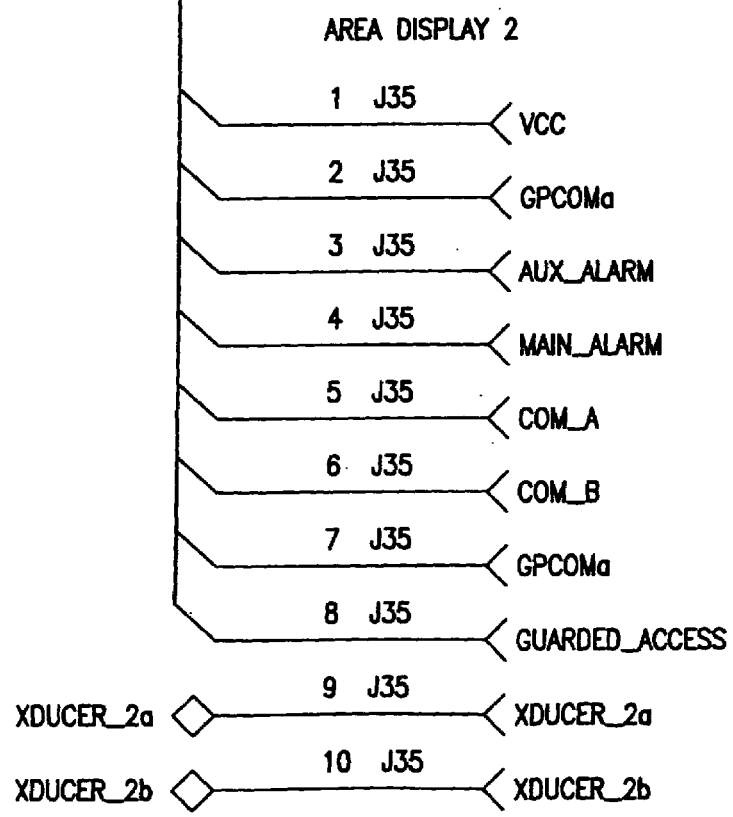
Figure 65J:
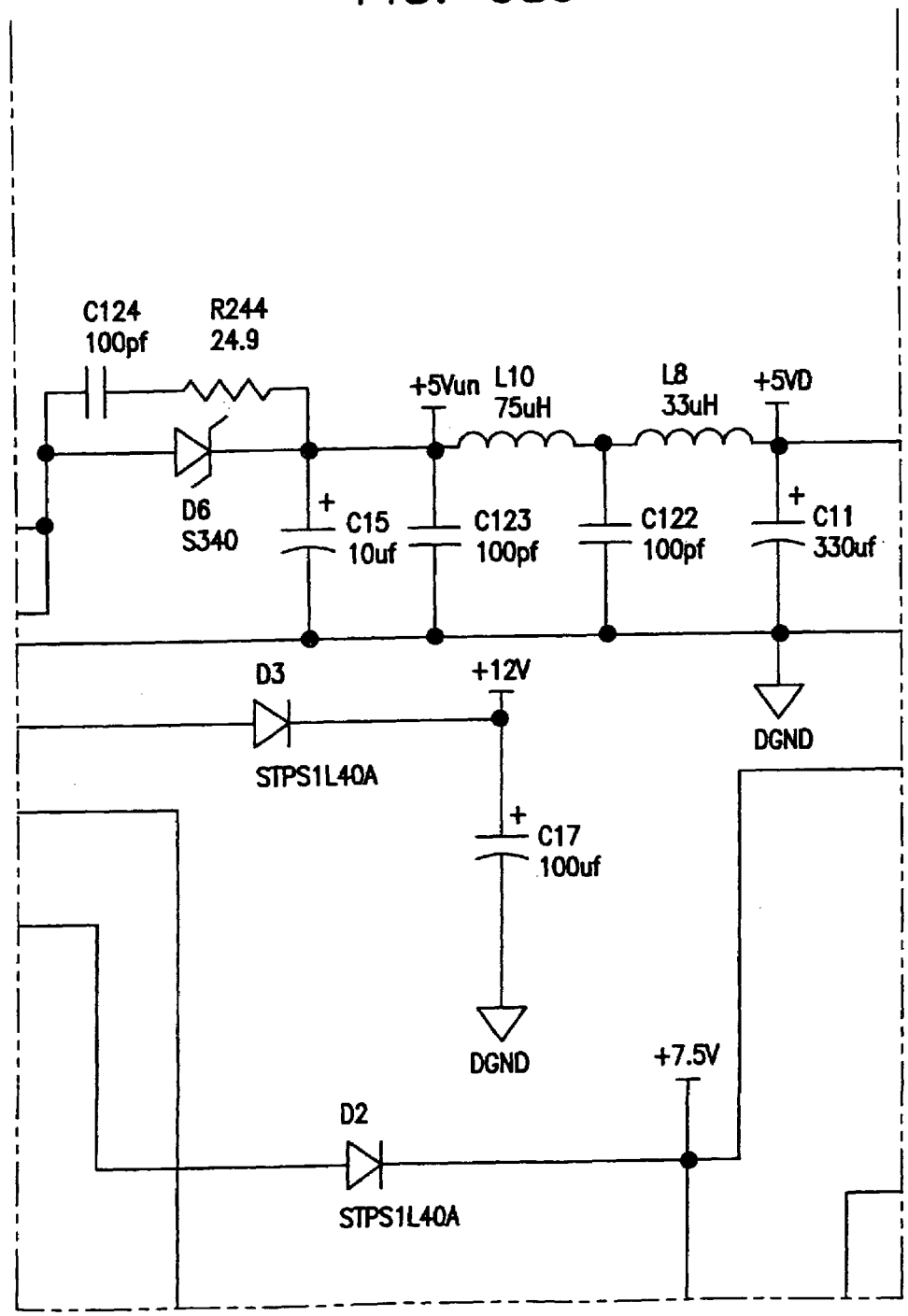
Figure 65K:
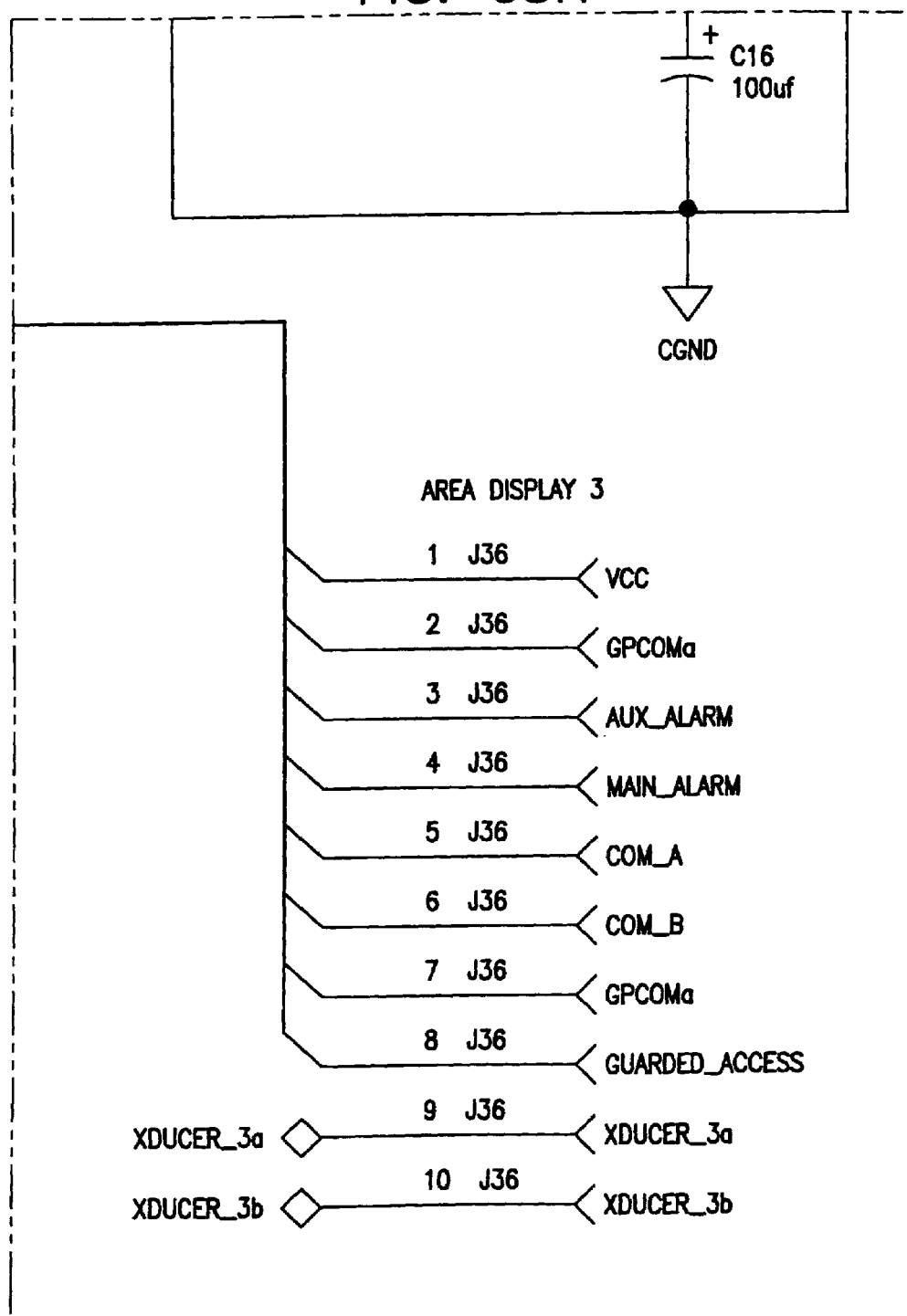

The VCC, GPCOMa, AUX_ALARM, COM_A, COM_B, CGND, MANUAL_ALARM, and GUARDED_ACCESS lines form a bus that illustratively couples to three different connectors (identified as connectors J34, J35, and J36 in FIGS. 65G, 65I, and 65K, respectively) that are couplable to associated display modules 156 (identified as AREA DISPLAY 1, AREA DISPLAY 2, and AREA DISPLAY 3 in FIGS. 65G, 65I, and 65K, respectively). In some alternative embodiments, an RS-485 communication port is included in circuit 70 in lieu of the connectors J34, J35, and J36 and in other alternative embodiments, circuit 70 includes additional connectors like connectors J34, J35, and J36 that permit more that three display modules 156 to be coupled to circuit 70. Each of the illustrative connectors J34, J35, and J36 includes pins 1–10 that couple to the VCC, GPCOMa, AUX_ALARM, MANUAL_ALARM, COM_A COM_B, GPCOMa, GUARDED_ACCESS, XDUCER_#A, and XDUCER_#B, respectively. The XDUCER_#A and XDUCER_#B lines carry the signals of the sensor module 54 associated with the display module 156, where "#" is "1" for the first display module 156, "2" for the second display module, and so on.

Circuit 70 includes a UC3845AD Current Mode Pulse Width Modulation (PWM) Controller chip which is available from STMicroelectronics and which is shown in FIG. 65F. Pin 1 of the UC3845AD chip is coupled to pin 2 thereof through a 100 pF capacitor and through a series combination of a 49.9 k.OMEGA. resistor and a 10 pF capacitor, the series combination being in parallel with the 100 pF capacitor. Pin 2 of the UC3845AD chip is also coupled to +5 Vun through the series combination of a 10 k.OMEGA. resistor and a 499.OMEGA. resistor as shown in FIGS. 65C and 65F. The common terminal of the 10 k.OMEGA. resistor and the 499.OMEGA. resistor is coupled to DGND through a 487.OMEGA. resistor as shown in FIG. 65C. Pin 7 of the UC3845AD chip is coupled to VCC through a set of four 3 k.OMEGA. resistor in series as shown in FIGS. 65C and 65F. In addition, pin 7 of the UC3845AD chip is coupled directly to +12V and is coupled to DGND through a 0.01 .mu.F capacitor as shown in FIGS. 65F and 65H.

Pin 4 of the UC3845AD chip is coupled to pin 8 thereof through a 7.32 k.OMEGA. resistor and is also coupled to DGND through a 470 pF capacitor as shown in FIGS. 65F and 65H. Pin 5 of the UC3845AD chip is coupled directly to DGND. Pin 6 of the UC3845AD chip is coupled to DGND through the series combination of a 4.99.OMEGA. resistor and a 100 k.OMEGA. resistor as shown in FIGS. 65F and 65H. The gate of a field effect transistor (FET) is coupled to the common terminal of the 4.99.OMEGA. resistor and the 100 k.OMEGA. resistor as shown in FIG. 65H. The source of the FET is coupled to DGND through a 0.5.OMEGA. resistor and through the series combination of a 4.99.OMEGA. resistor and a 1000 pF capacitor as also shown in FIG. 65H. Pin 3 of the UC3845AD chip is coupled to the common terminal of the 4.99.OMEGA. resistor and the 1000 pF capacitor as shown in FIGS. 65F and 65H.

VCC is coupled to the drain of the FET through the primary winding of a transformer as shown in FIGS. 65C, 65F and 65H. In addition, VCC is coupled to the anode of a zener diode (identified as circuit component D4). The cathode of the D4 zener diode is coupled to the cathode of a MURS160 ultrafast plastic rectifier available from General Semiconductor. The anode of the MURS160 rectifier is coupled to the drain of the FET as shown in FIG. 65H. The transformer of circuit 70 has three secondary windings as shown in FIG. 65H. The three secondary windings are hereinafter referred to as the top, middle, and bottom windings, respectively, the top winding having a pin 5 and a pin 6, the middle winding having a pin 3 and a pin 8, and the bottom winding having a pin 4 and a pin 7 as shown in FIG. 65H.

Figure 65L:
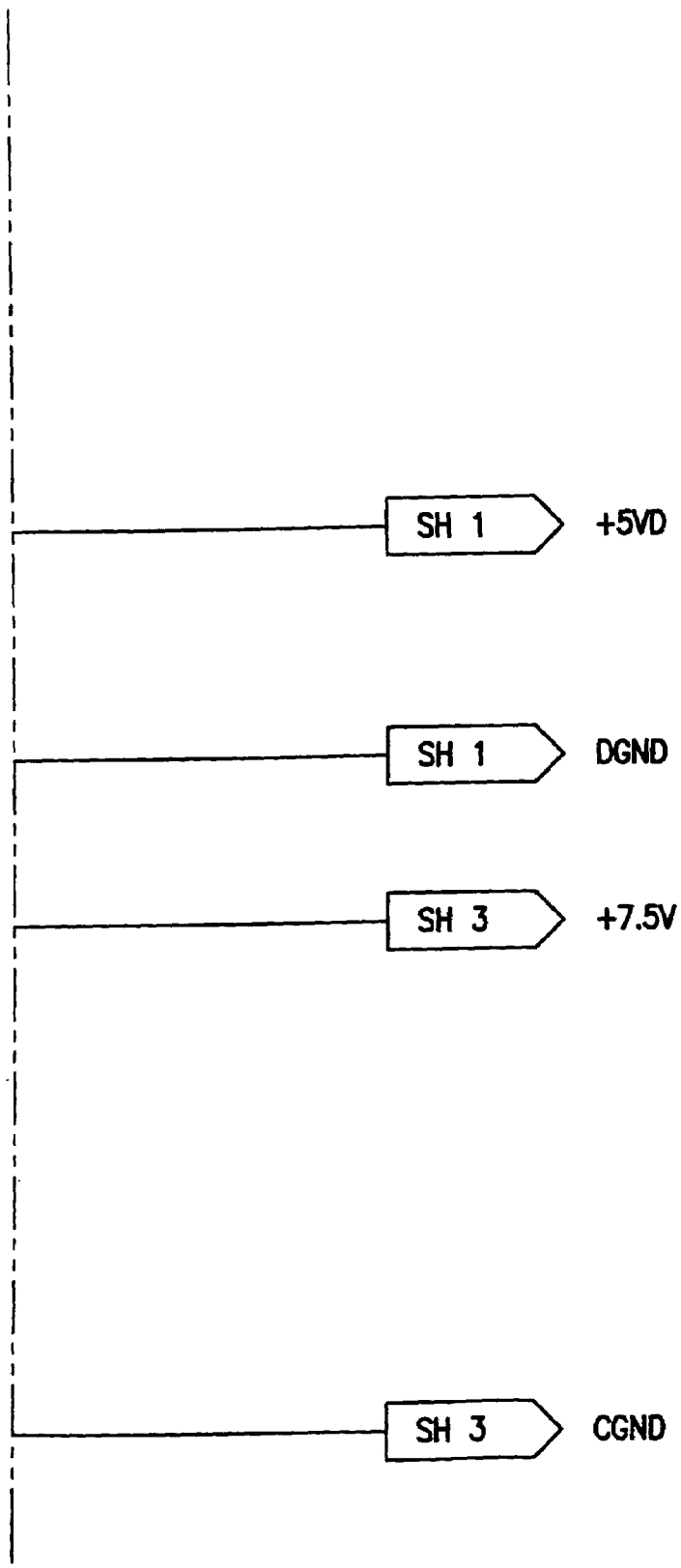

As shown in FIGS. 65H, 65J and 65L, pin 5 of the top winding establishes DGND and is coupled to the DGND line which, in turn, is coupled to the circuitry of FIGS. 62A–62U. Pin 6 of the top winding is coupled to the anode of an S340 diode or rectifier as shown in FIGS. 65H and 65J. Pin 6 of the top winding is coupled to the cathode of the S340 diode through a series combination of a 100 pF capacitor and a 24.9.OMEGA. resistor, such that the combination is in parallel with the S340 diode as also shown in FIGS. 65H and 65J. The cathode of the S340 diode is coupled to DGND through the parallel combination of a 10 .mu.F capacitor and a 100 pF capacitor as shown in FIG. 65J. The junction of the cathode of the S340 diode, the 10 .mu.F capacitor, and a 100 pF capacitor establishes +5 Vun. A first terminal of a 75 .mu.H inductor is coupled to +5 Vun and a second terminal of the 75 .mu.H inductor is coupled to DGND through a 100 pF capacitor as shown in FIG. 65J. The common terminal of the 75 .mu.H inductor and the 100 pF capacitor is coupled to the first terminal of a 33 .mu.H inductor. The second terminal of the 33 .mu.H inductor establishes +5 VD which is coupled to the circuitry of FIGS. 62A–62U by the +5 VD line as described above. The second terminal of the 33 .mu.H inductor is coupled to DGND through a 330 .mu.F capacitor as shown in FIG. 65J.

Pin 6 of the top winding is coupled to pin 3 of the middle winding as shown in FIGS. 65H and 65J. Pin 8 of the middle winding is coupled to the anode of a first STPS1L40A Low Drop Power Schottky Rectifier which is available form STMicroelectronics. The cathode of the first STPS1L40A rectifier establishes +12V and is coupled to DGND through a 100 .mu.F capacitor as shown in FIG. 65J. As shown in FIGS. 65H, 65J, 65K, and 65L, pin 4 of the bottom winding establishes CGND and is coupled to the CGND line which is, in turn, coupled to the circuitry of FIGS. 64A–64Q as described above. Pin 7 of the bottom winding is coupled to the anode of a second STPS1L40A Low Drop Power Schottky Rectifier. As shown in FIGS. 65J and 65L, the cathode of the second STPS1L40A rectifier establishes +7.5V and is coupled to the +7.5V line which is, in turn, coupled to the circuitry of FIGS. 64A–64Q. In addition, the cathode of the second STPS1L40A rectifier is coupled to CGND through a 100 .mu.F capacitor as shown in FIGS. 65J and 65K.

Figure 66D:
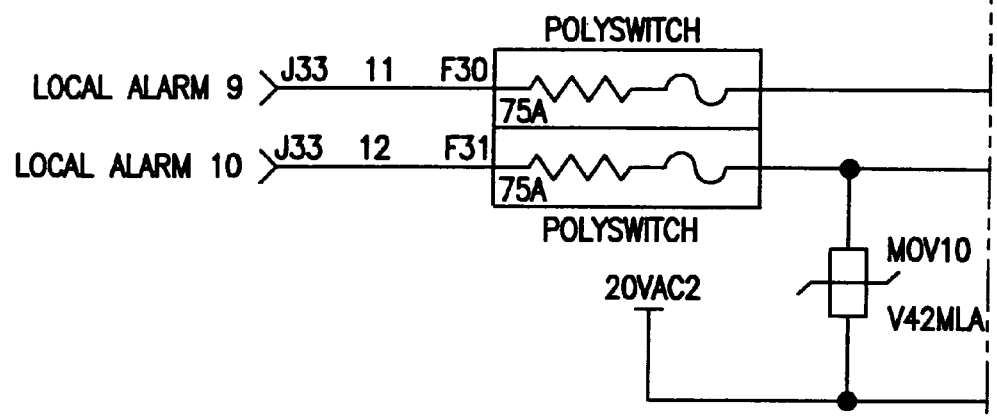
FIG. 66 is a circuit schematic map showing how to lay out FIGS. 66A–66X to form an electric circuit schematic of a fifth portion of the electric circuit of one of the master alarm controllers.
Figure 66E:
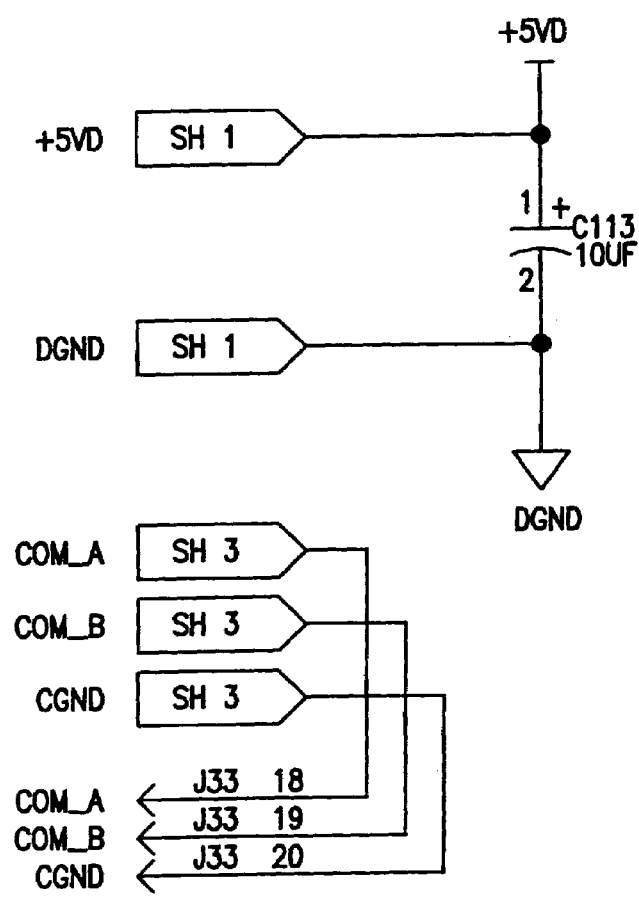
Figure 66F:
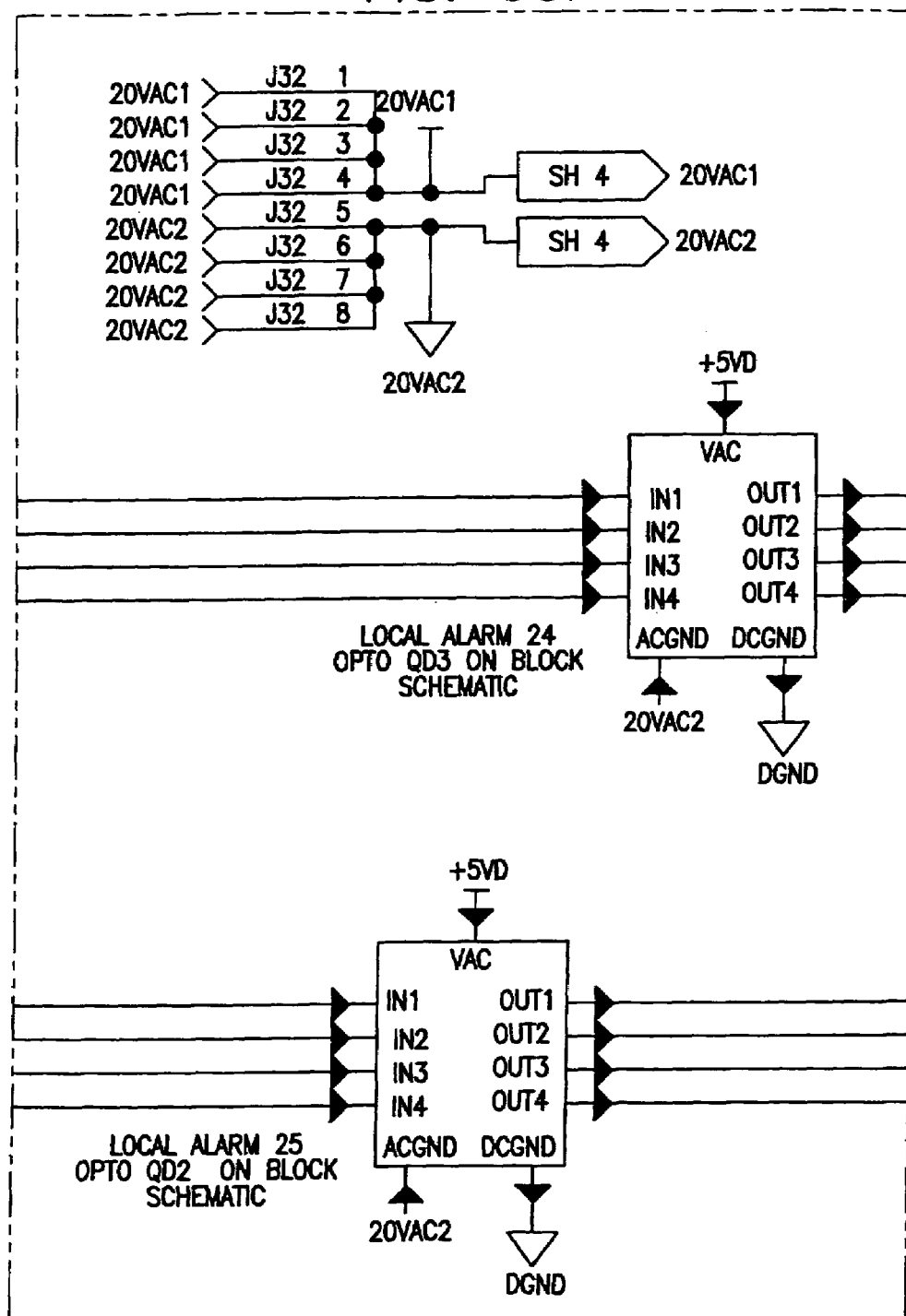
Figure 66G:
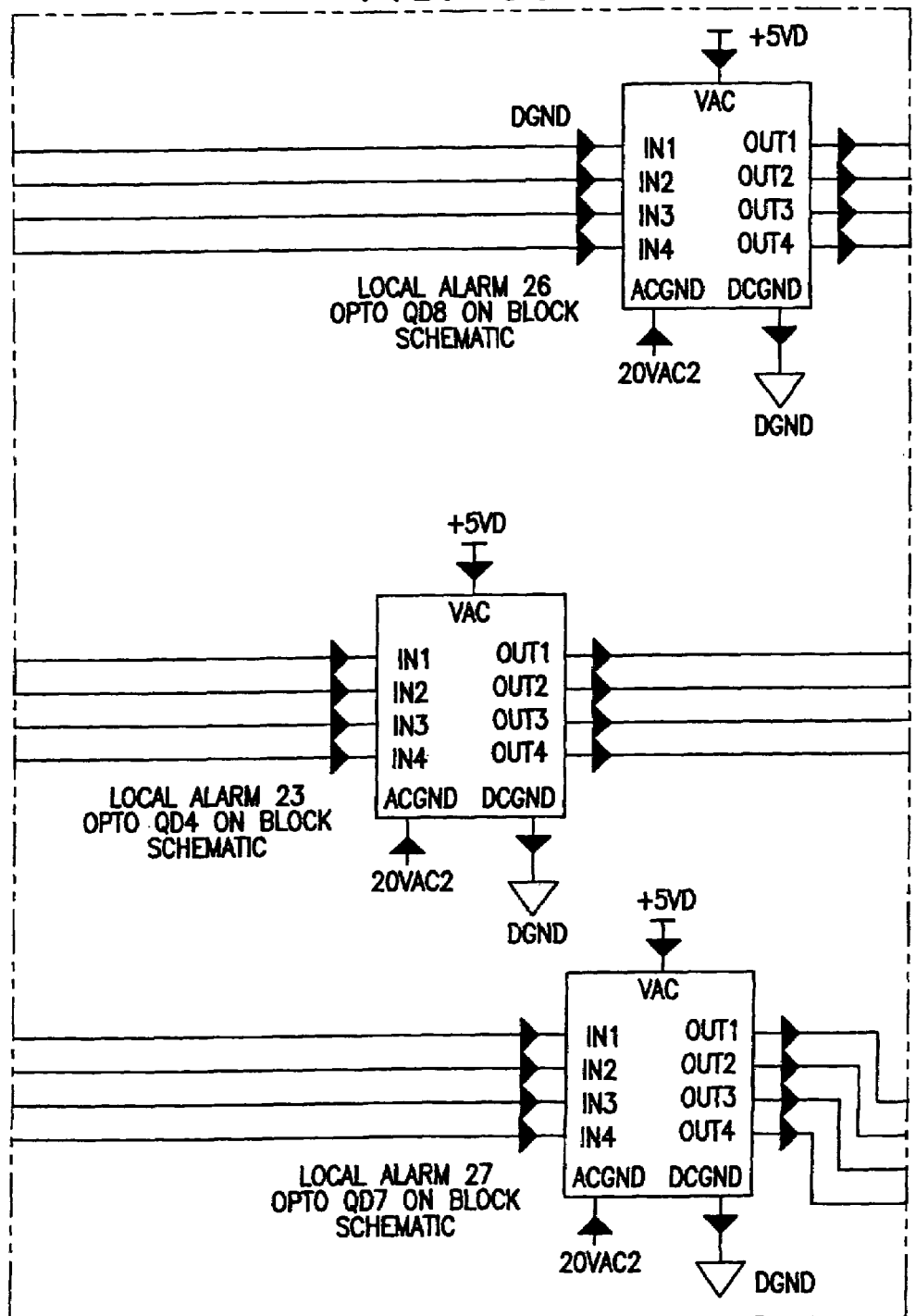
Figure 66H:
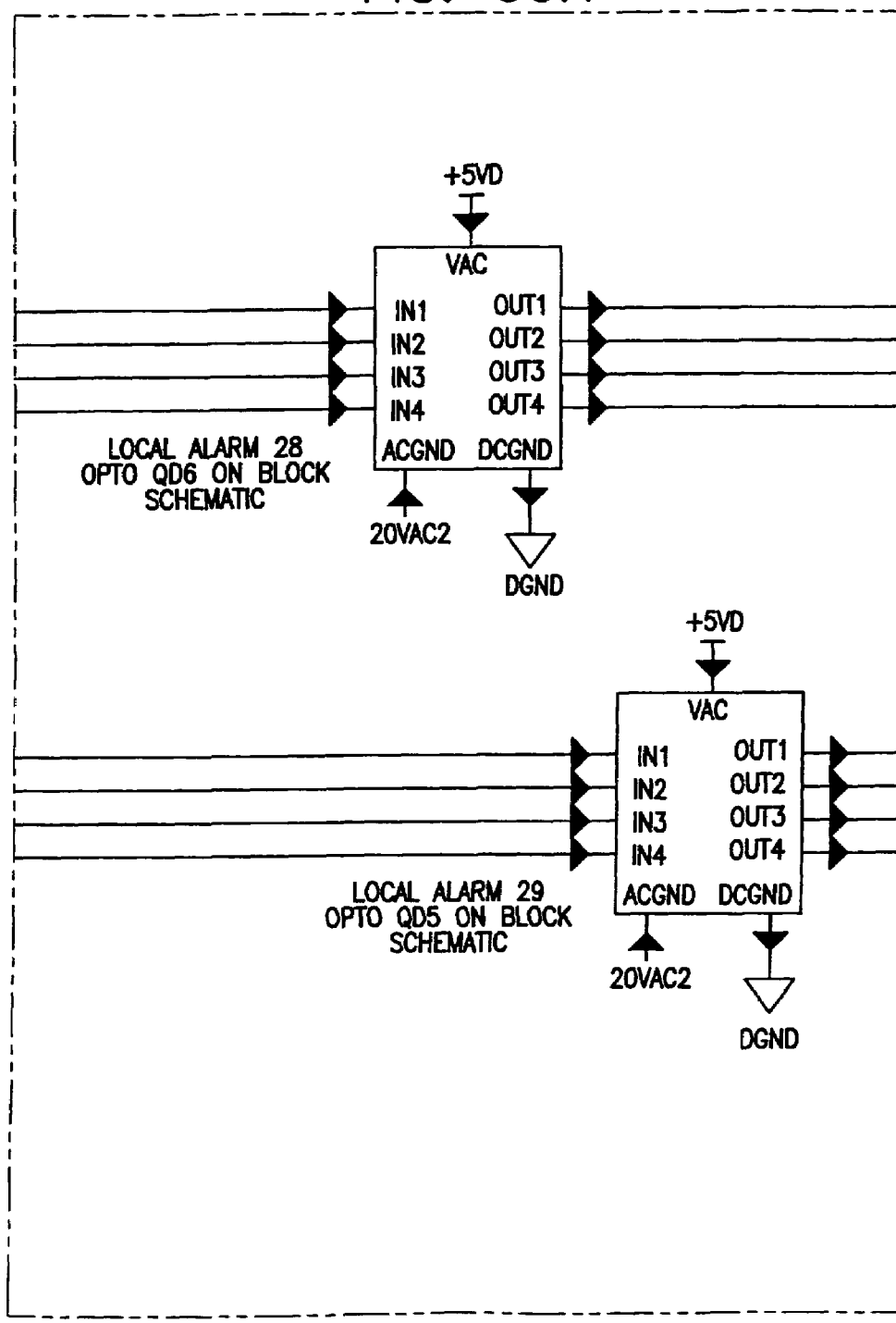
Figure 661:
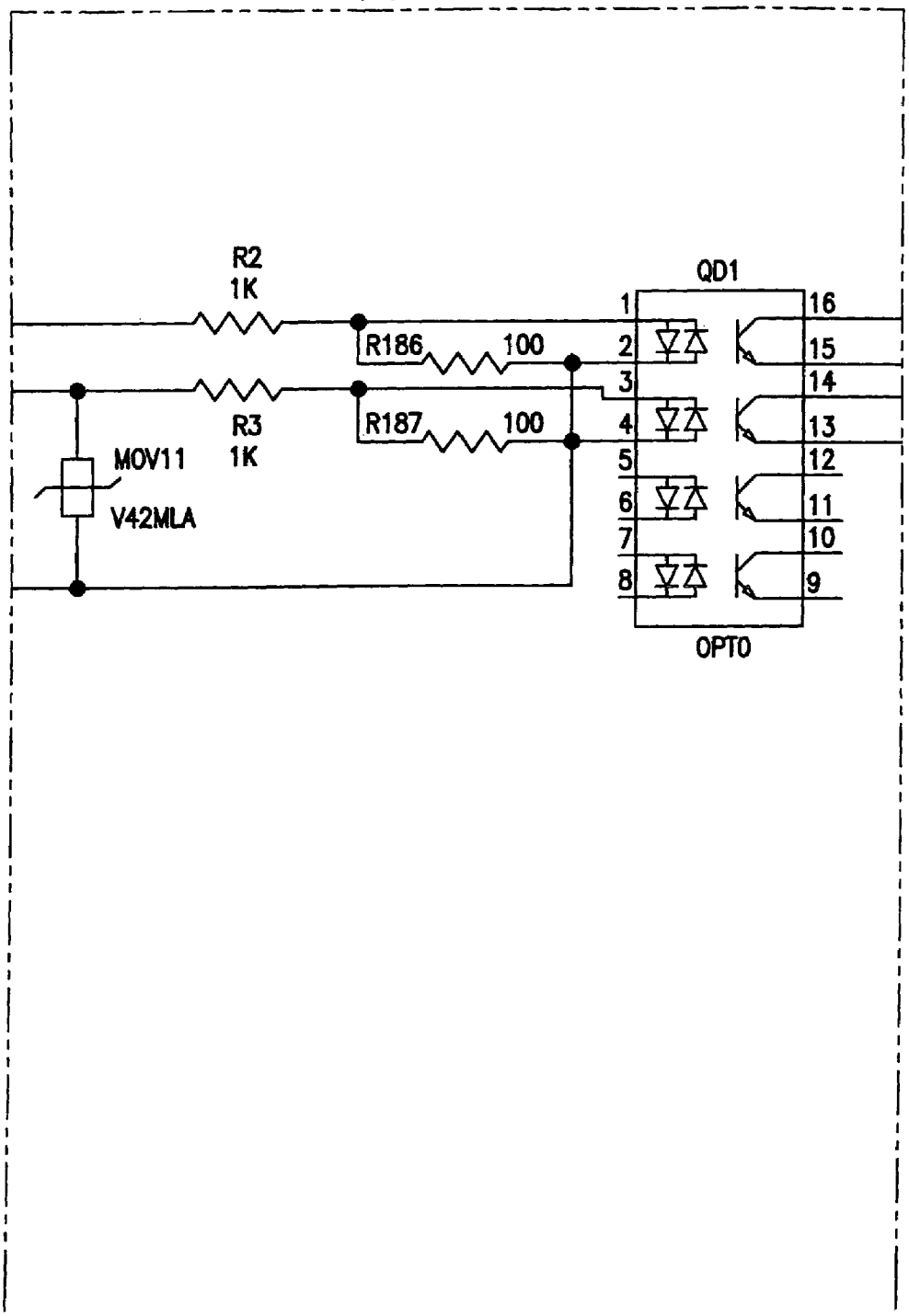
Figure 66J:
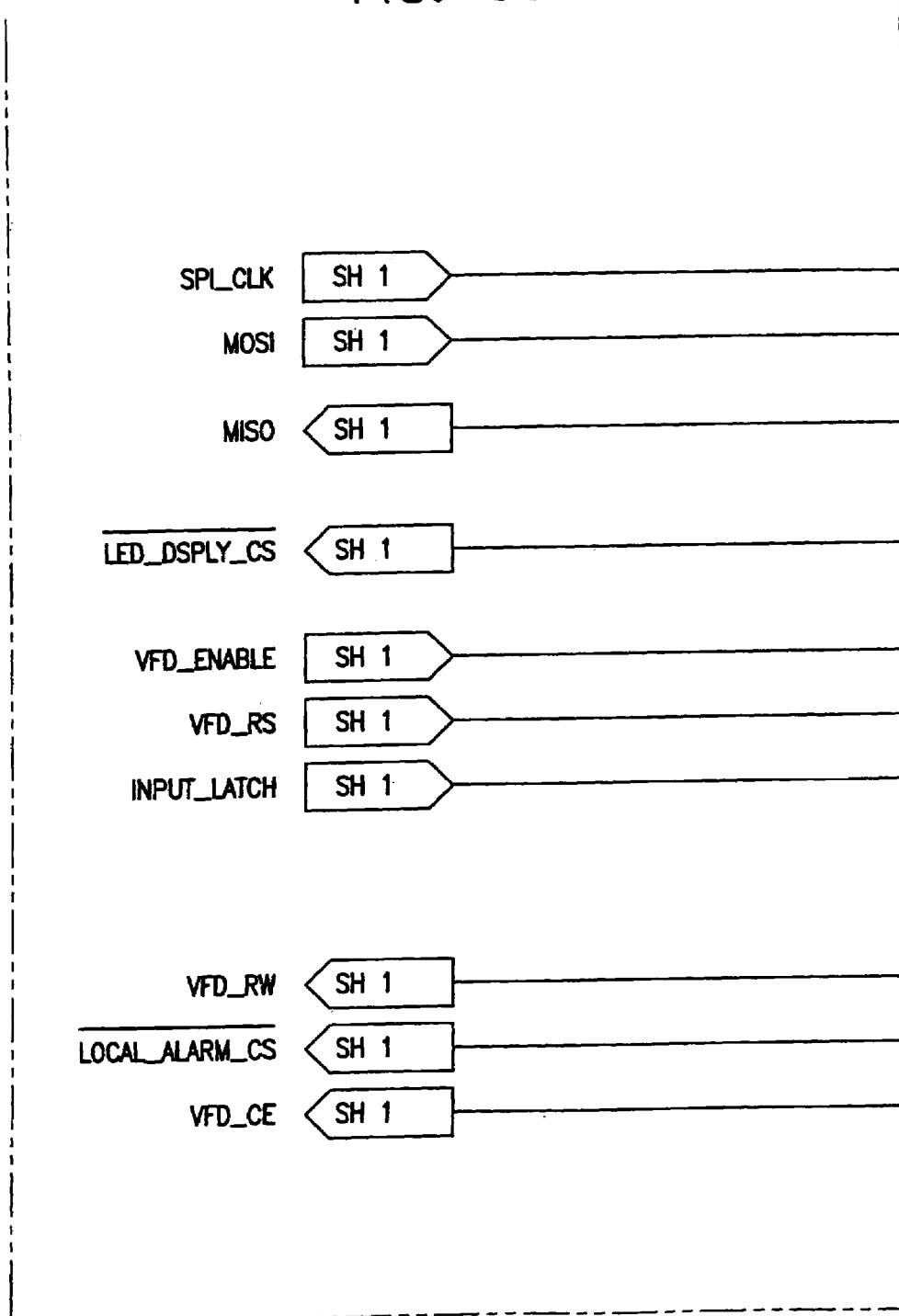
Figure 66K:
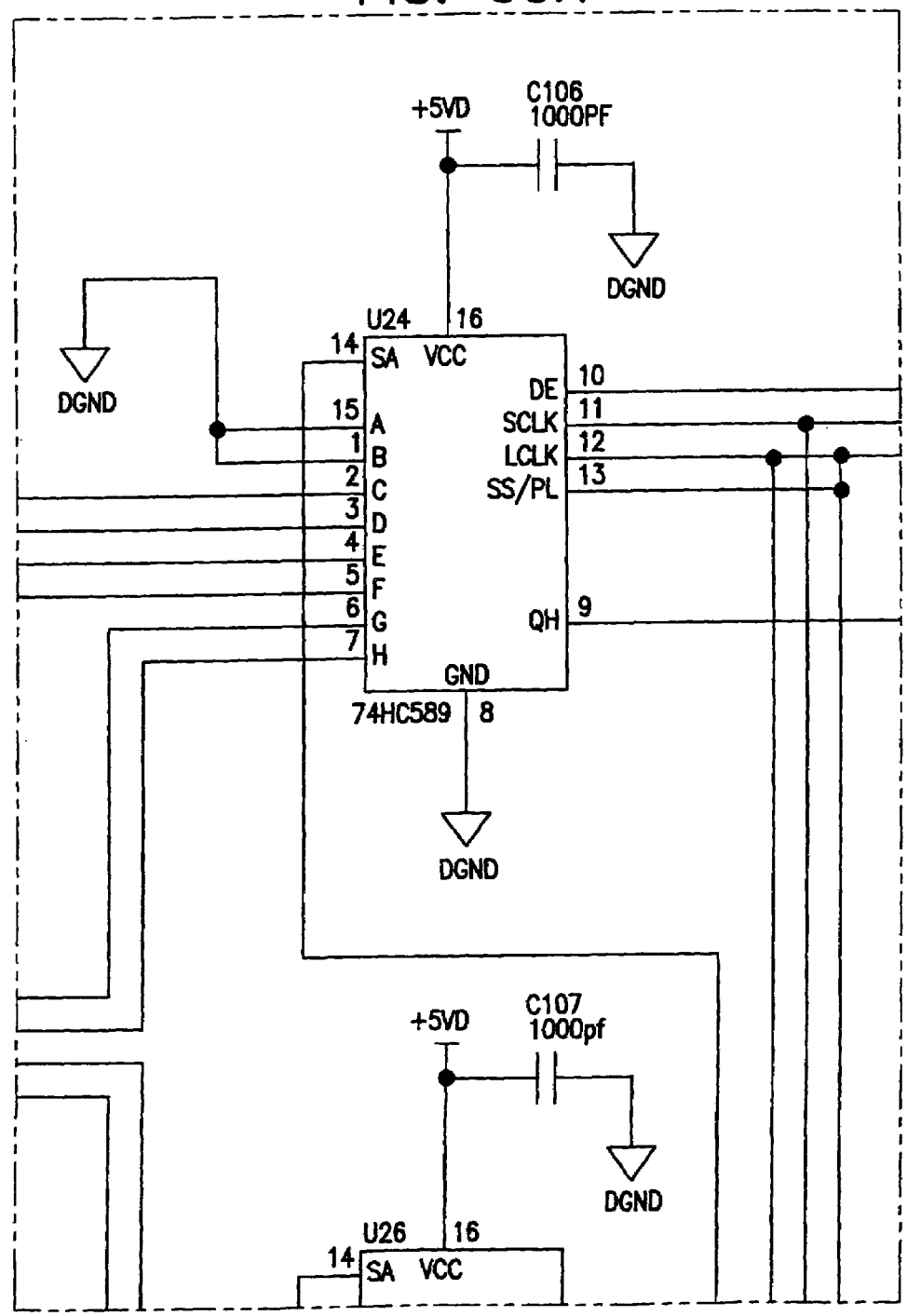
Figure 66L:
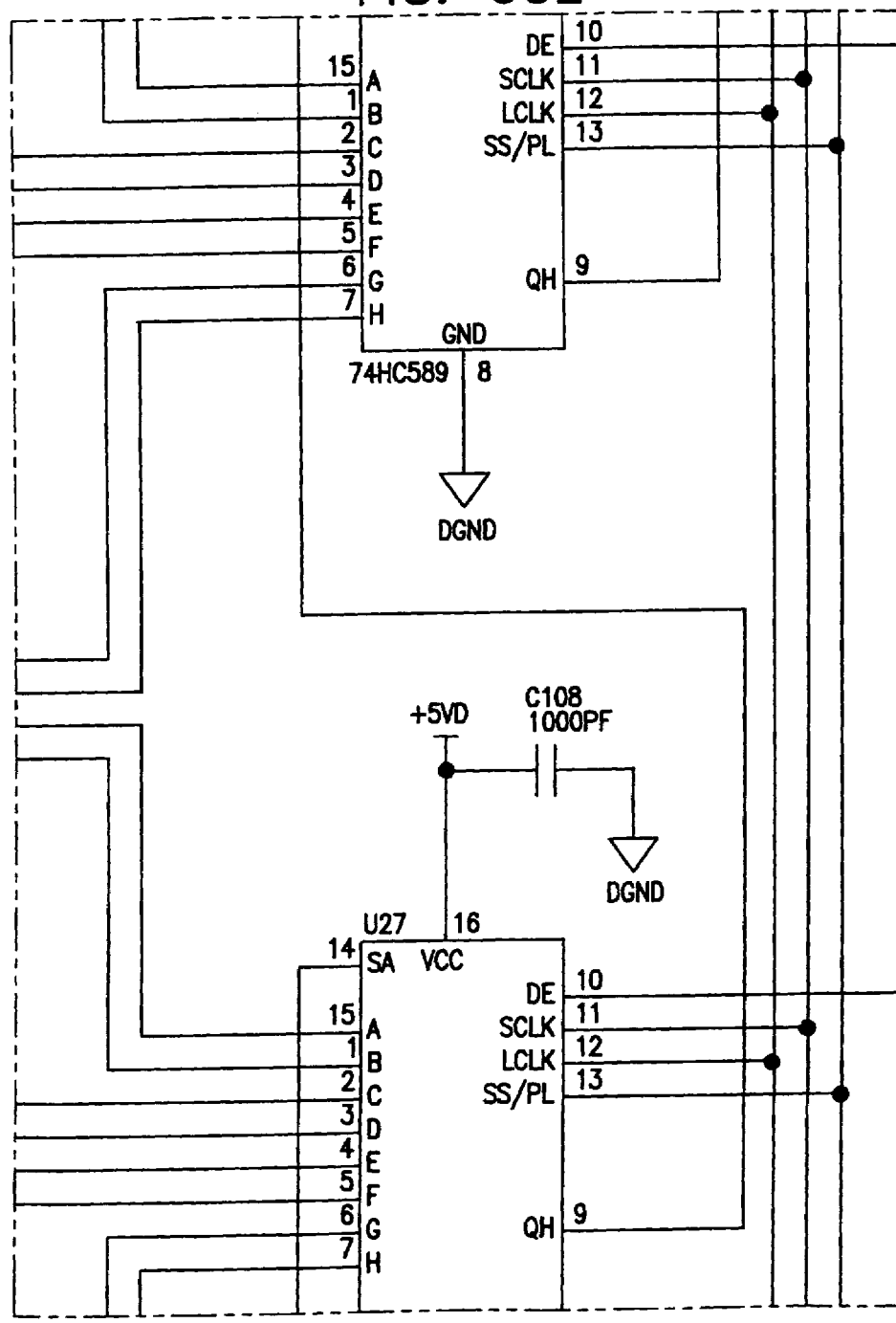
Figure 66M:
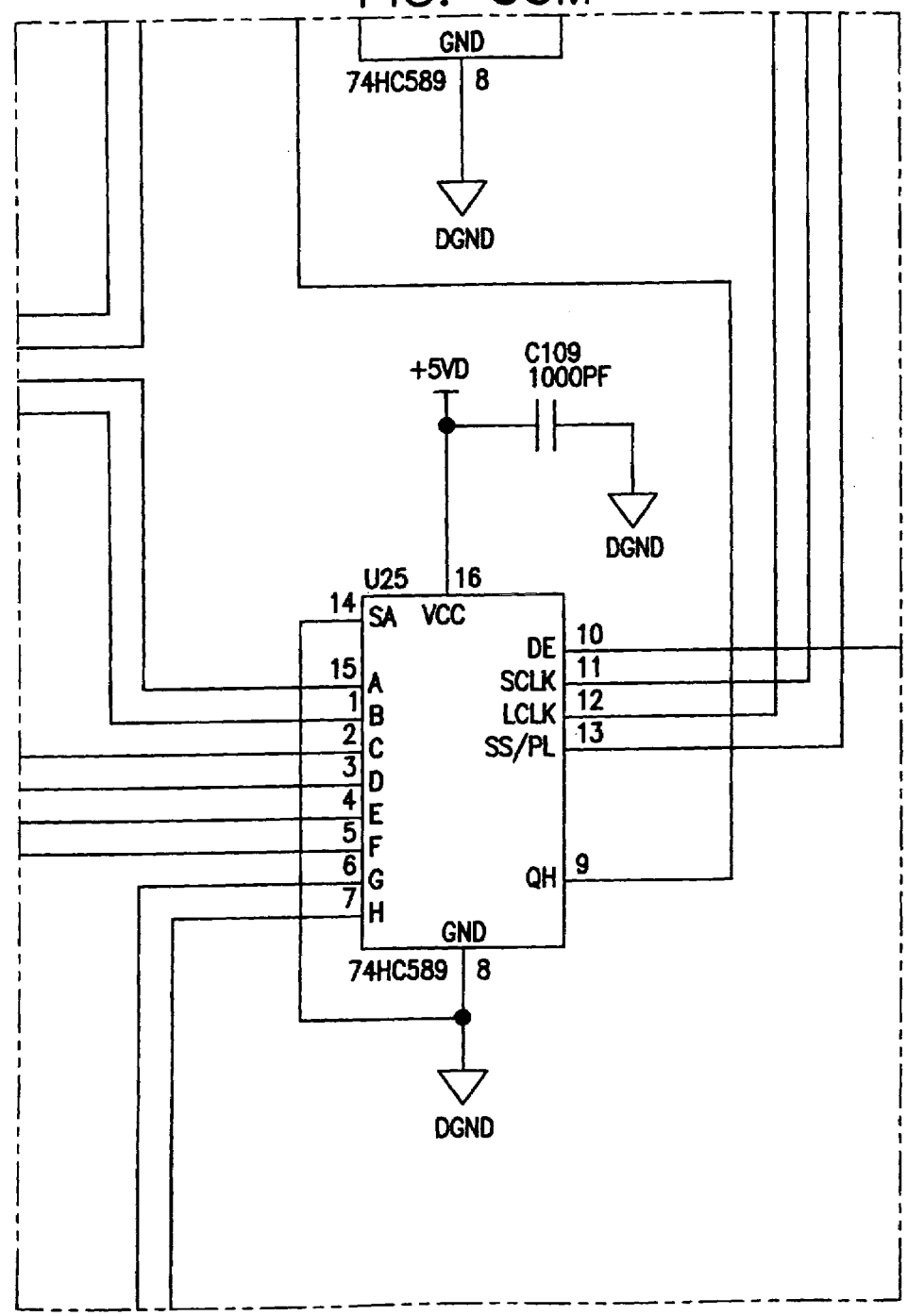
Figure 66N:
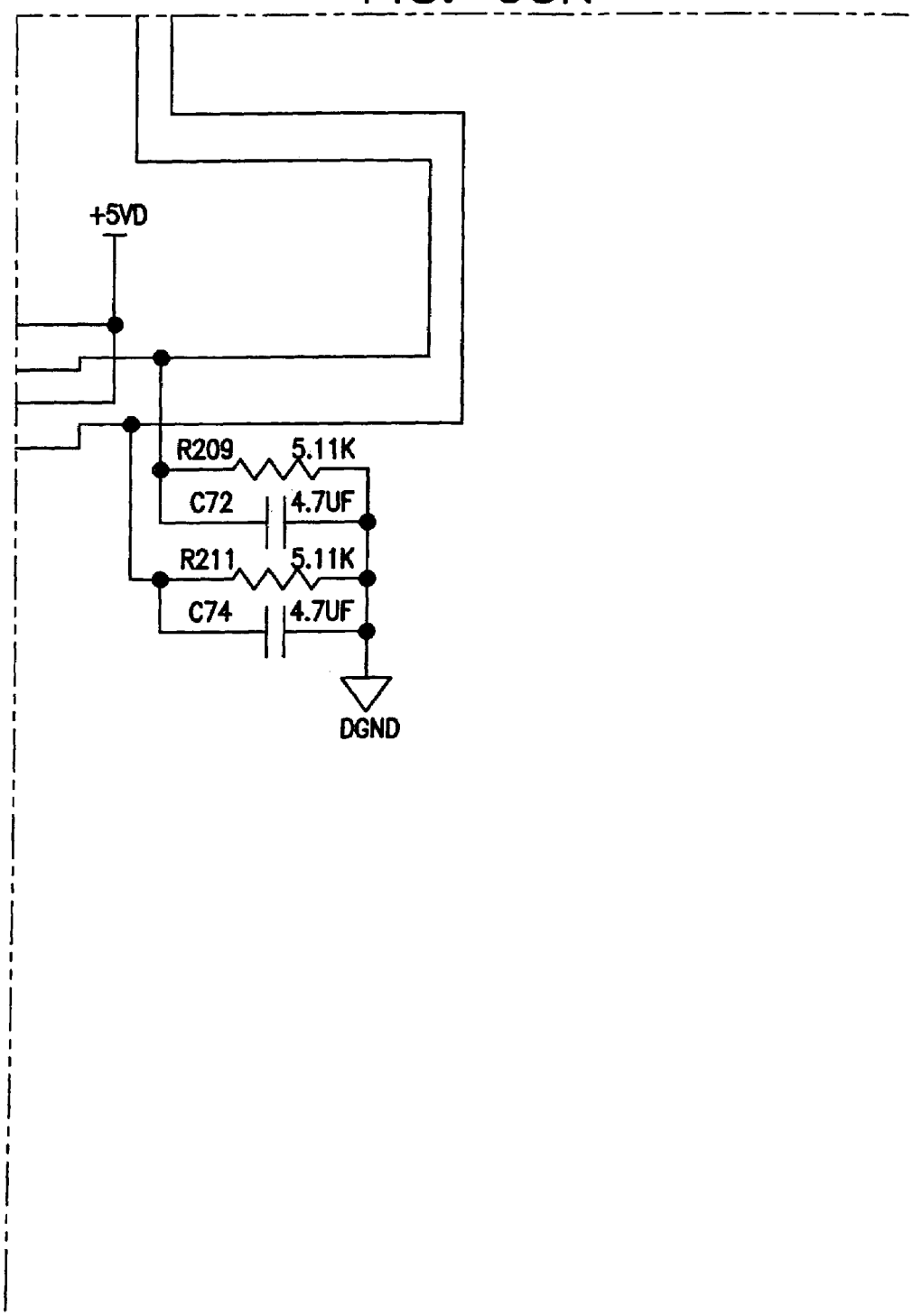
Figure 660:
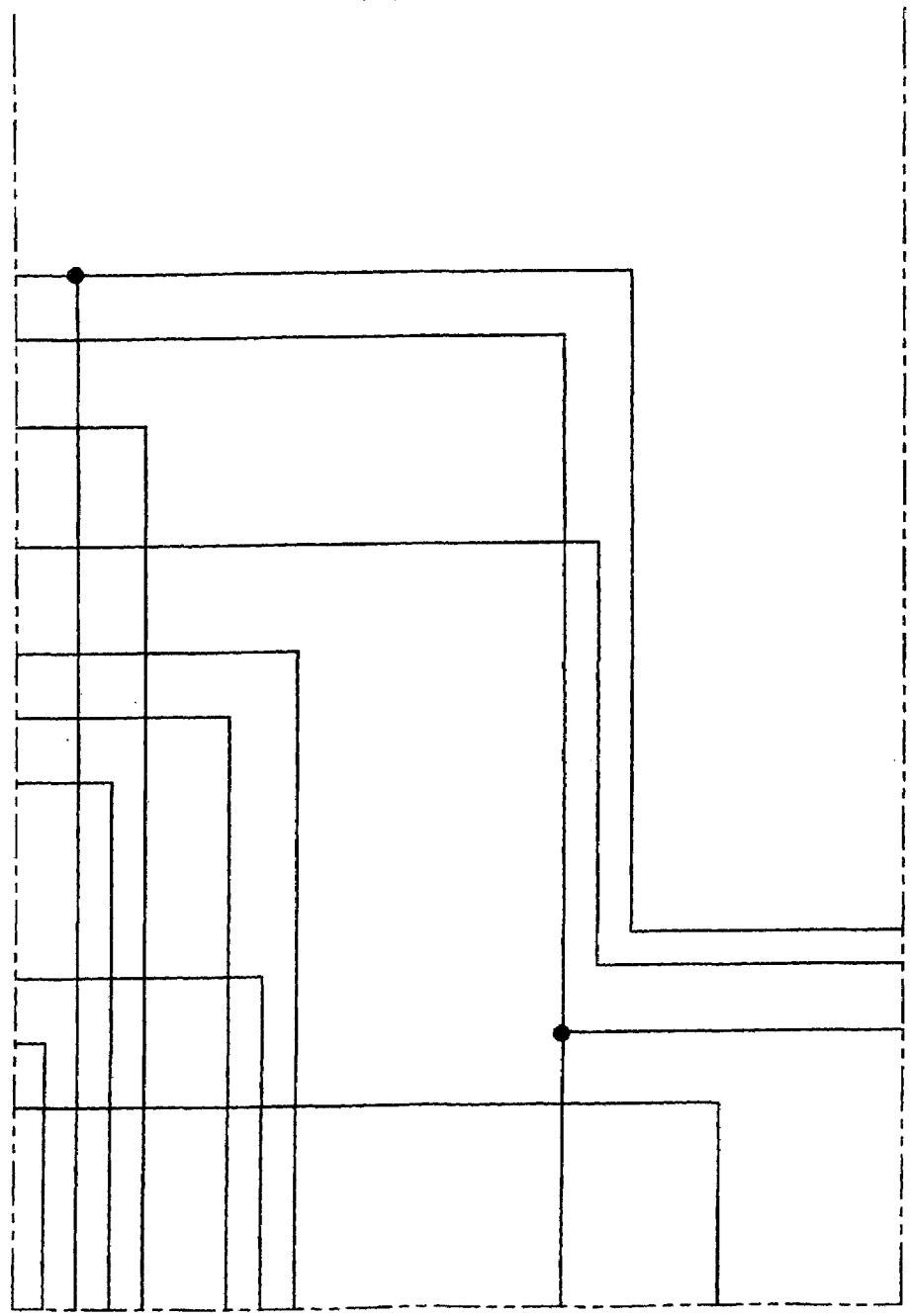
Figure 66P:
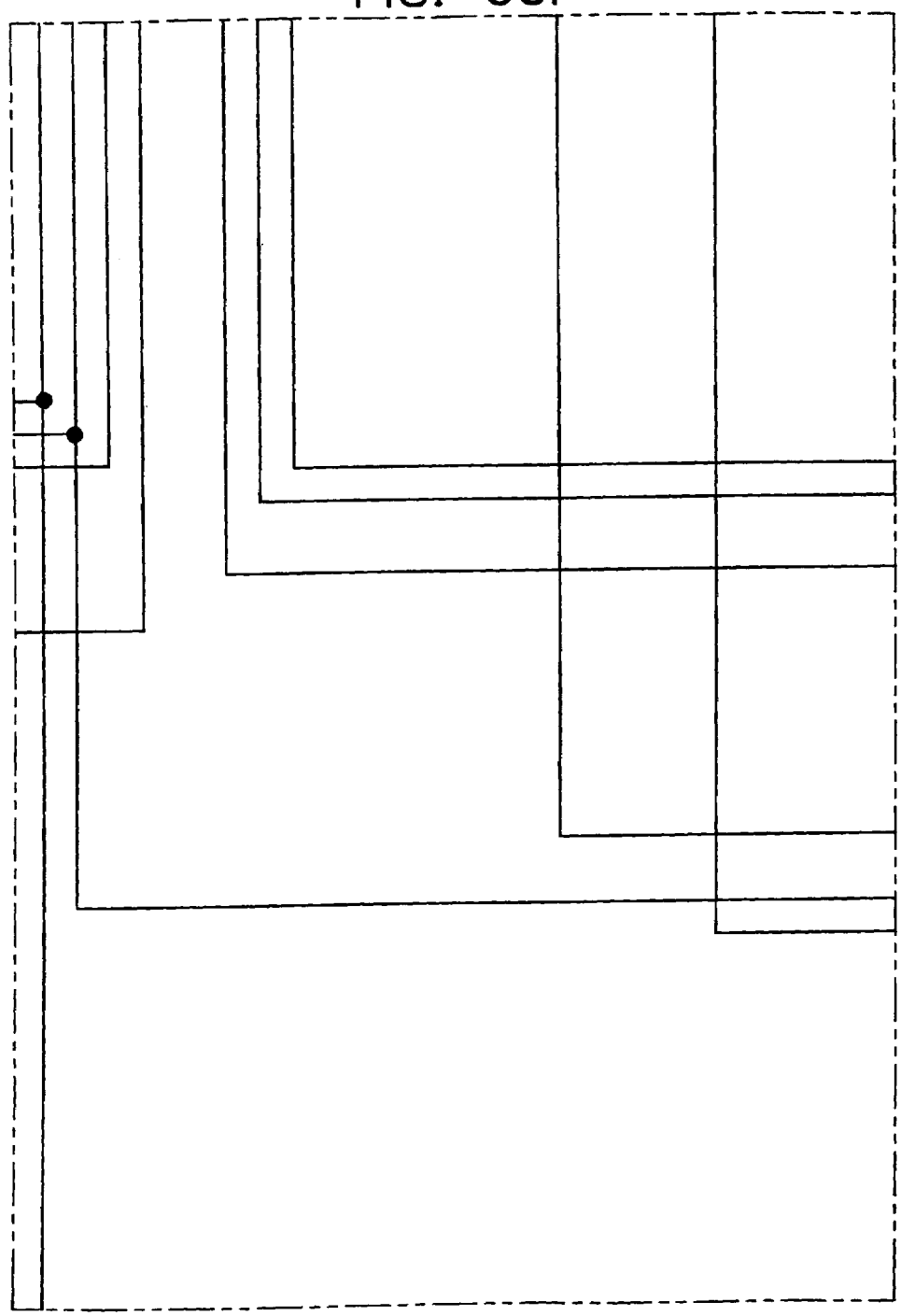
Figure 66Q:
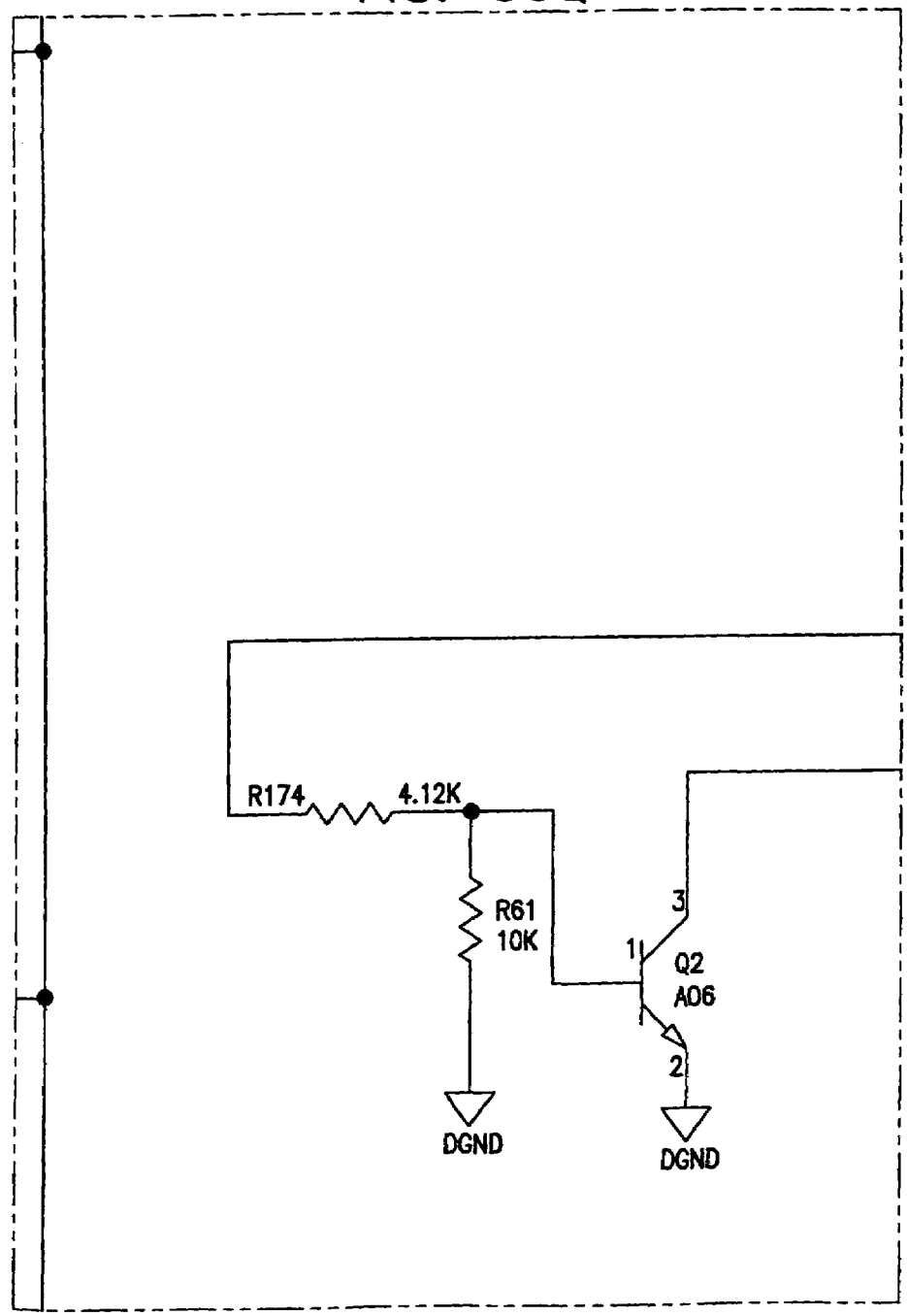
Figure 66R:
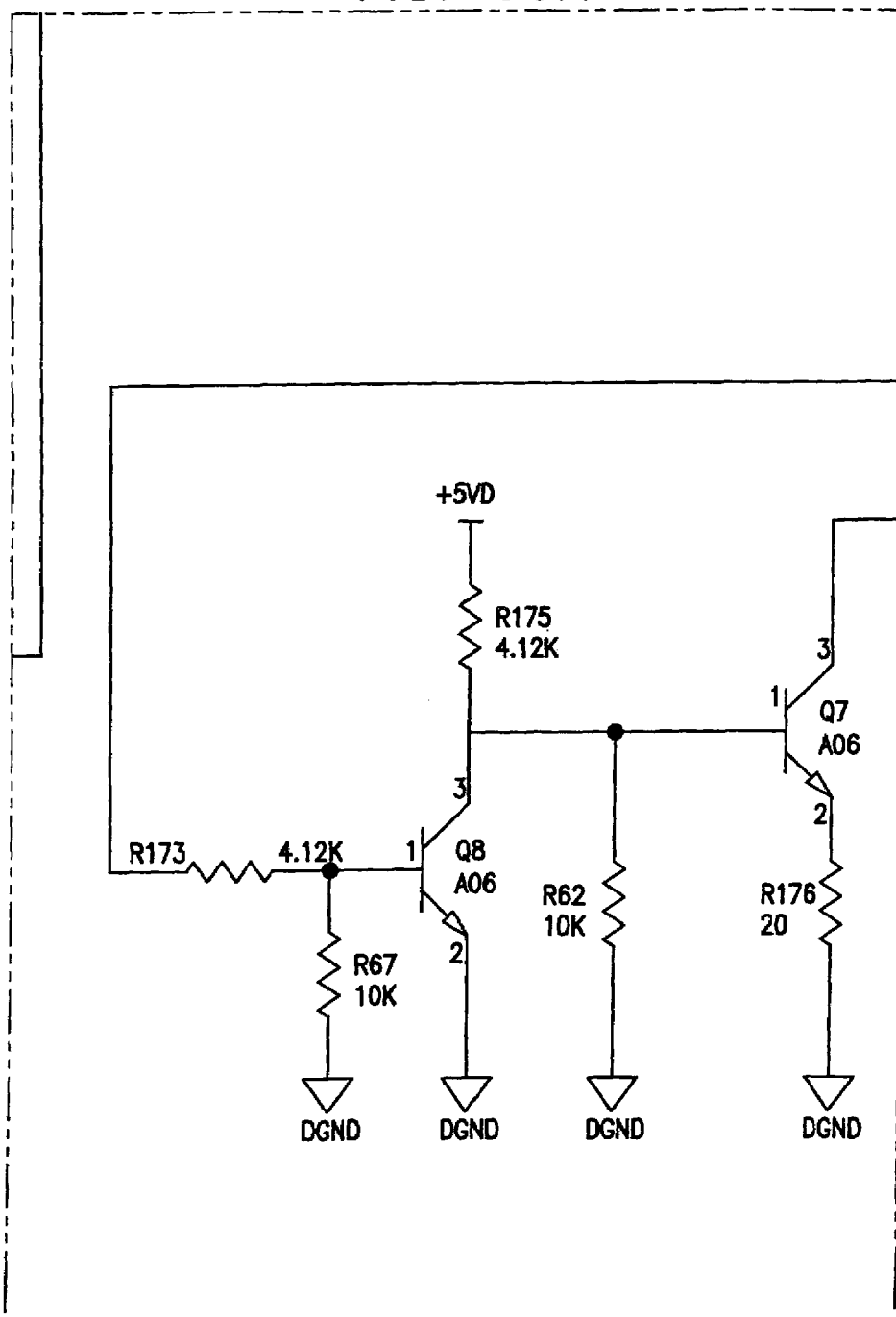
Figure 66S:
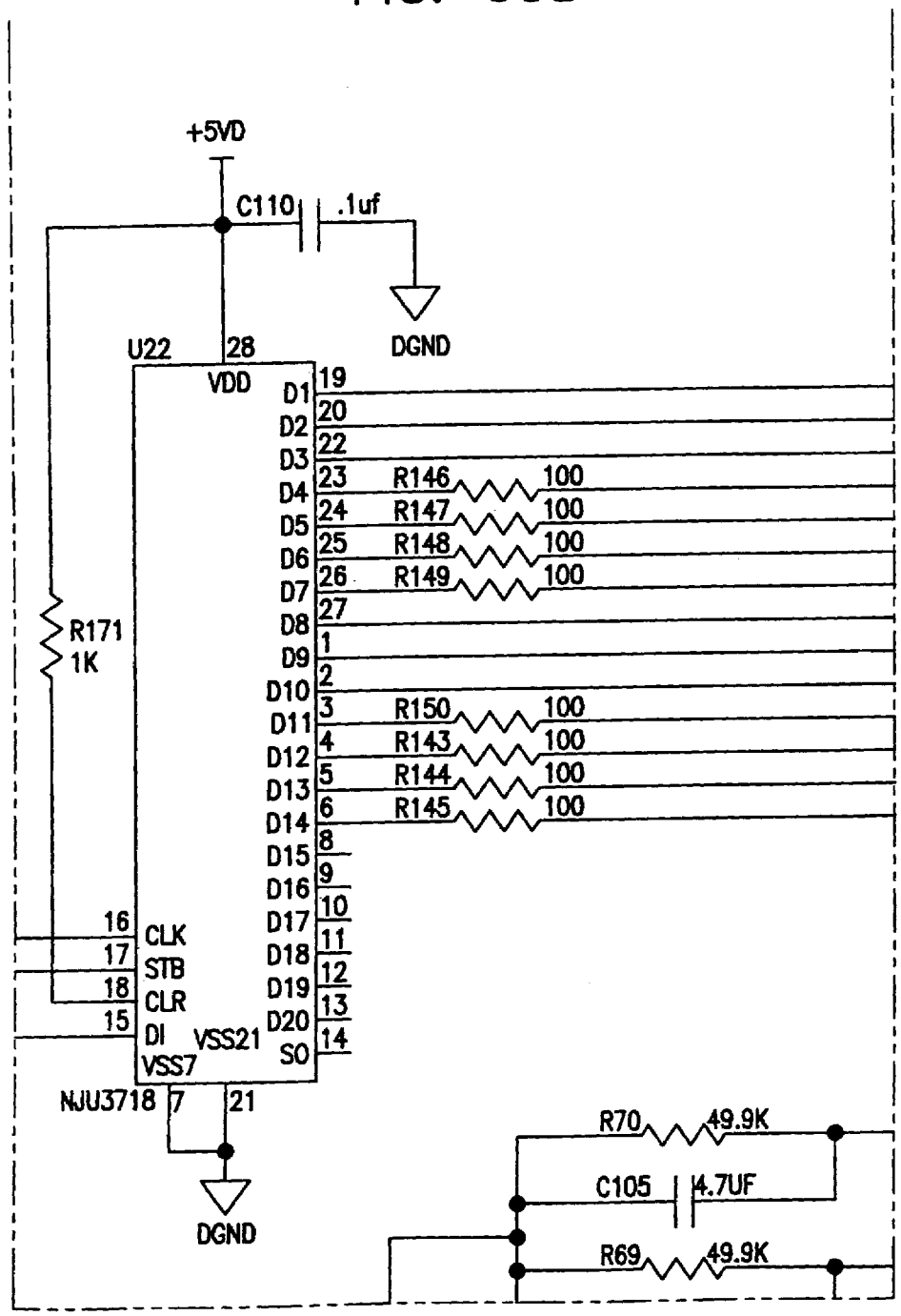
Figure 66T:
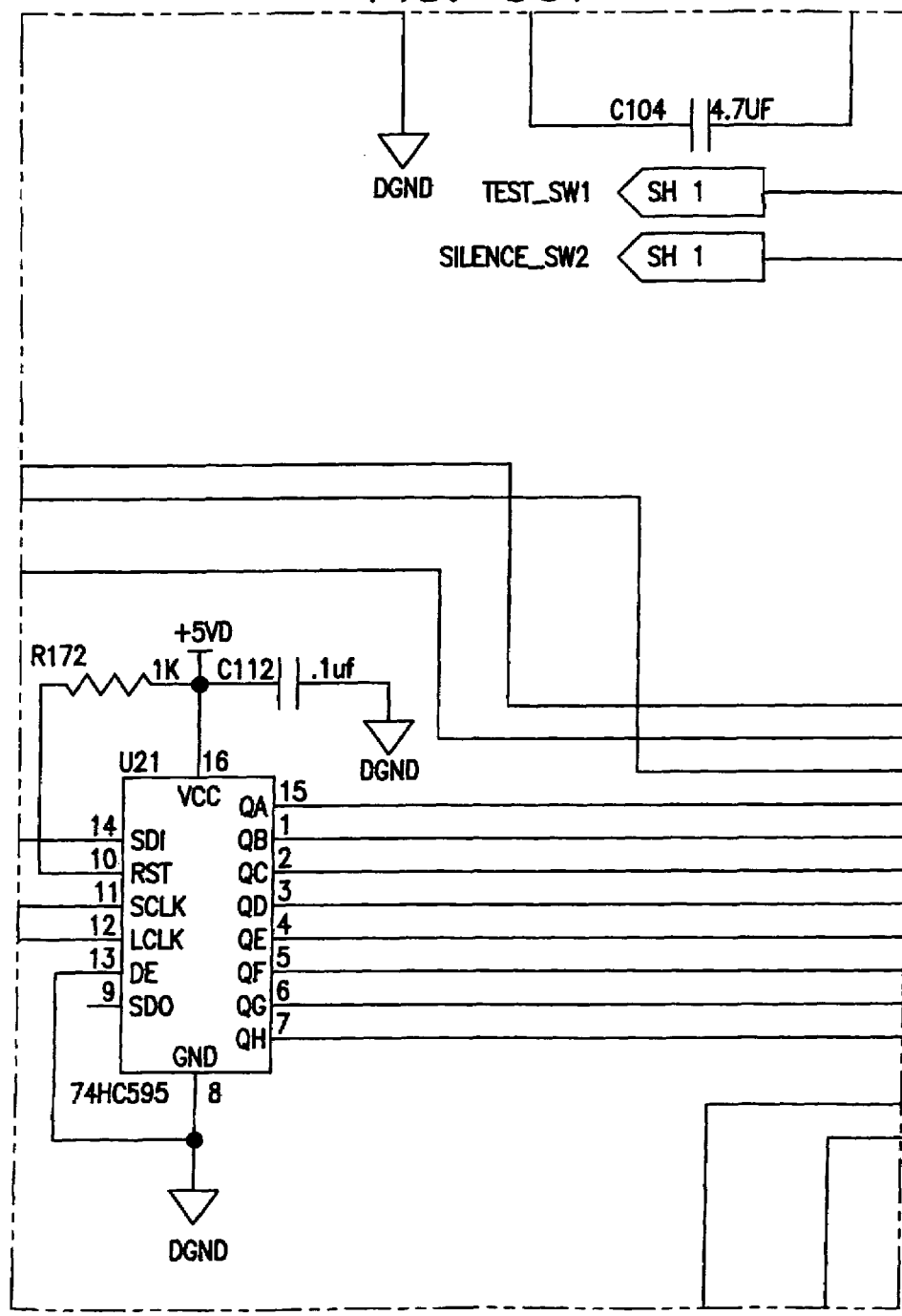
Figure 66U:
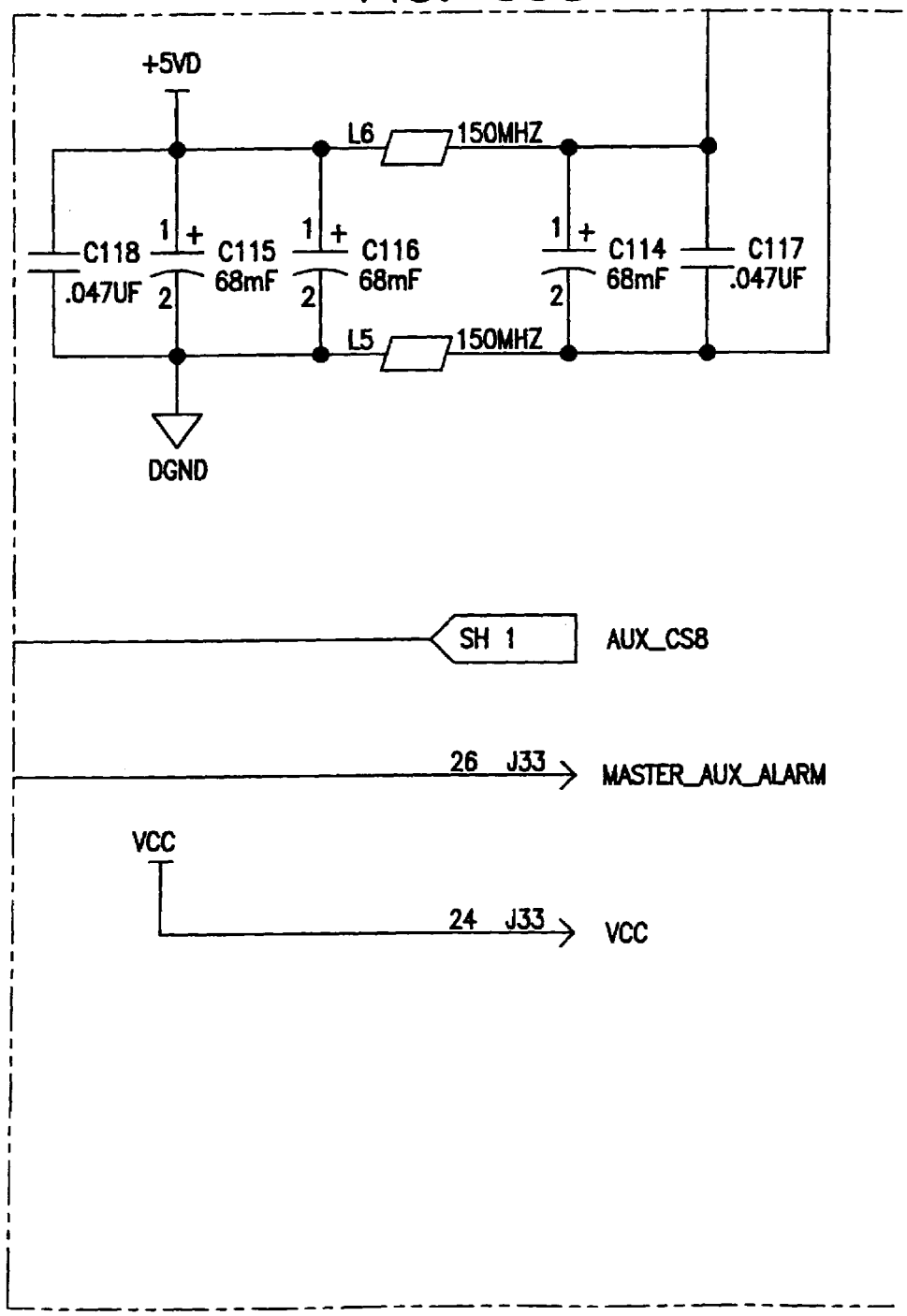
Figure 66V:
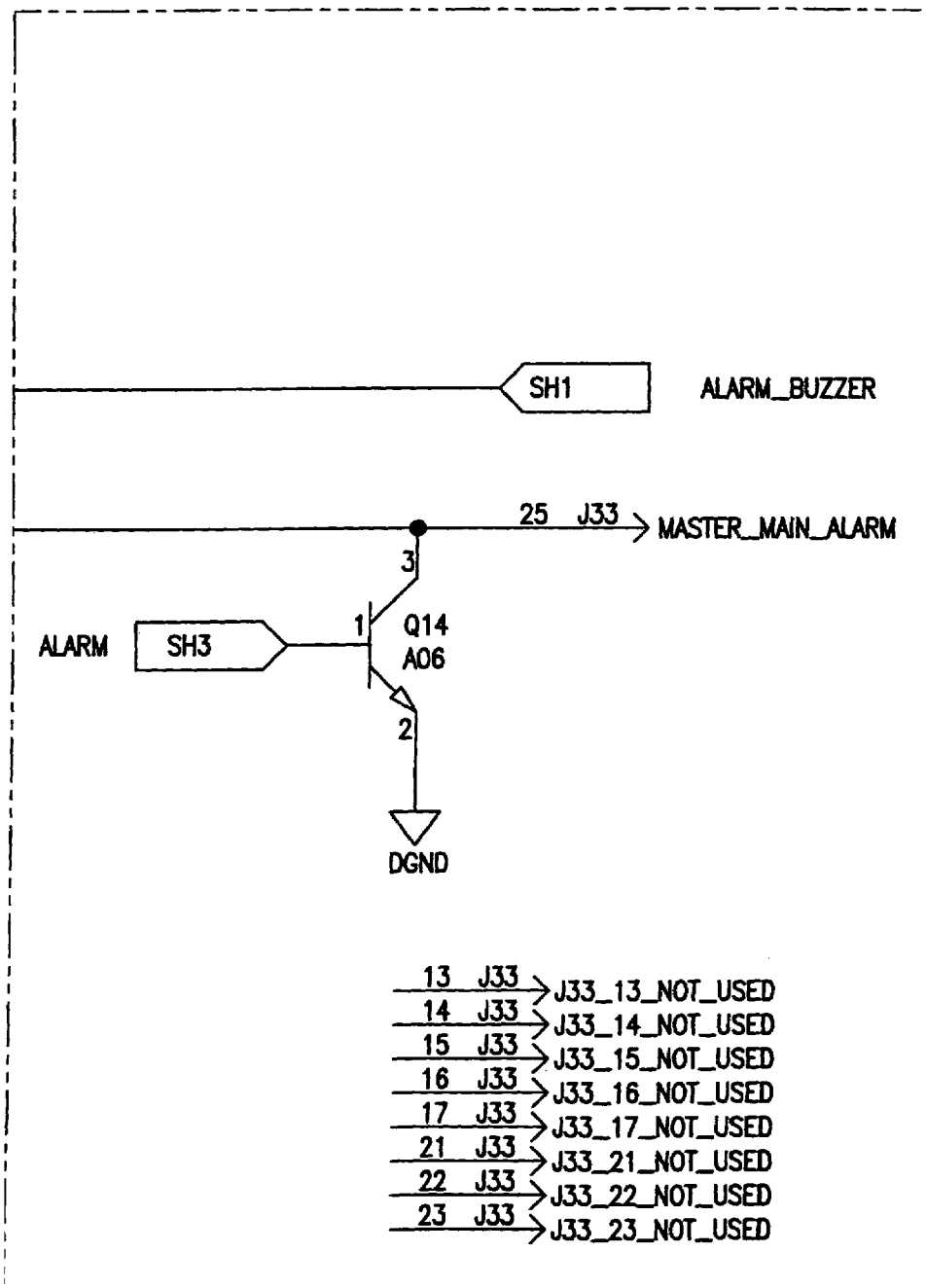
Figure 66W:
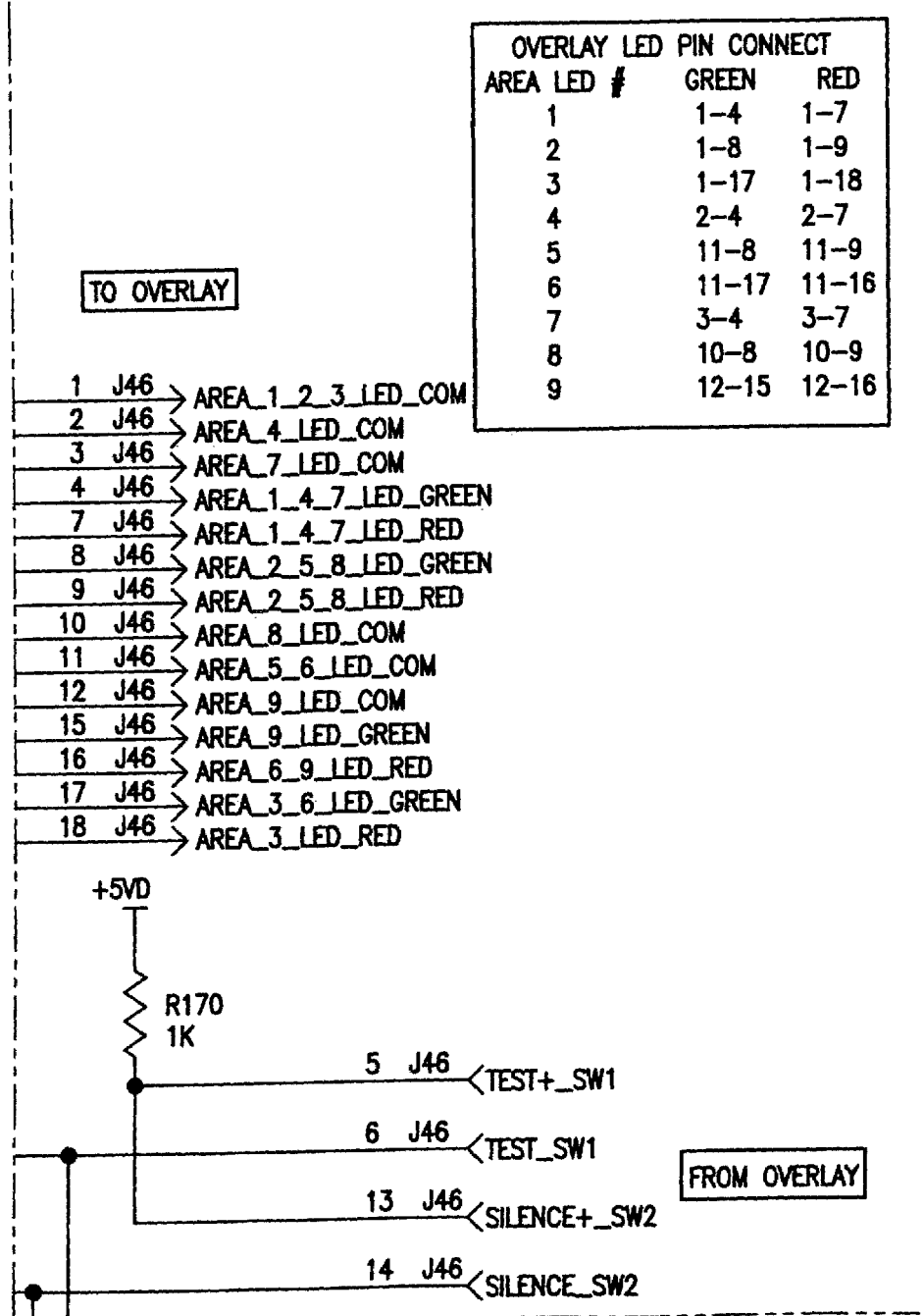
Figure 66X:
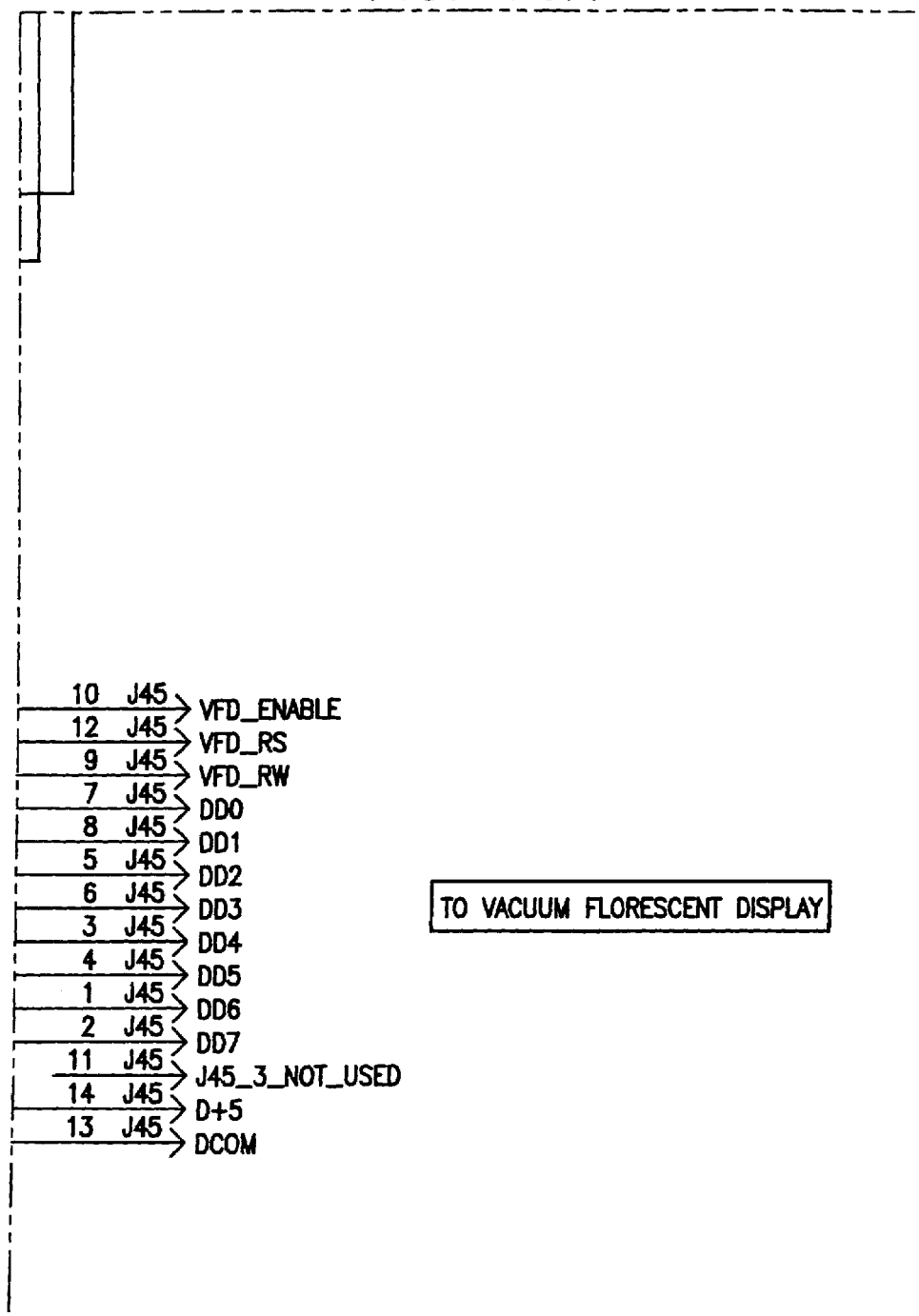

Referring now to FIGS. 66A–66X, circuit 70 includes eight PCT4216 optical isolator chips, which are available from Lumex Incorporated, and four 74HC589 8-bit shift register chips, which are available from Fairchild Semiconductor Corporation. Seven of the PCT4216 chips receive a total of 28 input signals from the switches that are coupled to source equipment 18 to monitor the condition thereof and the eighth PCT4216 chip receives input signals from two of the switches that are coupled to source equipment 18. Thus, the PCT4216 chips receive the 30 total input signals that are coupled to master alarm controller 48.

Circuit 70 includes a first 26-pin connector (identified as connector "J32") and a second 26-pin connector (identified as connector "J33"). As shown in FIG. 66F, pins 1–4 of the connector J32 are coupled to 20VAC1 and are coupled to the 20VAC1 line which is, in turn, coupled to the circuitry of FIGS. 65A–65L as described above. As also shown in FIG. 66F, pins 5–8 of the connector J32 are coupled to 20VAC2 and are coupled to the 20VAC2 line which is, in turn, coupled to the circuitry of FIGS. 65A–65L. Pins 9–26 of the connector J32 receive from source equipment 18 a number of the input signals, which are identified in FIGS. 66A and 66B as LOCAL ALARM 11, 12, 13, 14, 15, 16, 17, 18, 19, 20, 30, 29, 28, 27, 26, 25, 24, and 23, respectively.

Pins 1–12 of the connector J33 receive from source equipment 18 the other input signals, which are identified in FIGS. 66B, 66C, and 66D as LOCAL ALARM 22, 21, 1, 2, 3, 4, 5, 6, 7, 8, 9, and 10, respectively. Pins 13–17 and 21–23 of the connector J33 are not and such is indicated in FIG. 66V. As shown in FIG. 66E, pins 18–20 of the connector J33 are coupled to the COM_A, COM_B, and CGND lines that are received from the circuitry of FIGS. 64A–64Q. Pin 24 of the connector J33 is coupled to VCC as shown in FIG. 66U. Pin 25 of the connector J33 is associated with a MASTER_MAIN_ALARM line that is coupled to the collector of an first NPN transistor (identified as circuit component Q14) and that is coupled to the collector of a second NPN transistor (identified as circuit component Q7) as shown in FIGS. 66R and 66V. As shown in FIG. 66V, the base of the Q14 transistor is coupled to the ALARM line from the circuitry of FIGS. 64A–64Q and the emitter of the Q14 transistor is coupled to DGND.

The emitter of the Q7 transistor is coupled to DGND through a 20.OMEGA. resistor as shown in FIG. 66R. The base of the Q7 transistor is coupled to the collector of an NPN transistor (identified as circuit component Q8) and is also coupled to DGND through a 10 k.OMEGA. resistor. The collector of the Q8 transistor is coupled to +5 VD through a 4.12 k.OMEGA. resistor and the emitter of the Q8 transistor is coupled to DGND. As shown in FIGS. 66R and 66V, the base of the Q8 transistor is coupled to the ALARM_BUZZER line from the circuitry of FIGS. 62A–62U through a 4.12 k.OMEGA. resistor and is also coupled to DGND through a 10 k.OMEGA. resistor.

Pin 26 of the connector J33 is associated with a MASTER_AUX_ALARM line and is coupled to the collector of an NPN transistor (identified as circuit element Q2) as shown in FIGS. 66Q and 66U. The emitter of the Q2 transistor is coupled to DGND. As shown in FIGS. 66Q and 66U, the base of the Q2 transistor is coupled to the AUX_CS8 line from the circuitry of FIGS. 62A–62U through a 4.12 k.OMEGA. resistor and is also coupled to DGND through a 10 k.OMEGA. resistor. It will be appreciated that the connector J32 and J33 correspond to connectors 148, 150 that are associated with breakout board 138 and ribbon cables 146 as described above in connection with FIG. 4.

Pins 9–12 of the connector J32 are coupled to IN1, IN2, IN3, and IN4 lines, respectively, of the first PCT4216 chip and pins 13–16 of the connector J32 are coupled to IN1, IN2, IN3, and IN4 lines, respectively, of the second PCT4216 chip as shown in FIGS. 66A and 66F. Similarly, pins 17–20 of the connector J32 are coupled to IN1, IN2, IN3, and IN4 lines, respectively, of the third PCT4216 chip and pins 21–24 of the connector J32 are coupled to IN1, IN2, IN3, and IN4 lines, respectively, of the fourth PCT4216 chip as shown in FIGS. 66B and 66G. Pins 25 and 26 of the connector J32 and pins 1 and 2 of the connector J33 are coupled to IN1, IN2, IN3, and IN4 lines, respectively, of the fifth PCT4216 chip as also shown in FIGS. 66B and 66G. Pins 3–6 of the connector J33 are coupled to IN1, IN2, IN3, and IN4 lines, respectively, of the sixth PCT4216 chip and pins 7–10 of the connector J33 are coupled to IN1, IN2, IN3, and IN4 lines, respectively, of the seventh PCT4216 chip as shown in FIGS. 66C and 66H. The IN1, IN2, IN3, and IN4 lines of each PCT4216 chip are optically isolated from associated OUT1, OUT2, OUT3, and OUT4 lines, respectively.

Figure 71A:
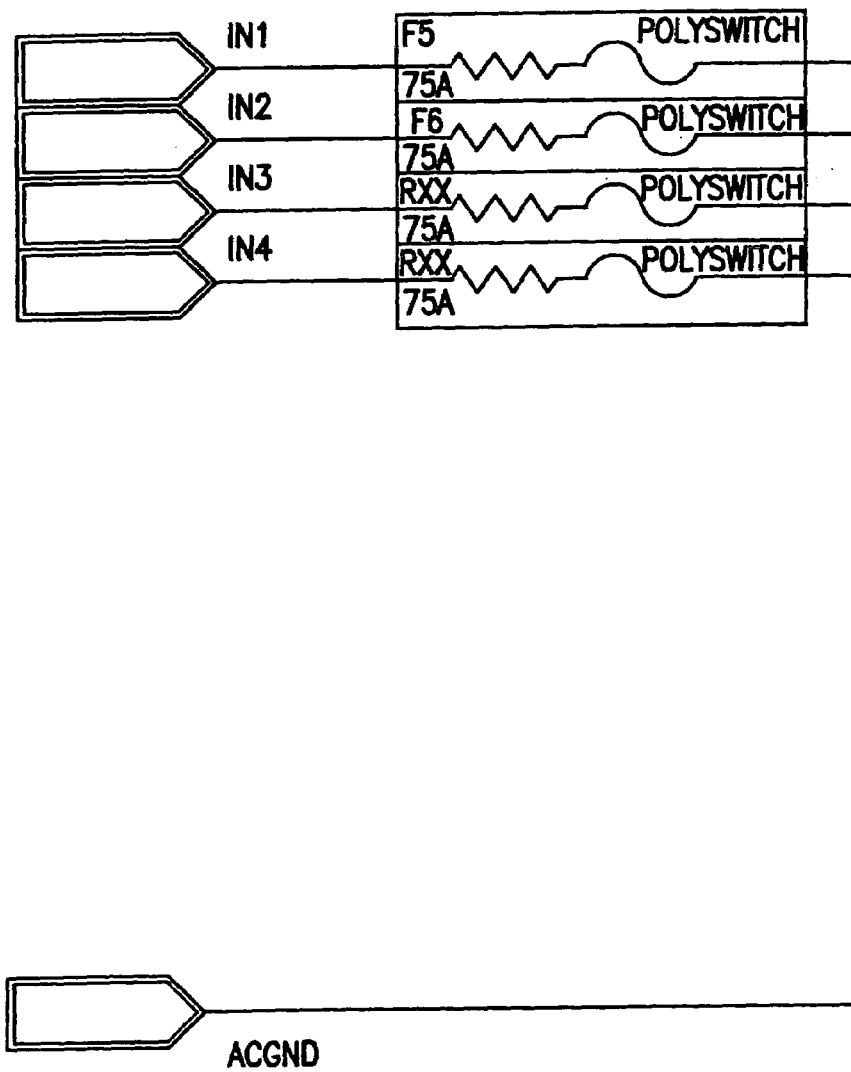
FIG. 71 is a circuit schematic map showing how to lay out FIGS. 71A–71D to form an electric circuit schematic of a subportion of the electric circuit of FIGS. 66A–66X.
Figure 71B:
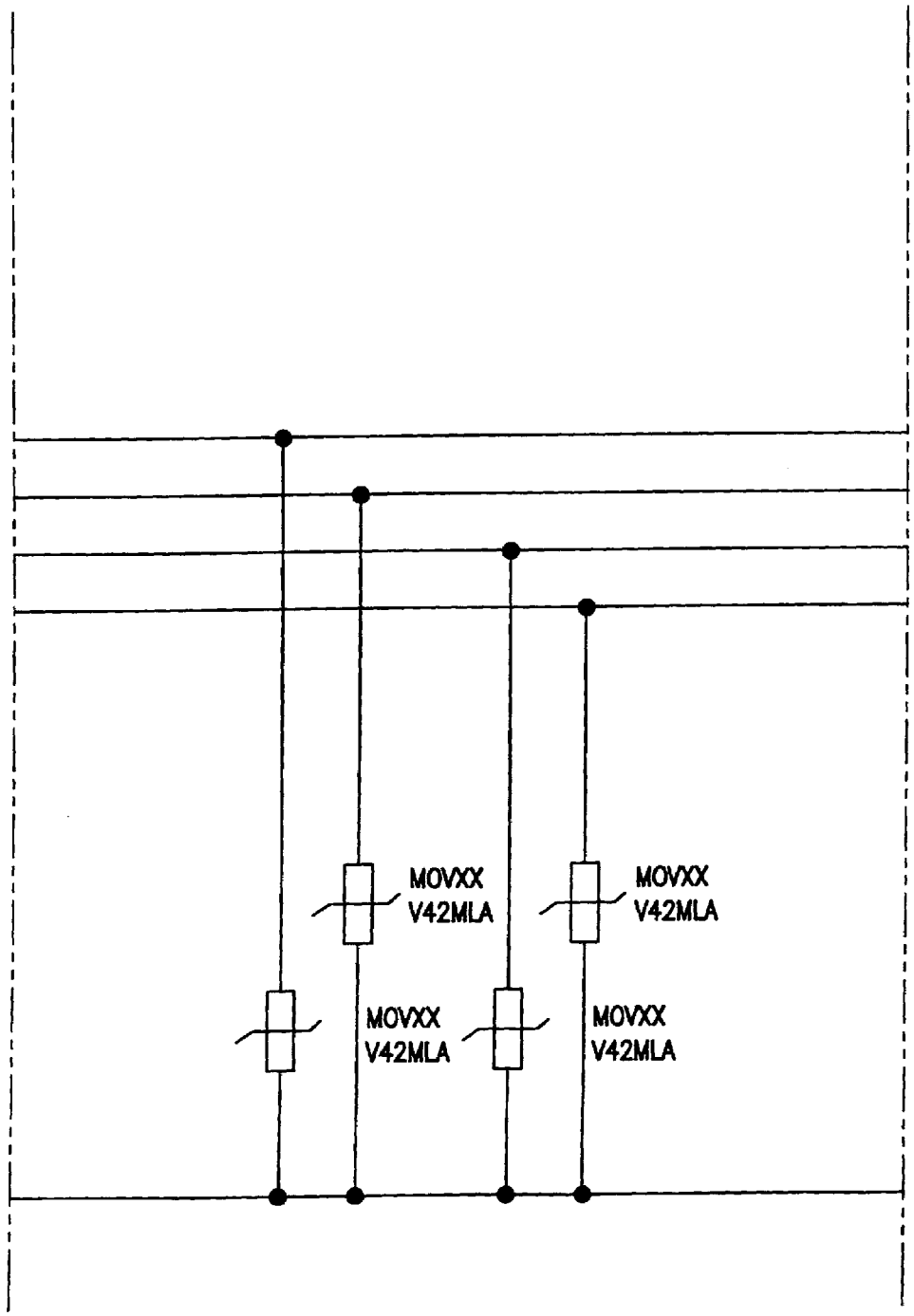
Figure 71C:
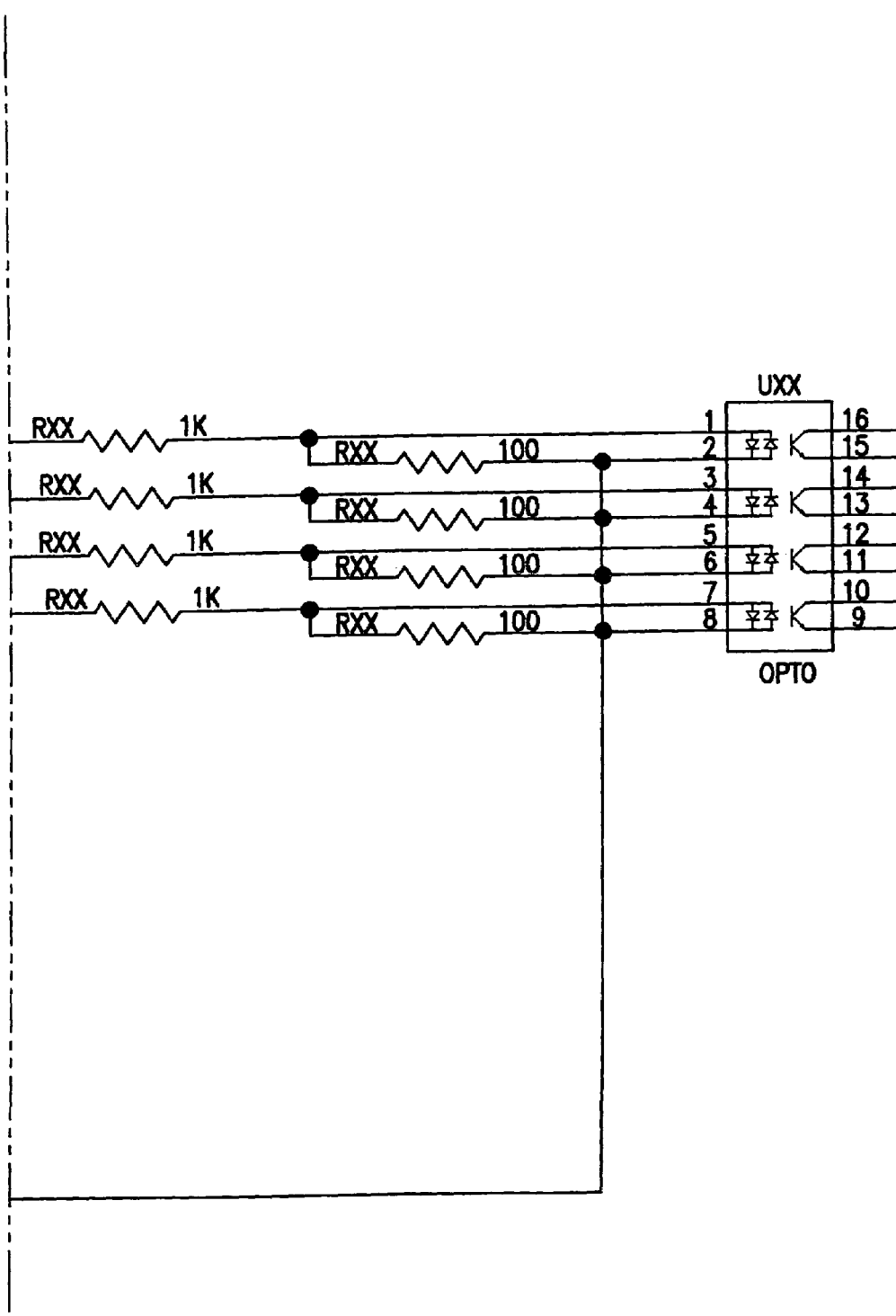

A schematic showing further circuit components that are used in connection with a representative PCT4216 chip is shown in FIGS. 71A–71D. These additional circuit components have been omitted from the schematic of FIGS. 66A–66X in connection with the first through seventh PCT4216 chips to save room on the schematic. Thus, the following description of FIGS. 71A–71D applies to each of the first through seventh PCT4216 chips unless specifically noted otherwise. The IN1, IN2, IN3, and IN4 lines are coupled to pins 1, 3, 5, and 7, respectively, of the representative PCT4216 chip through respective series combinations of a polyswitch and a 1 k.OMEGA. resistor as shown in FIGS. 71A, 71B, and 71C. In addition, pins 1, 3, 5, and 7 of the representative PCT4216 chip are coupled to pins 2, 4, 6, and 8, respectively, of the representative PCT4216 chip through respective 100.OMEGA. resistors as shown in FIG. 71C. Each of pins 2, 4, 6, and 8 of the representative PCT4216 chip are coupled to ACGND (sometimes referred to herein as 20VAC2) as shown in FIGS. 71A, 71B, and 71C.

Figure 71D:
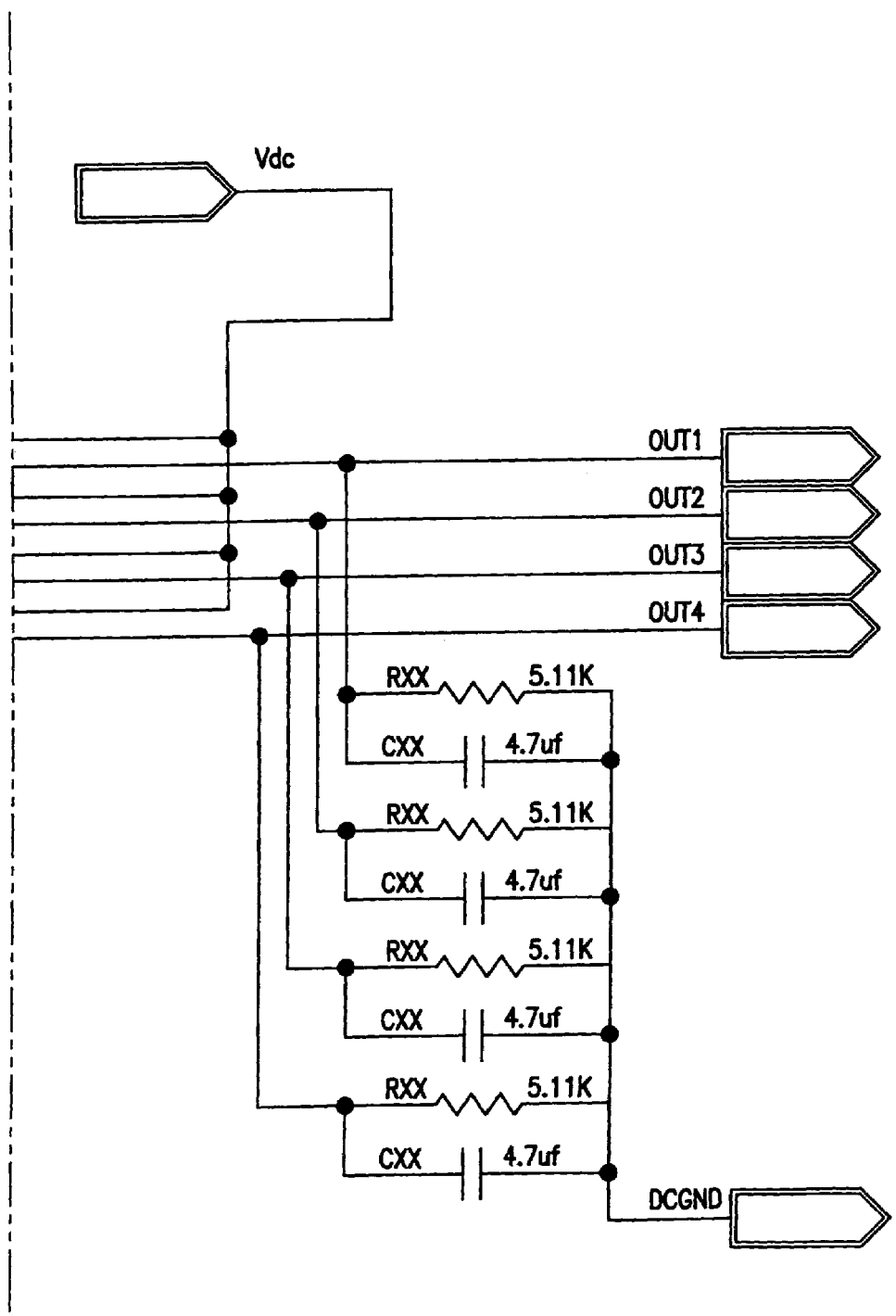

The common terminal of each polyswitch and each respective 1 k.OMEGA. resistor associated with the representative PCT4216 chip is coupled to ACGND through a respective metal oxide veristor (MOV) as shown in FIGS. 71A and 71B. Pins 15, 13, 11, and 9 of the representative PCT4216 chip are coupled to OUT1, OUT2, OUT3, and OUT4 lines, respectively, and are each coupled to DCGND (sometimes referred to herein as DGND) through respective parallel combination of a 5.11 k.OMEGA. resistor and a 4.7 .mu.F capacitor as shown in FIGS. 71C and 71D. Pins 10, 12, 14, 16 of the representative PCT4216 chip are coupled to Vdc (sometimes referred to herein as +5 VD) as also shown in FIGS. 71C and 71D.

Pins 11 and 12 of the connector J33 are coupled to are coupled to pins 1 and 3, respectively, of the eighth PCT4216 chip through respective series combinations of a polyswitch and a 1 k.OMEGA. resistor as shown in FIGS. 66D and 66I. In addition, pins 1 and 3 of the eighth PCT4216 chip are coupled to pins 2 and 4, respectively, of the eighth PCT4216 chip through respective 100.OMEGA. resistors as shown in FIG. 66I. Each of pins 2 and 4 of the eighth PCT4216 chip are coupled to 20VAC2 as shown in FIGS. 66D and 66I. The common terminal of each polyswitch and each respective 1 k.OMEGA. resistor associated with the eighth PCT4216 chip is coupled to 20VAC2 through a respective metal oxide veristor (MOV) as shown in FIGS. 66D and 66I. Pins 13 and 15 of the eighth PCT 4216 chip are coupled to pins 6 and 7, respectively, of the fourth 74HC589 chip and are each coupled to DGND through respective parallel combination of a 5.11 k.OMEGA. resistor and a 4.7 .mu.F capacitor as shown in FIGS. 66I, 66M, and 66N. Pins 14 and 16 of the eighth PCT4216 chip are coupled to +5 VD as shown in FIGS. 66I and 66N. Pins 5–12 of the eighth PCT4216 chip are open.

The OUT1, OUT2, OUT3, and OUT4 lines of the first PCT4216 chip are coupled to pins 2–5, respectively, of the first 74HC589 chip as shown in FIGS. 66F and 66K. The OUT1 and OUT2 lines of the second PCT4216 chip are couple to pins 6 and 7, respectively, of the first 74HC589 chip, as shown in FIGS. 66G and 66K, and the OUT3 and OUT4 lines of the second PCT4216 chip are coupled to pins 15 and 1, respectively, of the second 74HC589 chip, as shown in FIGS. 66F, 66K, and 66L. The OUT1, OUT2, OUT3, and OUT4 lines of the third PCT4216 chip are coupled to pins 2–5, respectively, of the second 74HC589 chip as shown in FIGS. 66G and 66L. The OUT1 and OUT2 lines of the fourth PCT4216 chip are couple to pins 6 and 7, respectively, of the second 74HC589 chip and the OUT3 and OUT4 lines of the fourth PCT4216 chip are coupled to pins 15 and 1, respectively, of the third 74HC589 chip, as also shown in FIGS. 66G and 66L. The OUT1, OUT2, OUT3, and OUT4 lines of the fifth PCT4216 chip are coupled to pins 2–5, respectively, of the third 74HC589 chip as shown in FIGS. 66G and 66L. The OUT1 and OUT2 lines of the sixth PCT4216 chip are couple to pins 6 and 7, respectively, of the third 74HC589 chip, as shown in FIGS. 66H, 66L, and 66M, and the OUT3 and OUT4 lines of the sixth PCT4216 chip are coupled to pins 15 and 1, respectively, of the fourth 74HC589 chip, as shown in FIGS. 66H and 66M. The OUT1, OUT2, OUT3, and OUT4 lines of the seventh PCT4216 chip are coupled to pins 2–5, respectively, of the fourth 74HC589 chip as shown in FIGS. 66H and 66M.

Pins 1 and 15 of the first 74HC589 chip are coupled to DGND as shown in FIG. 66K. Pin 16 of each of the four 74HC589 chips is coupled directly to +5 VD and is coupled to DGND through a respective 1000 pF capacitor as shown in FIGS. 66K, 66L, and 66M. Pin 8 of each of the four 74HC589 chips is coupled to DGND as also shown in FIGS. 66K, 66L, and 66M. In addition, pin 14 of the fourth 74HC589 chip is coupled to DGND as shown in FIG. 66M. Pin 14 of the first 74HC589 chip is coupled to pin 9 of the second 74HC589 chip as shown in FIGS. 66K and 66L. Pin 14 of the second 74HC589 chip is coupled to pin 9 of the third 74HC589 chip as also shown in FIGS. 66K and 66L. Pin 14 of the third 74HC589 chip is coupled to pin 9 of the fourth 74HC589 chip as shown in FIGS. 66L and 66M.

As shown in FIGS. 66J, 66K, 66O, and 66P, pin 9 of the first 74HC589 chip is coupled to the MISO line which is, in turn, coupled to the circuitry of FIGS. 62A–62U as described above. As shown in FIGS. 66J, 66K, 66L, 66M, 66O, 66P, 66Q, and 66R, pin 10 of each of the four 74HC589 chips is coupled to the notLOCAL_ALARM_CS line which is, in turn, coupled to the circuitry of FIGS. 62A–62U as described above. As shown in FIGS. 66J, 66K, 66L, 66M, 66O, and 66P, pin 11 of each of the four 74HC589 chips is coupled to the SPI_CLK line from the circuitry of FIGS. 62A–62U. As also shown in FIGS. 66J, 66K, 66L, 66M, 66O, and 66P, pins 12 and 13 of each of the four 74HC589 chips is coupled to the INPUT_LATCH line from the circuitry of FIGS. 62A–62U.

Circuit 70 includes a 74HC595 8-bit shift register chip as shown in FIG. 66T. Pin 9 of the 74HC595 chip is open. Pins 8 and 13 of the 74HC595 chip are coupled to DGND as shown in FIG. 66T. Pin 16 of the 74HC595 chip is coupled directly to +5 VD and is coupled to DGND through a 0.1 .mu.F capacitor. In addition, pin 16 of the 74HC595 chip is coupled to pin 10 thereof through a 1 k.OMEGA. resistor. As shown in FIGS. 66J, 66O, 66P, and 66T, pins 11, 12, and 14 of the 74HC595 chip are coupled to the SPI_CLK, notVFD_CE, and MOSI lines, respectively, which are, in turn, coupled to the circuitry of FIGS. 62A–62U as described above. As shown in FIGS. 66T and 66X, pins 15 and 1–7 of the 74HC595 chip are coupled to pins 7, 8, 5, 6, 3, 4, 1, and 2, respectively, which are included in a connector J45 and which are associated with DD0, DD1, ... DD7 lines, respectively. As shown in FIGS. 66J, 66O, 66P, 66T, and 66X, pins 9, 10, and 12 of the connector J45 are coupled to the lines VFD_RW, VFD_ENABLE, and VFD_RS, respectively, which are, in turn, coupled to the circuitry of FIGS. 62A–62U.

Pin 11 of the connector J45 is not used as shown in FIG. 66X. A parallel combination of a 0.047 .mu.F capacitor and a 68 mF capacitor are coupled across pins 13 and 14 of the connector J45 as shown in FIGS. 66T, 66U, and 66X. Pins 13 and 14 of the connector J45 are associated with D+5 and DCOM lines, respectively. In addition, pins 13 and 14 of the connector J45 are coupled through respective 150 MHz ferrite beads to the parallel combination of three capacitors, two of which are 68 mF capacitors and one of which is a 0.047 .mu.F capacitor as also shown in FIGS. 66T, 66U, and 66X. The positive terminals of the three parallel capacitors are coupled to +5 VD and the negative terminals of the three parallel capacitors are coupled to DGND as shown in FIG. 66U. As indicated in FIG. 66X, the J45 connector couples to a vacuum fluorescent display, which corresponds to display screen 86 described above. In one embodiment, the vacuum flourescent display is a Model No. CU 20025 ECP BU 1J display available from Noritake Company, Inc.

Circuit 70 includes an NJU3718 20-bit serial-to-parallel converter chip as shown in FIG. 66S. Pins 8–14 of the NJU3718 chip are open. Pins 7 and 21 of the NJU3718 chip couple to DGND. Pin 28 of the NJU3718 chip is coupled directly to +5 VD and is coupled through a 0.1 .mu.F capacitor to DGND. In addition, pin 28 of the NJU3718 chip is coupled to pin 18 thereof through a 1 k.OMEGA. resistor as shown in FIG. 66S. As shown in FIGS. 66J, 66O, and 66S, pins 15, 16, and 17 of the NJU3718 chip are coupled to the MOSI, SPI_CLK, and notLED_DSPLAY_CS lines, respectively, which, in turn, coupled to the circuitry of FIGS. 62A–62U as described above.

As shown in FIGS. 66S and 66W, pins 19, 20, 22, 27, 1, and 2 of the NJU3718 chip are coupled to pins 1, 2, 3, 10, 11, and 12, respectively, of a connector J46 which is included in circuit 70. Pins 23–26 and 3–6 of the NJU3718 chip are coupled through respective 100.OMEGA. resistors to pins 4, 7–9, and 15–18 of the connector J46 as also shown in FIGS. 66S and 66W. Pins 5 and 13 of the connector J46 are coupled to +5 VD through a single 1 k.OMEGA. resistor as shown in FIG. 66W. As shown in FIGS. 66S, 66T, 66W, and 66X, pin 6 of the connector J46 is coupled to DGND through the parallel combination of a 49.9 k.OMEGA. resistor and a 4.7 .mu.F capacitor and is also coupled directly to the TEST_SW1 line, which is, in turn, coupled to the circuitry of FIGS. 62A–62U as described above. As also shown in FIGS. 66S, 66T, 66W, and 66X, pin 14 of the connector J46 is coupled to DGND through the parallel combination of a 49.9 k.OMEGA. resistor and a 4.7 .mu.F capacitor and is also coupled directly to the SILENCE_SW2 line, which is, in turn, coupled to the circuitry of FIGS. 62A–62U as described above.

Signals are sent from the NJU3718 chip through pins 1–4, 7–12, and 15–18 of the connector J46 to control the illumination of the LED's 88 of master alarm controller 48. A table, which is shown in the upper right corner of FIG. 66W and which is titled "OVERLAY LED PIN CONNECT," shows which pins of the connector J46 cause respective LED's 88 (numbered 1 through 9) to shine green and to shine red. In addition, pins 5 and 6 of the connector J46 are coupled to test button 90 of master alarm controller 48 and pins 13 and 14 of the connector J46 are coupled to alarm silence button 92 of master alarm controller 48. As shown in FIG. 66E, the +5 VD line and the DGND line from the circuitry of FIGS. 62A–62U provide +5 VD and DGND to the circuitry of FIGS. 66A–66X and are coupled together through a 10 .mu.F capacitor.

The above description of circuit 70, shown in FIGS. 62–65, of master alarm controller 48 applies as well to circuit 74 of each area alarm controller 50 with certain exceptions. Area alarm controller 50 does not include circuitry corresponding to that shown in FIGS. 66A–66X, and thus, any signal communication lines that are indicated in FIGS. 62–65 as a connection to or from "SH5" (i.e. FIGS. 66A–66X) are omitted in circuit 74. For example, the VFD_AS, VFD_notAW, VFD_ENABLE, and INPUT_LATCH lines, shown in FIG. 62B, and the notLOCAL_ALARM_CS and notLED_DISPLAY_CS lines, shown in FIG. 62O, are omitted in circuit 74. Circuit 74 includes circuitry that is the same as that shown in FIGS. 63A–63L and FIGS. 64A–64Q.

Circuit 74 includes circuitry that is substantially the same as that shown in FIGS. 65A–65L with two main exceptions. One exception is that the 20VAC1 and 20VAC2 lines in circuit 74, which are coupled to the two coils of the 1 mH pulse suppression transformer of circuit 74 (see FIG. 65A for reference) are associated with the same connector that has the XDUCER_1A, XDUCER1B, XDUCER_2A, ..., XDUCER_6B lines of circuit 74. Thus, the pins of the connector in circuit 74 that are correspond to pins 1–6 of the connector J40 in circuit 70, connect the 20VAC1 and 20VAC2 power lines to the 1 mH transformer of circuit 74. The other exception is that, in circuit 74, the bus formed by the VCC, GPCOMa, AUX_ALARM, COM_A, COM_B, CGND, MANUAL_ALARM, and GUARDED_ACCESS lines couple to six different connectors, rather than three (see connectors J34, J35, and J36 in FIGS. 65G, 65I, and 65K for reference) and the six connectors in circuit 74 are couplable to six associated display modules 156 (i.e. AREA DISPLAY 1, AREA DISPLAY 2, AREA DISPLAY 3, AREA DISPLAY 4, AREA DISPLAY 5, and AREA DISPLAY 6). It should also be noted that circuit 74 includes button 912 in lieu of button 910 (see FIG. 65E for reference) as mentioned above.

Circuit 254 of local annunciator 52 is substantially the same as a portion of the circuitry shown in FIGS. 66A–66X with a few exceptions. One exception is that circuit 254 does not include a 74HC595 chip or any type of display screen and therefore, the 74HC595 chip and its associated circuitry is omitted in circuit 254. In addition, in some embodiments, circuit 254 does not include any microprocessor and therefore, in such embodiments, any lines shown in FIGS. 66A–66X as coming from or leading to SH1 (i.e. FIGS. 62A–62U) or SH3 (i.e. FIGS. 64A–64Q) are omitted in circuit 254. Thus, it will be appreciated that circuit 254 includes a set of PCT4216 optical isolator chips that receive input signals from source equipment 18, one or more NJU3718 chips to control the operation of LED's 250 of local annunciator 52, and a set of 74HC589 shift register chips that receive outputs from the PCT4216 chips and that provide inputs to the one or more NJU3718 chips. In addition, circuit 254 includes an audible alarm of some type as mentioned above. The activation of such an audible alarm may be controlled, for example, via one or more of pins 8–13 of the one or more NJU3718 chips, which pins in the circuitry shown in FIGS. 66A–66X are unused as described above.

The description below of the circuitry of one of display modules 156, shown in FIGS. 67 and 68, is descriptive of the circuitry of all display modules 156 unless specifically noted otherwise. In addition, a portion of the circuit shown in FIG. 67 is included as part of circuit 74 of the associated area alarm controller 50 and the description of this portion is applicable to all area alarm controller 50 unless specifically noted otherwise.

Figure 67A:
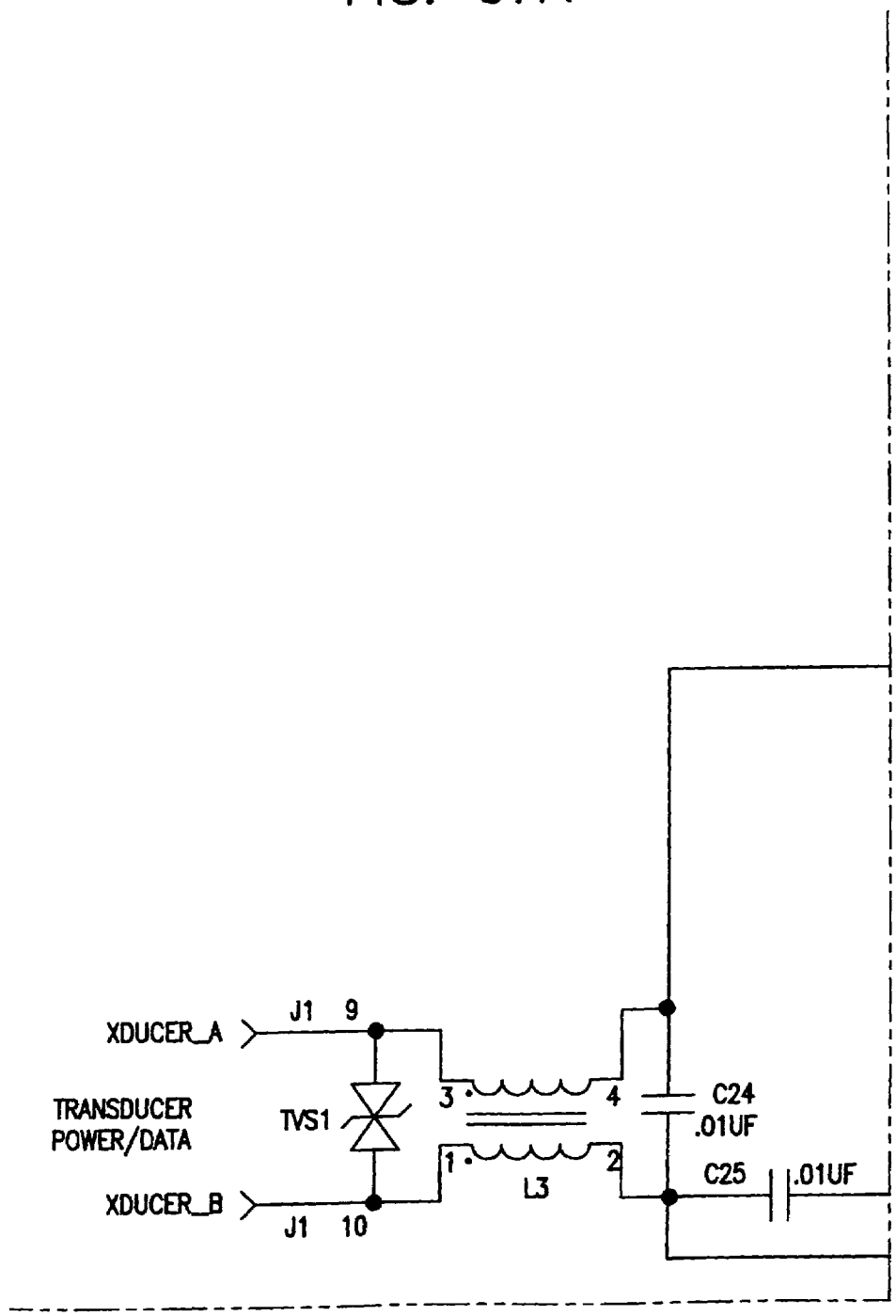
FIG. 67 is a circuit schematic map showing how to lay out FIGS. 67A–67U to form an electric circuit schematic of a first portion of an electric circuit of one of the display modules included in one of the area alarm controllers.
Figure 67B:
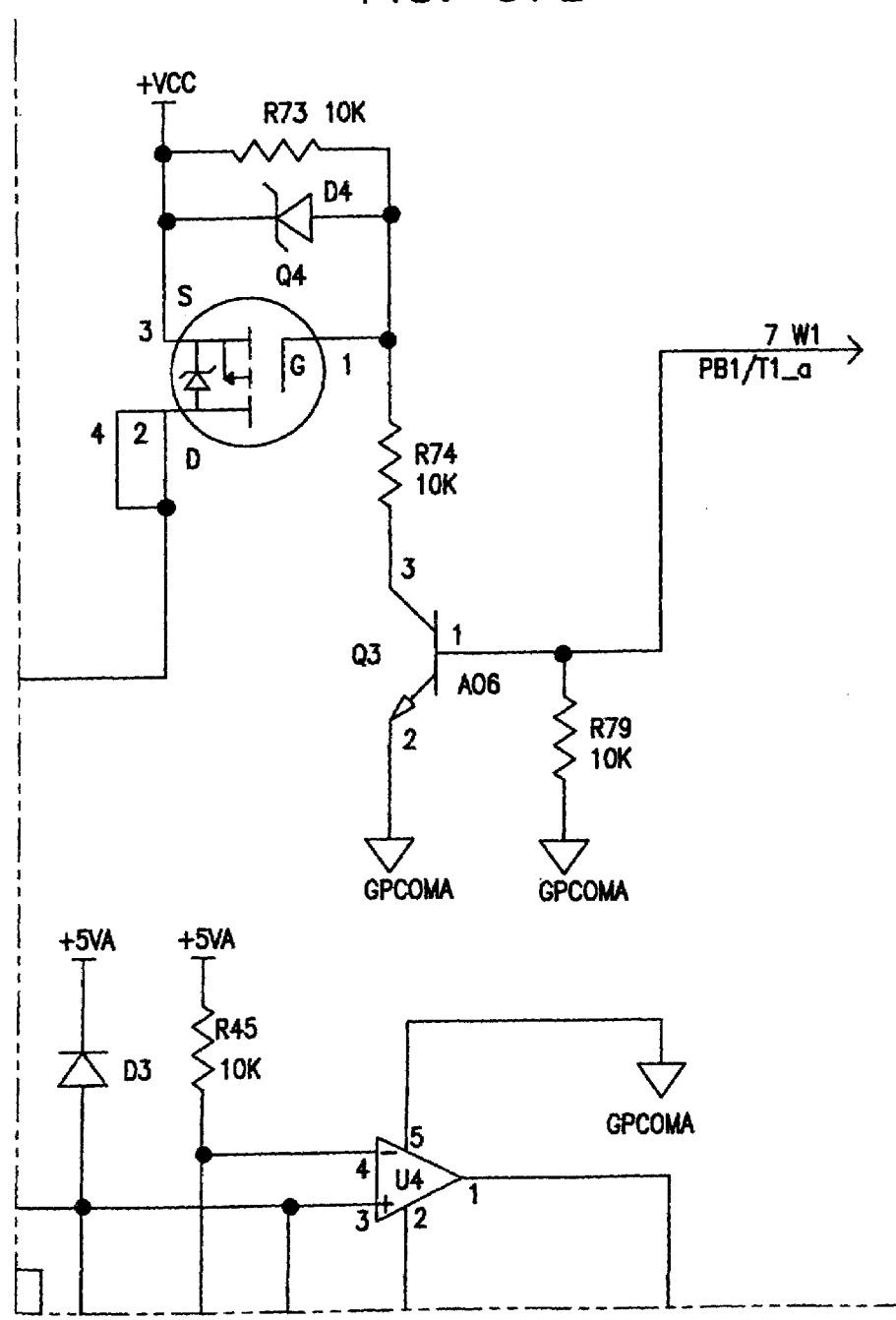
Figure 67C:
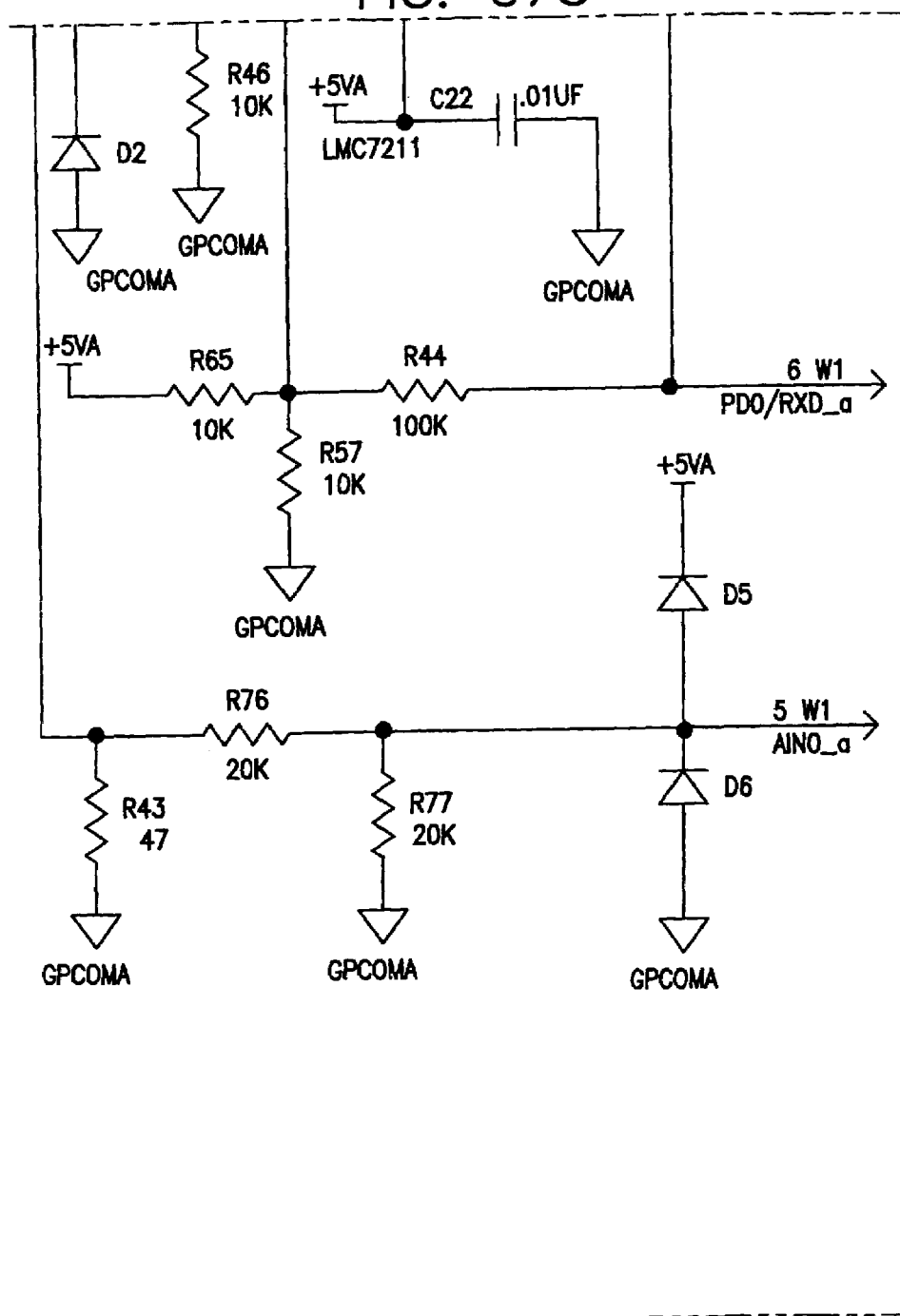
Figure 67D:
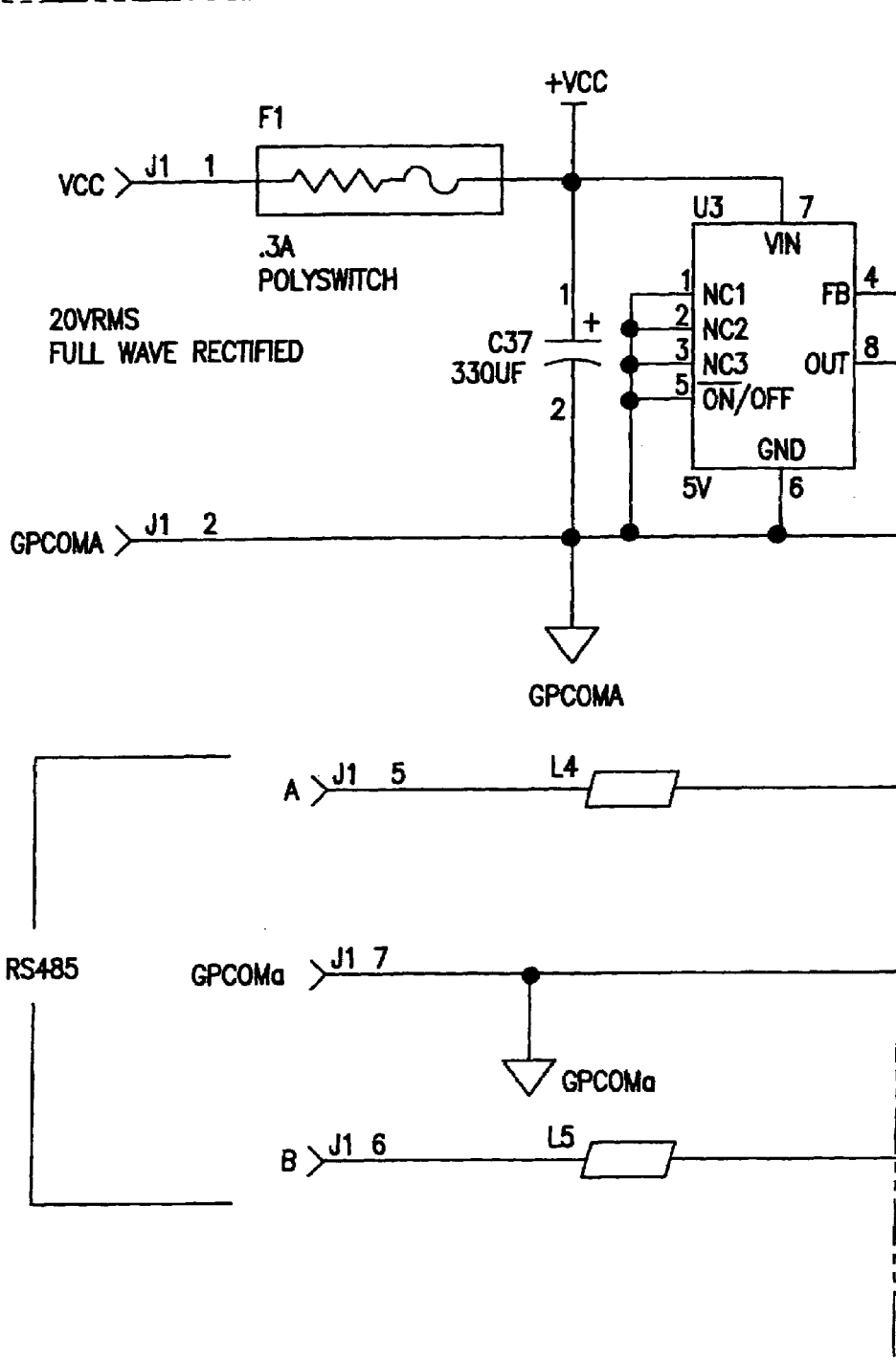
Figure 67F:
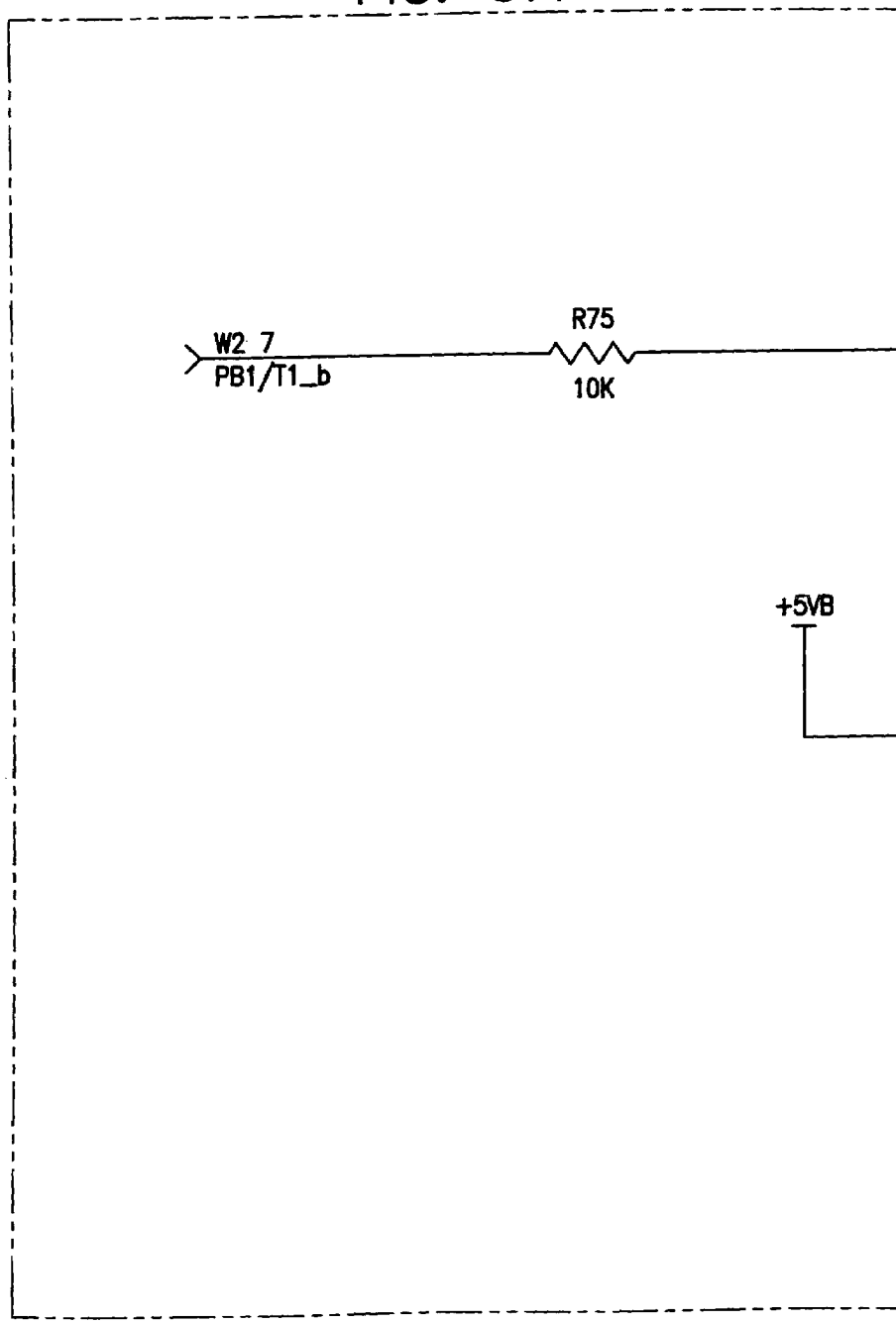
Figure 67G:
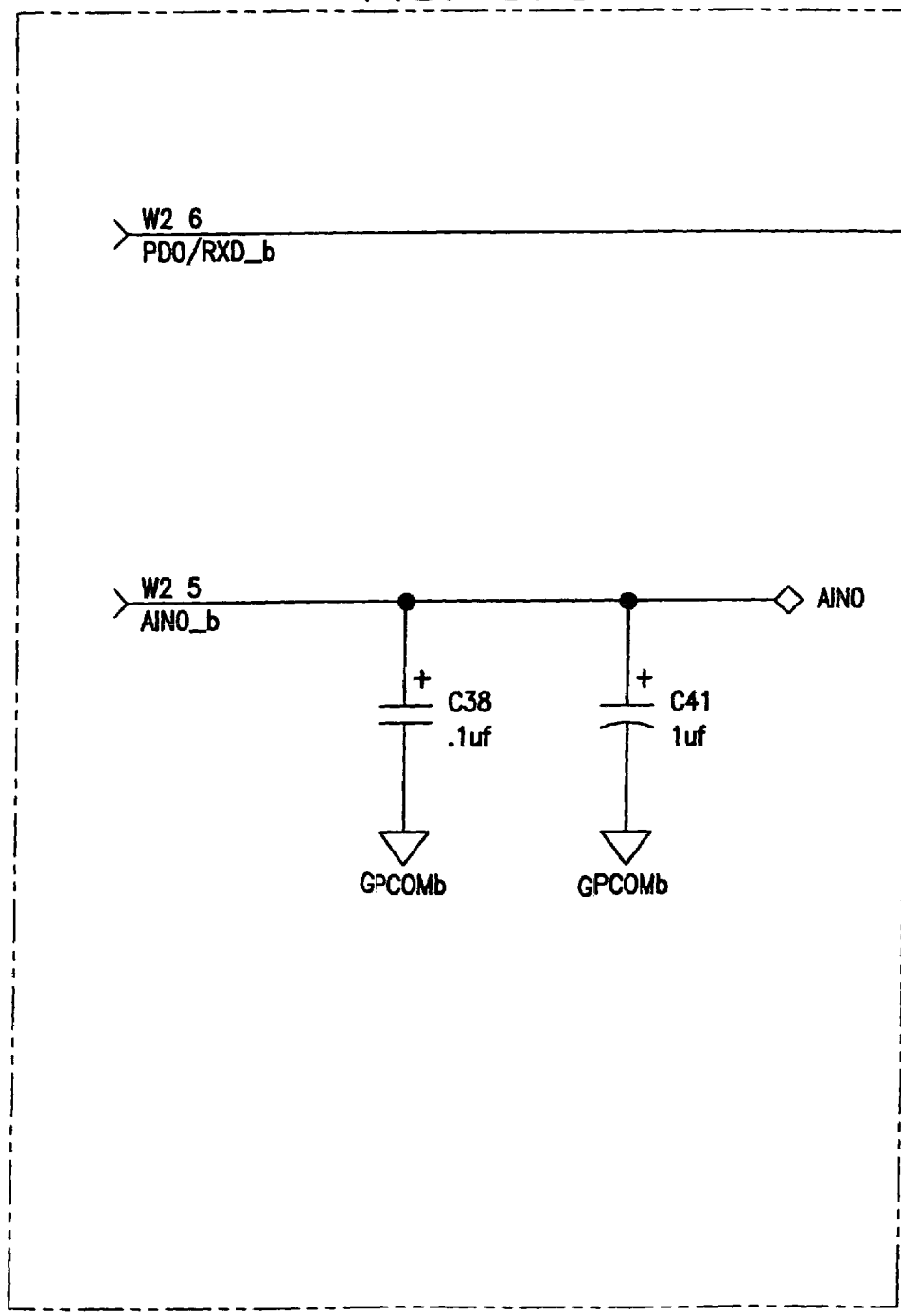
Figure 67H:
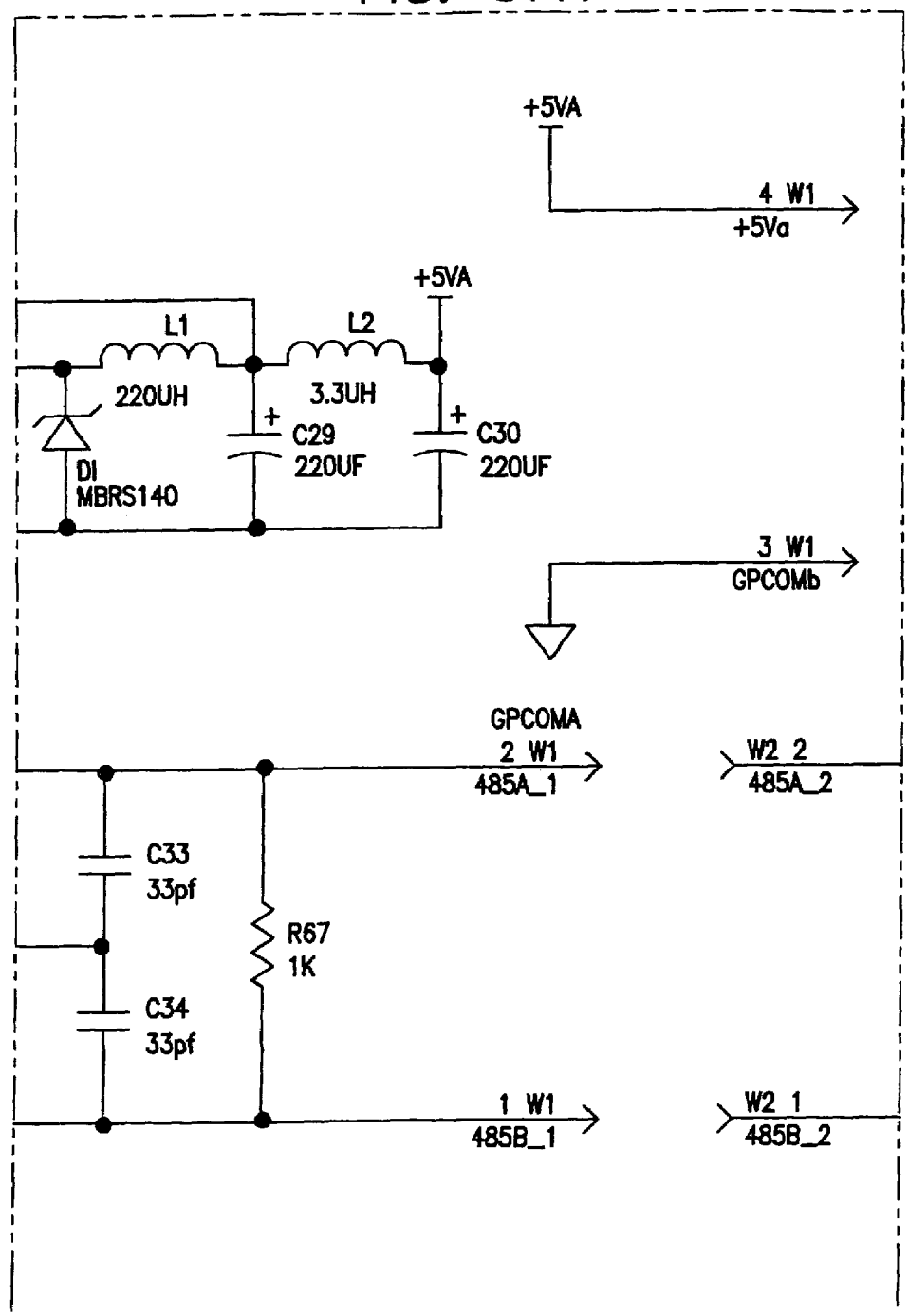
Figure 671:
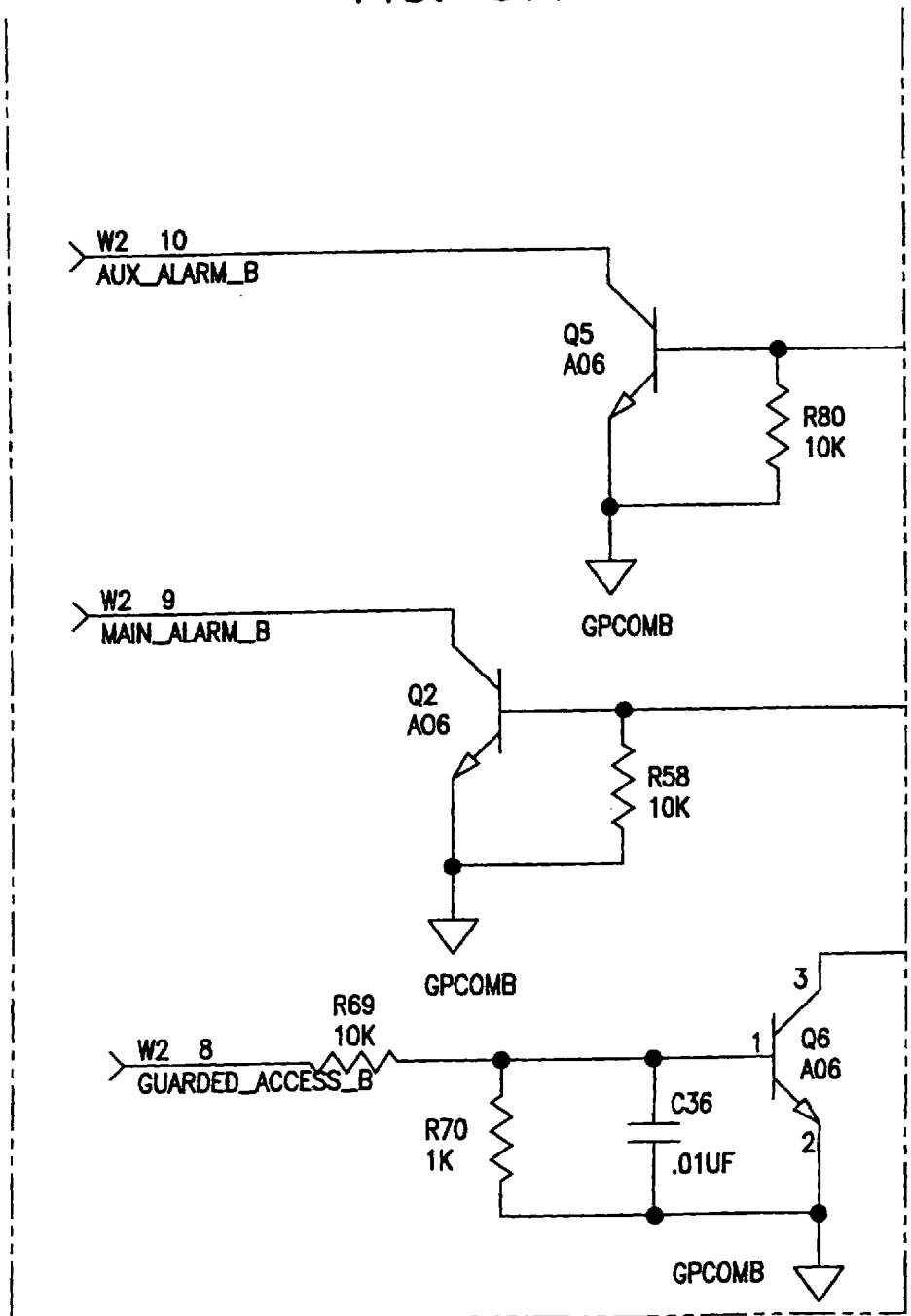
Figure 67J:
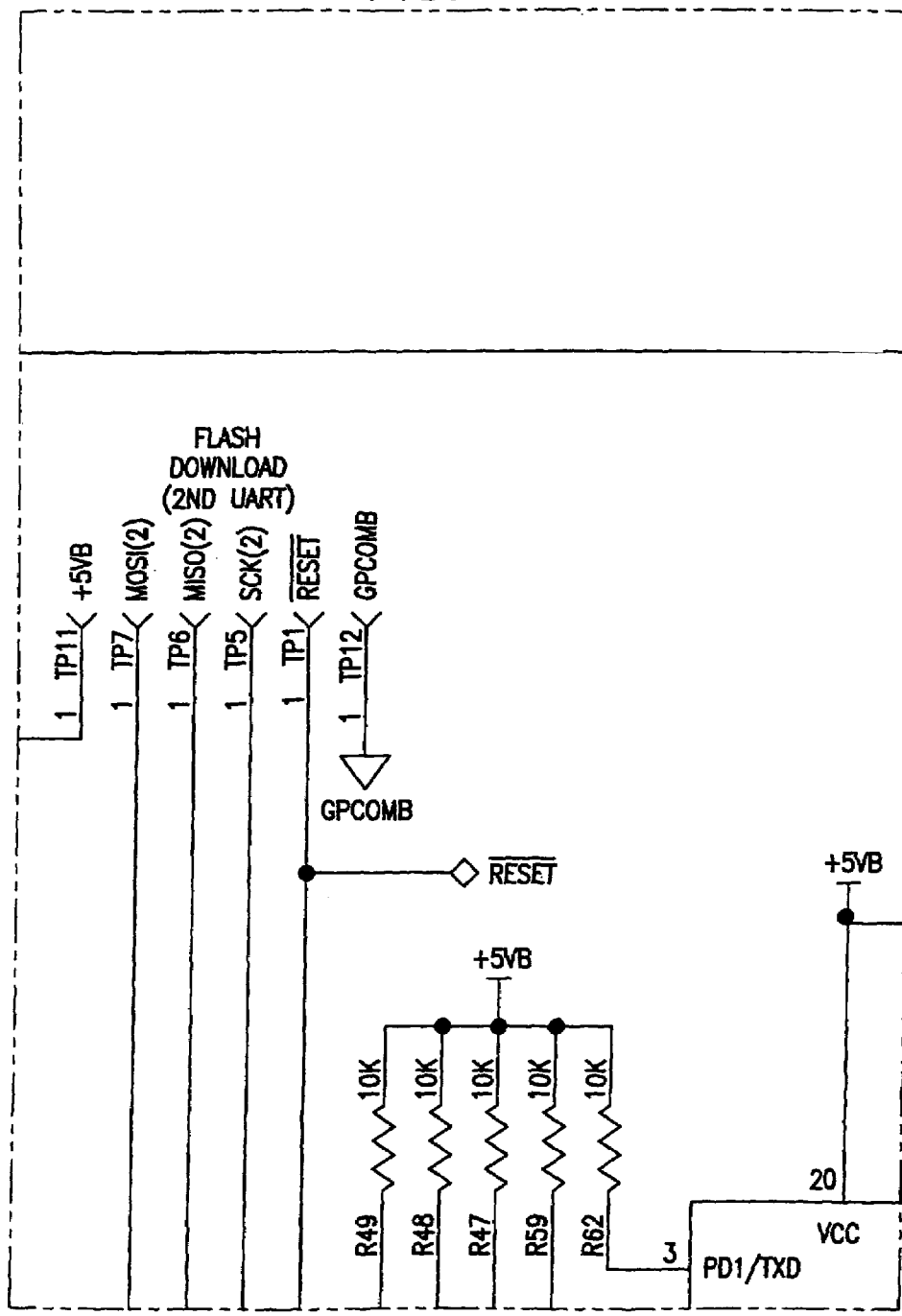
Figure 67K:
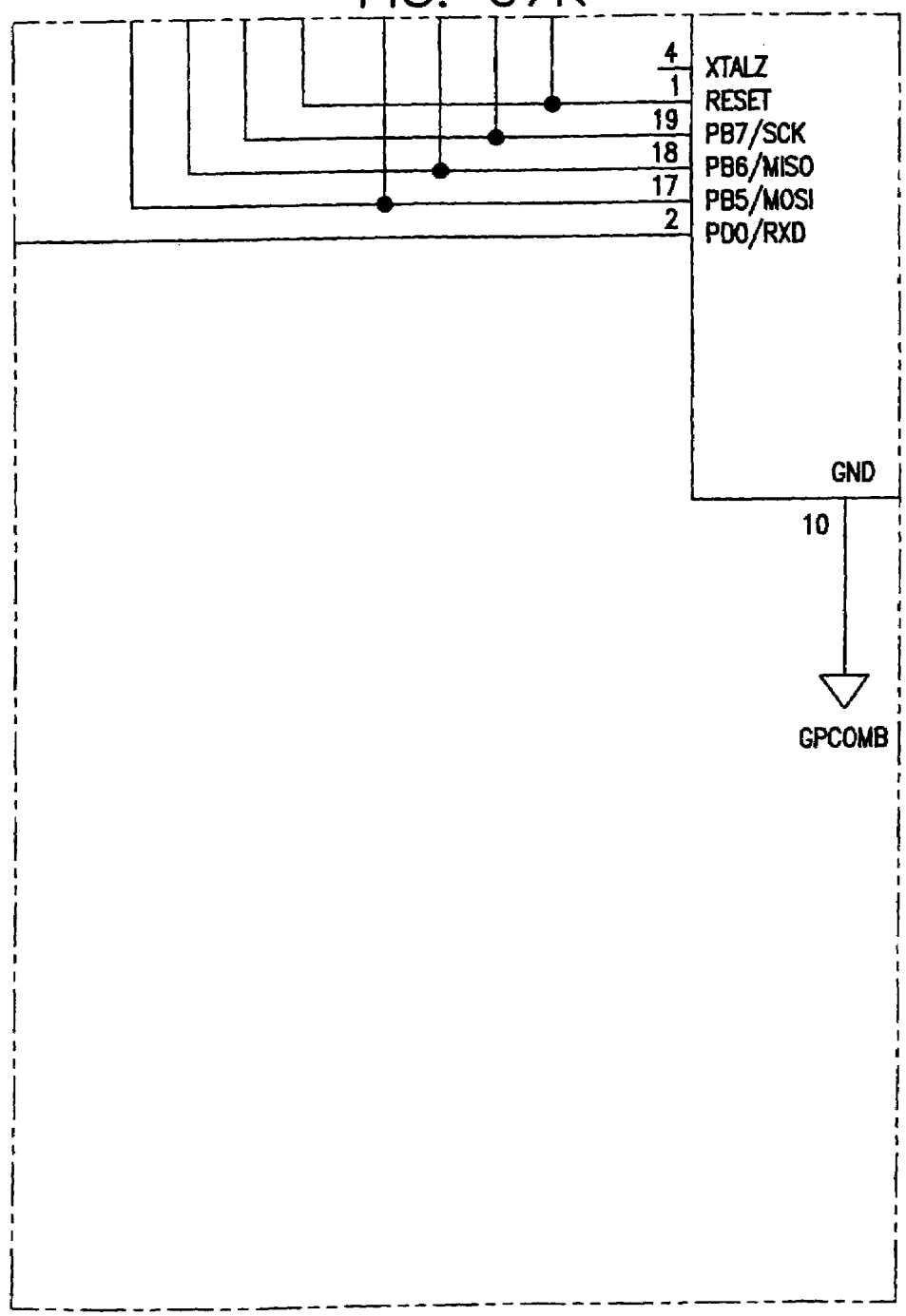
Figure 67L:
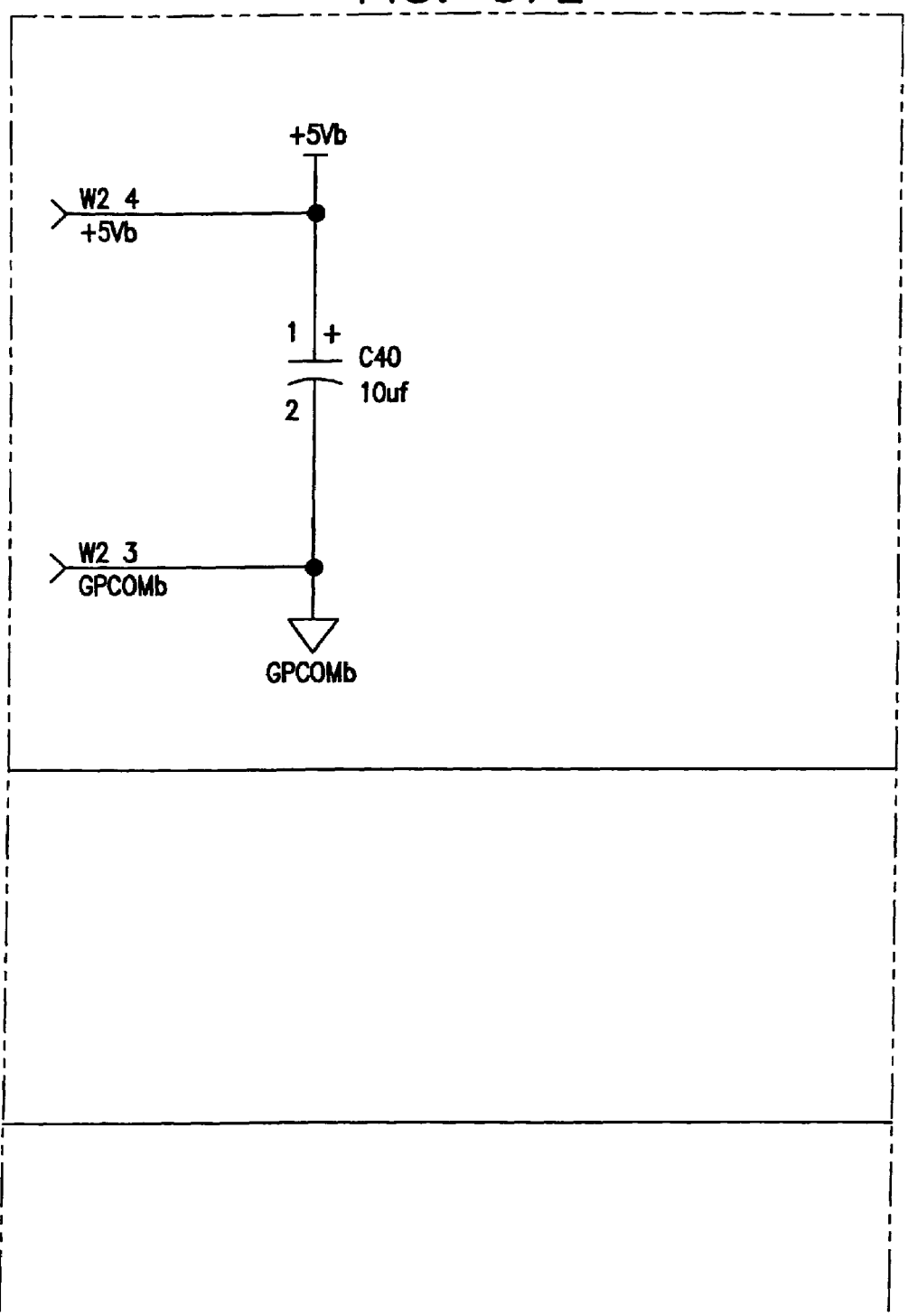
Figure 67M:
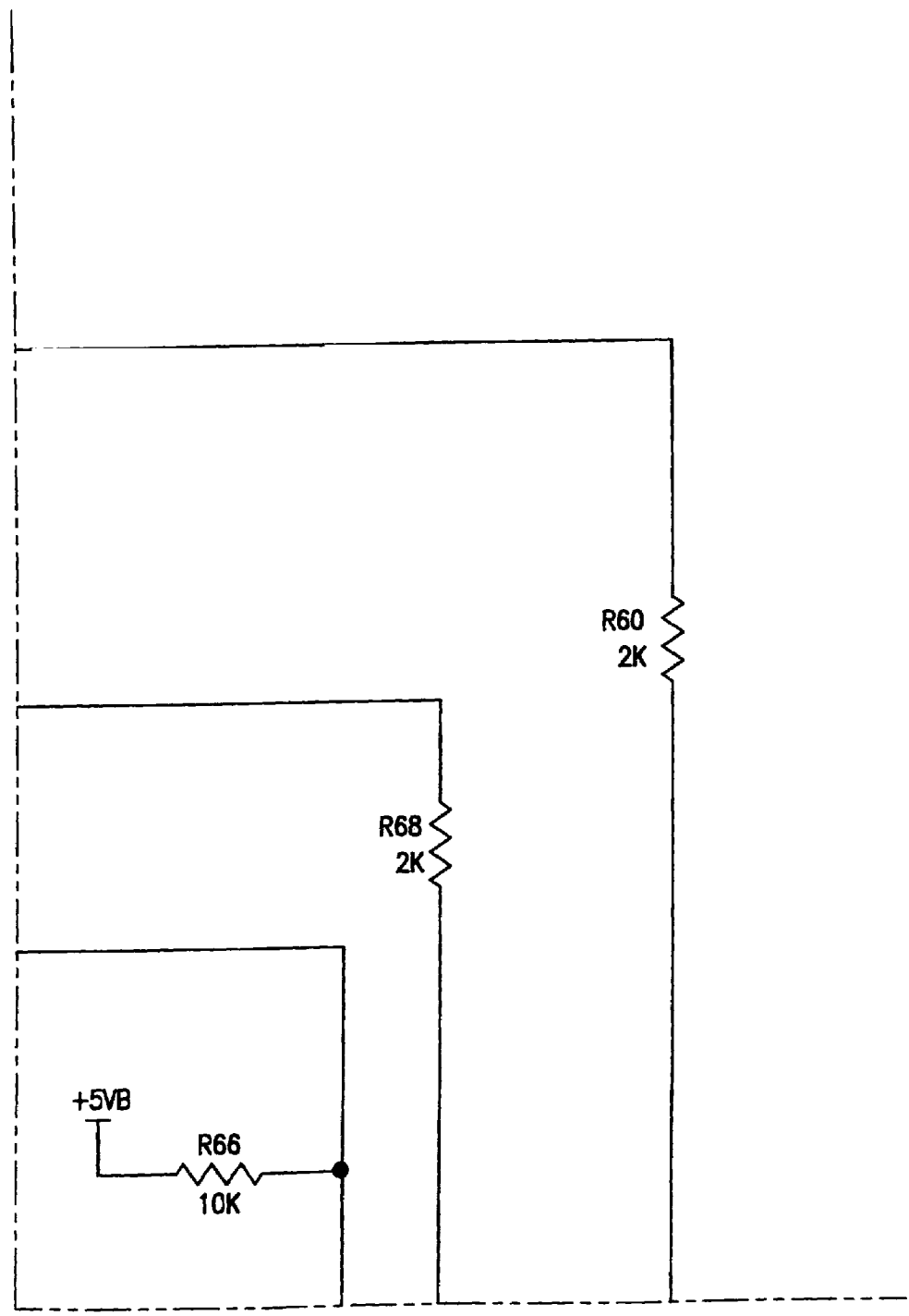
Figure 670:
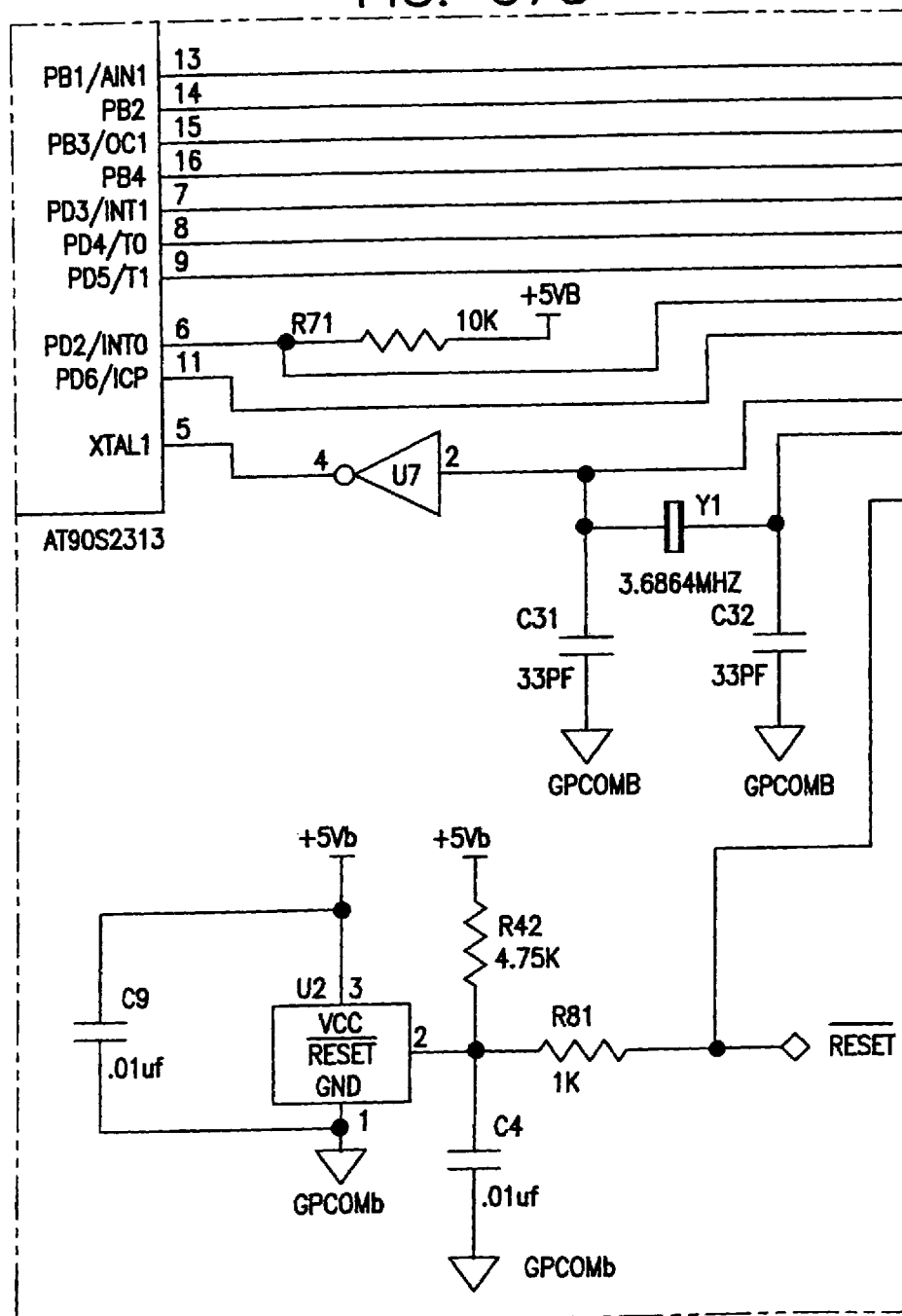
Figure 67P:
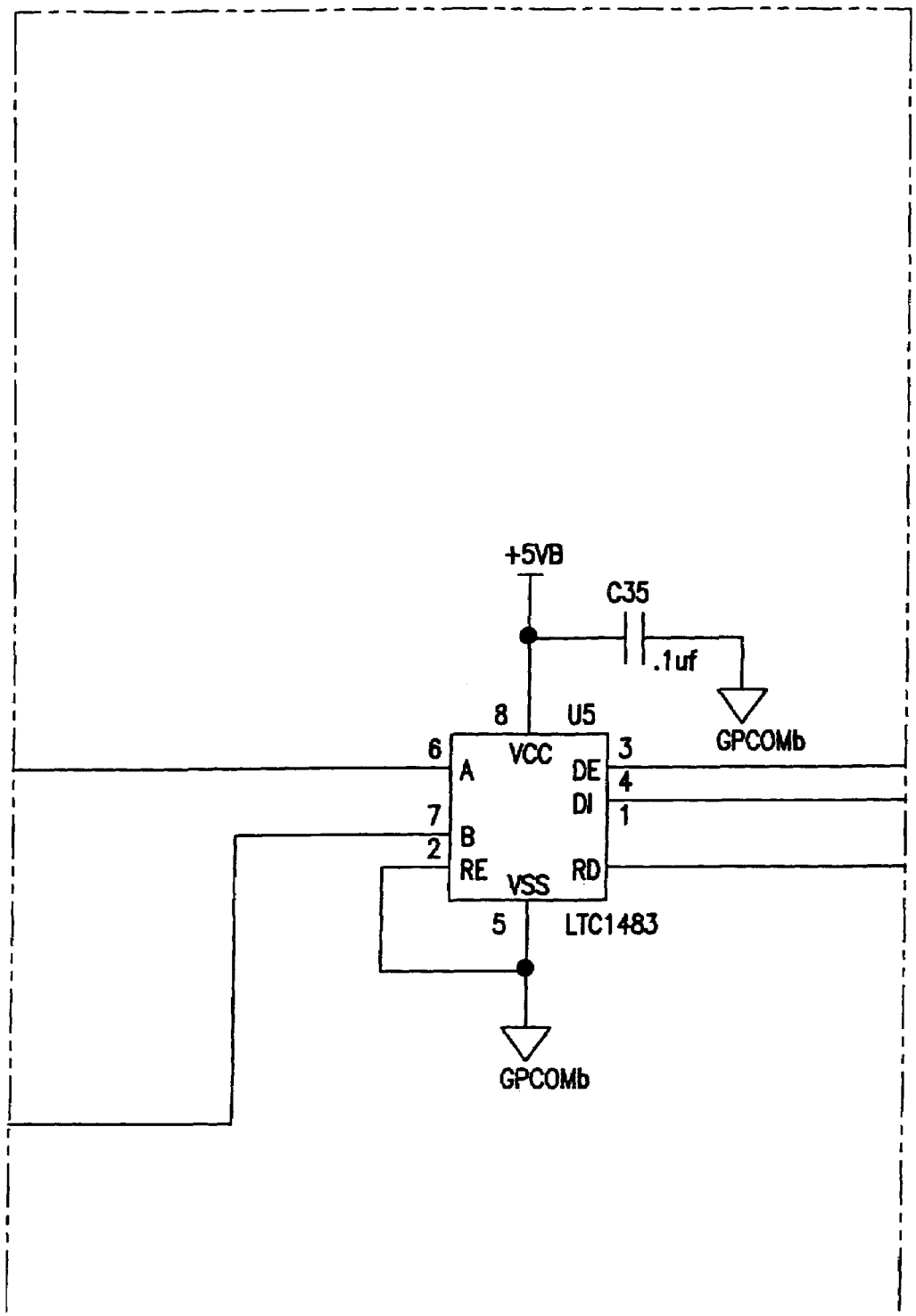
Figure 67Q:
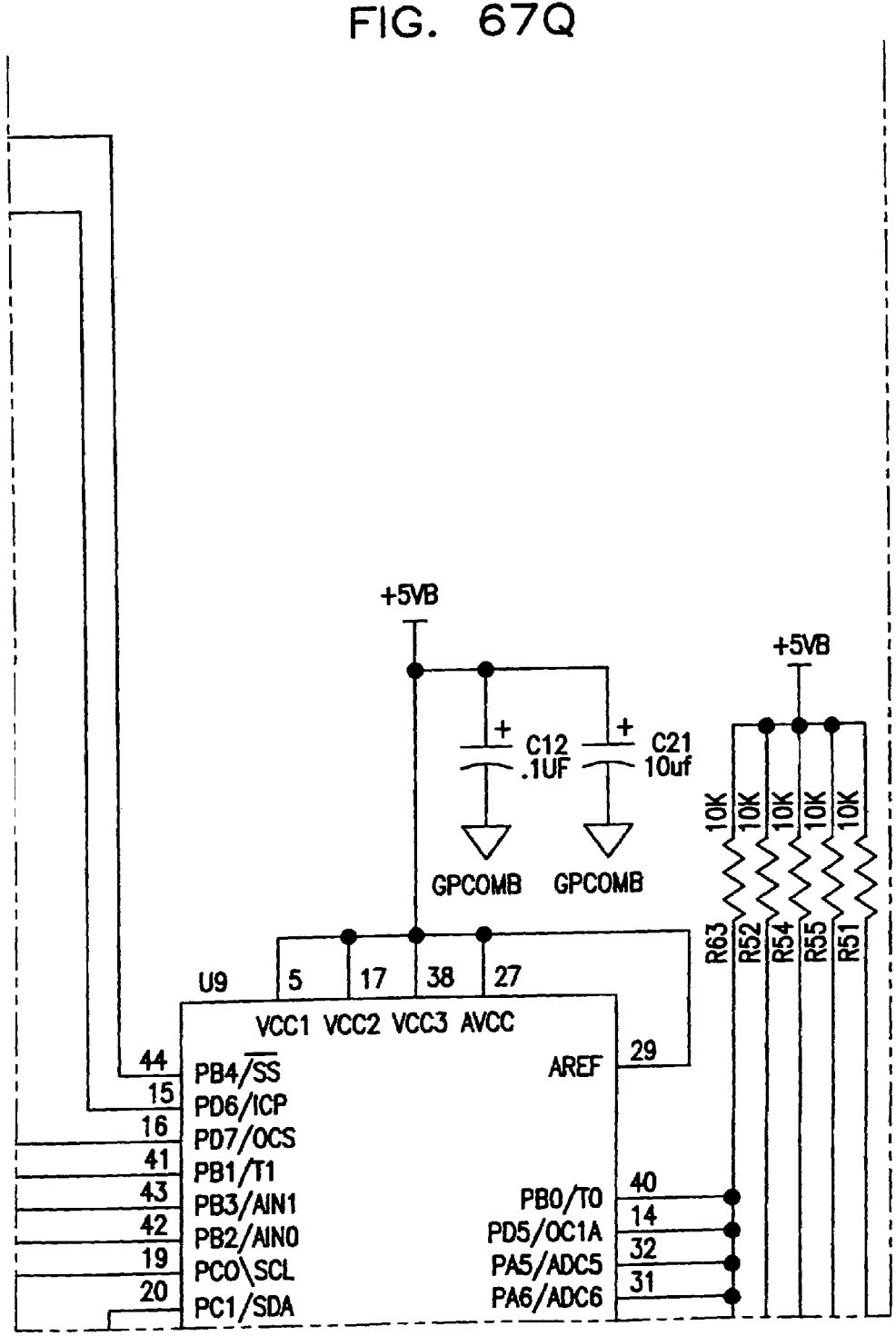
Figure 67R:
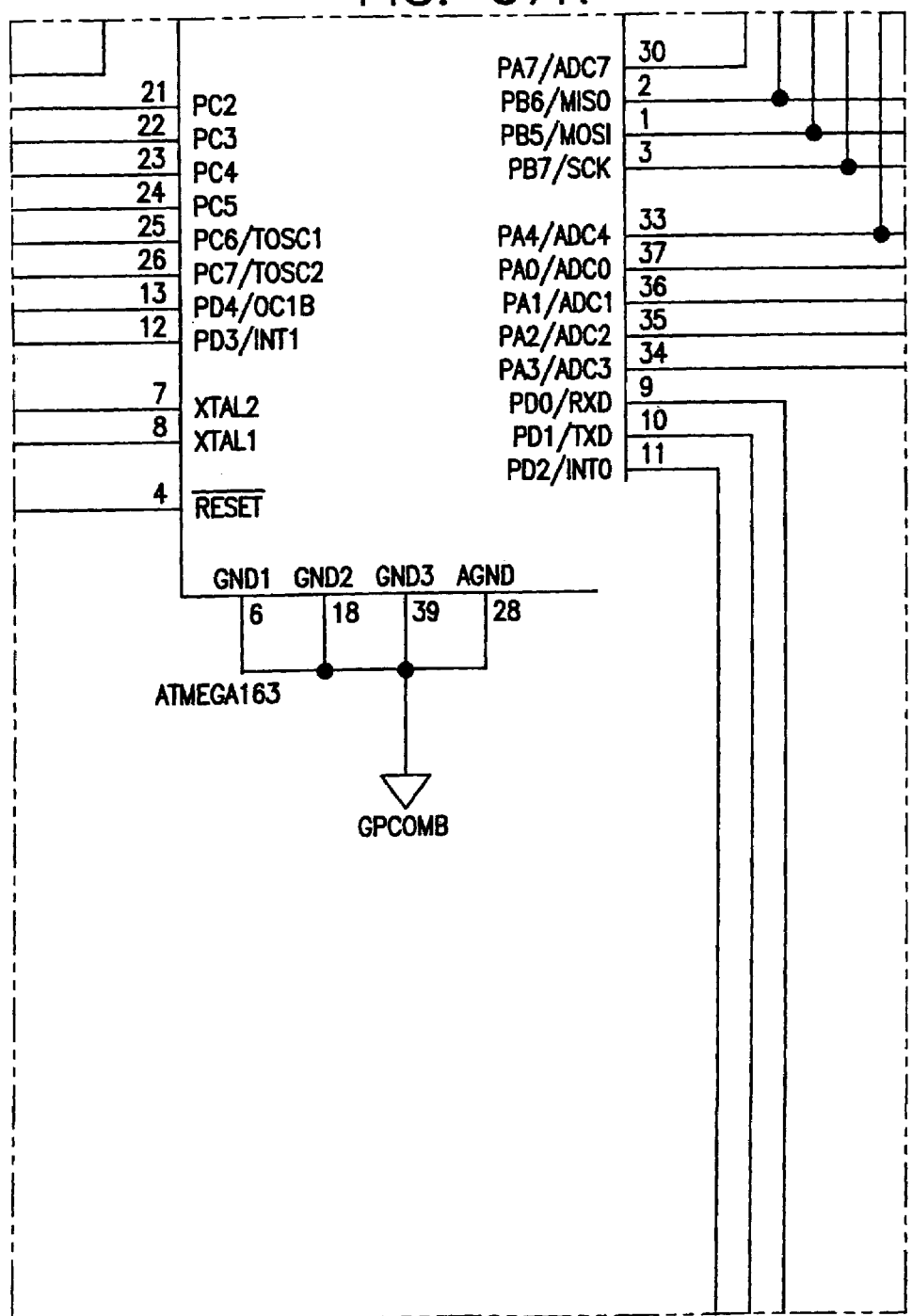
Figure 67S:
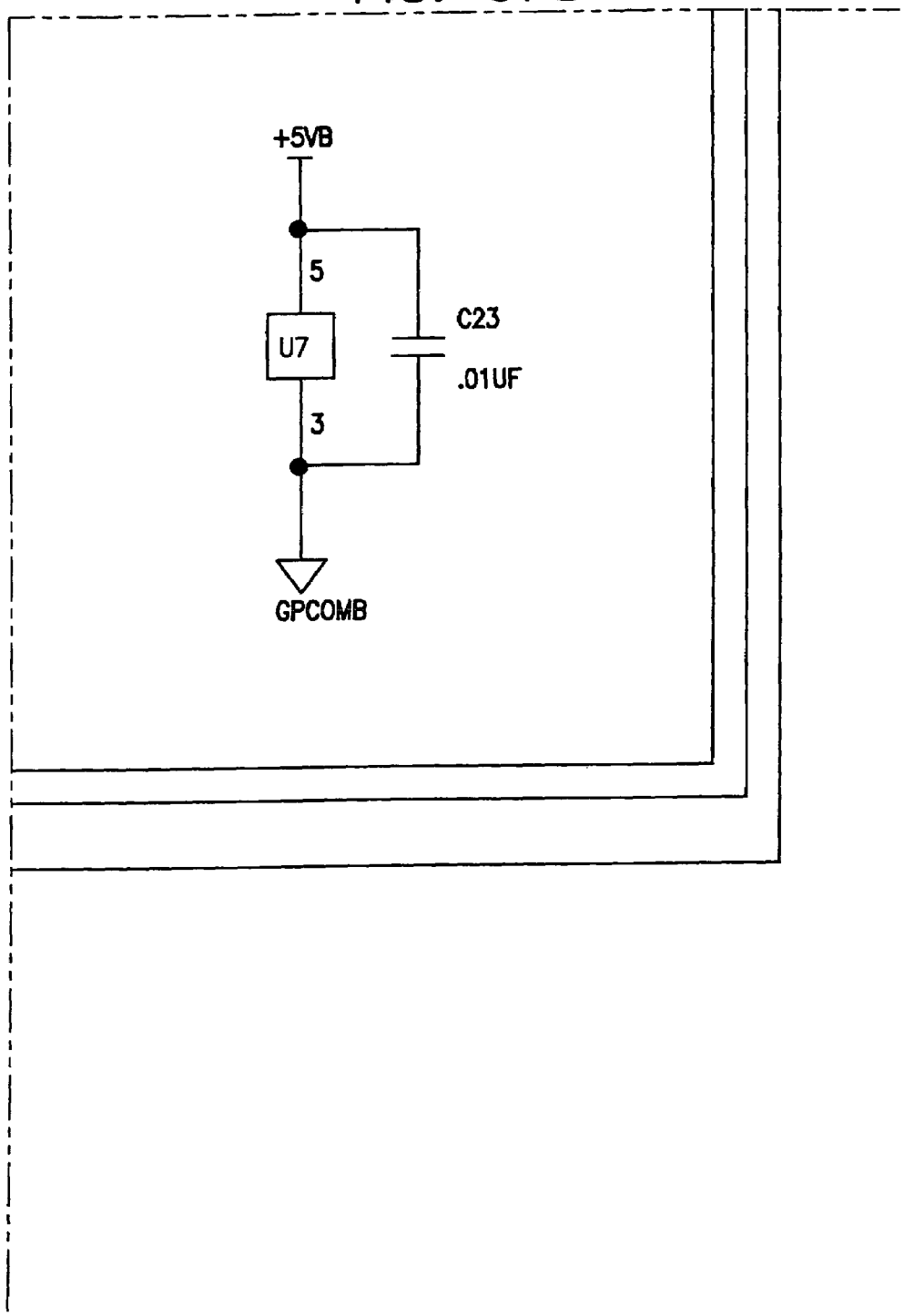
Figure 67T:
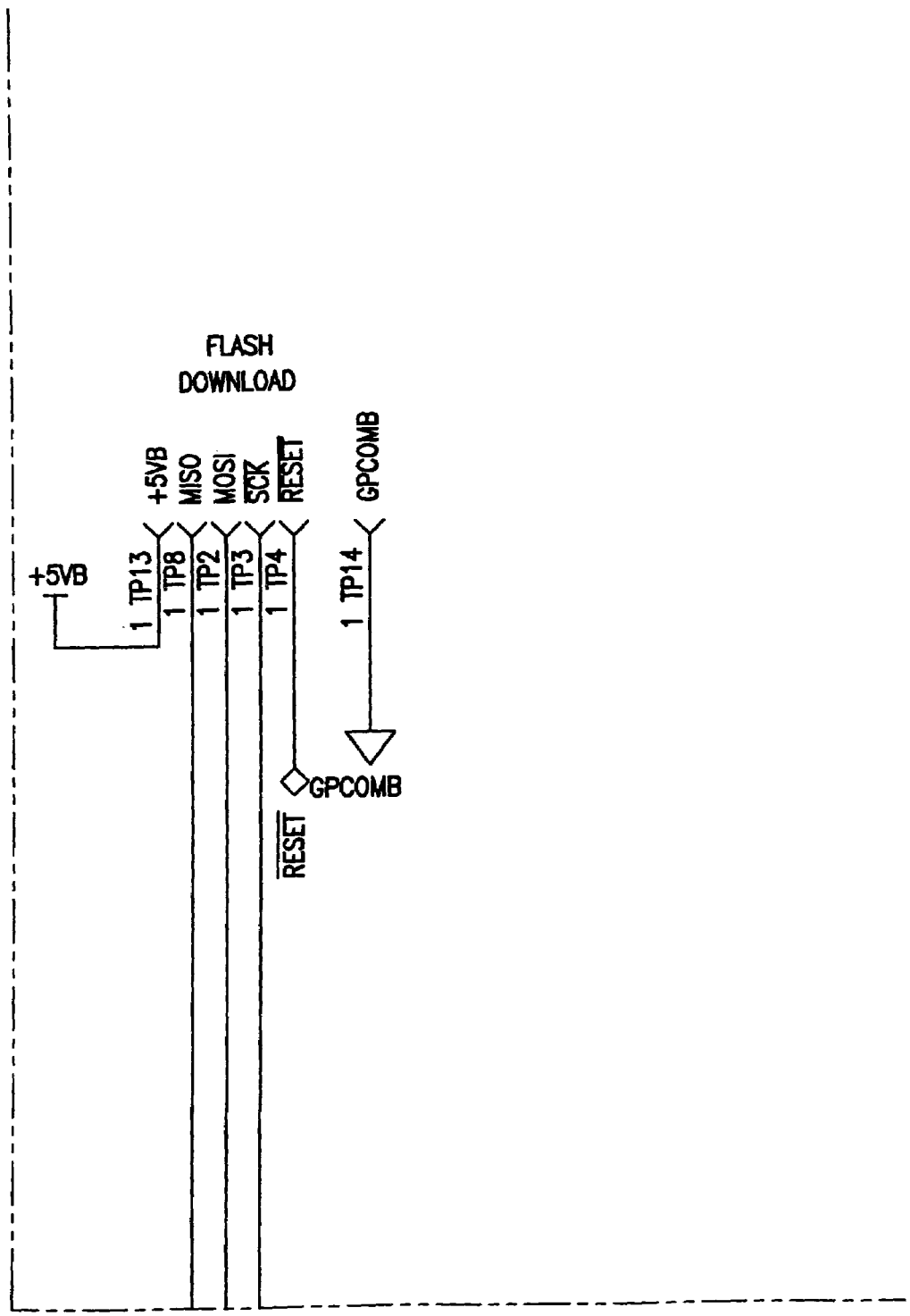
Figure 67U:
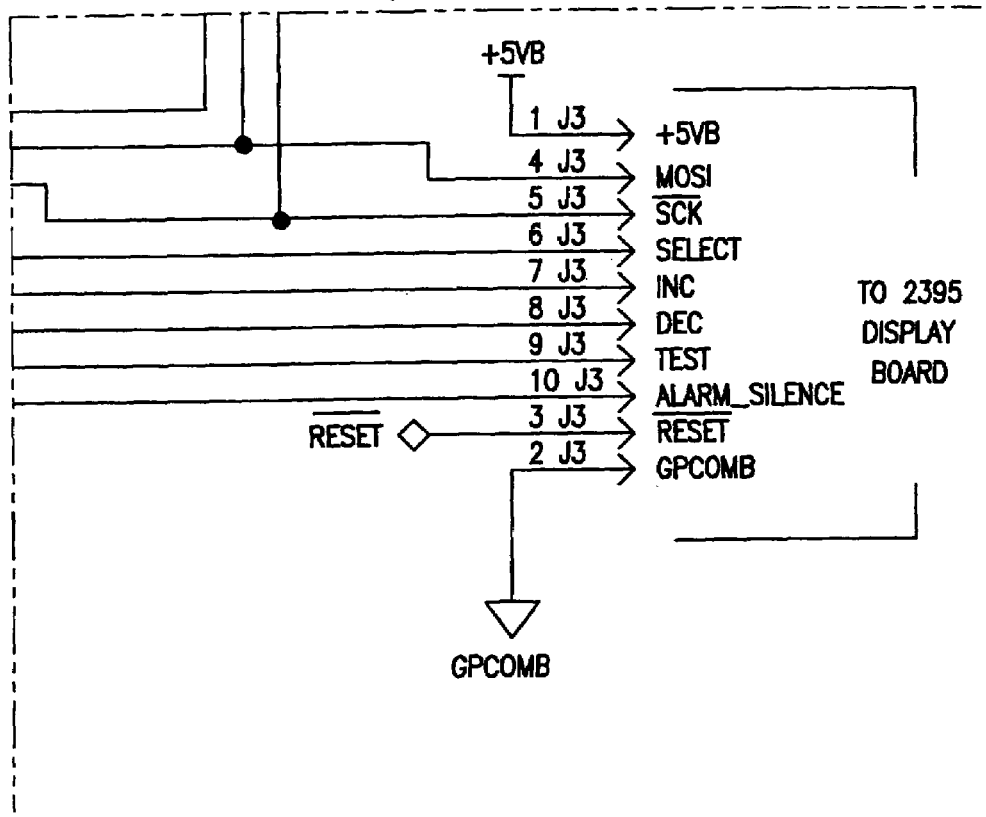

Referring now to FIGS. 67A–67U, display module 156 includes an ATmega163 microcontroller (.mu.C) and an AT90S2313 microcontroller (.mu.C), both of which are available from Atmel Corporation. Pins 6, 18, 28, and 39 of the ATmega163 .mu.C are coupled to GPCOMB as shown in FIG. 67R. Pins 5, 17, 27, 29, and 38 of the ATmega163 .mu.C are each coupled directly to +5 VB and are each coupled to GPCOMB through the same parallel combination of a 10 .mu.F capacitor and a 0.1 .mu.F capacitor as shown in FIG. 67Q.

Pins 14, 30, 31, 32, and 40 of the ATmega163 .mu.C are tied together and are coupled to +5 VB through a single 10 k.OMEGA. resistor as shown in FIGS. 67Q and 67R. Pins 1, 2, 3, and 33 of the ATmega163 .mu.C are each coupled to +5 VB through respective 10 k.OMEGA. resistors as also shown in FIGS. 67Q and 67R. Pins 1, 2, and 3 of the ATmega163 .mu.C are also coupled to MOSI, MISO, and notSCK lines as shown in FIGS. 67R, 67T, and 67U. The MOSI, MISO, and notSCK lines terminate at respective test points as indicated in FIG. 67T. Test points are also provided for +5 VB, notRESET, and GPCOMB lines as also shown in FIG. 67T.

Pins 1 and 3 of the ATmega163 .mu.C connector to pins 4 and 5, respectively, of a connector J3 as shown in FIGS. 67R and 67U. Pins 1, 2, and 3 of the connector J3 couple to +5 VB, GPCOMB, and notRESET lines, respectively, as shown in FIG. 67U. Pins 33, 37, 36, 35, and 34 of the ATmega163 .mu.C are coupled to pins 6–10, respetively, of the connector J3 as shown in FIGS. 67R and 67U. Pins 1–10 of the connector J3 couple to +5 VB, GPCOMB, notRESET, MOSI, notSCK, SELECT, INC, DEC, TEST, and ALARM_SILENCE lines that are indicated in FIG. 67U as being routed to the 2395 display board, which is the circuitry shown in FIGS. 68A–68J.

Display module 156 includes an LTC1483 differential line transceiver chip which is available from Linear Technology Corporation and which is shown in FIG. 67P. Pins 9, 10, and 11 of the ATmega163 .mu.C are coupled to pins 1, 3, and 4, respectively, of the LTC1483 chip as shown in FIGS. 67P, 67R, and 67S. Pins 2 and 5 of the LTC1483 chip are coupled to GPCOMb (referred to elsewhere herein as GPCOMB) as shown in FIG. 67P. Pin 8 of the LTC chip is coupled directly to +5 VB and is coupled to GPCOMb through a 0.1 .mu.F capacitor as also shown in FIG. 67P. Pins 6 and 7 of the LTC1483 chip are coupled to 485A_2 and 485B_2 lines, respectively, as shown in FIGS. 67H, 67L, and 67P.

Pin 4 of the ATmega163 .mu.C is coupled to the notRESET line and is also coupled through a 1 k.OMEGA. resistor to pin 2 of a reset chip, such as a MAX809 reset chip like that shown in FIG. 62E, as shown in FIGS. 67O and 67R. Pin 2 of the reset chip is coupled to +5 Vb (referred to elsewhere herein as +5 VB) through a 4.75 k.OMEGA. resistor and is coupled to GPCOMb through a 0.01 .mu.F capacitor as shown in FIG. 67O. Pin 1 of the reset chip is coupled to GPCOMb and pin 3 of the reset chip is coupled to +5 Vb. In addition, pin 1 of the reset chip is coupled to pin 3 of the reset chip through a 0.01 .mu.F capacitor.

Pin 7 of the ATmega163 .mu.C is coupled to a first terminal of a 3.6864 MHz oscillator or clock and pin 8 of the ATmega163 .mu.C is coupled to a second terminal of the 3.6864 clock as shown in FIGS. 67O and 67R. In addition, pins 7 and 8 of the ATmega163 .mu.C are each coupled to GPCOMB through a respective 33 pF capacitor. Furthermore, pin 7 of the ATmega163 .mu.C is coupled to the input of a NOT gate (identified as circuit component U7 in FIG. 67O), of the type included in, for example, an NC7ST04 chip, and the output of the NOT gate is coupled to pin 5 of the AT90S2313 .mu.C as shown in FIGS. 67O and 67R. As shown in FIG. 67S, the U7 circuit component in which the NOT gate of FIG. 67O is included includes pins 5 and 3 that are coupled to +5 VB and to GPCOMB, respectively, and that are coupled together by a 0.01 .mu.F capacitor.

Pins 12 and 13 of the ATmega163 .mu.C are coupled to pins 11 and 6, respectively, of the AT90S2313 .mu.C as shown in FIGS. 67O and 67R. In addition, pin 13 of the ATmega163 .mu.C and pin 6 of the AT90S2313 .mu.C are coupled to +5 VB through a single 10 k.OMEGA. resistor. Pins 19, 20, 21, 22, 23, 24, 25, and 26 of the ATmega163 .mu.C are coupled to pins 12, 13, 14, 15, 16, 7, 8, and 9, respectively, of the AT90S2313 .mu.C as shown in FIGS. 67N, 67O, 67Q, and 67R. Pin 42 of the ATmega163 .mu.C is coupled to an AIN0 line as shown in FIGS. 67N and 67Q. Pin 43 of the ATmega163 .mu.C is coupled to +5 VB through a 15 k.OMEGA. resistor and is coupled to GPCOMB through the parallel combination of a 10 k.OMEGA. resistor and a 0.1 .mu.F capacitor as also shown in FIGS. 67N and 67Q.

Pin 4 of the AT90S2313 .mu.C is open and pin 10 of the AT90S2313 .mu.C is coupled to GPCOMB as shown in FIG. 67K. Pin 20 of the AT90S2313 .mu.C is coupled directly to +5 VB and is coupled to GPCOMB through the parallel combination of a 0.1 .mu.F capacitor and a 10 .mu.F capacitor as shown in FIGS. 67J and 67N. Pins 1, 3, 17, 18, and 19 of the AT90S2313 .mu.C are each coupled to +5 VB through respective 10 k.OMEGA. resistors as shown in FIGS. 67J and 67K. Pins 1, 17, 18, and 19 of the AT90S2313 .mu.C are also coupled to notRESET, MOSI(2), MISO(2), and SCK(2) lines as also shown in FIGS. 67J and 67K. The notRESET, MOSI(2), MISO(2), and SCK(2) lines terminate at respective test points as indicated in FIG. 67J. Test points are also provided for +5 VB, and GPCOMB lines as shown in FIGS. 67F and 67J. Pin 2 of the AT90S2313 .mu.C is coupled to a PDO/RXD b line as shown in FIGS. 67G and 67K.

Pin 44 of the ATmega163 .mu.C is coupled to the base of an NPN transistor (identified as circuit component Q5) through a 2 k.OMEGA. resistor as shown in FIGS. 67I, 67M, 67N, and 67Q. The emitter of the Q5 transistor is coupled directly to GPCOMB and is coupled to the base of the Q5 transistor through a 10 k.OMEGA. resistor as shown in FIG. 67I. The collector of the Q5 transistor is coupled to an AUX_ALARM_B line as also shown in FIG. 67I. Pin 15 of the ATmega163 .mu.C is coupled to the base of an NPN transistor (identified as circuit component Q2) through a 2 k.OMEGA. resistor as shown in FIGS. 67I, 67M, 67N, and 67Q. The emitter of the Q2 transistor is coupled directly to GPCOMB and is coupled to the base of the Q2 transistor through a 10 k.OMEGA. resistor as shown in FIG. 67I. The collector of the Q2 transistor is coupled to a MAIN_ALARM_B line as also shown in FIG. 67I.

Pin 16 of the ATmega163 .mu.C is coupled to +5 VB through a 10 k.OMEGA. resistor and is also coupled to the collector of an NPN transistor (identified as circuit component Q6) as shown in FIGS. 67I, 67M, 67N, and 67Q. The emitter of the Q6 transistor is coupled directly to GPCOMB and is coupled to the base of the Q6 transistor through the parallel combination of a 1 k.OMEGA. resistor and a 0.01 .mu.F capacitor as shown in FIG. 67I. The base of the Q6 transistor is coupled to a GUARDED_ACCESS_B line through a 10 k.OMEGA. resistor as also shown in FIG. 67I.

Pin 41 of the ATmega163 .mu.C is coupled to a PB1/T1_b line through a 10 k.OMEGA. resistor as shown in FIGS. 67F, 67I, 67J, 67N, and 67Q. The AIN0 line that is coupled to pin 42 of the ATmega163 .mu.C is also referred to an AIN0_b line and is coupled to GPCOMb through the parallel combination of a 0.1 .mu.F capacitor and a 1 .mu.F capacitor as shown in FIG. 67G. As shown in FIG. 67L, a +5 Vb line is coupled to a GPCOMb line through a 10 .mu.F capacitor.

The AUX_ALARM_B, MAIN_ALARM_B, GUARDED_ACCESS_B, PB1_T1_b, PDO/RXD_b, AIN0_b, +5 VB, GPCOMb, 485A__2, and 485B__2 lines of display module 156 are coupled through associated wires of ribbon cable 236 (not shown in FIGS. 67A–67U) to circuitry included in circuit 74 of area alarm controller 50. For example, circuit 74 includes AUX_ALARM_A, MAIN_ALARM_A, GUARDED_ACCESS_A, PB1/T1_a, PDO/RXD_a, AIN0_a, +5 Va, GPCOMa, 485A__1, and 485B__1 lines that couple through the wires of ribbon cable 236 to the AUX_ALARM_B, MAIN_ALARM_B, GUARDED_ACCESS_B, PB1_T1_b, PD0RXD_b, AIN0_b, +5 VB, GPCOMb, 485A__2, and 485B__2 lines, respectively. FIG. 67E shows the AUX_ALARM_A, MAIN_ALARM_A, and GUARDED_ACCESS_A lines of circuit 74; FIG. 67B shows the PB1/T1_a line of circuit 74; FIG. 67C shows the PDO/RXD_a and AIN0_a lines of circuit 74; and FIG. 67H shows the +5 Va, GPCOMa, 485A__1, and 485B__1 lines of circuit 74.

The 485A__2 and 485B__2 lines are coupled through ribbon cable 236 (not shown in FIGS. 67A-67U) to the 485A__1 and 485B__1 lines included in circuit 74 as shown in FIG. 67H. The 485A__1 line is coupled to the 485B__1 line through a 1 k.OMEGA. resistor. In addition, each of the 485A__1 and 485B__1 lines are coupled to GPCOMa (referred to elsewhere herein as GPCOMA) through a respective 33 pF capacitor as shown in FIGS. 67D and 67H. The 485A__1 and 485B__1 lines are coupled through respective ferrite beads to pins 5 and 6, respectively, of a connector J1 included in circuit 74. Pin 7 of the connector J1 is coupled to GPCOMa. Pins 5, 6, and 7 of the connector J1 provide circuit 74 with an RS-485 port as indicated in FIG. 67D. Pins 3, 4, and 8 of the connector J1 are coupled to AUX_ALARM, MAIN_ALARM, and GUARDED_ACCESS lines as shown in FIG. 67E. Pins 9 and 10 of the connector J1 are coupled to XDUCER_A and XDUCER_B lines as shown in FIG. 67A. Pins 1 and 2 of the connector J1 are coupled to VCC and GPCOMA as shown in FIG. 67D.

Pin 1 of the connector J1 is coupled to pin 7 of a 5V voltage regulator chip through a 0.3 A polyswitch as shown in FIG. 67D. Pin 7 of the 5V voltage regulator chip is coupled directly to +VCC and is coupled to GPCOMA (i.e. pin 2 of the connector J1) thorugh a 330 .mu.F capacitor as also shown in FIG. 67D. Pins 1, 2, 3, 5, and 6 of the 5V voltage regulator chip are each coupled directly to GPCOMA. Pin 8 of the 5V voltage regulator chip is coupled to the cathode of an MBRS140 diode and the anode of the MBRS140 diode is coupled to GPCOMA as shown in FIGS. 67D and 67H. Pin 4 of the 5V voltage regulator chip is coupled to a junction formed by a first terminal of a 220 .mu.H inductor, a first terminal of a 3.3 .mu.H inductor, and a first terminal of a 220 .mu.F capacitor as also shown in FIGS. 67D and 67H. The second terminal of the 220 .mu.H inductor is coupled to pin 8 of the 5V voltage regulator chip. The second terminal of the 220 .mu.F capacitor is coupled to GPCOMA as shown in FIG. 67H. The second terminal of the 3.3 .mu.H inductor is coupled directly to +5 VA and is coupled to GPCOMA through a 220 .mu.F capacitor as shown in FIGS. 67D and 67H.

Pins 9 and 10 (i.e. XDUCER_A and XDUCER_B) of the connector J1 receive data from the associated sensor module 54 as will be described in further detail below in connection with FIG. 70. In addition, power is provided to the associated sensor module 54 through pins 9 and 10 of the connector J1. Pins 9 and 10 of the connector J1 are coupled to respective terminals of a bidirectional diode as shown in FIG. 67A. In addition, pin 10 of the connector J1 is coupled to terminal 1 of a 4-terminal transformer having two windings on a common core to serve as a common mode noise suppressor and pin 9 of the connector J1 is coupled to terminal 3 of the 4-terminal transformer as also shown in FIG. 67A. Terminal 4 of the 4-terminal transformer is coupled to terminal 2 thereof through a 0.01 .mu.F capacitor.

Terminal 4 of the 4-terminal transformer is coupled to the drain of a field effect transistor (FET) as shown in FIGS. 67A and 67B. The source of the FET is coupled directly to VCC and is coupled to the gate of the FET through a 10 k.OMEGA. resistor as shown in FIG. 67B. In addition, the source of the FET is coupled to the cathode of a diode (identified as circuit component D4) and the gate of the FET is coupled to the anode of the D4 diode. The gate of the FET is coupled to the collector of an NPN transistor (identified as circuit component Q3) through a 10 k.OMEGA. resistor as shown in FIG. 67B. The emitter of the Q3 transistor is coupled to GPCOMA. The base of the Q3 transistor is coupled to GPCOMA through a 10 k.OMEGA. resistor and is also coupled to the PB1/T1_a line.

Terminal 2 of the 4-terminal transformer is coupled to GPCOMA through a 47.OMEGA. resistor as shown in FIGS. 67A, 67B, and 67C. Terminal 2 of the 4-terminal transformer is also coupled to the AIN0_a line through a 20 k.OMEGA. resistor as also shown in FIGS. 67A, 67B, and 67C. The AIN0_a line is coupled to GPCOMA through a 20 k.OMEGA. resistor, is coupled to the anode of a first diode (identified as circuit component D5), and is coupled to the cathode of a second diode (identified as circuit component D6), as shown in FIG. 67C. The cathode of the D5 diode is coupled to +5 VA. The anode of the D6 diode is coupled to GPCOMA.

As shown in FIG. 67B, circuit 74 includes a comparator, such as an LMC7211 CMOS comparator chip available from National Semiconductor Corporation. Terminal 2 of the 4-terminal transformer is coupled to pin 3 of the LMC7211 chip through a 0.01 .mu.F capacitor as shown in FIGS. 67A and 67B. Pin 3 of the LMC7211 chip is coupled to GPCOMA and to +5 VA through respective 10 k.OMEGA. resistors as shown in FIGS. 67B and 67C. Pin 3 of the LMC7211 chip is also coupled to the cathode of a first diode (identified as circuit component D2) and to the anode of a second diode (identified as circuit component D3) as also shown in FIGS. 67B and 67C. The anode of the D2 diode is coupled to GPCOMA, as shown in FIG. 67C, and the cathode of the D3 diode is coupled to +5 VA, as shown in FIG. 67B. Pin 4 of the LMC7211 chip is coupled to +5 VA and to GPCOMA through respective 10 k.OMEGA. resistors as shown in FIGS. 67B and 67C. Pin 5 of the LMC7211 chip is coupled to GPCOMA as shown in FIG. 67B. Pin 2 of the LMC7211 chip is coupled directly to +5 VA and is coupled to GPCOMA through a 0.01 .mu.F capacitor. Pin 1 of the LMC7211 chip is coupled directly to the PD0/RXD_a line and is coupled to pin 3 of the LMC7211 chip through a 100 k.OMEGA. resistor as shown in FIGS. 67B and 67C.

The FET of FIG. 67B serves as a switch that controls the supply of voltage from VCC to the associated sensor module 54 through the XDUCER_A and XDUCER_B lines. The ATmega163 .mu.C operates through pin 41 thereof and through the PB1/T1_b line, the PB1/T1_a line, and the Q3 transistor of FIG. 67B to control whether the FET switch is in an "ON" state or an "OFF" state. The AIN0 line provides feedback to the ATmega163 .mu.C through pin 42 thereof regarding the state of the FET switch. The serial data transmitted from the associated sensor module 54 on the XDUCER_A and XDUCER_B lines is coupled to the comparator of FIG. 67B and the comparator provides a HIGH output signal at pin 1 thereof when pin 3 thereof receives an input signal that is greater than approximately 2.5 V. The comparator provides a LOW signal when pin 3 thereof receives an input signal that is less than approximately 2.5 V. The output of the comparator, therefore, provides the serial data from the associated sensor module 54 to pin 2 of the AT90S2313 .mu.C via the PD0/RXD_a and PD0/RXD_b lines.

Figure 68A:
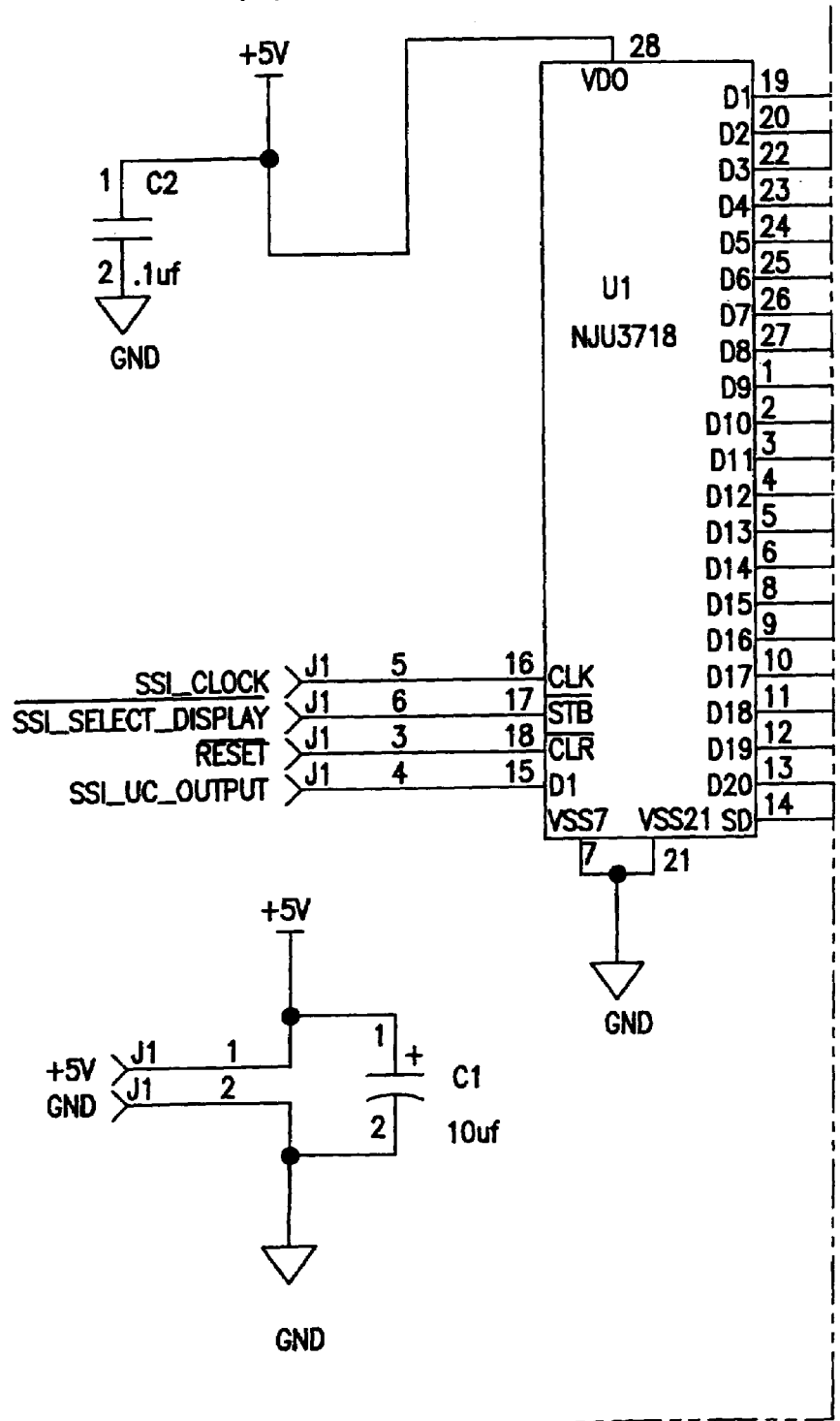
FIG. 68 is a circuit schematic map showing how to lay out FIGS. 68A–68J to form an electric circuit schematic of a second portion of an electric circuit of one of the display modules included in one of the area alarm controllers.

Each display module 156 includes an NJU3718 20-bit serial-to-parallel converter chip as shown in FIG. 68A. Pins 15, 16, 17, and 18 of the NJU3718 chip are coupled to pins 4, 5, 6, and 3, respectively, of a connector J1 as also shown in FIG. 68A. The connector J1 couples to the connector J3 shown in FIG. 67U such that the numbered pins of the connector J3 are coupled to similarly numbered pins of the connector J1. Thus, pins 3, 4, 5, and 6 of the connector J1, which are associated with notRESET, SSI_U_OUTPUT, SSI_CLOCK, and notSSI_SELECT_DISPLAY lines, respectively, as shown in FIG. 68A, couple to pins 3, 4, 5, and 6 of the connector J3, which are associated with notRESET, MOSI, notSCK, and SELECT lines, respectively, as shown in FIG. 67U. Pin 1 of the connector J1 is coupled to +5V and pin 2 of the connector J1 is coupled to GND as shown in FIG. 68A. In addition, pin 1 of the connector J1 is coupled to pin 2 thereof through a 10 .mu.F capacitor.

Figure 68B:
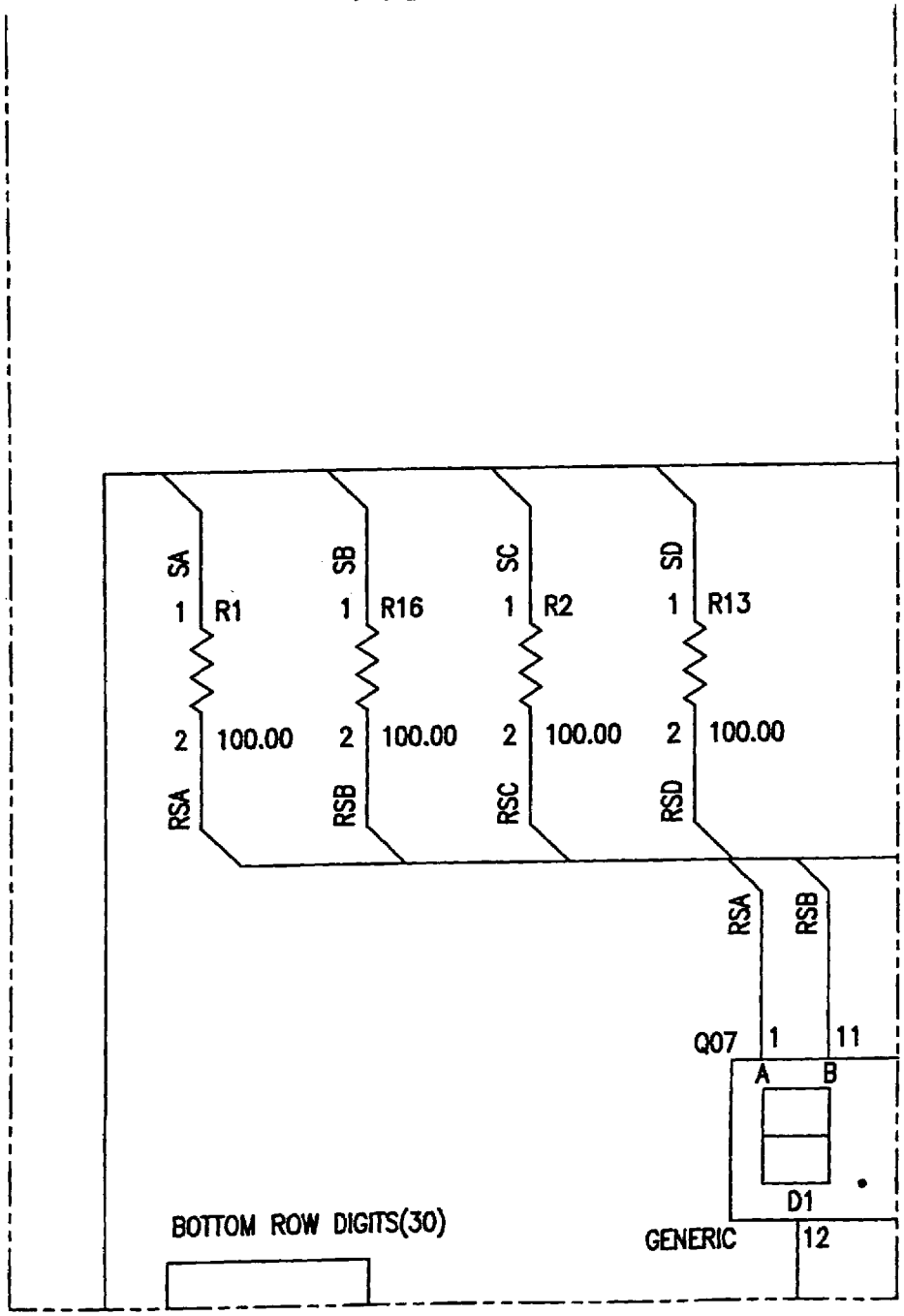
Figure 68C:
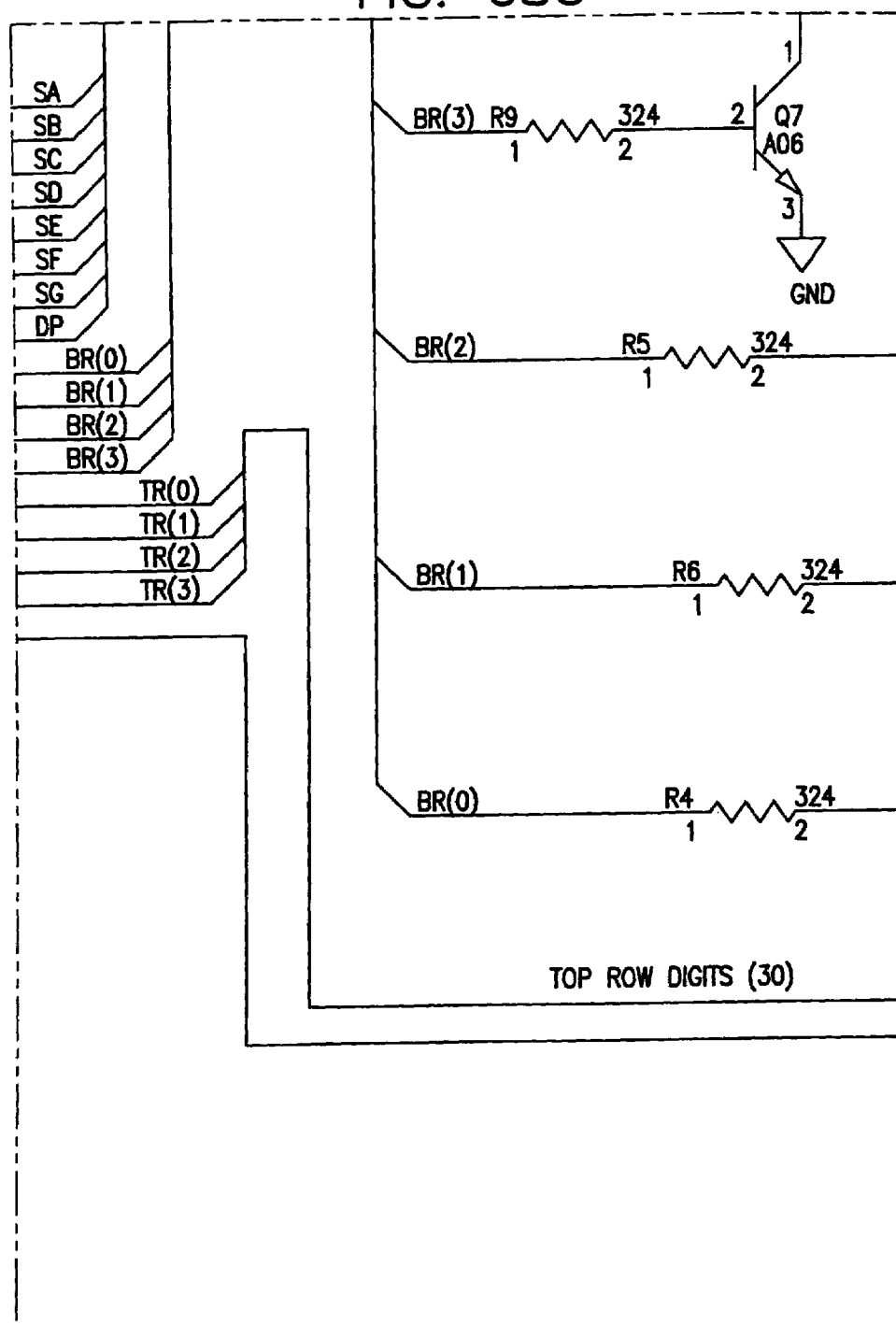
Figure 68D:
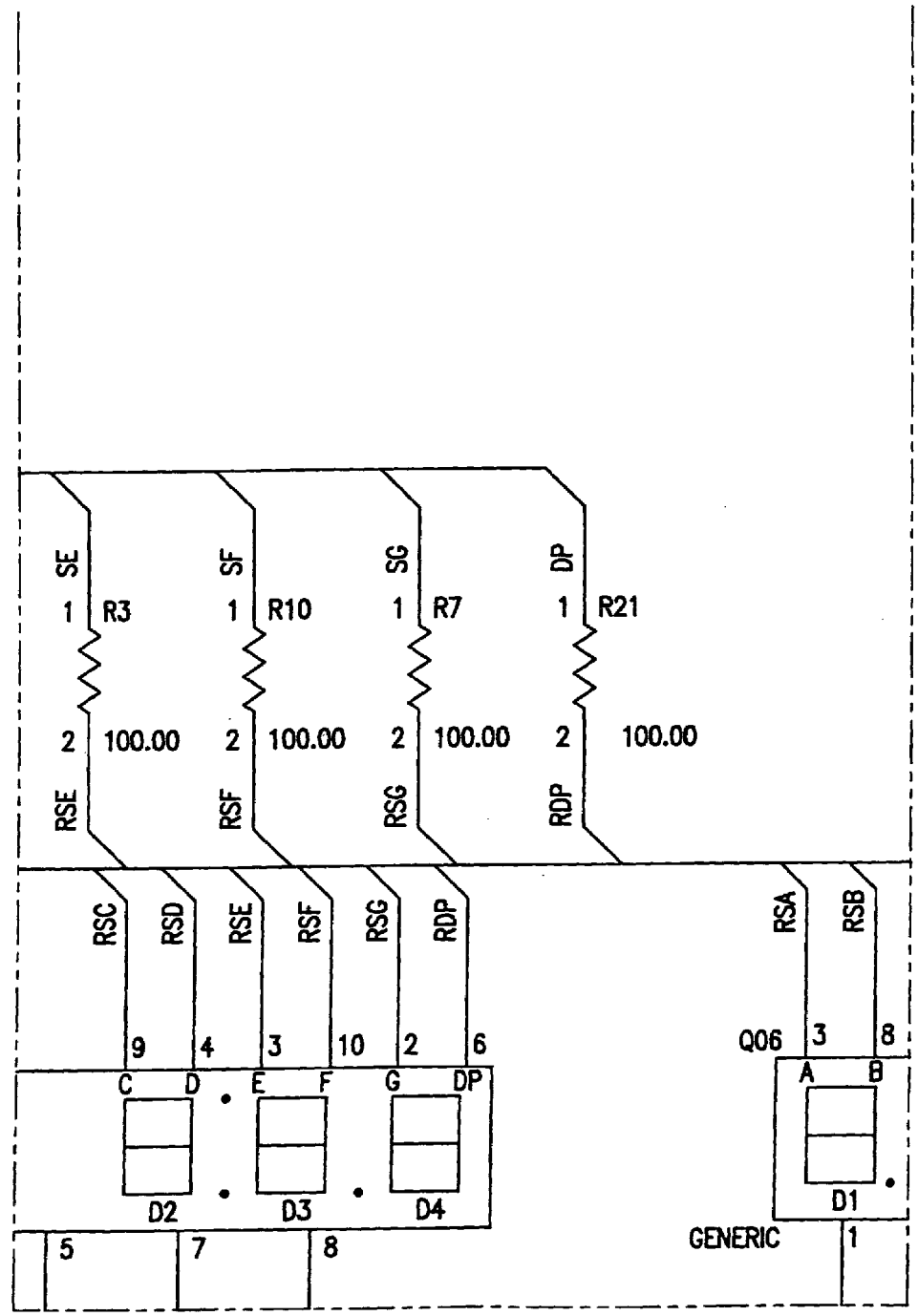
Figure 68E:
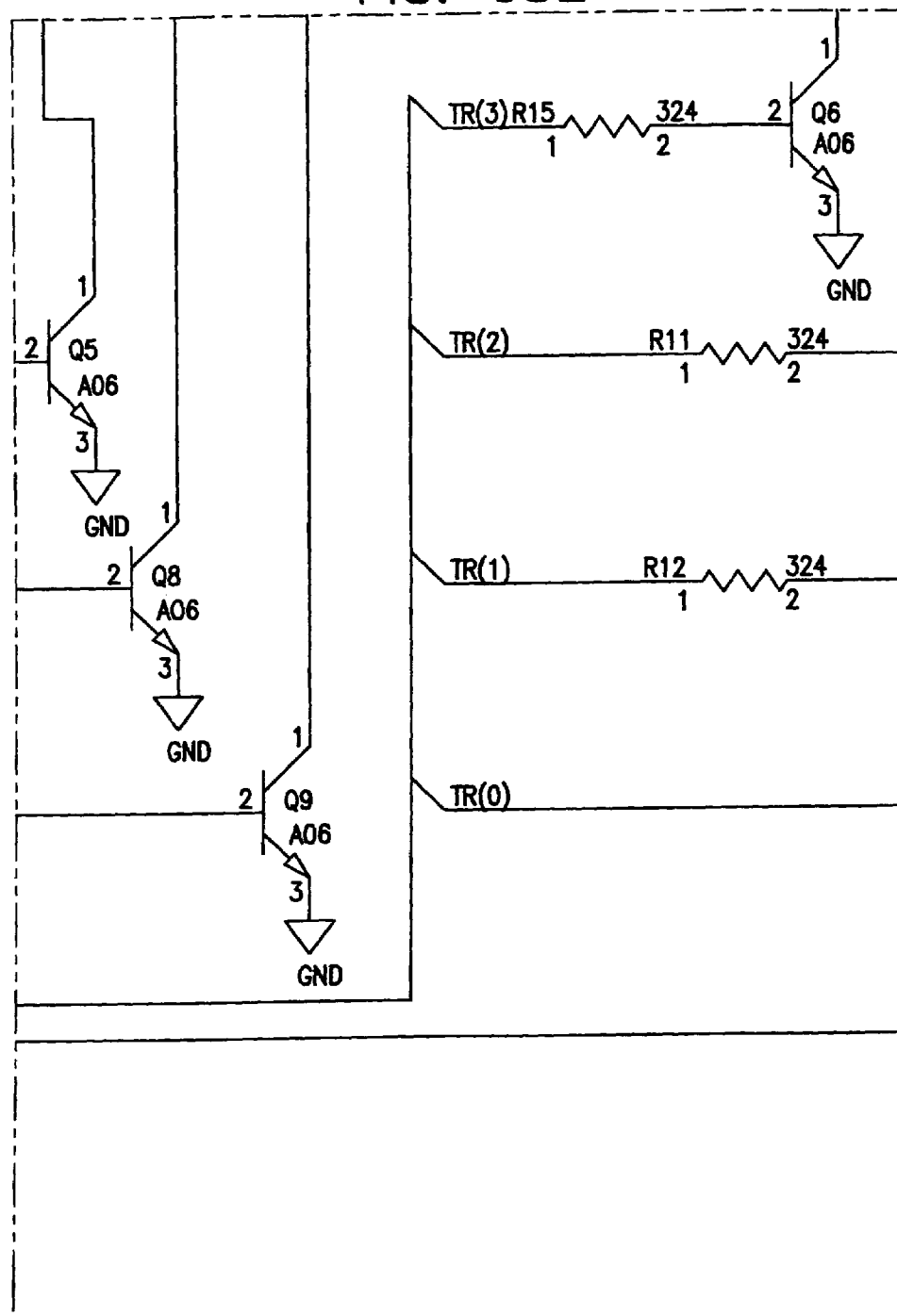
Figure 68F:
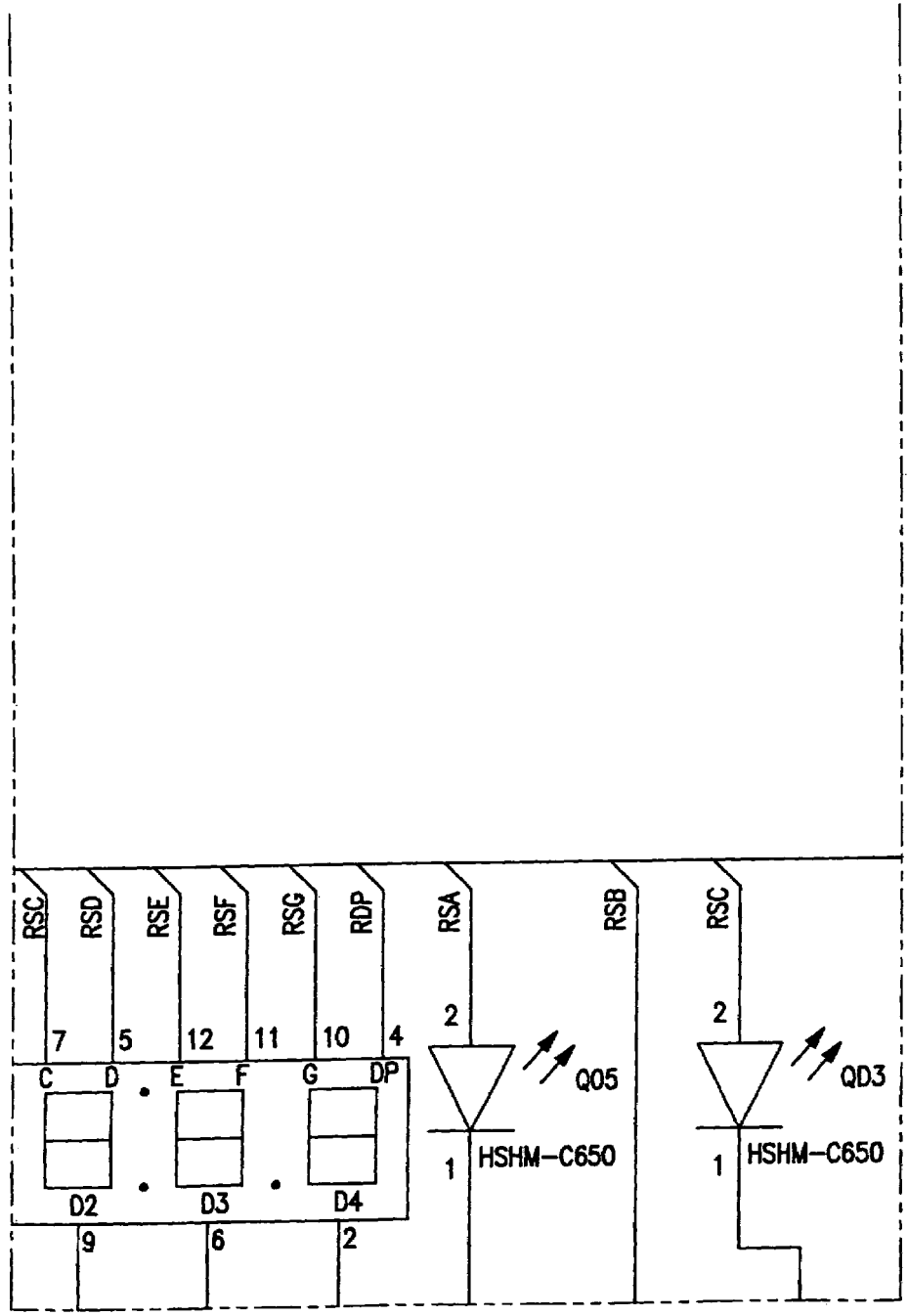
Figure 68G:
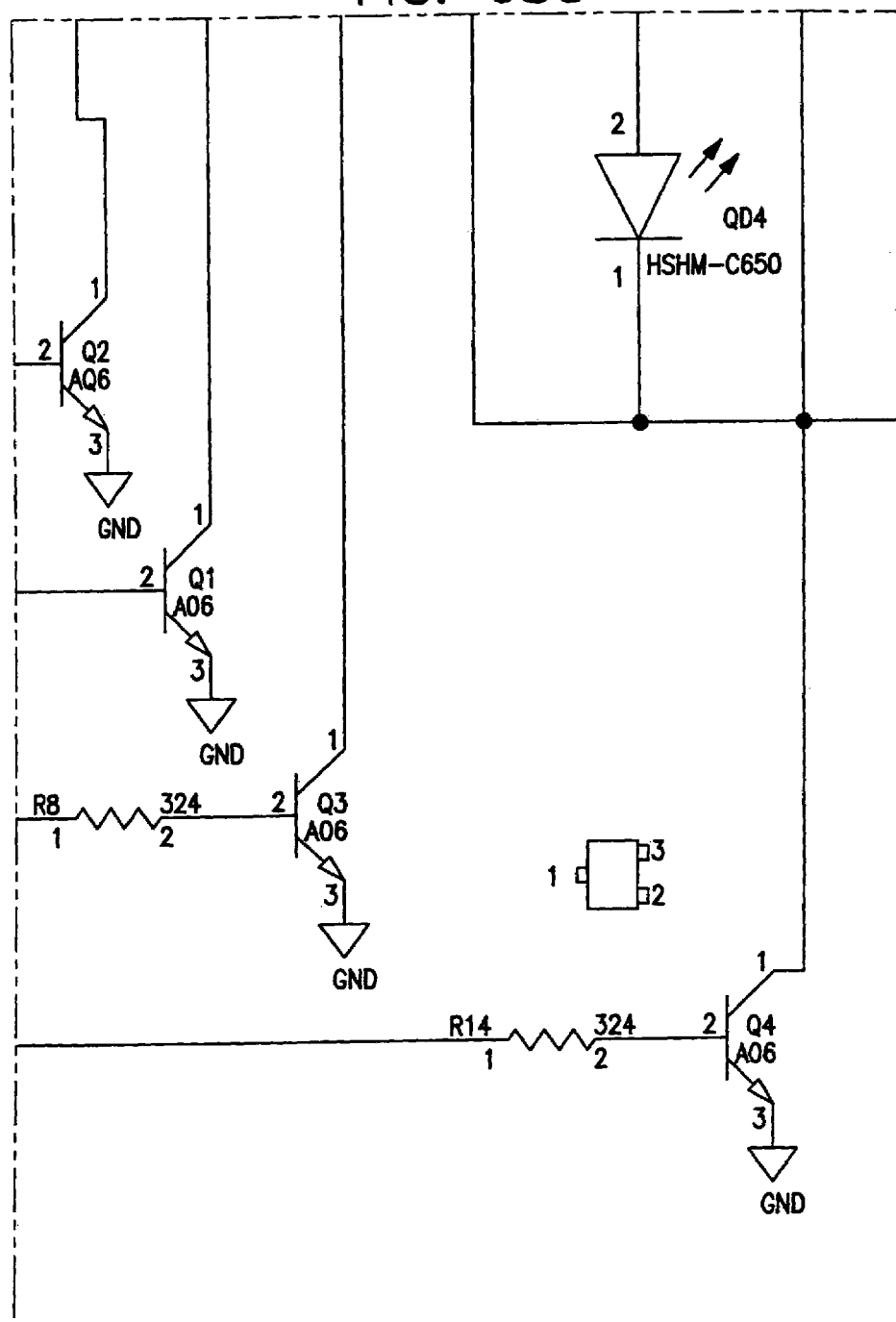
Figure 68H:
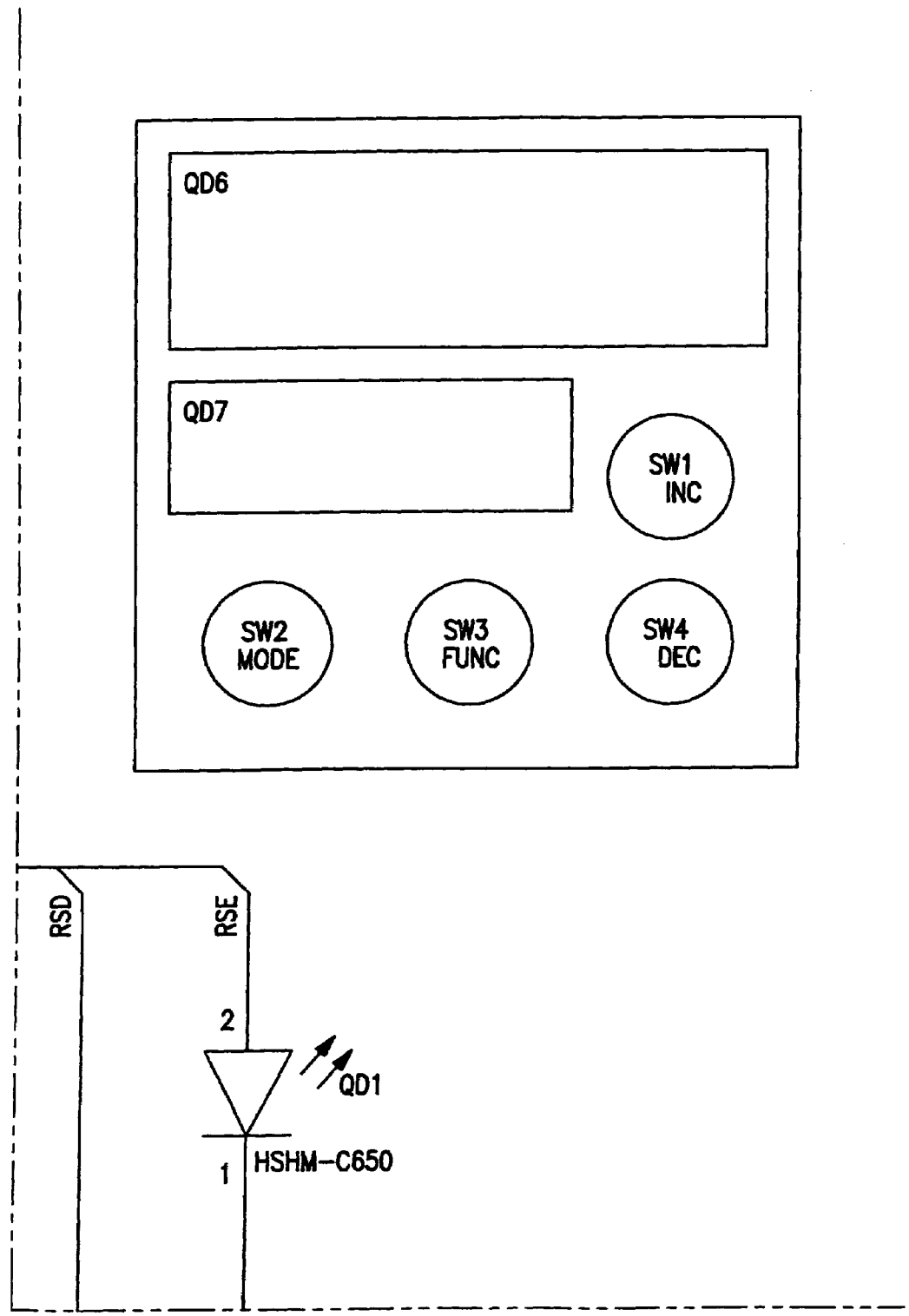
Figure 681:
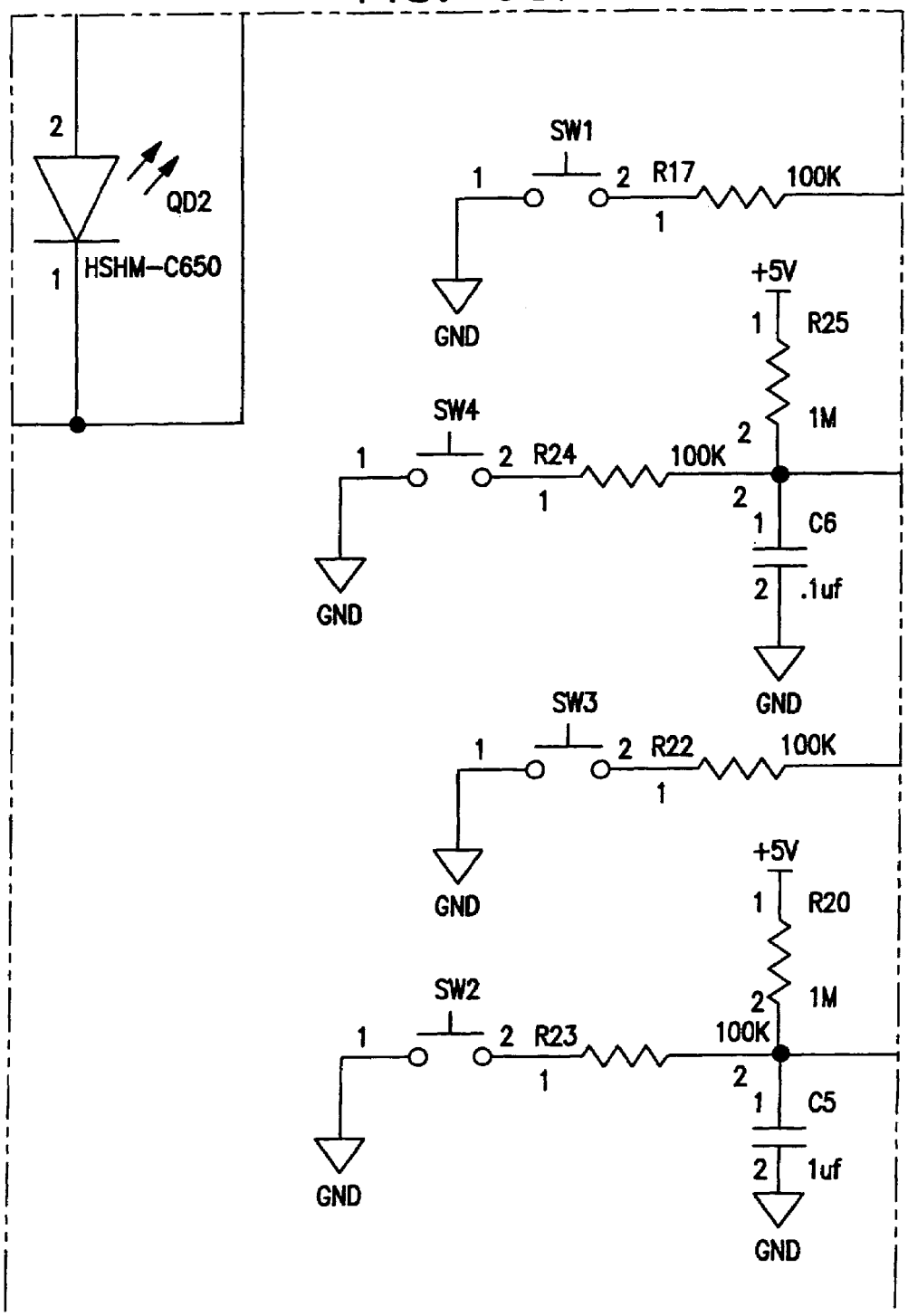

Pins 7 and 21 of the NJU3718 chip are coupled to GND as shown in FIG. 68A. Pin 28 of the NJU3718 chip is coupled directly to +5V and is coupled to GND through a 0.1 .mu.F capacitor as also shown in FIG. 68A. Pins 11, 12, 13, and 14 of the NJU3718 chip are open as shown in FIG. 68A. Pins 19, 20, 22, 23, 24, 25, 26, and 27 are coupled to RSA, RSB, RSC, RSD, RSE, RSF, RSG, and RDP lines, respectively, through respective 100.OMEGA. resistors as shown in FIGS. 68A–68D. Each display module includes a first 4-digit display (identified as circuit component QD6) and a second 4-digit display (identified as circuit component QD7) as shown in FIGS. 68B, 68D, and 68F. The four digits of the QD6 and QD7 displays, which are designated as D1, D2, D3, and D4 in each of the QD6 and QD7 displays, are in the 7-segment display format, having A, B, C, D, E, F, and G segments for each digit. In addition each digit of the QD6 and QD7 displays is separated from the next adjacent digit by a decimal point (DP) segment.

The RSA, RSB, RSC, RSD, RSE, RSF, RSG, and RDP lines are coupled to pins of the QD6 and QD7 displays that correspond to the A, B, C, D, E, F, G, and DP segments, respectively, as shown in FIGS. 68B and 68D. In addition, the RSA, RSB, RSC, RSD, and RSE lines are coupled to the anodes of respective HSHM-C650 LED's as shown in FIG. 68F–68I. Each display module 156 includes nine NPN transistors and pins 1–6 and 8–10 of the NJU3718 chip are coupled to the base of respective NPN transistors through respective 324.OMEGA. resistors as shown in FIGS. 68A–C, 68E, and 68G. The emitter of each of the nine NPN transistors is coupled to GND.

The collectors of the four NPN transistors associated with pins 1, 2, 3, and 4, respectively, of the NJU3718 chip are coupled to pins of the QD7 display that correspond to D1, D2, D3, and D4, respectively, of the QD7 display as shown in FIGS. 68B–68E. Similarly, the collectors of the four NPN transistors associated with pins 5, 6, 8, and 9 of the NJU3718 chip are coupled to the pins of the QD6 display that correspond to D1, D2, D3, and D4, respectively, of the QD6 display as shown in FIGS. 68D–68G. The collector of the NPN transistor associated with pin 10 of the NJU3718 chip is coupled to the cathode of each of the HSHM-C650 LED's as shown in FIGS. 68F–68I.

Figure 68J:
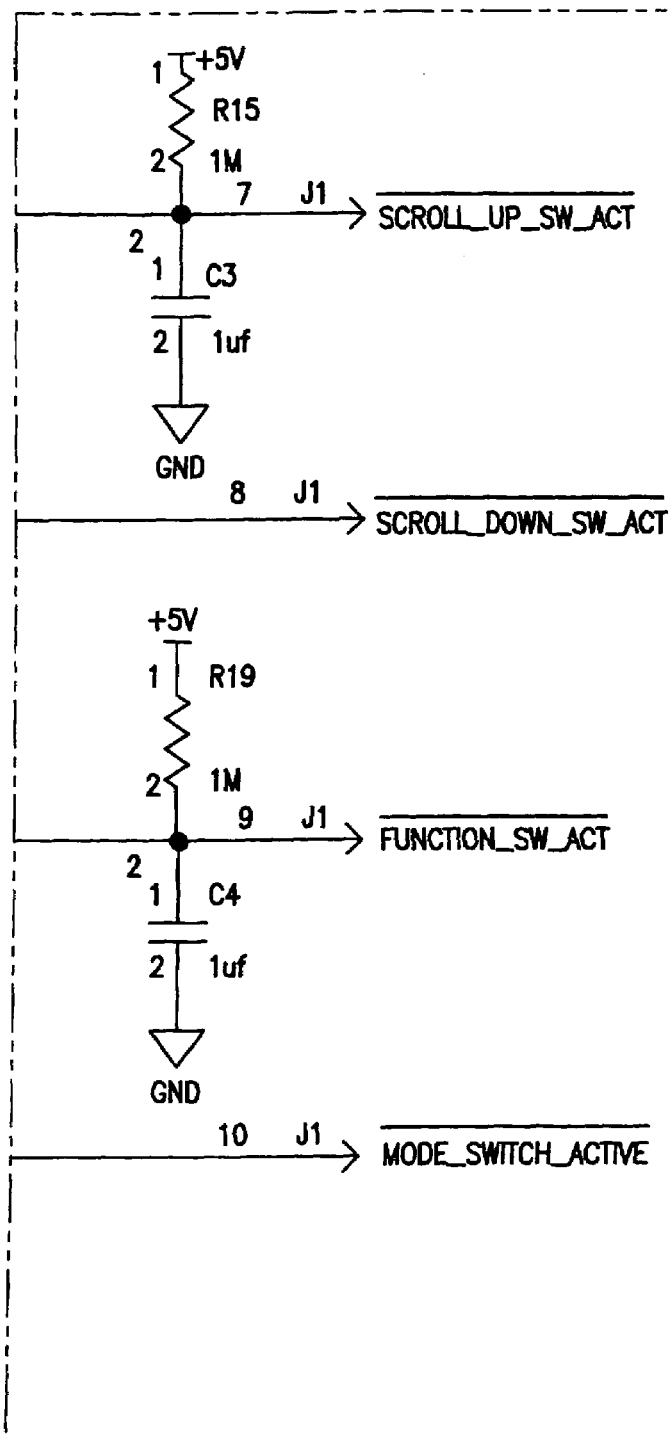

Pins 7, 8, 9, and 10 of the connector J1, which are associated with notSCROLL_UP_SW_ACT, notSCROLL_DOWN_SW_ACT, notFUNCTION_SW_ACT, and notMODE_SWITCH_ACTIVE lines, respectively, as shown in FIG. 68J, couple to pins 7, 8, 9, and 10 of the connector J3, which are associated with INC, DEC, TEST, and ALARM_SILENCE lines, respectively, as shown in FIG. 67U. Pins 7, 8, 9, and 10 of the connector J1 are each coupled to +5V through respective 1 M.OMEGA. resistors and are each coupled to GND through respective 1 .mu.F capacitors as shown in FIGS. 68I and 68J. In addition, pins 7, 8, 9, and 10 of the connector J1 are coupled through respective 100 k.OMEGA. resistors to respective switch terminals of respective momentary switches (identified as circuit components SW1, SW2, SW3, SW4) as also shown in FIGS. 68I and 68J. The other terminal of the SW1, SW2, SW3, and SW4 switches is coupled to GND. The SW1, SW2, SW3, and SW4 switches, shown in FIG. 1, correspond to buttons 170, 168, 166, 172, respectively, mentioned above in connection with FIG. 5.

Figure 69:
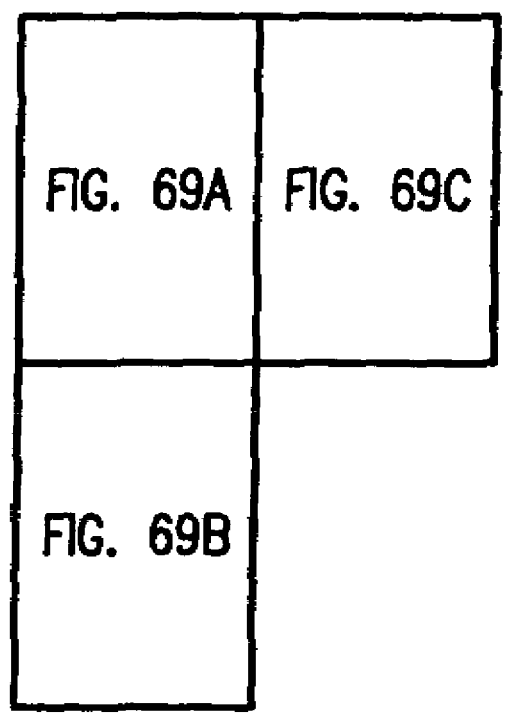
FIG. 69 is a circuit schematic map showing how to lay out FIGS. 69A–69C to form an electric circuit schematic of a portion of an electric circuit of one of the area alarm controllers.
Figure 69A:
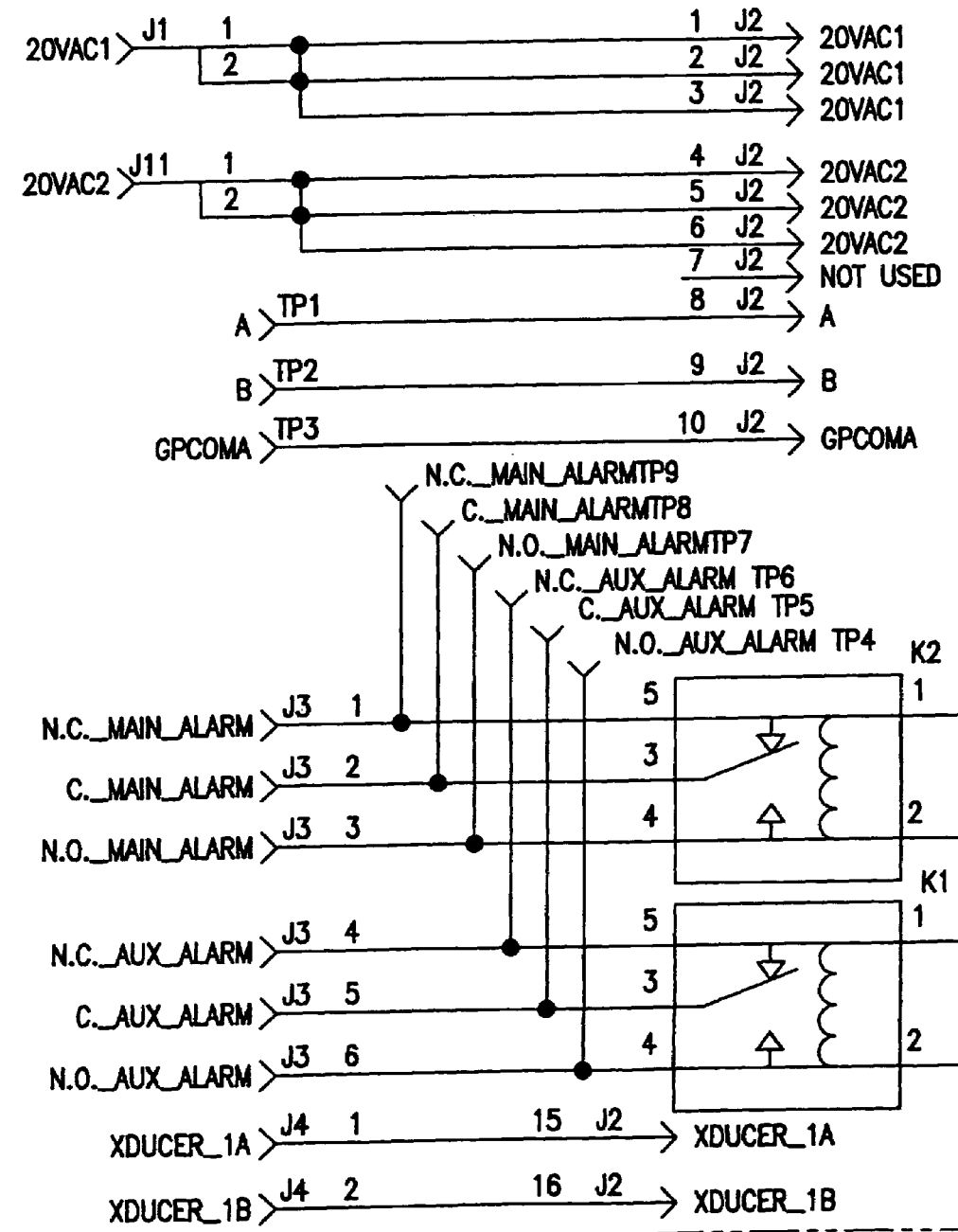
Figure 69B:
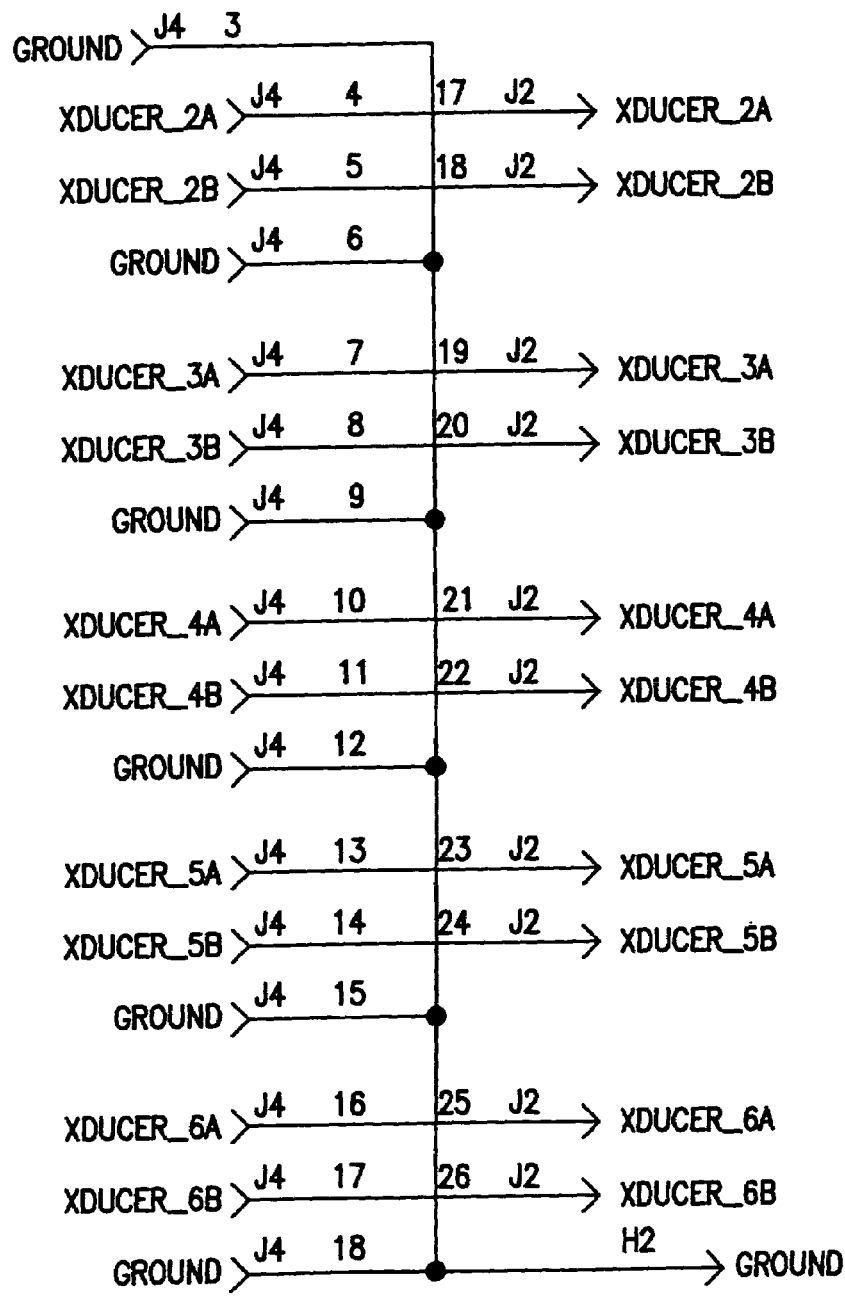
Figure 69C:
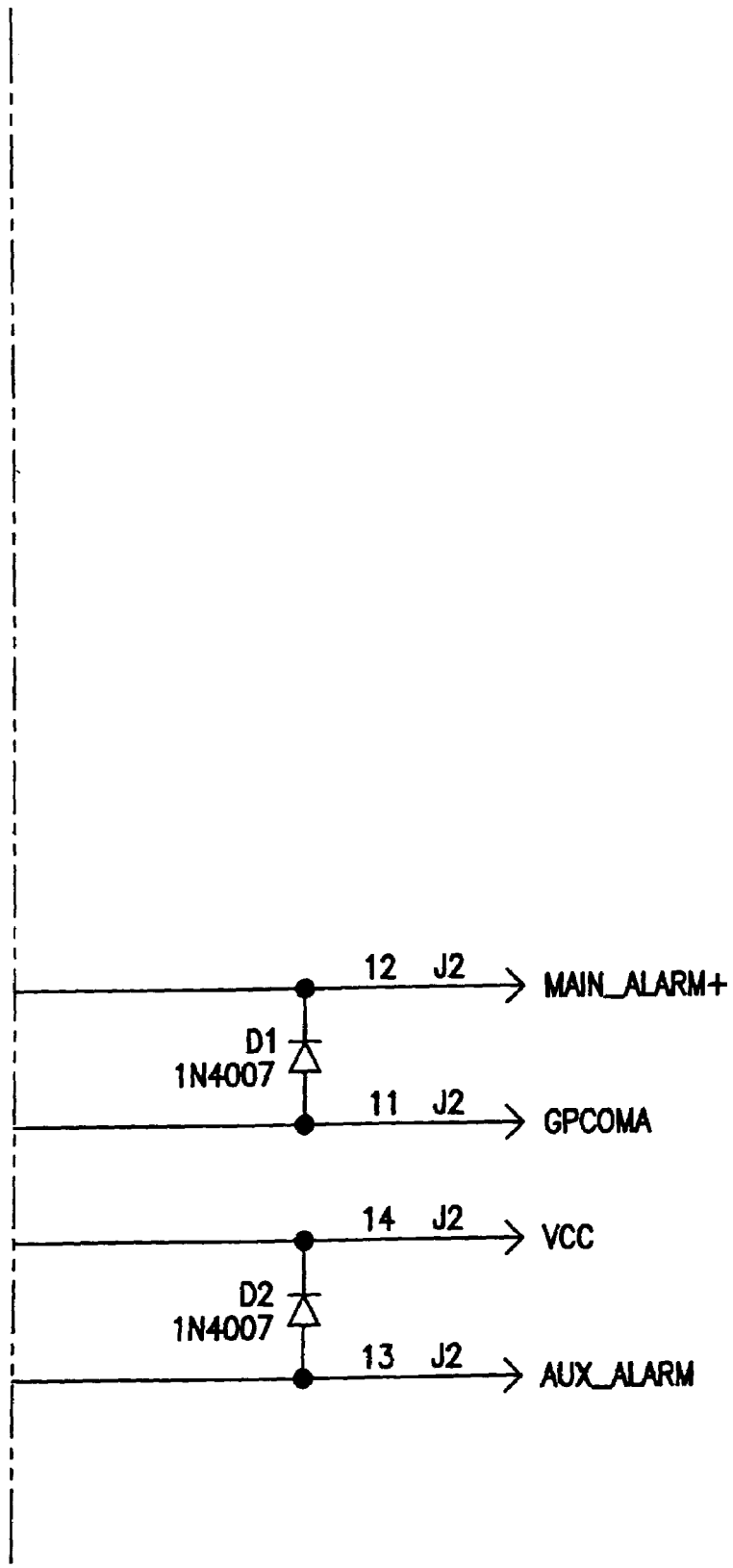

FIGS. 69A–69C show a schematic of breakout board 222 of area alarm controller 50. Breakout board 222 includes a connector J2 to which ribbon cable 230 couples and a connector J4 to which the shielded, twisted pair wires from the respective sensor modules 54 couple as shown in FIGS. 69A–69C. Breakout board 222 further includes a J1 connector that couples to 20VAC1 power provided by the associated transformer and a connector J11 that couples to 20VAC2. Pins 1 and 2 of the connector J11 couple to pins 1–3 of the connector J2 and pins 1 and 2 of the connector J11 couple to pins 4–6 of the J2 connector as shown in FIG. 69A. Pin 7 of the connector J2 is not used. Pins 8, 9, and 10 of the connector J2 provide test points (identified as TP1, TP2, and TP3) for A, B, and GPCOMa lines, respectively, as shown in FIG. 69A.

Breakout board 222 further includes a connector J3 having pins 1–6 that couple to N.C._MAIN_ALARM, C._MAIN_ALARM, N.O._MAIN_ALARM, N.C._AUX_ALARM, C._AUX_ALARM, and N.O._AUX_ALARM lines, respectively, and that provide test points (identified as TP9, TP8, TP7, TP6, TP5, and TP4, respectively) for these lines as shown in FIG. 69A. Pins 1, 2, and 3 of the connector J3 couple to pins 5, 3, and 4, respectively, of a first 5-terminal relay and pins 4, 5, and 6 of the connector J3 couple to pins 5, 3 and 4, respectively, of a second 5-terminal relay as shown in FIG. 69A.

Pin 1 of the first 5-terminal relay couples to pin 12 of the connector J2, which corresponds to the MAIN_ALARM+ line, and pin 2 of the first 5-terminal relay couples to pin 11 of the connector J2, which corresponds to the GPCOMA line, as shown in FIGS. 69A and 69C. In addition, pin 1 of the of the first 5-terminal relay couples to the cathode of a first IN4007 diode, which is available from Fairchild Semiconductor Corporation, and pin 2 of the first 5-terminal relay coupled to the anode of the first 1N4007 diode. Pin 1 of the second 5-terminal relay couples to pin 14 of the connector J2, which corresponds to the VCC line, and pin 2 of the second 5-terminal relay couples to pin 13 of the connector J2, which corresponds to the AUX_ALARM line, as shown in FIGS. 69A and 69C. In addition, pin 1 of the of the second 5-terminal relay couples to the cathode of a second 1N4007 diode and pin 2 of the second 5-terminal relay coupled to the anode of the second 1N4007 diode.

Pins 3, 6, 9, 12, 15, and 18 of the connector J4 couple to GROUND as shown in FIG. 69B. In addition, pins 3, 6, 9, 12, 15 and 18 couple to the shielding of the shielded, twisted pair wires associated with the first through sixth sensor modules 54, respectively, that are associated with area alarm controller 50. Pins 1, 2, 4, 5, 7, 8, 10, 11, 13, 14, 16, and 17 of the connector J4 couple to pins 15, 16, 17, 18, 19, 20, 21, 22, 23, 24, 25, and 26, respectively, of the connector J2 as shown in FIGS. 69A and 69B. Pins 1, 2, 4, 5, 7, 8, 10, 11, 13, 14, 16, and 17 of the connector J4 and pins 15, 16, 17, 18, 19, 20, 21, 22, 23, 24, 25, and 26 of the connector J2 are associated with XDUCER_1A, XDUCER_1B, XDUCER_2A, XDUCER_2B, XDUCER_3A, XDUCER_3B, XDUCER_4A, XDUCER_4B, XDUCER_5A, XDUCER_5B, XDUCER_6A, and XDUCER_6B lines, respectively.

Figure 70A:
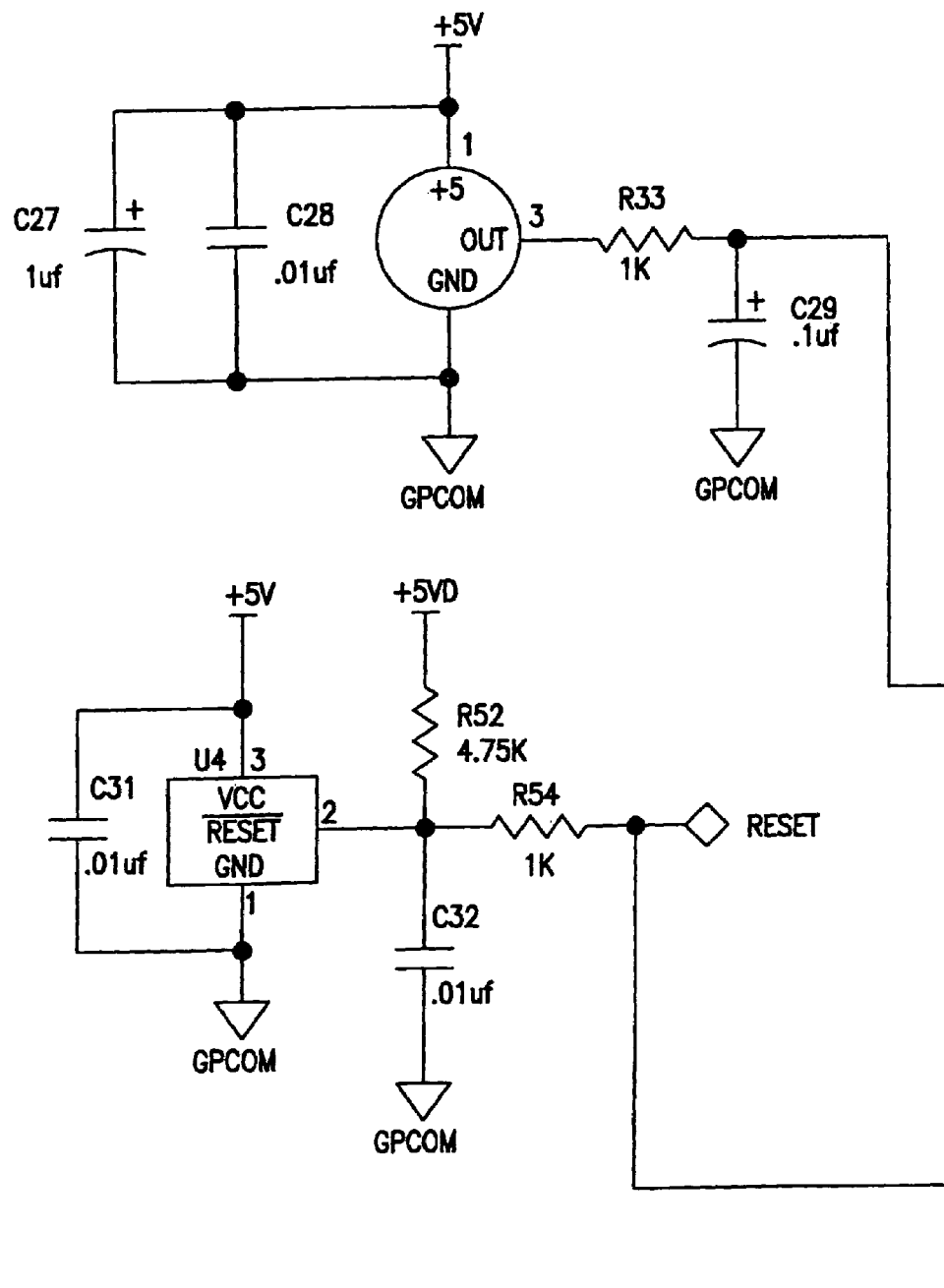
FIG. 70 is a circuit schematic map showing how to lay out FIGS. 70A–70J to form an electric circuit schematic of an electric circuit of one of the sensor modules.
Figure 70B:
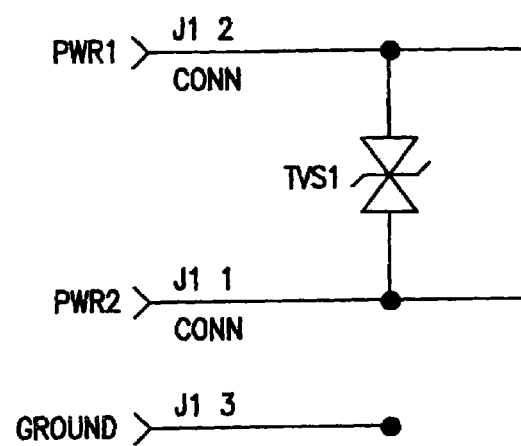
Figure 70C:
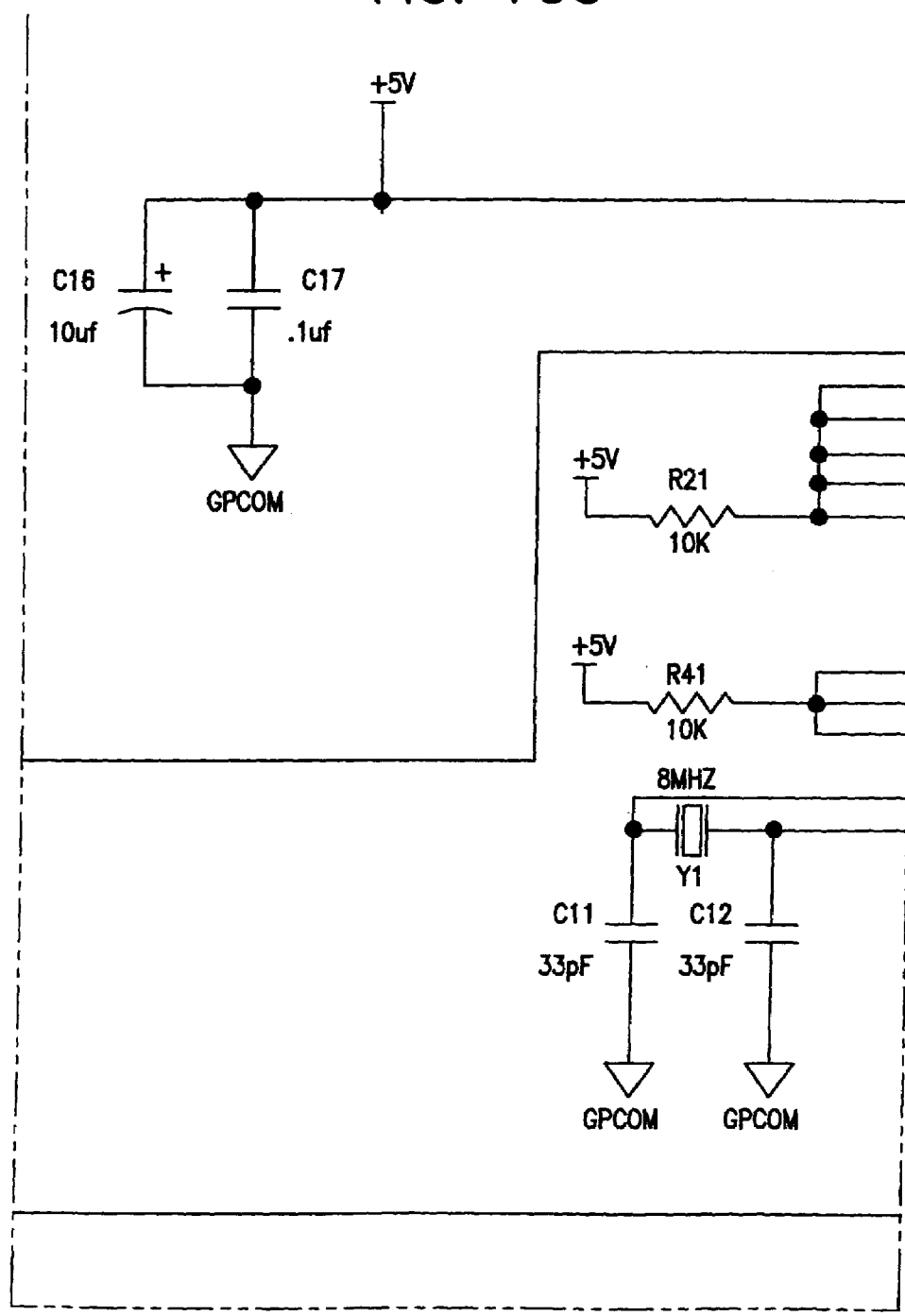
Figure 70E:
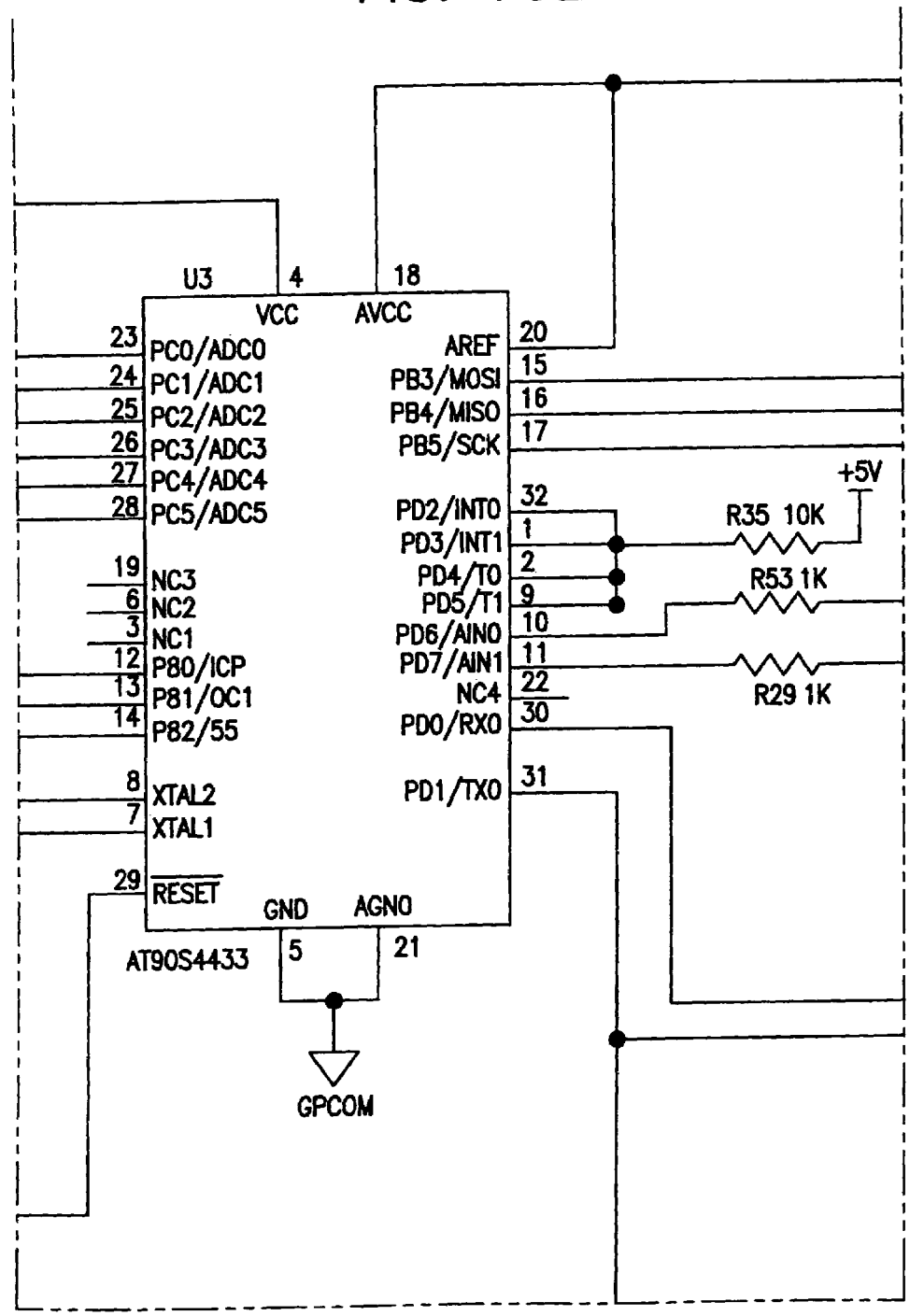

Referring now to FIGS. 70A–70J, each sensor module 54 includes an AT90S4433 microcontroller (.mu.C) which is available from Atmel Corporation. Pins 3, 6, 19, and 22 of the AT90S4422 .mu.C are open as shown in FIG. 70E. Pins 5 and 21 of the AT90S4422 .mu.C are coupled to GPCOM as also shown in FIG. 70E. Pins 1, 2, 9, and 32 of the AT90S4422 .mu.C are coupled to +5V through a single 10 k.OMEGA. resistor. Pins 12, 13, and 14 of the AT90S4422 .mu.C are coupled to +5V through a single 10 k.OMEGA. resistor as shown in FIGS. 70C and 70E. Similarly, pins 24, 25, 26, 27 and 28 are coupled to +5V through a single 10 k.OMEGA. resistor as also shown in FIGS. 70C and 70E. Pin 4 of the AT90S4422 .mu.C is coupled directly to +5V and is coupled to GPCOM through the parallel combination of a 10 .mu.F capacitor and a 0.1 .mu.F capacitor as further shown in FIGS. 70C and 70E.

Pins 7 and 8 of the AT90S4422 .mu.C are each coupled to GPCOM through a respective 33 pF capacitor as shown in FIGS. 70C and 70E. In addition, pin 7 of the AT90S4422 .mu.C is coupled to the first terminal of an 8 MHz oscillator or clock and pin 8 is coupled to the other terminal of the 8 MHz clock as also shown in FIGS. 70C and 70E. Pins 18 and 20 of the AT90S4422 .mu.C are each coupled to +5V through a single ferrite bead and are each coupled to GPCOM through a single 0.01 .mu.F capacitor as shown in FIGS. 70E, 70G, and 70I. As shown in FIGS. 70A, 70C, and 70E, pin 29 of the AT90S4422 .mu.C is coupled to a RESET line and is coupled through a 1 k.OMEGA. resistor to pin 2 of a Reset chip, such as, for example, a MAX809 reset chip. Pin 2 of the Reset chip is coupled to +5V through a 4.75 k.OMEGA. resistor and is coupled to GPCOM through a 0.01 .mu.F capacitor as shown in FIG. 70A. Pin 3 of the Reset chip is coupled to +5V and pin 1 of the Reset chip is coupled to GPCOM as also shown in FIG. 70A. In addition, pin 3 of the Reset chip is coupled to pin 1 thereof through a 0.01 .mu.F capacitor.

In some embodiments, transducer 286 of each sensor module 54 is either a Model No. 40PC250G2A transducer (if positive pressure is to be measured) available from Honeywell Corporation or a Model No. 40PC015V2A transducer (if negative pressure is to be measured) which is also available from Honeywell Corporation. Each of these Honeywell transducers have three pins as shown, for example, in FIG. 70A. Pin 23 of the AT90S4422 .mu.C is coupled to GPCOM through a 0.1 .mu.F capacitor and is coupled to pin 3 of the Honeywell transducer through a 1 k.OMEGA. resistor as shown in FIGS. 70A, 70C, and 70E. Pin 1 of the Honeywell transducer is coupled to +5V and pin 2 of the Honeywell transducer is coupled to GPCOM. In addition, pin 1 of the Honeywell transducer is coupled to pin 2 thereof through the parallel combination of a 1 .mu.F capacitor and a 0.01 .mu.F capacitor as shown in FIG. 70A. The Honeywell transducer operates to provide an analog pressure signal to pin 23 of the AT90S4422 .mu.C.

Pin 10 of the AT90S4422 .mu.C is coupled to the cathode of a first LED through a 1 k.OMEGA. resistor and pin 11 of the AT90S4422 .mu.C is coupled to the cathode of a second LED through a 1 k.OMEGA. resistor as shown in FIGS. 70E and 70G. The anodes of the first and second LED's are coupled to +5V as shown in FIG. 70G. The LED's shown in FIG. 70G correspond to LED's 338 mentioned above in connection with FIG. 9. Sensor modules 54 each include a connector J2 as shown in FIG. 70G. Pin 3 of the connector J2 is not connected to any circuitry. Pin 2 of the connector J2 is coupled to +5V. Pins 4 and 6 of the connector J2 are coupled to GPCOM. Pin 5 of the connector J2 is coupled to the RESET line.

Pins 15, 16, and 17 of the AT90S4422 .mu.C are coupled to +5V through respective 10 k.OMEGA. resistors as shown in FIGS. 70E and 70G. In addition, pins 15, 16, and 17 of the AT90S4422 .mu.C are coupled to pins 1, 9, and 7, respectively, of the connector J2. Pins 1, 9, and 7 of the connector J2 correspond to MOSI, MISO, and SCK lines, respectively, as shown in FIG. 70G. Pins 30 and 31 of the AT90S4422 .mu.C are coupled to +5V through respective 10 k.OMEGA. resistors as shown in FIGS. 70E and 70G. In addition, pins 30 and 31 of the AT90S4422 .mu.C are coupled to pins 8 and 10, respectively, of the connector J2. Pins 8 and 10 of the connector J2 correspond to RX and TX lines, respectively, as shown in FIG. 70G. The connector J2 serves as a connection point to permit FLASH downloads of updated application software to the AT90S4422 .mu.C from a device, such as a personal computer, that is connected to the connector J2.

Figure 70F:
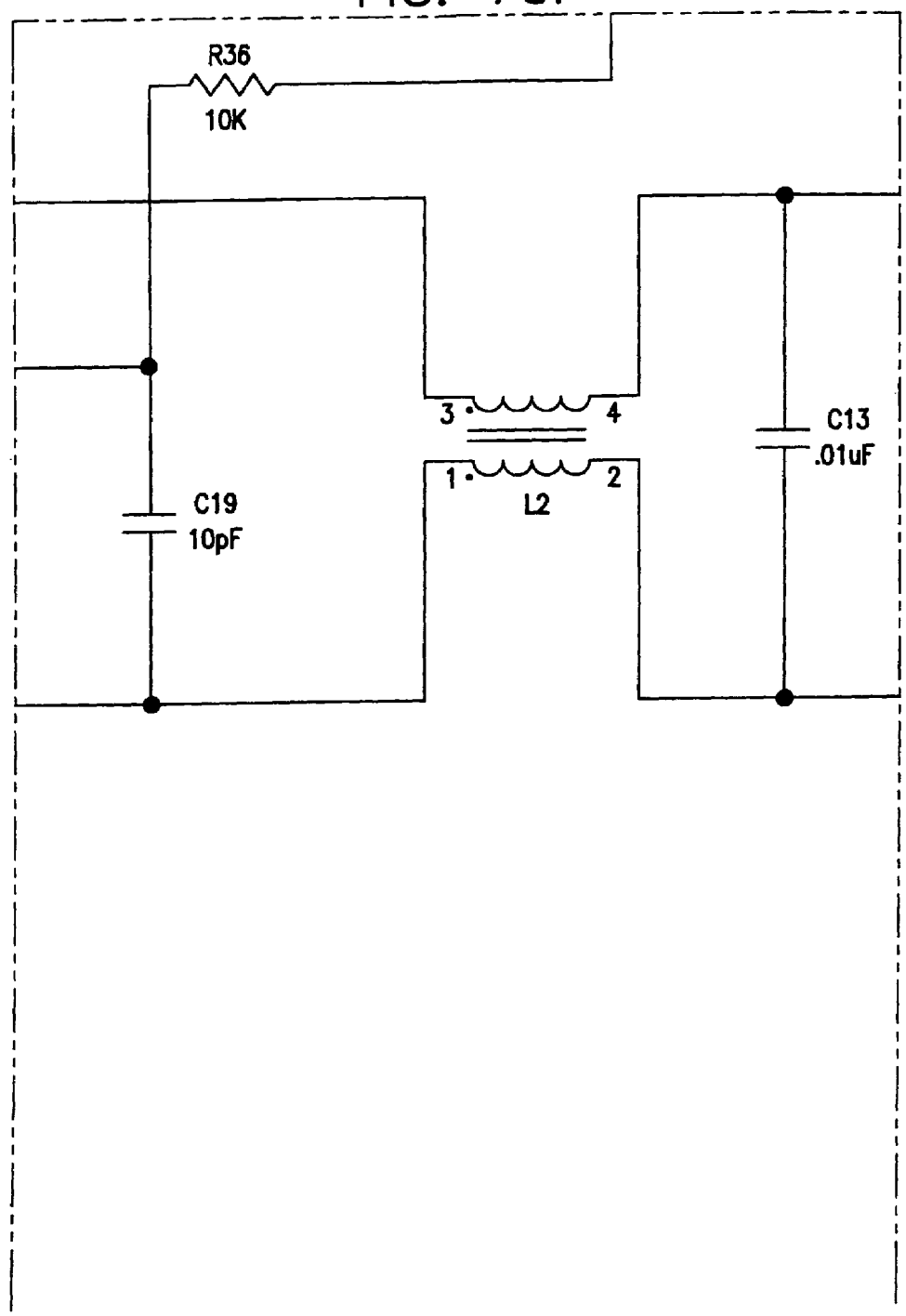
Figure 70G:
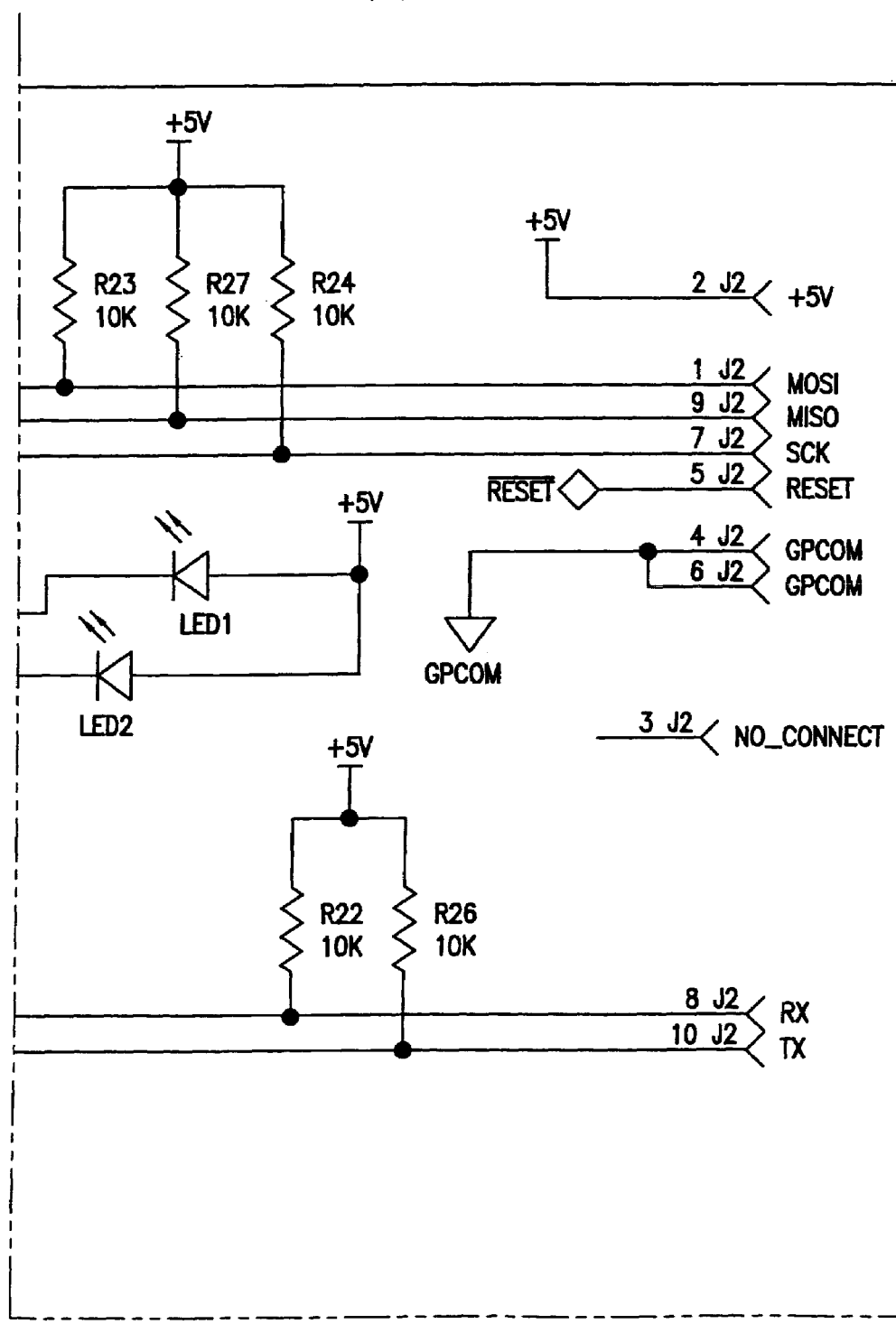

Pin 31 of the AT90S4422 .mu.C is coupled to the base of an NPN transistor (identified as circuit component Q5) through a 10 k.OMEGA. resistor as shown in FIGS. 70D–70F. The base of the Q5 transistor is coupled directly to the collector of an NPN transistor (identified as circuit component Q1) and is coupled to the emitter of the Q1 transistor through a 10 pF capacitor as shown in FIGS. 70D and 70F. The emitter of the Q5 transistor is coupled directly to the base of the Q1 transistor and is coupled to the emitter of the Q1 transistor through a 30.1.OMEGA. resistor as shown in FIG. 70D. Each sensor module 54 includes a 4-terminal diode bridge rectifier, shown in FIG. 70D and a 4-terminal transformer, shown in FIG. 70F, having two coils wound on a common core. The collector of the Q5 transistor is coupled to terminal 1 of the diode bridge rectifier and is coupled to terminal 3 of the 4-terminal transformer as shown in FIGS. 70D and 70F. The emitter of the Q1 transistor is coupled to terminal 2 of the diode bridge rectifier and is coupled to terminal 1 of the 4-terminal transformer as also shown in FIGS. 70D and 70F.

Figure 70H:
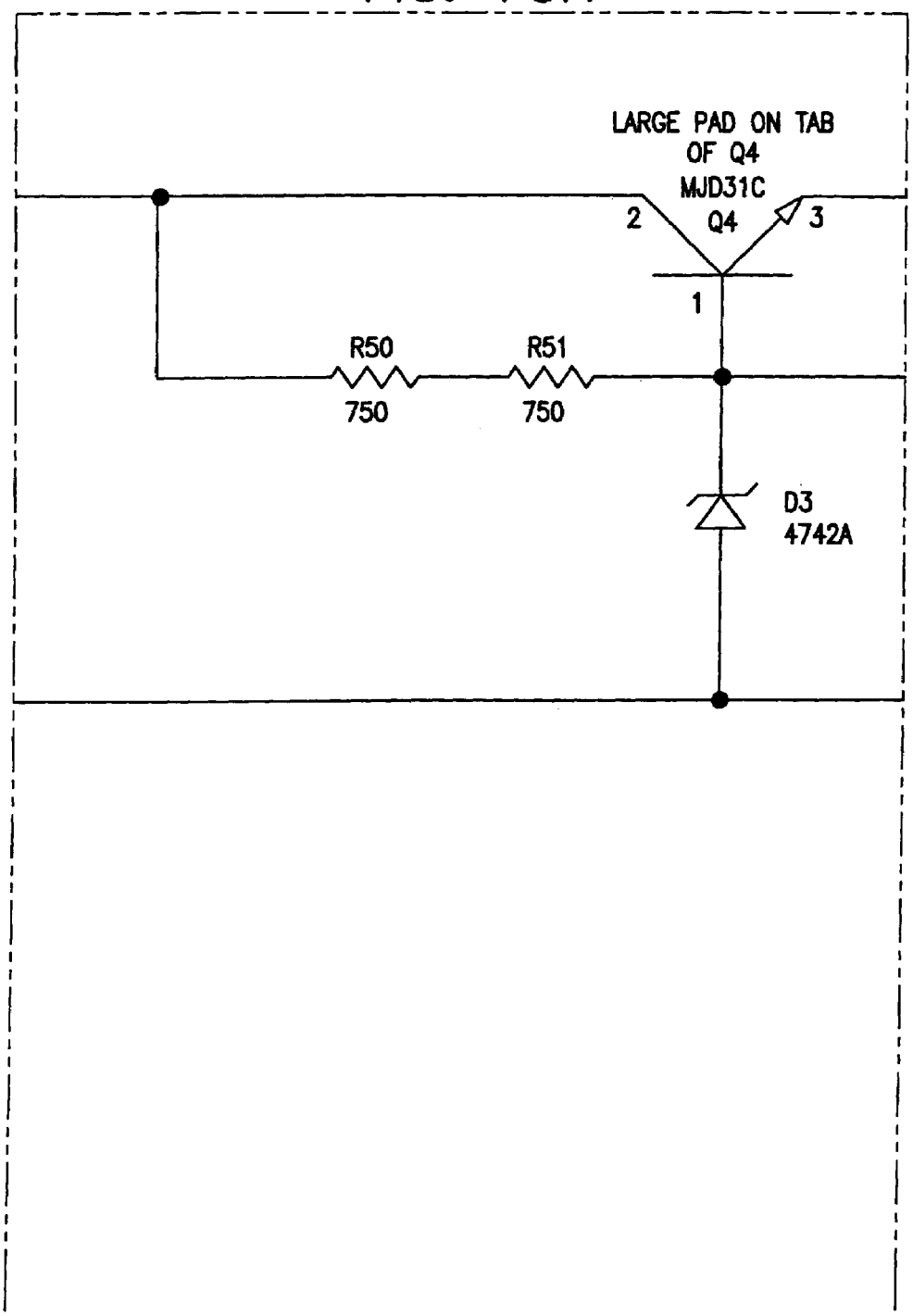
Figure 701:
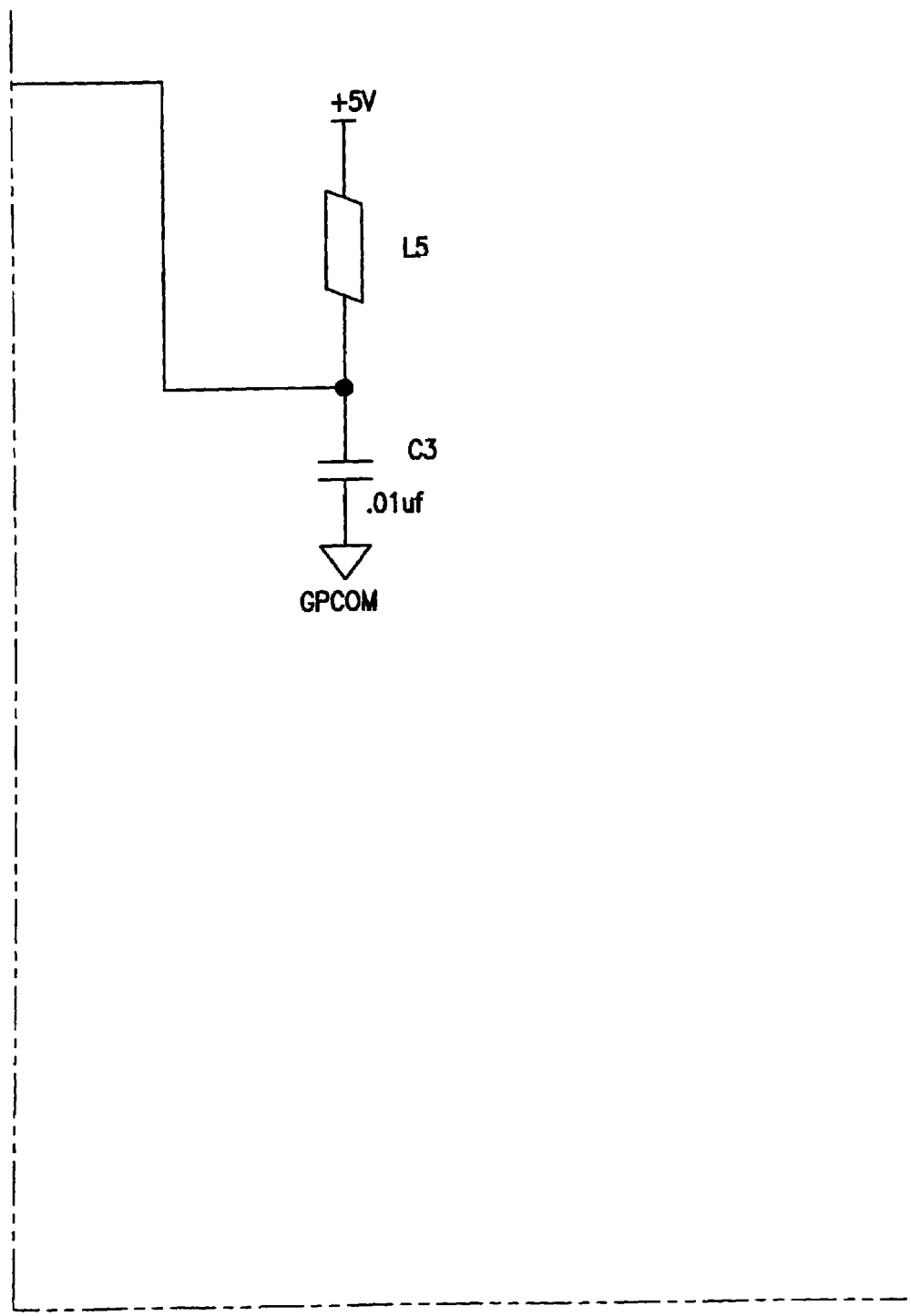
Figure 70J:
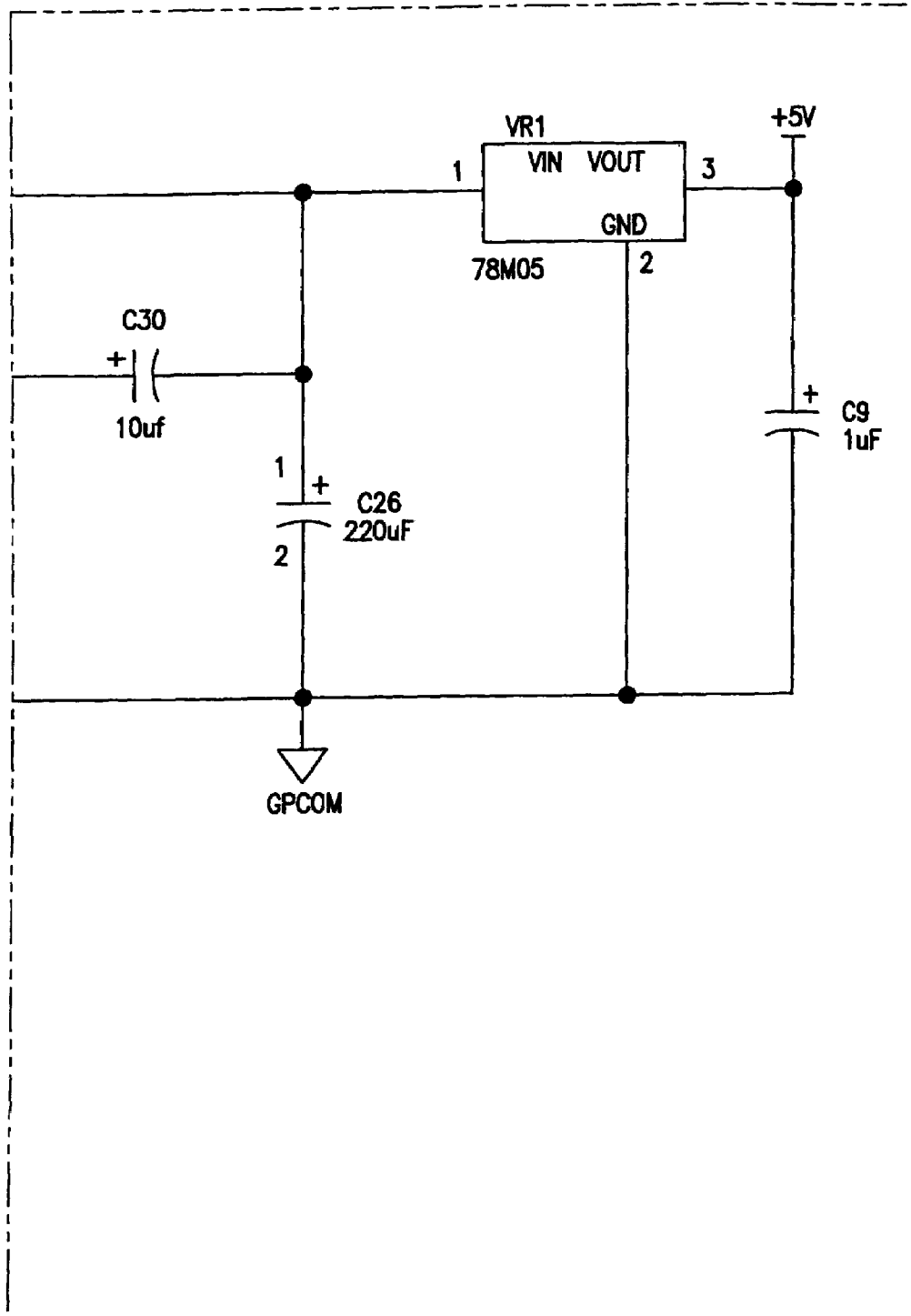

Terminal 2 of the 4-terminal transformer is coupled to GPCOM as shown in FIGS. 70F, 70H, and 70J. Terminal 4 of the 4-terminal transformer is coupled to the collector of an NPN transistor (identified as circuit component Q4) as shown in FIGS. 70F and 70H. In addition, terminal 2 of the 4-terminal transformer is coupled to terminal 4 thereof through a 0.01 .mu.F capacitor as shown in FIG. 70F. The collector of the Q4 transistor is coupled to the base of the Q4 transistor through the series combination of a pair of 750.OMEGA. resistors as shown in FIG. 70H. The base of the Q4 transistor is coupled to the cathode of a Zener diode as also shown in FIG. 70H. The anode of the Zener diode is coupled to GPCOM.

The base of the Q4 transistor is coupled to the emitter of the Q4 transistor through a 10 .mu.F capacitor as shown in FIGS. 70H and 70J. The emitter of the Q4 transistor is coupled to GPCOM through a 220 .mu.F capacitor as also shown in FIGS. 70H and 70J. In addition, the emitter of the Q4 transistor is coupled to pin 1 of a 5 Volt voltage regulator, such a 78M05 voltage regulator available from National Semiconductor Corporation, as shown in FIGS. 70H and 70J. Pin 2 of the 78M05 voltage regulator is coupled to GPCOM as shown in FIG. 70J. Pin 3 of the 78M05 voltage regulator is coupled directly to +5V and is coupled to GPCOM through a 1 .mu.F capacitor as also shown in FIG. 70J.

As shown in FIGS. 70B and 70D, terminal 3 is of the diode bridge rectifier is coupled to pin 2 of a connector J 1 to which the shielded, twisted pair wires couple. Terminal 4 of the diode bridge rectifier is coupled to pin 1 of the connector J 1 as also shown in FIGS. 70B and 70D. In addition, terminal 3 of the diode bridge rectifier is coupled to one terminal of a bidirectional diode and terminal 4 of the diode bridge rectifier is coupled to the other terminal of the bidirectional diode. Pin 3 of the connector J1 is open as shown in FIG. 70B. Pins 1, 2, and 3 of the connector J1 are associated with PWR2, PWR1, and GROUND lines, respectively, of the shielded, twisted pair wires.

In operation, a stream of serial data is transmitted from pin 31 of the AT90S4433 .mu.C through the Q5 transistor and through the diode bridge rectifier to the PWR2 line which is coupled through the twisted wire pair to the XDUCER_B line shown in FIG. 67A. The 10 pF capacitor coupled to the base of the Q5 transistor is normally charged to +5V because one of its terminals is coupled to GPCOM and the other of its terminals is coupled to +5V through the series combination of two 10 k.OMEGA. resistors. When the pin 31 of the AT90S4433 .mu.C changes from outputting a HIGH signal of about +5V to outputting a LOW signal of about 0V, the 10 pF capacitor discharges, thereby causing current to flow into the base of the Q5 transistor and switching the Q5 transistor from an OFF state to an ON state. When the Q5 transistor is in the ON state, current is drawn through the PWR1 and PWR2 lines through the Q5 transistor. The current draw through the Q5 transistor is sensed by the circuitry of FIGS. 67A–67U. Thus, pin 31 of the AT90S4433 .mu.C modulates the current draw through the Q5 transistor to transmit the serial data to the circuitry of FIGS. 67A–67U. The data sent from sensor module 54 to the associated alarm controller 50 is unidirectional and is sent two times per second in datagram format at a rate of 2400 baud.

Although the invention has been described in detail with reference to a certain illustrative embodiment, variations and modifications exist within the scope and spirit of the invention as described and as defined in the following claims.

What is claimed is:

1. A medical gas alarm system for use in a healthcare facility having a medical gas system and having a network of computer devices, the medical gas alarm system comprising:
   at least one area alarm controller adapted to receive a first signal indicative of a condition of a first portion of the medical gas system and adapted to communicate with the network; and
   at least one master alarm controller adapted to receive a second signal indicative of a condition of a second portion of the medical gas system and adapted to communicate with the network, the at least one area alarm controller being adapted to communicate with the at least one master alarm controller through the network, and
   wherein self-diagnostic tests may be run by the medical gas alarm system.

2. A medical gas alarm system according to claim 1, further comprising a plurality of sensor modules configured to sense gas pressures in respective gas pipes of the medical gas system,
   wherein the area alarm controller includes a plurality of display modules, each display module being associated with a respective sensor module, and each display module being configured to display the gas pressure sensed by the respective sensor module.

3. A medical gas alarm system according to claim 2, wherein the self-diagnostic tests may be run for each of the plurality of display modules of the area alarm controller.

4. A medical gas alarm system according to claim 1, wherein the self-diagnostic tests may be run by the master alarm controller.

5. A medical gas alarm system according to claim 1, wherein the area alarm controller is adapted to couple to a first network hub of the network.

6. A medical gas alarm system according to claim 5, wherein the master alarm controller is adapted to couple to a second network hub of the network.

7. A medical gas alarm system according to claim 6, wherein the master alarm controller communicates with a server of the network through the second network hub.

8. A medical gas alarm system according to claim 6, wherein the alarm controller communicates with a server of the network through the first network hub.

9. A medical gas alarm system according to claim 6, wherein the area alarm controller communicates with the master alarm controller through the first and second network hubs.

10. A medical gas alarm system for use in a healthcare facility having a medical gas system which delivers a plurality of medical gases to a plurality of locations in the healthcare facility including source equipment through a number of lines that are routed from the source equipment to outlets located throughout the healthcare facility, and a plurality of sensor modules, the medical gas alarm system comprising:
- a master alarm controller adapted to receive a plurality of alarm signals, each alarm signal being indicative of a respective alarm condition in the source equipment; and
- an alarm controller adapted to receive an input signal indicative of a condition of the medical gas system, the alarm controller being adapted to couple to the network,
- wherein the master alarm controller including a display screen that displays text messages identifying any alarm conditions that occur, and
- wherein the plurality of sensors monitors medical gas levels of the plurality of medical gases such that when the medical gas level falls below a predetermined level of a main supply the medical gas alarm system switches to a back-up supply and contacts supplier of the medical gas.

11. A medical gas alarm system according to claim 10, wherein the master alarm controller includes buttons that are operable to program the text messages that appear on the display screen for each of the alarm conditions.

12. A medical gas alarm system according to claim 11, wherein the master alarm controller is configured to host a website that is used to program the master alarm controller with the text messages that appear on the display screen for each of the alarm conditions.

13. A medical gas alarm system according to claim 12, wherein each web page of the website is identified by a respective network address.

14. A medical gas alarm system according to claim 10, wherein the alarm controller is programmed to send an e-mail to at least one designated e-mail address to provide notification of any alarm conditions that occur.

15. A medical gas alarm system according to claim 14, wherein the alarm controller is programmed to send an e-mail to the supplier of the medical gas when the medical gas alarm system switches over to the back-up supply of medical gas.

* * * * *